(12) United States Patent
Phan et al.

(10) Patent No.: US 7,029,912 B1
(45) Date of Patent: Apr. 18, 2006

(54) TYROSINE KINASE SUBSTRATE(TKS) PROTEINS

(75) Inventors: Huan Phan, Belmont, CA (US); Sara A. Courtneidge, Ada, MI (US)

(73) Assignee: Sugen, Inc., South San Francisco, CA (US)

( * ) Notice: Subject to any disclaimer, the term of this patent is extended or adjusted under 35 U.S.C. 154(b) by 0 days.

(21) Appl. No.: 09/958,359

(22) PCT Filed: Apr. 6, 2000

(86) PCT No.: PCT/US00/09277

§ 371 (c)(1),
(2), (4) Date: Feb. 5, 2002

(87) PCT Pub. No.: WO00/61750

PCT Pub. Date: Oct. 19, 2000

Related U.S. Application Data

(60) Provisional application No. 60/128,492, filed on Apr. 9, 1999.

(51) Int. Cl.
*C12N 15/12* (2006.01)
*C07K 16/16* (2006.01)

(52) U.S. Cl. .................. 435/325; 435/6; 435/69.1; 435/320.1; 435/252.3; 530/350; 536/23.5

(58) Field of Classification Search ............... 435/69.1, 435/6, 325, 320.1; 530/350; 536/23.5
See application file for complete search history.

(56) References Cited

FOREIGN PATENT DOCUMENTS

WO  96/31625  10/1996
WO  99/55858  11/1996

OTHER PUBLICATIONS

Schaller D.M et. al. Identification and characterization of Novel substrates for Protein tyrosine kinases 1993: Progress in Nucleic acid research and Molecular Biology, 44:205-227.*
GeneBank Accession NO. AA402736 WashU-NCI human EST project, 1996.*
GeneBank Accession NO. AA778210 WashU-NCI human EST project, 1998.*
GeneBank Accession NO. R18386 WashU-MERCK- EST project, 1995.*
GenBank Accsession NO. W65329 WashU-MERCK- EST project, 1996.*
D. Ensenat et al., "A Novel SRC Homology 3 Domain-containing Adaptor Protein, HIP-55, That Interacts with Hematopoietic Progenitor Kinase 1," *Journal of Biological Chemistry* 274(48):33945-33950 (1999).
P. Lock et al., "A New Method for Isolating Tyrosine Kinase Substrates Used to Identify Fish, an SH3 and PX Domain-containing Protein, and Src Substrate," *The EMBO Journal* 17(15):4345-4357 (1998).
A.B. Sparks et al., "Cloning of Ligand Targets: Systematic Isolation of SH3 Domain-containing Proteins," *Nature Biotechnology* 14(6):741-744 (1996).
Hillier et al., "The WashU-Merck EST Project,", DATABASE EMBL 'Online! Accession No. R18386, (1995) XP002146969 (Abstract).
Hillier et al., "The WashU-Merck EST Project,", DATABASE EMBL 'Online! Accession No. W65329, (1996) XP002146970 (Abstract).
Hillier et al., "The WashU-NCI Human EST Project,", DATABASE EMBL 'Online! Accession No. AA402736; (1995) XP002146971 (Abstract).
Hillier et al., "The WashU-Merck EST Project,", DATABASE EMBL 'Online! Accession No. W68106, (1996) XP002156940 (Abstract).
J. Takeda, "Large Scale Collection of Expressed Sequence Tags (ESTs) From Human Pancreatic Islet cDNA Library," DATABASE EMBL 'Online! Accession No. C75612, (1997) XP002156941 (Abstract).
R. Strausberg, "National Cancer Institute, Cancer Genome Anatomy Project," DATABASE EMBL 'Online! Accession No. AA470519. (1997) XP002156942 (Abstract).

* cited by examiner

*Primary Examiner*—Rebecca E. Prouty
(74) *Attorney, Agent, or Firm*—Beth A. Burrous; Gregg C. Benson; Nicholas I. Slepchuk, Jr.

(57) ABSTRACT

The present invention relates to novel Tks 107, Tks 113, Tks 118 and Tks 202 polypeptides, nucleotide sequences encoding the novel polypeptides, as well as various products and methods useful for the diagnosis and treatment of various related diseases and conditions.

20 Claims, 25 Drawing Sheets

FIG. 1

```
CGCTGAAGGGCGGGGCGGGGAGGGGCGGCCGTCTCGGCCCTCCCTGGCGGGGCCCCGCGGCCTGGAAGCCGGAGCGGGCC
GAGCCGCCACCGCGGCCGGAGCTGTCCCTTAGCCAGACCCGGCGAGACACGAGCGGCGGGAGGGAGGCGGTGGCGCGCCC
GGCCCCGCCCGCCCGACCAAGCGTCGGACGCGGCCCGGCGCCGAGCCATGGAGCCTGAGCCAGTGGAGGACTGTGTGCAG
AGGACTCTCGCCGCCCTGTATCCACCCTTTGAGGCAACAGCCCCCACCCTGTTGGGCCAGGTGTTCCAGGTGGTGGAGAG
GACTTATCGGGAGGACGCACTGAGGTACACGCTGGACTTCCTGGTACCAGCCAAGCACCTGCTTGCCAAGGTCCAGCAGG
AAGCCTGTGCCCAATACAGTGGATTCCTCTTCTTCCATGAGGGGTGGCCGCTCTGCCTGCATGAACAGGTGGTGGTGCAG
CTAGCAGCCCTACCCTGGCAACTGCTGCGCCCAGGAGACTTCTATCTGCAGGTGGTGCCCTCAGCTGCCCAAGCACCCCG
ACTAGCACTCAAGTGTCTGGCCCCTGGGGGTGGGCGGGTGCAGGAGGTTCCTGTGCCCAATGAGGCTTGTGCCTACCTAT
TCACACCTGAGTGGCTACAAGGCATCAACAAGGACCGGCCAACAGGTCGCCTCAGTACCTGCCTACTGTCTGCGCCCTCT
GGGATTCAGCGGCTGCCCTGGGCTGAGCTCATCTGTCCACGATTTGTGCACAAAGAGGGCCTCATGGTTGGACATCAGCC
AAGTACACTGCCCCAGAACTGCCCTCTGGACCTCCAGGGCTTCCCAGCCCTCCACTTCCTGAGGAGGCGCTGGGTACCC
GGAGTCCTGGGGATGGGCACAATGCCCCTGTGGAAGGACCTGAGGGCGAGTATGTGGAGCTGTTAGAGGTGACGCTGCCC
GTGAGGGGGAGCCCAACAGATGCTGAAGGCTCCCCAGGCCCTCCAGAGTCCGGACGGTACCCACCCGCAAGGGCGCTGG
AGGGAAGGGCCGCCACCGGAGACACCGGGCGTGGATGCACCAGAAGGGCCTGGGGCCTCGGGGGCCAGGATGGAGCACGCC
CACCCGGCGAGGGGAGCAGCACCGGAGCCTCCCCTGAGTCTCCCCCAGGAGCTGAGGCTGTCCCAGAGGCAGCAGTCTTG
GAGGTGTTTGAGCCCCAGCAGAGGCTGTGGGAGAAGCCTCCGGATCTTGCCCCCTGAGGCCAGGGGAGCTTAGAGGAGG
AGGAGGAGGAGGCCAGGGGGCTGAAGGACCACCTGGTACCCCTCGGAGAACAGGCAAAGGAAACAGAAGAAAGAAGCGAG
CTGCAGGTCGAGGGGCTCTTAGCCGAGGAGGGGACAGTGCCCCACTGAGCCCTGGGGACAAGGAAGATGCCAGCCACCAA
GAAGCCCTTGGCAATCTGCCCTCACCAAGTGAGCACAAGCTTCCAGAATGCCACCTGGTTAAGGAGGAATATGAAGCCTC
AGGGAAGCCAGAATCTGAGCCAAAAGAGCTCAAAACAGCAGGCGAGAAAAGAGCCTCAGCTCTCTGAAGCCTGTGGGCCTA
CAGAAGAGGGGCCGGAGAGAGAGAGCTGGAGGGGCCAGGCCTGCTGTGTATGGCAGACACACAGGCCCAGAAGGCCCC
CTGTCTGACACTCCAACACCTCCGCTGGAGACTGTGCAGGAAGGAAAAGGGGACAACATTCCAGAAGAGGCCCTTGCAGT
CTCCGTCTCTGATCACCCTGATGTAGCTTGGGACTTGATGGCATCTGGATTCCTCATCCTGACGGGAGGGGTGGACCAGA
GTGGGCGAGCTCTGCTGACCATTACCCCACCGTGCCCTCCTGAGGAGCCCCCACCCTCCCGAGACACGCTGAACACAACT
CTTCATTACCTCCACTCACTGCTCAGGCCTGATCTACAGACACTGGGGCTGTCCGTCCTGCTGGACCTTCGTCAGGCACC
TCCACTGCCTCCAGCACTCATTCCTGCCTTGAGCCAACTTCAGGACTCAGGAGATCCTCCCCTTGTTCAGCGGCTGCTGA
TTCTCATTCATGATGACCTTCCAACTGAACTCTGTGATTCAGGGTGCTGAGGTGCTGTCAGAGAATGATCTGAAAAGA
GTGGCCAAGCCAGAGGAGCTGCAGTGGGAGTTAGGAGGTCACAGGGACCCCTCTCCCAGTCACTGGGTAGAGATACACCA
GGAAGTGGTAAGGCTATGTCGCCTGTGCCAAGGTGTGCTGGGCTCGGTACGGCAGGCCATTGAGGAGCTGGAGGGAGCAG
CAGAGCCAGAGGAAGAGGAGGCAGTGGGAATGCCCAAGCCACTGCAGAAGGTGCTGGACAGATCCCCGGCTGACGGCACTG
CAGAGGGATGGGGGGGCCATCCTGATGAGGCTGCGCTCCACTCCCAGCAGCAAGCTGGAGGCCAAGGCCCAGCTACACT
GTATCAGGAAGTGGACGAGGCCATTCACCAGCTTGTGCGCCTCTCCAACCTGCACGTGCAGCAGCAAGAGCAGCGGCAGT
GCCTGCGGCGACTCCAGCAGGTGTTGCAGTGGCTCTGCAGGCCCAGGGGAGGGAGCAGCTGGCAAGCTTTGCTATGCCTGGG
GACACCTTGTCTGCCCTGCAGGAGACAGAGCTGCGATTCCGTCTTTCAGCGCTGAGGTCCAGGAGCGCCTGGCCCAGGC
ACGGGAGGCCCTGGCTCTGGAGGAGAATGCCACCTCCCAGAAGGTGCTGGATATCTTTGAACAGCGGCTGGAGCAGGTTG
AGAGTGGCCTCCATCGGGCCCTGCGGCTACAGCGCTTCTTCCAGCAGGCACATGAATGGGTGGATGAGGGCTTTGCTCGG
CTGGCAGGAGCTGGGCCGGGTCGGGAGGCTGTGCTGGCTGCACTGGCCCTGCGGCGGGCCCCAGAGCCCAGTGCCGGCAC
CTTCCAGGAGATGCGGGCCCTGGCCCTGGACCTGGGCAGCCCAGCAGCCCTGCGAGAATGGGGCCGCTGCCAGGCCCGCT
GCCAAGAGCTAGAGAGGAGGATCCAGCAACACCTGGGAGAGGAGGCGAGCCCACGGGGCTACCGACGACGGCGGGCAGAC
GGTGCCAGCAGTGGAGGGGCCCAGTGGGGGCCCCGCAGCCCCTCGCCCAGCCTCAGCTCCTTGCTGCTCCCAGCAGCCC
TGGGCCACGGCCAGCCCCATCCCCATTGCTCCCTGGCCCCATGTGGAGGACTATGAGGAAGAGGGGCCCTGAGCTGGCTC
CAGAAGCAGAGGCGAGGCCCCCAAGAGCTGTGCTGATCCGAGGCCTGGAGGTCACCAGCACTGAGGTGGTAGACAGGACG
TGCTCACCACGGGAACACGTGCTGCTGGGCCGGGCTAGGGGGCCAGACGGACCCTGGGGAGTAGGCGCCCCCCGGATGGA
GCGCAAGCGAAGCATCAGTGCCCAGCAGCGGCTGGTGTCTGAGCTGATTGCCTGTGAACAAGATTACGTGGCCACCTTGA
GTGAGCCAGTGCCACCCCCTGGGCCTGAGCTGACGCCTGAACTTCGGGGCACCTGGGCTGCTGCCCTGAGTGCCCGGGAA
AGGCTTCGCAGCTTCCACCGGACACACTTTCTGCGGGAGCTTCAGGGCTGCGCCACCCACCCCCTACGCATTGGGGCCTG
CTTCCTTCGCCACGGGGACCAGTTCAGCCTTTATGCACAGTACGTGAAGCACCGACACAAACTGGAGAATGGTCTGGCTG
CGCTCAGTCCCTTAAGCAAGGGCTCCATGGAGGCTGGCCCTTACCTGCCCCCGAGCCCTGCAGCAGCCTCTGGAACAGCTG
ACTCGGTATGGGCGGCTCCTGGAGGAGCTCCTGAGGGAAGCTGGGCCTGAGCTCAGTTCTGAGTGCCGGGCCCTTGGGGC
TGCTGTACAGCTGCTCCGGGAACAAGAGGCCCGTGGCAGAGACCTGCTGGCCGTGGAGGCGGTGCGGGCTGTGAGATAG
ATCTGAAGGAGCAGGGACAGCTCTTGCATCGAGACCCCTTCACTGTCATCTGTGGCCGAAAGAAGTGCCTTCGCCATGTC
TTCTTCTTCGAGCATCTCCTCCTGTTCAGCAAGCTCAAGGGCCCTGAAGGGGGGTCAGAGATGTTTGTTTACAAGCAGGC
CTTTAAGACTGCTGATATGGGGCTGACAGAAAACATCGGGGACAGCGGACTCTGCTTTGAGTTGTGGTTTCGGCGGCGGC
GTGCACGAGAGGCATACACTCTGCAGGCAACCTCACCAGAGATCAAACTCAAGTGGACAAGTTCTATTGCCCAGCTGCTG
TGGAGACAGGCAGCCCACAACAAGGAGCTCCGAGTGCAGACGATGGTGTCCATGGGCATTGGGAATAAACCCTTCCTGGA
CATCAAAGCCCTTTGGGGAGCGGACGCTGAGTGCCCTGCTCACTGGAGAAGAGCCGCCCGCACCCGGGCCCTCCGTGGCCGTGT
CATCCTTTGAGCATGCCGGCCCCTCCCTTCCCGGCCTTTCGCCGGGAGCCTGCTCCCTGCCTGCCCGCGTCGAGGAGGAG
GCCTGGGATCTGGACGTCAAGCAAATTTCCCTGGCCCCAGAAACACTTGACTCTTCTGGAGATGTGTCCCCAGGAGCAAG
AAACAGCCCCAGCCTGCAACCCCCCCACCCTGGGAGCAGCACTCCCACCCTGGCCAGTCGAGGGATCTTAGGGCTATCCC
GACAGAGTCATGCTCGAGCCCTGAGTGACCCCACCACGCCTCTGTGACCTGGAGAAGATCCAGAACTTGCGTGCAGCTTC
TCCTCTCAGCACACTTTGGGCTGGGATGGCAGTGGGGCATAATGGAGCCCTGGGCGATCGCTGAATTTCTTCCCTCTGCT
TCCTGGACACAGAGGAgGCTAACGACCAGAGTATTGCCCTGCCACCACTATCTCTAGTCTCCCTAGCTTGGTGCCTTCT
CCTGCAGGAGTCAGAGCAGCCACATTGCTTGCCTTCATACCCTGgAGGTgGGGAAGTTATCCCTCTTCCGGTGCTTTCCC
ATCCTGGGCCACTGTATCCAGGACATCACTCcCATGCCAGCCCTCCCTGGCAGCCCATGTTCcCCTCTTTTCTCACCCCC
TGACTTTCCCTGAGAAGAATCATCTCTGCCAGGTCAACTGGAGTCCCTGGTGACTCCATTCTGAGGTGTCACAAGCAATG
AAGCTATGCAAACAATAGGAGGGTGTGACAGGGGAACCGTAGACTTTATATATGTAATTACTGTTATTATAATACTATTG
TTATATTAAATGTATTTACTCACACTTTGCCCTCTAAAAAAAAAAAAAAAAAAAAA
```

FIG. 2

```
GAATTCGGCACGAGCAACTACGGCGGCGGCGGCAGAACCCAGCAGTGATGT
GGAGGTGGAGACCCACAGGAGCCCCGGAC
TTCACCTGAGCTACCTCAGTGGTCACCAAGAGTGGCAAGATAAAGAAAACCC
TGAGTTGGGCGGGACCAGGATGCCTGAC
CGGGACAGCTATGCCAACGGTACCGGGAGCAGCGGTGGAGGCCCTGGAGGT
GGTGGCAGCAAGGAGGCCAGTGGGGCAGG
GGTAGGCAGTGGCGGGGCCAGCTCAGATGCCATCTGTAGAGACTTCTTGAGG
AATGTGTGCAAGCGAGGCAAGCGTTGCC
GATATCGCCACCCAGACATGAGCGAGGTGTCCAACTTGGGGGTGAGCAAAAA
CGAGTTCATCTTCTGCCATGACTTCCAG
AACAAGGAGTGTAGCCGCCCAAATTGCCGTTTCATCCATGGCTCCAAGGAGG
ATGAGGATGGCTATAAGAAGACAGGAGA
GCTTCCCCCACGGCTGAGGCAGAAAGTAGCAGCTGGCCTTGGCCTTTCACCG
GCTGACCTACCAAATGGCAAGGAGGAGG
TCCCTATCTGCCGTGACTTTCTCAAGGGTGACTGTCAGAGAGGAGCCAAGTG
CAAGTTCCGTCACCTGCAACGGGATTTT
GAGTTTGATGCTCGGGGTGGAGGAGGCACTGGTGGGGGCTCAACAGGCTCAG
TCCTCCCAGGACGACGTCATGATCTCTA
TGATATCTATGACCTTCCTGACAGGGGCTTTGAGGACCATGAGCCAGGCCCA
AAACGCCGGCGAGGTGGATGCTGCCCCC
CTGATGGCCCTCATTTTGAGTCATATGAATATAGTTTGGCTCCACCGCGAGGG
GTGGAGTGCAGACTGCTAGAGGAGGAG
AATGCCATGCTCAGGAAGCGGGTAGAGGAGTTAAAGAAGCAGGTCAGCAAC
CTGCTGGCCACCAATGAGGTACTACTGGA
ACAAAATGCTCAGTTCCGCAATCAGGCCAAGGTCATAACCCTGAGCTCCACT
GCACCAGCGACTGAGCAGACTCTGGCCC
CCACTGTGGGCACTGTTGCCACTTTTAACCATGGCATTGCCCAGACTCACACT
ACTCTCAGCAGCCAGGCTCTACAGCCT
CGTCCAGTGTCCCAGCAAGAACTGGTGGCCCCTGCTGGAGCTCCAGCTGCTG
CCCCAACTAATGCTGCACCTCCTGCTGC
GCCCTGGCTCAAACAATTGCCCAGGGAA
TGGCACCTCCACCTGTCTCCATGGCTCCTGTGGCTGTATCTGTGGCTCCTGTG
GCCCCTGTGGCTGTATCGATGGCCCAA
CCCTTGGCAGAAATCACAATGAGCCACACCACCACTCCCATGGTGACTTACC
CTATCGCTCCCCCTCGAG
```

FIG. 3

```
TTCGACACGAGCTGCGGGGCGGGCCATGGCGGCGAACCTGAGCCGGAACGGGCCAGCGCTGCAAGAGGCCTACGTGCGGG
TGGTCACCGAGAAGTCCCCGACCGACTGGGCTCTCTTTACCTATGAAGGCAACAGCAATGACATCCGCGTGGCTGGCACA
GGGGAGGGTGGCCTGGAGGAGATGGTGGAGGAGCTCAACAGCGGGAAGGTGATGTACGCCTTCTGCAGAGTGAAGGACCC
CAACTCTGGACTGCCCAAATTTGTCCTCATCAACTGGACAGGCGAGGGCGTGAACGATGTGCGGAAGGGAGCCTGTGCCA
GCCACGTCAGCACCATGGCCAGCTTCCTGAAGGGGGCCCATGTGACCATCAACGCACGGGCCGAGGAGGATGTGGAGCCT
GAGTGCATCATGGAGAAGGTGGCCAAGGCTTCAGGTGCCAACTACAGCTTTCACAAGGAGAGTGGCCGCTTCCAGGACGT
GGGACCCCAGGCCCCAGTGGGCTCTGTGTACCAGAAGACCAATGCCGTGTCTGAGATTAAAAGGGTTGGTAAAGACAGCT
TCTGGGCCAAAGCAGAGAAGGAGGAGGAGAACCGTCGGCTGGAGAAAAGCGGCGGGCCGAGGAGGCACAGCGGCAGCTG
GAGCAGGAGCGCCGGGAGCGTGAGCTGCGTGAGGCTGCACGCCGGGAGCAGCGCTATCAGGAGCAGGGTGGCGAGGCCAG
CCCCCAGAGCAGGACGTGGGAGCAGCAGCAAGAAGTGGTTTCAAGGAACCGAAATGAGCAGGAGTCTGCCGTGCACCCGA
GGGAGATTTTCAAGCAGAAGGAGAGGGCCATGTCCACCACCTCCATCTCCAGTCCTCAGCCTGGCAAGCTGAGGAGCCCC
TTCCTGCAGAAGCAGCTCACCCAACCAGAGACCCACTTTGGCAGAGAGCCAGCTGCTGCCATCTCAAGGCCCAGGGCAGA
TCTCCcTGcTGAGGAGCCGGCGCCCAGCACTCCTCCATGTCTGGTGCAGGCAGAAGAGGAGGcTGTGTATGAGGAACCTC
CAGAGCAGGAGACCTTCTACGAGCAGCCCCACTGGTGCAGCAGCAAGGTGCTGGCTCTGAGCACATTGACCACCACATT
CAGGGCCAGGGGCTCACTGGGCAAGGGCTCTGTGCCCGTGCCCTGTACGACTACCAGGCAGCCGACGACACAGAGATCTC
CTTTGACCCCGAGAACCTCATCACGGGCATCGAGGTGATCGACGAAGGCTGGTGGCGTGGCTATGGGCCGGATGGCCATT
TTGGCATGTTCCCTGCCAACTACGTGGAGCTCATTGAGTGAGGCTGAGGGCACATCTTGCCCTTCCCCTCTCAGACATGG
CTTCCTTATTGCTGGAAGAGGAGGCCTGGGAGTTGACATTCAGCACTCTTCCAGGAATAGGACCCCCAGTGAGGATGAGG
CCTCAGGGCTCCCTCCGGCTTGGCAGACTCAGCCTGTCACCCCAAATGCAGCAATGGCCTGGTGATTCCCACACATCCTT
CCTGCATCCCCCGAC
```

FIG. 4

```
CAGTCGCAGGAGGCGCTCCTTGGCGGTGCCTGGAGCCCGGGCGCACCCCACCGCTCCCGGGACCTGTTGGGCGCTGGCCC
GACCCGTCGTCGAAGGGAGCCGCTCGGCCACCCCCGACGTTCCTCGCCCCGCCCGACGTTCCCTCAAGTGGCCGAACCAG
CCGGACGAGCCAAACTCGCCGGGCCTCCCGGCGGCAGCAGGTGGCCCCGTCCTTCCAGGGAGGGCCCTGCGCCCCGCGGC
GCTCCGGAGCCCTCTCGGCCGCCCCCGCCAGGCGGATGGAGGCGGATGGGGACGGAGAGGAGCTGGCCCGGCTGCGCTC
AGTCTTCGCCGCCTGCGACGCGAACCGCTCGGGGCGCCTGGAGCGCGAGGAGTTCCGGGCAcTGTGCACGGAGCTGCGGG
TGCGGCCGGCCGACGCCGAggCAGTATTCCAGCGGCTGGACGCCGACCGTGACGGCGCAATCACCTTCCAGGAGTTCGCG
CGTGGCTTCCTCGGGTCCCTCCGCGGGGGGCGGCGCCGGGACTGGGGTCCTCTGGATCCCGCGCCCGCCGTGTCTGAGGC
GGGGCCGGAgACACACGACAGCGAGGAGGACGAAGGCGACgAGGACgCGGCGGCGGCGCTGGCCACCTCGTGCGGCCCGG
CGAGTCCCGGCCGGGCTTGGCAGGATTTCCAGGCGCGACTTGGGGACGAAGCCAAGTTCATTCCCAGAGAAGAGCAAGTT
AGTACCTTGTACCAAAACATCAACCTTGTGGAGCCAAGATTAATTCAGCCATATGAACATGTTATAAAGAACTTCATCCG
TGAGATCAGACTTCAAAGCACAGAAATGGAAAATTTGGCCATTGCGGTGAAGAGAGCCCAGGACAAGGCAGCTATGCAGT
TGAGTGAGTTGGAAGAGGAAATGGATCAGAGGATTCAGGCTGCAGAACATAAGACACGGAAAGACGAAAAACGCAAAGCT
GAGGAAGCCCTCAGTGACCTCAGACGTCAGTATGAAACTGAAGTAGGAGATCTGCAGGTGACCATTAAAAAGCTAAGAAA
GCTCGAAGAACAATCAAAAcGCGTAAGTCAAAAGGAAGATGTGGCTGCATTGAAAAAACAAATTTATGATTTATCAATGG
AAAACCAGAAAGTTAAGAAAGACCTTTTAGAAGCACAGACAAACATAGCCTTTCTTCAGAGTGAGTTAGATGCTTTGAAA
AGTGATTATGCTGATCAGAGTCTGAATACTGAAAGGGATCTGGAAATAATCCGAGCATACACAGAAGATCGAAATAGTCT
TGAGAGGCAAATTGAAATACTCCAAACAGCTAACCGGAAGCTACATGACAGTAATGATGGCCTTAGAAGTGCCCTTGAAA
ACAGTTATAGCAAGTTCAACAGATCTTTGCATATAAATAATACTCACCAGGGAATACAATTTCTAGAAGCAGTCCCAAA
TTCATTGGTCATTCCCCTCAACCTCTAGGCTATGACAGGTCATCCCGCTCTTCCTATGTGGATGAGGACTGTGACTCCCT
GGCCCTCTGTGATCCTCTGCAGAGGACAAATTGTGAAGTTGACAGCCTGCCTGAAAGCTGCTTGGACAGCGGCTTGTCTA
CCTTGAGAGATCCCAATGAGTATGACTCAGAAGTGGAATACAAGCACCAGAGGGGATTTCAGAGGTCACACGGGGTGCAG
GAGAGCTTTGGAGGTGATGCTTCAGACACAGATGTTCCTGACATAAGGGATGAAGAGACATTTGGTTTAGAAGATGTGGC
TTCCGTCTTAGACTGGAAGCCCCAAGGGTCTGTTAGTGAAGGCAGCATTGTTAGTTCATCAAGAAAGCCCATCTCAGCAC
TCTCGCCCCAGACAGACCTGGTAGATGACAACGTCAAATCTTTTAGCTCACAGAAGGCTTACAAGATTGTACTTGCTGGG
GACGCTGCAGTGGGGAAGTCTAGTTTCCTCATGAGACTTTGCAAGAATGAATTTCGAGAAAATATAAGCGCCACCCTGGG
AGTTGATTTCCAAATGAAAACCCTCATTGTGGATGGAGAACGAACAGTTCTGCAGCTCTGGGATACAGCTGGTCAGGAGA
GATTCAGAAGTATTGCCAAGTCTTACTTCAGAAAGGCAGATGGTGTTTTGCTGCTGTATGATGTTACATGTGAGAAAAGC
TTTCTTAACATACGAGAATGGGTAGATATGATTGAGGATGCAGCCCATGAGACTGTTCCCATTATGCTGGTAGGAAACAA
GGCTGACATTCGTGACACTGCTGCTACAGAGGGACAAAAATGTGTCCCAGGGCACTTTGGAGAGAAACTGGCCATGACGT
ATGGGGCATTATTCTGTGAAACAAGTGCCAAAGATGGTTCTAACATAGTGGAGGCTGTTCTGCACCTTGCTCGAGAAGTG
AAAAAGAGAACTGACAAGGATGACAGCAGATCCATTACCAATCTAACCGGGACCAATTCCAAAAAGTCACCACAGATGAA
GAATTGTTGCAATGGCTAAATCCCAAACATCCTTGGCCTGTGAAGTCTTCATTTCCAGAATACTGAATTTGTGTGACTTA
TTTGGCTCTTAACAGAGTGGCACATCCTACTGACACTGTCCATGGAGAGTTTACAGTGCAGGGAAACCTGAACCCAGCT
CTCAGGTCCCTCTGGAACTTTGGCTCTTCTTTGTTTTGTCTCAGTGAGTGATTTGGGCCCTCTGGCTAAATAGACTAGTC
ATGTCCTTACAGGTCTTAAAAGATAACATGTAAATGTTTTTAAAATGGTAAAAAAAAAAAAAAAAAA
```

FIG. 6

```
NSARATTAAAAEPSSDVEVETHRSPGLHLSYLSGHQEWQDKENPELGGTRMPDR
DSYANGTGSSGGGPGGGGSKEASGAG
VGSGGASSDAICRDFLRNVCKRGKRCRYRHPDMSEVSNLGVSKNEFIFCHDFQN
KECSRPNCRFIHGSKEDEDGYKKTGE
LPPRLRQKVAAGLGLSPADLPNGKEEVPICRDFLKGDCQRGAKCKFRHLQRDFE
FDARGGGGTGGGSTGSVLPGRRHDLY
DIYDLPDRGFEDHEPGPKRRRGGCCPPDGPHFESYEYSLAPPRGVECRLLEEENA
MLRKRVEELKKQVSNLLATNEVLLE
QNAQFRNQAKVITLSSTAPATEQTLAPTVGTVATFNHGIAQTHTTLSSQALQPRP
VSQQELVAPAGAPAAPPTNAAPPAA
PPPPPPHLTPEITPLSAALAQTIAQGMAPPPVSMAPVAVSVAPVAPVAVSMAQPL
AGITMSHTTTPMVTYPIAPPR
```

FIG. 5

MEPEPVEDCVQSTLAALYPPFEATAPLLGQVFQVVERTYREDALRYTLDFLVP
AKHLLAKVQQEACAQYSGFLFFHEGW
PLCLHEQVVVQLAALPWQLLRPGDFYLQVVPSAAQAPRLALKCLAPGGGRVQE
VPVPNEACAYLFTPEWLQGINKDRPTG
RLSTCLLSAPSGIORLPWAELICPRFVHKEGLMVGHQPSTLPPELPSGPPGLPSPPL
PEEALGTRSPGDGHNAPVEGPEG
EYVELLEVTLPVRGSPTDAEGSPGLSRVRTVPTRKGAGGKGRHRRHRAWMHQK
GLGPRGQDARPPGEGSSTGASPESPP
GAEAVPEAAVLEVFEPPAEAVGEASGSCPLRPGELRGGGGGGQGAEGPPGTPRR
TGKGNRRKKRAAGRGALSRGGDSAPL
SPGDKEDASHQEALGNLPSPSEHKLPECHLVKEEYEGSGKPESEPKELKTAGEKE
PQLSEACGPTEEGAGERELEGPGLL
CMAGHTGPEGPLSDTPTPPLETVQEGKGDNIPEEALAVSVSDHPDVAWDLMASG
FLILTGGVDQSRALLTITPPCPPEE
PPPSRDTLNTTLHYLHSLLRPDLQTLGLSVLLDLRQAPPLPPALIPALSQLQDSGD
PPLVQRLLILIHDDLPTELCGFQG
AEVLSENDLKRVAKPEELQWELGGHRDPSPSHWVEIHQEVVRLCRLCQGVLGSV
RQAIEELEGAAEPEEEEAVGMPKPLQ
KVLADPRLTALQRDGGAILMRLRSTPSSKLEGQGPATLYQEVDEAIHQLVRLSNL
HVQQQEQRQCLRRLQQVLQWLSGPG
EEQLASFAMPGDTLSALQETELRFRAFSAEVQERLAQAREALALEENATSQKVL
DIFEQRLEQVESGLHRALRLQRFFQQ
AHEWVDEGFARLAGAGPGREAVLAALALRRAPEPSAGTFQEMRALALDLGSPA
ALREWGRCQARCQELERRIQQHLGEEA
SPRGYRRRRADGASSGGAQWGPRSPSPSLSSLLLPSSPGPRPAPSHCSLAPCGEDY
EEEGPELAPEAEGRPPRAVLIRGL
EVTSTEVVDRTCSPREHVLLGRARGPDGPWGVGAPRMERKRSISAQQRLVSELI
ACEQDYVATLSEPVPPPGPELTPELR
GTWAAALSARERLRSFHRTHFLRELQGGCATHPLRIGACFLRHGDQFSLYAQYVK
HRHKLENGLAALSPLSKGSMEAGPYL
PRALQQPLEQLTRYGRLLEELLREAGPELSSECRALGAAVQLLREQEARGRDLLA
VEAVRGCEIDLKEQGQLLHRDPFTV
ICGRKKCLRHVFLFEHLLLFSKLKGPEGGSEMFVYKQAFKTADMGLTENIGDSG
LCFELWFRRRRAREAYTLQATSPEIK
LKWTSSIAQLLWRQAAHNKELRVQQMVSMGIGNKPFLDIKALGERTLSALLTGR
AARTRASVAVSSFEHAGPLPGLSPG
ACSLPARVEEEAWDLDVKQISLAPETLDSSGDVSPGPRNSPSLQPPHPGSSTPLA
SRGILGLSRQSHARALSDPTTPL

FIG. 7

MAANLSRNGPALQEAYVRVVTEKSPTDWALFTYEGNSNDIRVAGTGEGGLEEM
VEELNSGKVMYAFCRVKDPNSGLPKFV
LINWTGEGVNDVRKGACASHVSTMASFLKGAHVTINARAEEDVEPECIMEKVA
KASGANYSFHKESGRFQDVGPQAPVGS
VYQKTNAVSEIKRVGKDSFWAKAEKEEENRRLEEKRRAEEAQRQLEQERREREL
REAARREQRYQEQGGEASPQSRTWEQ
QQEVSRNRNEQESAVHPREIFKQKERAMSTTSISSPQPGKLRSPFLQKQLPET
HFGREPAAAISRPRADLPAEEPAP
STPPCLVQAEEEAVYEEPPEQETFYEQPPLVQQQGAGSEHIDHHIQGQGLSGQGL
CARALYDYQAADDTEISFDPENLIT
GIEVIDEGWWRGYGPDGHFGMFPANYVELIE

FIG. 8

QSQEALLGGAWSPGAPHRSRDLLGAGPNRRRREPLGHRRSSPRPTFPQVAEPAG
RAKLAGPPGGSRWPRPSREGPAPRG
APEPSRPPPPGGMEADGDEELARLSVFAACDANRSGRLEREEFRALCTELRVR
PADAEAVFQRLDADRDGAITFQEFA
RGFLGSLRGGRRRDWGPLDPAPAVSEAGPETHDSEEDEGDAAAALATSCGPA
SPGRAWQDFQARLGDEAKFIPREEQV
STLYQNINLVEPRLIQPYEHVIKNFIREIRLQSTEMENLAIAVKRAQDKAAMQLSE
LEEEMDQRIQAAEHKTRKDEKRKA
EEALSDLRRQYETEVGDLQVTIKKLRKLEEQSKRVSQKEDVAALKKQIYDLSME
NQKVKKDLLEAQTNIAFLQSELDALK
SDYADOSLNTERDLEIIRAYTEDRNSLERQIEILQTANRKLHDSNDGLRSALENSY
SKFNRSLHINNISPGNTISRSSPK
FIGHSPQPLGYDRSSRSSYVDEDCDSLALCDPLQRTNCEVDSLPESCFDSGLSTLR
DPNEYDSEVEYKHQRGFQRSHGVQ
ESFGGDASDTDVPDIRDEETFGLEDVASVLDWKPQGSVSEGSIVSSSRKPISALSP
QTDLVDDNAKSFSSQKAYKIVLAG
DAAVGKSSFLMRLCKNEFRENISATLGVDFQMKTLIVDGERTVLQLWDTAGQER
FRSIAKSYFRKADGVLLLYDVTCEKS
FLNIREWVDMIEDAAHETVPIMLVGKADIRDTAATEGQKCVPGHFGEKLAMTY
GALFCETSAKDGSNIVEAVLHLAREV
KKRTDKDDSRSITNLTGTNSKKSPQMKNCCNG

FIG. 10

| | | | |
|---|---|---|---|
| Dbl | 687 | NLNELGKMIMQGgfsvwighkkgatkmKDL-ARFKPMQRHLFLYEKA-IV | |
| tiam | 433 | TVRKAGALAVKNflvhk.....knkkvESA-TRRKWKHYWVSLKGCT-LF | |
| fgd1 | 820 | NSVICSFLHYME...............KGG-KG--WHKAWFVVPENEPLV | |
| Grub | 1265 | DLKEQGQLLHRDp.............fTVICGR-KKCLRHVFLFEHL-LL | |

| | | | |
|---|---|---|---|
| Dbl | 735 | FCKRRvESGEG..SDRYPSYSFKHCWKMDEVGITEYVKG..DNRKFEIWY | |
| tiam | 476 | FYESD.GRSG-...-IDHNSIPKHAVWVENSIVQAV-PEHpkKDFVFCLS- | |
| fgd1 | 852 | LYIYGaPQDV-...-KAQRSLPLIGFEVGPPE--AG-ERP.dRRHVFKIT- | |
| Grub | 1300 | FSKLKgPEGGSemFVYKQAFKTADMGLTENIGDSG-LC-.....-FELW- | |

| | | | |
|---|---|---|---|
| Dbl | 781 | GEKEEV....YIVQASNVDVKMTWLKELRNILL | 809 |
| tiam | 519 | NSLGDA....FLFQTTSQLELENWITALHSACA | 547 |
| fgd1 | 893 | -QSHLS....WFYSPETEELQRRWMAVLGRAGR | 901 |
| Grub | 1341 | -FRRRRareaYTLQATSPEIKLKWTSSLAQLLW | 1372 |

FIG. 9

```
                          CR1
                  H1a                               H2a
dbl     493  DVLKNHVLNEL IQTERVYVREL YTVLLGYRAEMD-NPEMFDLMPPLLRNK
cdc24   276  HNEYVKI IKEFVATERKYVHDHE ILDKYRQQLLD------SNLITSEELY
vav     192  YDKRCCCLREIQQTEEKYTDTLGSIQQHFMKPLQ-------RFLKPQDME
tiam   1038  ADNVRKVICELLETERIYVKDLNCLMERYLKPLQ-----KETFLTQDELD
fgd1    370  QQKVFHIANELLQTEKAYVSRLHLLDQVFCARLL-EEARNRSSFPADVVH
Grub   1083  ISAQQRLVSELIACEQDYVATLSEPVPPPGPELT--PELRGTWAAALSAR CR2
              H2a       H2b
dbl     542  KdIEFGNMAEIYEFHNDIFLSSLEN---CAHAPE...........--RVCP
cdc24   320  M.-LFPNLGDAIDFQRRFLISLEIN-ALVEPSKQ...........--RICA
vav     235  T.-LFVNIEELLSVHTHFLKELKDA--LSGPGAT...........--MLYQ
tiam   1083  V.-LFGNLTEMVEFQVEFLKTLEDGVRLVPDLEKIekvdqfkkvLFSLGG
fgd1    419  G.-LFSNICSIYCFHQQFLLPELEKRMEEWDRYP...........--RICD
Grub   1131  E.--.----RLRSFHRTHFLRELQG---CATHPL...........--RIGA H3           H4
dbl     577  CFLERKDDF--QMYAKYCQNKPRSETI-WRKYSECA-FFQECQRKLKHR-
cdc24   355  LFMHSKHFF--KLYEPWSIGQNAAIEFLSSTLHKM--RVDESQRFIINND
vav     269  VFIKYKERF--LVYGRYCSQVESAIKHLDQVATAR-EDVQMKLEECSQRA
tiam   1131  SFLYYADRF--KLYSAFCAIHTKVPKVLVKAKTDK--AFKAFLDAQNPK-
fgd1    455  IFQKLAPFL--KMYGEYVKNFDRAVELVNTWTERST-QFKVIIHEVQKE-
Grub   1158  CFLRHGDQF--SLYAQYVKHRHKLENGLAALSPLS-----KGSMEAGPY- CR3
                    H7b        H8
dbl     622  ---LR.....LDSYLLKPVQRITKMQLLLKELLKYS--KDCEGSALLK--
cdc24   400  ......KLELQSFLYKPVQRLCRMPLLVKELLAESSDDN-NTKELEA--
vav     316  N-NGR...-FTLRDLLMVPMQRVLKMHLLLQELVKHTQ-DTTEKENLRL--
tiam   1176  ---QQ.hSSTLESYLIKPIQRILKMPLLLRELFALTDAES-EEHYHLD--
fgd1    501  ---EAcrNLTLQHHMLEPVQRIPRMELLLKDYLLKLPHGSPDSKDAQK--
Grub   1158  --------.---LPRALQQPLEQLTRMGRLLEELLREAG---PELSSECR-- dbl     660  KALDAMLDLL-KSVND-SMHQIAIN      682
cdc24   440  -ALDISKNIA-RSINE-NQRRTENH     461
vav     359  -ALDAMRDLA-QCVNEVKRDNETLR     381
tiam   1219  VAIKTMNKVA-SHINE--MQKIHEE    1240
fgd1    546  -SLELIATAA-EHSNA-AIRKMERM     567
Grub   1235  -ALGAAVQLL-REQEARGRDLLAVE    1257
```

FIG. 14
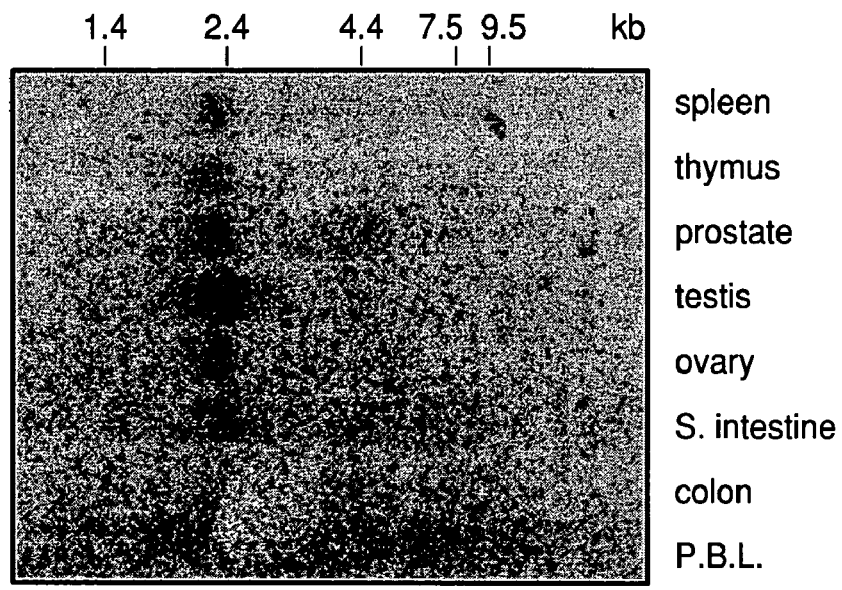
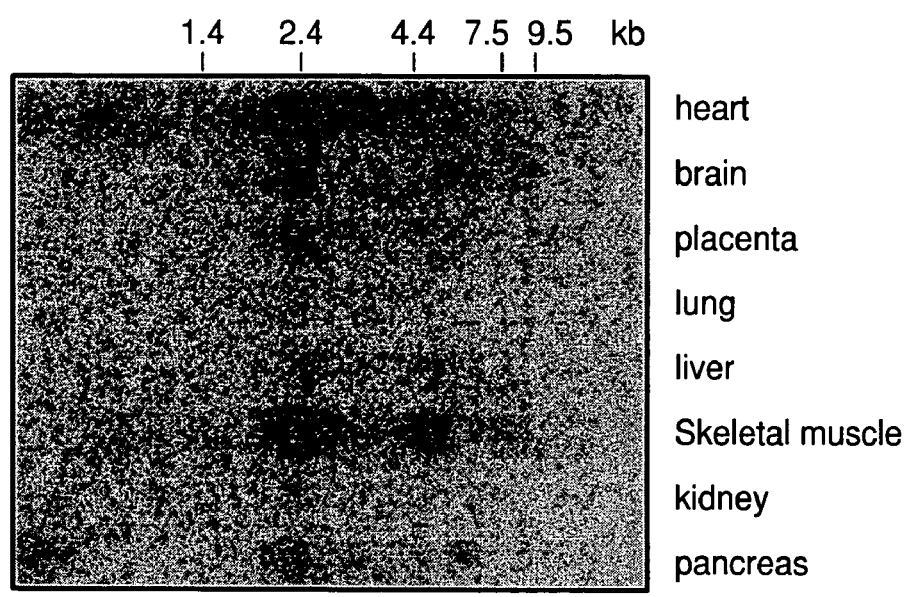

FIG. 16

```
1   MAGVSFSGHRLELLAAYEEVIREESAADWALYTYEDGSDD          Drebrin E
1   MAA-NLSRNGPALQEAYVRVVTEKSPTDWALFTYEGNSND          Tks118
1   MAV-NLSRNGPALQEAYVRVVTEKSPTDWALFTYEGNSND          mSH3P7
84  ----------------------------------------          SRC-human 41  LKLAASGEGGLQELSGHFENQKVMYGECSVKDSQAALPKY          Drebrin E
40  LRVAGTGEGGLEEMVEELNSGKVMYAECRVKDPNSGLPKF          Tks118
40  LRVAGTGEGGLEELVEELNSGKVMYAECRVKDPNSGLPKF          mSH3P7
84  ----------------------------------------          SRC-human 81  VLINWVGEDVPDARKCACASHVAKVAEFFQGVDVIVNASS          Drebrin E
80  VLINWTGECVNDVRKGACASHVSTMASFLKGAHVTENARA          Tks118
80  VLINWTGECVNDVRKGACANHVSTMANFLKGAHVTENARA          mSH3P7
84  ----------------------------------------          SRC-human 121 VEDIDAGALGQRLSNGLARLSSPVLHRLRLREDENAEPVG          Drebrin E
120 EEDVEPECLMEKVAKASGANYSFHKESGRFQDVCPQAPVG          Tks118
120 EEDVEPECLMEKVAKASGANYSFHKESTSFQDVCPQAPVG          mSH3P7
84  ----------------------------------------          SRC-human 161 TTYQKTDAAVEMKRINREQFWEQAKKEEELRKEEERKKAL          Drebrin E
160 SVYQKTNAVSEIKRVGKDSFWAKAEKEEENRRLEEKRRAR          Tks118
160 SVYQKTNAISEIKRVGKDNFWAKAEKEEENRRLEEKRRAR          mSH3P7
84  ----------------------------------------          SRC-human 201 DERLRFEQERMEQERCEQEERERRYRER                      Drebrin E
200 EAQRQEEQERRERELREAARRECRYCEQGGEASPQSRTWE          Tks118
200 EERQREEFERRERELREAARRECRYCEQHRSAGAPSRTGE          mSH3P7
84  ----------------------------------------          SRC-human 228                                                   Drebrin E
240 QQQEVVGRNRNE----QESAVHPRETFKQKERAMSTTSIS          Tks118
240 PEQEAVGRTRQEWESAGQQAPHPRETFKQKERAMSTTSVT          mSH3P7
84  ----------------------------------------          SRC-human 228                                                   Drebrin E
276 SPQPGKLRSPFLQKQLTQPETHFCREPAAAISRPRADLPA          Tks118
280 SSQPGKLRSPFLQKQLTQPETSYCREPTAPVSRPAAGV-C          mSH3P7
84  ----------------------------------------          SRC-human 228                                                   Drebrin E
316 EEPAPSTPPCLVQAEEEAVYEEPPEQETFYEQPPLVQQQG          Tks118
319 EEPAPSTLSS-AQTEEEPTYEVPPEQDTLYEEPPLVQQQG          mSH3P7
84  ----------------------------------------          SRC-human 228                                                   Drebrin E
356 AGSEHIDHHIQGQGLSGQGLCARALYDYQAADDTEISFDP          Tks118
358 AGSEHIDHYNQSQGFSGQGLCARALYDYQAADDTEISFDP          mSH3P7
84  ---------------GGVTTFVALYDYESRTETDLSFKK           SRC-human 228                                                   Drebrin E
396 ENLITGLEVIDEGWWRGYG-PDGHFGMFPANYVELIE              Tks118
398 ENLITGLEVIDEGWWRGYG-PDGHFGMFPANYVELIE              mSH3P7
108 GERLQIVNNTEGDWWLAHSLSTGQTGYIPSNYVAPSDSIQ          SRC-human
```

FIG. 21

```
1   MAKTYDYLEKLLLLGESGVGKTCVLERESEDAFNSTFIST      c-mel
1   MAKTYDYLEKLLLLGESGVGKTCVLERESEDAFNSTFIST      rab8
630 SQKAY----KIVLAGEAAVGKSSFLMRLCKNEFRENISAT      Tks202

41  IGIDFKIRTIELDGKRIKLQIWDTAGQERERTITTAYYRG      c-mel
41  IGIDFKIRTIELDGKRIKLQIWDTAGQERERTITTAYYRG      rab8
666 LGVDFQMKTLIVDGERTVLQLWDTAGQERERSIAKSYFRK      Tks202

81  AMGIMLVYEFTNEKSEDNLRNWIRNLEEHAGADVEKMILG      c-mel
81  AMGIMLVYEFTNEKSEDNLRNWIRNLEEHAGADVEKMILG      rab8
706 ADGVLLLYEVTCEKSELNLREWVDMLEDAAHETVPIMLVG      Tks202

121 NKGDWNDKRQVSKER------GEKLALDYGLKEMETSAKA      c-mel
121 NKGDWNDKRQVSKER------GEKLALDYGLKEMETSAKA      rab8
746 NKADIRDTAATEGQKCVPGHFGEKLAMTYGALECETSAKD      Tks202

155 NINVENAFFTEARDIKAKMDKNWKATAA-GSSHGVKITVE      c-mel
155 NINVENAFFTEARDIKAKMDKKLEGNSPQGSNQGVKITPD      rab8
786 GSNIVEAVLHEAREVKKRTDKDDSRSITNLTGTNSKKSPQ      Tks202

194 QQKRTSFFRGSLE                                 c-mel
194 QQKRSSFFRGVLE                                 rab8
826 MKN------GCNG                                 Tks202
```

FIG. 22
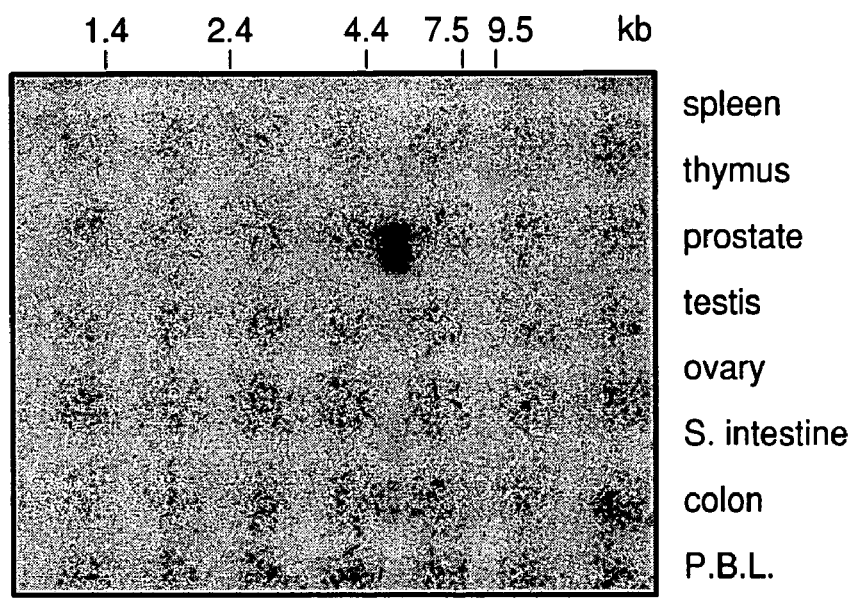
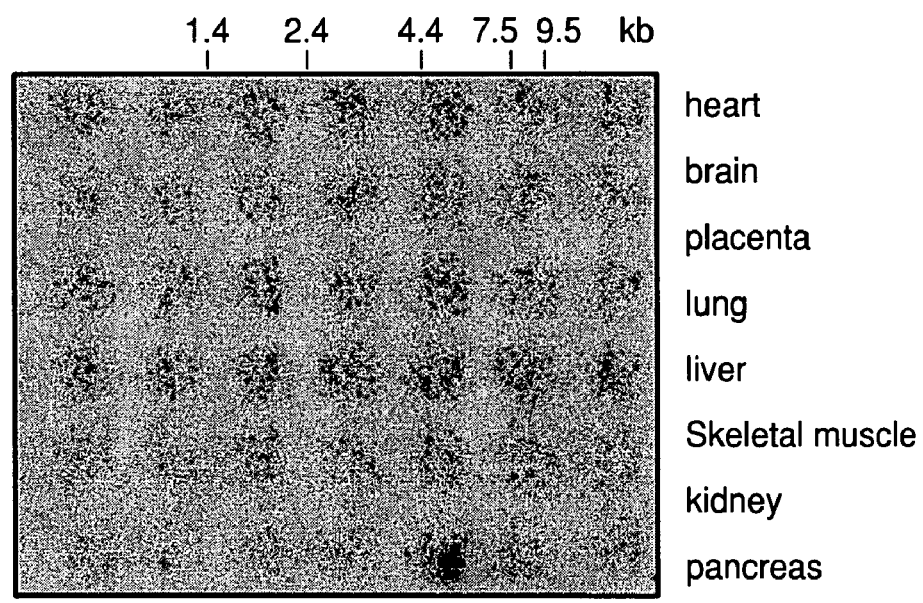

AEGRGGEGRPSRPSLAGPRGLEAGAGRAATAAGAVP.PDPARHERREGGGGAPG
PARPTKRRTRPGAEPWSLSQWRTVCR
ALSPPCIHPLRQQPPPCWARCSRWWRGLIGRTH.GTRWTSWYQPSTCLPRSSRKP
VPNTVDSSSSMRGGRSACMNRWWCS
.QPYPGNCCAQETSICRWCPQLPKHPD.HSSVWPLGVGGCRRFLCPMRLVPTYSH
LSGYKASTRTGQQVASVPAYCLRPL
GFSGCPGLSSSVHDLCTKRASWLDISQVHCPQNCPLDLQGFPALHFLRRRWVPG
VLGMGTMPLWKDLRASMWSC.R.RCP
.GGAQQMLKAPQASPESGRYPPARALEGRAATGDTGRGCTRRAWGLGARMEHA
HPARGAAPEPPLSLPQELRLSQRQQSW
RCLSPQQRLWEKPPDLAP.GQGSLEEEEEEARGLKDHLVPLGEQAKETEERSELQ
VEGLLAEEGTVPH.ALGTRKMPATK
KPLAICPHQVSTSFQNATWLRRNMKAQGSQNLSQKSSKQQARKSLSSLKPVGLQ
KRGPERESWRGQACCVWQDTQAQKAP
CLTLQHLRWRLCRKEKGTTFQKRPLQSPSLITLM.LGT.WHLDSSS.REGWTRVGE
LC.PLPHRALLRSPHPPETR.TQL
FITSTHCSGLIYRHWGCPSCWTFVRHLHCLQHSFLP.ANFRTQEILPLFSGC.FSFM
MTFQLNSVDFRVLRCCQRMI.KE
WPSQRSCSGS.EVTGTPLPVTG.RYTRKW.GYVACAKVCWARYGRPLRSWREQQ
SQRKRRQWECPSHCRRCWQIPG.RHC
RGMGGPS..GCAPLPAASWRAKAQLHCIRKWTRPFTSLCASPTCTCSSKSSGSACG
DSSRCCSGSRAQGRSSWQALLCLG
TPCLPCRRQSCDSVLSALRSRSAWPRHGRPWLWRRMPPPRRCWISLNSGWSRLR
VASIGPCGYSASSSRHMNGWMRALLG
WQELGRVGRLCWLHWPCGGPQSPVPAPSRRCGPWPWTWAAQQPCENGAAARP
AAKS.RGGSSNTWERRRAHGATDDGGQT
VPAVEGPSGGPAAPRPASAPCCSPAALGHGQPHPIAPWPHVERTMRKRALSWLQ
KQRAGPQELC.SEAWRSPALRW.TGR
AHHGNTCCWAGLGGQTDPGE.APPGWSASEASVPSSGWCLS.LPVNKITWPP.VS
QCHPLGLS.RLNFGAPGLLP.VPGK
GFAASTGHTFCGSFRAAPPTPYALGPASFATGTSSAFMHST.STDTNWRMVWLRS
VP.ARAPWRLALTCPEPCSSLWNS.
LGMGGSWRSS.GKLGLSSVLSAGPLGLLYSCSGNKRPVAETCWPWRRCVAVR.I.
RSRDSSCIETPSLSSVAERSAFAMS
FSSSISSCSASSRALKGGQRCLFTSRPLRLLIWG.QKTSGTADSALSCGFGGGVHER
HTLCRQPHQRSNSSGQVLLPSCC
GDRQPTTRSSECSRWCPWALGINPSWTSKPLGSGR.VPCSLEEPPAPGPPWPCHPL
SMPAPPFPAFRREPAPCLPASRRR
PGIWTSSKFPWPQKHLTLLEMCPQDQETAPACNPPTLGAALPPWPVEGS.GYPDR
VMLEP.VTPPRLCDLEKIQNLRAAS
PLSTLWAGMAVGHNGALGDR.ISSLCFLDTEEV.RPEYCPATTISSLPSLVPSPAGV
RAATLLAFIPWRWGSYPSSGAFP
SWATVSRTSLPCQPSLAAHVPLFSHPLTFPEKNHLCQVNWSPW.LHSEVSQAMKL
CKQ.EGVTGEP.TLYM.LLLL.YYC
YIKCIYSHFASKKKKKKK
LKGGAGRGGRLGPPWRGPAAWKPERAEPPPRPELSLSQTRRDTSGGREAVARPA
PPARPSVGRGPAPSHGA.ASGGLCAE
HSRRPVSTL.GNSPHPVGPGVPGGGEDLSGGRTEVHAGLPGTSQAPACQGPAGSL
CPIQWIPLLP.GVAALPA.TGGGAA
SSPTLATAAPRRLLSAGGALSCPSTPTSQVSGPWGWAGAGGSCAQ.GLCLPIHT.
VATRHQQGPANRSPQYLPTVCALW
DSAAALG.AHLSTICAQRGPHGWTSAKYTAPRTALWTSRASQPSTS.GGAGYPES
WGWAQCPCGRT.GRVCGAVRGDAAR
EGEPNRC.RLPRPLQSPDGTHPQGRWREGPPPETPGVDAPEGPGASGPGWSTPTR
RGEQHRSLP.VSPRS.GCPRGSSLG
GV.APSRGCGRSLRILPPEARGA.RRRRRRPGG.RTTWYPSENRQRKQKKEASCRS
RGS.PRRGQCPTEPWGQGRCQPPR
SPWQSALTK.AQASRMPPG.GGI.RLREARI.AKRAQNSRRERASAL.SLWAYRRGG
RRERAGGARPAVYGRTHRPRRPP
V.HSNTSAGDCAGRKRGQHSRRGPCSLRL.SP.CSLGLDGIWIPHPDGRGGPEWAS
SADHYPTVPS.GAPTLPRHAEHNS
SLPPLTAQA.STDTGAVRPAGPSSGTSTASSTHSCLEPTSGLRRSSPCSAAADSHS..
PSN.TLWISGC.GAVRE.SEKS
GQARGAAVGVRRSQGPLSQSLGRDTPGSGKAMSPVPRCAGLGTAGH.GAGGSSR
ARGRGGSGNAQATAEGAGRSPADGTA
EGWGGHPDEAALHSQQQAGGPRPSYTVSGSGRGHSPACAPLQPARAAARAAAW

FIG. 23A

To FIG. 23B

To FIG. 23B

From FIG. 23A          From FIG. 23A

```
    PAATPAGVAVALGPRGGAAGKLCYAWG
HLVCPAGDRAAIPCFQR.GPGAPGPGTGGPGSGGECHLPEGAGYL.TAAGAG.EW
PPSGPAATALLPAGT.MGG.GLCSA
GRSWAGSGGCAGCTGPAAGPRAQCRHLPGDAGPGPGPGQPSSPARMGPLPGPLP
RAREEDPATPGRGGEPTGLPTTAGRR
CQQWRGPVGAPQPLAQPQLLAAPQQPWATASPIPLLPGPMWRGL.GRGP.AGSRS
RGQAPKSCADPRPGGHQH.GGRQDV
LTTGTRAAGPG.GARRTLGSRRPPDGAQAKHQCPAAAGV.ADCL.TRLRGHLE.AS
ATPWA.ADA.TSGHLGCCPECPGK
ASQLPPDTLSAGASGLRHPPPTHWGLLPSPRGPVQPLCTVREAPTQTGEWSGCAQ
SLKQGLHGGWPLPAPSPAAASGTAD
SVWAAPGGAPEGSWA.AQF.VPGPWGCCTAAPGTRGPWQRPAGRGGGAWL.DR
SEGAGTALASRPLHCHLWPKEVPSPCL
SLRASPPVQQAQGP.RGVRDVCLQAGL.DC.YGADRKHRGQRTLL.VVVSAAACT
RGIHSAGNLTRDQTQVDKFYCPAAV
ETGSPQQGAPSAADGVHGHWE.TLPGHQSPWGADAECPAHWKSRPHPGLRGRVI
L.ACRPLPSRPFAGSLLPACPRRGGG
LGSGRQANFPGPRNT.LFWRCVPRTKKQPQPATPPPWEQHSHPGQSRDLRAIPTES
CSSPE.PHHASVTWRRSRTCVQLL
LSAHFGLGWQWGIMEPWAIAEFLPSASWTQRRSNDQSIALPPLSLVSLAWCLLL
QESEQPHCLPSYPGGGEVIPLPVLSH
PGPLYPGHHSHASPPWQPMFPSFLTP.LSLRRIISARSTGVPGDSILRCHKQ.SYANN
RRV.QGNRRLYICNYCYYNTIV
ILNVFTHTLPLKKKKKK
FFFFFFFRGKV.VNTFNITIVL..Q.LHI.SLRFPCHTLLLFA.LHCL.HLRMESPGTPVD
LAEMILLRESQGVRKEGNM
GCQGGLAWE.CPGYSGPGWESTGRGITSPPPGYEGKQCGCSDSCRRRHQARETR
DSGGRAILWSLDLLCVQEAEGRNSAI
AQGSIMPHCHPSPKCAERRSCTQVLDLLQVTEAWWGHSGLEHDSVGIALRSLD
WPGWECCSQGGGVAGWGCFLVLGTHLQ
KSQVFLGPGKFA.RPDPRPPPRRGQAGSRLPAKGREGRGRHAQRMTRPRRPGCG
RLFQ.AGHSASAPQGL.CPGRVYSQC
PWTPSAALGAPCCGLPVSTAAGQ.NLST.V.SLVRLPAECMPLVHAAAETTTQSRV
RCPRCFLSAPYQQS.RPACKQTSL
TPLQGP.AC.TGGDARRERHGEGTSFGHR.Q.RGLDARAVPAPSDLSHSHAPPPRPA
GLCHGPLVPGAAVQQPQGPGTQN
.AQAQLPSGAPPGAAHTESAVPEAAAGLGAGKGQPPWSPCLRD.AQPDHSPVCV
GASRTVHKG.TGPRGEGSRPQCVGGG
WRSPEAPAESVSGGSCEAFPGHSGQQPRCPEVQASAQAQGVALAHSRWPRNLV
HRQSAQTPAAAGH.CFACAPSGGRLLP
RVRLAP.PGPAARVPVVSTSCLPPQCW.PPGLGSAQLLGACPLLLEPAQGPLPHSPL
HMGPGSNGMGLAVAQGCWGAARS
.GWARGCGAPTGPLHCWHRLPAVVGSPVGSPPLPGVAGSSSLALGSGPGSGPILA
GLLGCPGPGPGPASPGRCRHWALGP
AAGPVQPAQPPDPAQLLPAEQSPHPPIHVPAGRSAVAAGPDGGHSQPAPAAVQR
YPAPSGRWHSPPEPGPPVPGPGAPGP
QR.KHGIAALSPAGQTRCPQA.QSLPAAPPLGPRATATPAGVAAGTAAALAAARA
GWRGAQAGEWPRPLPDTV.LGLGPP
ACCWEWSAASSGWPPHPSAVPSAGDLPAPSAVAWAFPLPPLPLALLLPPAPQWP
AVPSPAHLGTGDIALPLPGVSLPSDW
ERGPCDLLTPTAAPLAWPLFSDHSLTAPQHPEIHRVQLEGHHE.ESAAAEQGEDLL
SPEVGSRQE.VLEAVEVPDEGPAG
RTAPVSVDQA.AVSGGNEELCSACLGRVGAPQEGTVG.WSAELAHSGPPLPSG.GI
QMPSSPKLHQGDQRRRLQGPLLEC
CPLFLPAQSPAEVLECQTGGLLGLCVLPYTAGLAPPALSLRPPLL.AHRLQRAEAL
SRLLF.ALLAQILASLSLHIPP.P
GGILEACAHLVRADCQGLLGGWHLPCPQGSVGHCPLLG.EPLDLQLASFFCFLCL
FSEGYQVVLQPPGLLLLLL.APLAS
GGKIRRLLPQPLLGAQTPPRLLPLGQPQLLGETQGRLRCCSPRRVGVLHPGPEAP
GPSGASTPGVSGGGPSLQRPCGWVP
SGLWRGLGSLQHLLGSPSRAASPLTAPHTRPQVLPQGHCAHPQDSGYPAPPQEV
EGWEALEVQRAVLGAVYLADVQP.GP
LCAQIVDR.AQPRAAAESQRAQTVGRY.GDLLAGPC.CLVATQV.IGRHKPHWAQE
PPAPAHPQGPDT.VLVGVLGQLRA
    PPADRSLLGAAVARVGLLAAPPPVHAGRAATPHGRRGIHCIGHRLPAGPWQAGA
```

From FIG. 23B — From FIG. 23B

```
WLVPGSPACTSVRPPDKSSPPPGTPG
PTGWGLLPQRVDTGRRECSAHSPPLAQAPWLGAGPRPTLGRAGGAGRATASLPP
LVSRRVWLRDSSGRGGGSARSGFQAA
GPRQGGPRRPPLPAPPFS
FFFFFFLEAKCE.IHLI.Q.YYNNSNYIYKVYGSPVTPSYCLHSFIACDTSEWSHQGL
QLTWQR.FFSGKVRG.EKRGTW
AAREGWHGSDVLDTVAQDGKAPEEG.LPHLQGMKASNVAALTPAGEGTKLGRL
EIVVAGQYSGR.TSSVSRKQREEIQRS
PRAPLCPTAIPAQSVLRGEAARKFWIFSRSQRRGGVTQGSSMTLSG.P.DPSTGQG
GSAAPRVGGLQAGAVSWSWGHISR
RVKCFWGQGNLLDVQIPGLLLDAGRQGAGSRRKAGKGGAGMLKG.HGHGGPG
AGGSSSEQGTQRPLPKGFDVQEGFIPNA
HGHHLLHSELLVVGCLSPQQLGNRTCPLEFDLW.GCLQSVCLSCTPPPKPQLKAE
SAVPDVFCQPHISSLKGLLVNKHL.
PPFRALELAEQEEMLEEKDMAKALLSATDDSEGVSMQELSLLLQIYLTATHRLH
GQQVSATGLLFPEQLYSSPKGPALRT
ELRPSFPQELLQEPPIPSQLFQRLLQGSGQVRASLHGALA.GTERSQTILQFVSVLH
VLCIKAELVPVAKEAGPNA.GVG
GAALKLPQKVCPVEAAKPFPGTQGSSPGAPKFRRQLRPRGWHWLTQGGHVILFT
GNQLRHQPLLGTDASLALHPGGAYSP
GSVWPPSPAQQHVFPW.ARPVYHLSAGDLQASDQHSSWGPALCFWSQLRALFLI
VLSTWGQGAMGWGWPWPRAAGEQQGA
EAGRGAAGPPLGPSTAGTVCPPSSVAPWARLLSQVLLDPPL.LLAAGLAAAPFSQ
GCWAAQVQGQGPHLLEGAGTGLWGP
PQGQCSQHSLPTRPSSCQPSKALIHPFMCLLEEAL.PQGPMEATLNLLQPLFKDIQH
LLGGGILLQSQGLPCLGQALLDL
SAESTESQLCLLQGRQGVPRHSKACQLLLPWAREPLQHLLESPQALPLLLLLHVQ
VGEAHKLVNGLVHFLIQCSWALALQ
LAAGSGAQPHQDGPPIPLQCRQPGICQHLLQWLGHSHCLLFLWLCCSLQLLNGLP
YRAQHTLAQAT.PYHFLVYLYPVTG
RGVPVTS.LPLQLLWLGHSFQIIL.QHLSTLKSTEFSWKVIMNENQQPLNKGRIS.VL
KLAQGRNECWRQWRCLTKVQQD
GQPQCL.IRPEQ.VEVMKSCVQRVSGGWGLLRRARWGNGQQSSPTLVHPSRQDE
ESRCHQVPSYIRVIRDGDCKGLFWNV
VPFSFLHSLQRRCWSVRQGAFWACVSCHTQQAWPLQLSLSGPLFCRPTGFRELR
LFLACCFELFWLRFWLP.AFIFLLNQ
VAFWKLVLTW.GQIAKGFLVAGIFLVPRAQWGTVPSSAKSPSTCSSLLSSVSFACS
PRGTRWSFSPLASSSSSSKLPWPQ
GARSGGFSHSLCWGLKHLQDCCLWDSLSSWGRLRGGSGAAPLAGWACSILAPR
PQALLVHPRPVSPVAALPSSALAGGYR
PDSGEAWGAFSICWAPPHGQRHL.QLHILALRSFHRGIVPIPRTPGTQRLLRKWRA
GKPWRSRGQFWGQCTWLMSNHEAL
FVHKSWTDELSPGQPLNPRGRRQ.AGTEATCWPVLVDAL.PLRCE.VGTSLIGHRN
LLHPPTPRGQTLEC.SGCLGS.GH
HLQIEVSWAQQLPG.GC.LHHHLFMQAERPPLMEEEESTVLGTGFLLDLGKQVLG
WYQEVQRVPQCVLPISPLHHLEHLA
QQGGGCCLKGWIQGGESALHTVLHWLRLHGSAPGRVRRLVGRAGPGAPPPPSR
RSCLAGSG.GTAPAAVAARPAPASRPR
GPAREGRDGRPSPPRPSA
FFFFFF.RQSVSKYI.YNNSIIITVITYIKSTVPLSHPPIVCIASLLVTPQNGVTRDSS.P
GRDDSSQGKSGGEKRGEHG
LPGRAGMGVMSWIQWPRMGKHRKRDNFPTSRV.RQAMWLL.LLQEKAPS.GD.R.
WWQGNTLVVRPPLCPGSRGKKFSDR
PGLHYAPLPSQPKVC.EEKLHASSGSSPGHRGVVGSLRARA.LCRDSPKIPRLARV
GVLLPGWGGCRLGLFLGPGDTSPE
ESSVSGAREICLTSRSQASSSTRAGREQAPGERPGREGPACSKDDTATEARVRAA
LPVSRALSVRSPRALMSRKGLFPMP
MDTICCTRSSLLWAACLHSSWAIELVHLSLISGEVACRVYASRARRRRNHNSKQS
PLSPMFSVSPISAVLKACL.TNISD
PPSGPLSLLNRRRCSKRKTWRRHFFRPQMTVKGSRCKSCPCSFRSISQPRTASTAS
RSLPRASCSRSSCTAAPRARIISEL
SSGPASLRSSSRSRPYRVSCSRGCCRARGR.GPASMEPLLKGLSAARPFSSLCRCFT
YCA.RLNWSPWRRKQAPMRRGWV
AQP.SSRRKCVRWKLRSLSRALRAAAQVPRSSGVSSGPGGGTGSLKVAT.SCSQAI
SSDTSRCWALMLRLRSIRGAPTPQ
```

From FIG. 23C            From FIG. 23C

```
GPSGPLARPSSTCSRGEHVLSTTSVLVTSRPRISTALGGLPSASGASSGPSSS.SSPH
GAREQWDGAGRGPGLLGSSKEL
RLGEGLRGPHWAPPLLAPSARRRR.PRGLASSPRCCWILLSSSWQRAWQRPHSRR
AAGLPRSRARARISWKVPALGSGAR
RRASAASTASRPGPAPASRAKPSSTHSCACWKKRCSRRARWRPLSTCSSRCSKIS
STFWEVAFSSRARASRAWARRSWTS
ALKARNRSSVSCRADKVSPGIAKLASCSSPGPESHCNTCWSRRRHCRCSCCCTCR
LERRTSW.MASSTS.YSVAGPWPSS
LLLGVERSLIRMAPPSLCSAVSRGSASTFCSGLGIPTASSSSGSAAPSSSSMACRTE
PSTPWHRRHSLTTSWCISTQ.LG
EGSL.PPNSHCSSSGLATLFRSFSDSTSAP.NPQSSVGRSS.MRISSR.TRGGSPES.SW
LKAGMSAGGSGGA.RRSSRT
DSPSVCRSGLSSEWR..RVVFSVSREGGGSSGGHGGVMVSRARPLWSTPPVRMRN
PDAIKSQATSG.SETETARASSGML
SPFPSCTVSSGGVGVSDRGPSGPVCPAIHSRPGPSSSLSPAPSSVGPQASES.GSFSP
AVLSSFGSDSGFPEPSYSSLTR
WHSGSLCSLGEGRLPRASWWLASSLSPGLSGALSPPRLRAPRPAARFFLLFPLPVL
RGVPGGPSAPWPPPPPPLSSPGLR
GQDPEASPTASAGGSNTSKTAASGTASAPGGDSGEAPVLLPSPGGRAPSWPRGPR
PFWCIHARCLRWRPFPPAPLRVGTV
RTLERPGEPSASVGLPLTGSVTSNSSTYSPSGPSTGALCPSPGLRVPSASSGSGGLG
SPGGPEGSSGGSVLG.CPTMRPS
LCTNRGQMSSAQGSR.IPEGADSRQVLRRPVGRSLLMPCSHSGVNR.AQASLGTG
TSCTRPPPGARHLSASRGAWAAEGT
TCR.KSPGRSSCQGRAASCTTTCSCRQSGHPSWKKRNPLYWAQASCWTLASRCL
AGTRKSSVYLSASSR.VLSTTWNTWP
NRVGAVASKGGYRAARVLCTQSSTGSGSMARRRAASDAWSGGRGRARHRLPP
AARVSPGLAKGQLRPRWRLGPLRLPGRG
APPGRAETAAPPRPALQ
```

EFGTSNYGGGGRTQQ.CGGGDPQEPRTSPELPQWSPRVAR.RKP.VGRDQDA.PGQ
LCQRYREQRWRPWRWWQQGGQWGR
GRQWRGQLRCHL.RLLEECVQARQALPISPPRHERGVQLGGEQKRVHLLP.LPEQ
GV.PPKLPFHPWLQGG.GWL.EDRR
ASPTAEAESSSWPWPFTG.PTKWQGGGPYLP.LSQG.LSERSQVQVPSPATGF.V.CS
GWRRHWWGLNRLSPPRTTS.SL
.YL.PS.QGL.GP.ARPKTPARWMLPP.WPSF.VI.I.FGSTARGGVQTARGGECHAQEA
GRGVKEAGQQPAGHQ.GTTG
TKCSVPQSGQGHNPELHCTSD.ADSGPHCGHCCHF.PWHCPDSHYSQQPGSTASS
SVPARTGGPCWSSSCSPN.CCTSCC
STTPTPTLDPRDHATVSCPGSNNCPGNGTSTCLHGSCGCICGSCGPCGCIDGPTLG
RNHNEPHHHSHGDLPYRSPS
IRHEQLRRRRQNPAVMWRPTGAPDFT.ATSVVTKSGKIKKTLSWAGPGCLTG
TAMPTVPGAAVEALEVVAARRPVGQG
.AVAGPAQMPSVETS.GMCASEASVADIATQT.ARCPTWG.AKTSSSSAMTSRTRS
VAAQIAVSSMAPRRMRMAIRRQES
FPHG.GRK.QLALAFHRLTYQMARRRSLSAVTFSRVTVREEPSASSVTCNGILSLM
LGVEEALVGAQQAQSSQDDVMISM
ISMTFLTGALRTMSQAQNAGEVDAAPLMALILSHMNIVWLHREGWSADC.RRR
MPCSGSG.RS.RSRSATCWPPMRYYWN
KMLSSAIRPRS.P.APLHQRLSRLWPPLWALLPLLTMALPRLTLLSAARLYSLVQC
PSKNWWPLLELQLLPQLMLHLLLL
HHPHPHT.PQRSRHCQLPWLKQLPREWHLHLSPWLLWLYLWLLWPLWLYRWPN
PWQESQ.ATPPLPW.LTLSLPLE
LEGER.GKSPWEWWCGSL.FLPRVGPSIQPQGPQEPQIQPQEPWRQVEVPFPGQLF
EPGQLTVA.SLGSSVGVGVVEQQE
VQH.LGEQLELQQGPPVLAGTLDEAVEPGC.E.CESGQCHG.KWQQCPQWGPESA
QSLVQWSSGL.PWPDCGTEHFVPVV
PHWWPAGC.PASLTPLPAS.AWHSPPLAVCTPPLAVEPNYIHMTQNEGHQGGSIH
LAGVLGLAHGPQSPCQEGHRYHRDH
DVVLGGLSLLSPHQCLLHPEHQTQNPVAGDGTCTWLLSDSHP.ESHGR.GPPPCHL
VGQPVKGQGQLLLSASAVGEALLS
SYSHPHPPWSHG.NGNLGGYTPCSGSHGRR.TRFCSPPSWTPRSCLGGDIGNACLA
CTHSSRSLYRWHLSWPRHCLPLPH
WPPCCHHLQGLHRCSRYRWHSCPGQASWSRPTQGFLYLATLGDH.GSSGEVRGS
CGSPPPIIHCWVLPPPP.LLVPN
SRGSDRVSHHGSGGVAHCDSCQGLGHRYSHRGHRSHRYSHRSHGDRWRCHSLG
NCLSQGS.QWRDLWGQVWGWGWWSSRR
CSISWGSSWSSSRGHQFLLGHWTRL.SLAAESSVSLGNAMVKSGNSAHSGGQSLL
SRWCSGAQGYDLGLIAELSILFQ.Y
LIGGQQVADLLL.LLYPLPEHGILLL.QSALHPSRWSQTIFI.LKMRAIRGAASTSPAF
WAWLMVLKAPVRKVIDIIEIM
TSSWED.AC.APTSASSTPSIKLKIPLQVTELALGSSLTVTLEKVTADRDLLLAIW.V
SR.KAKASCYFLPQPWGKLSCL
LIAILILLGAMDETAIWAATLLVLEVMAEDELVFAHPQVGHLAHVWVAISATLAS
LAHIPQEVSTDGI.AGPATAYPCPT
GLLAATTSRASTAAPGTVGIAVPVRHPGPAQLRVFFILPLLVTTEVAQVKSGAPV
GLHLHITAGFCRRRRSCSCRI
RGGAIG.VTMGVVVWLIVIPAKGWAIDTATGATGATDTATGAMETGGGAIPWAI
V.ARAADSGVISGVKCGGGGGGAAGG
AALVGGAAGAPAGATSSCWDTGRGCRAWLLRVV.VWAMPWLKVATVPTVGA
RVCSVAGAVELRVMTLA.LRN.AFCSSST
SLVASRLLTCFFNSSTRFLSMAFSSSSSLHSTPRGGAKLYSYDSK.GPSGGQHPPRR
RFGPGSWSSKPLSGRS.IS.RS.
RRPGRTEPVEPPPVPPPPRASNSKSRCR.RNLHLAPL.QSPLRKSRQIGTSSLPFGRS
AGERPRPAATFCLSRGGSSPVF
RGS.PRRGQCPTEPWGQGRCQPPR
L.PSSSSLEPWMKRQFGRLHSLFWKSWQKMNSFLLTPKLDTSLMSGWRYRQRLP
RLHTFLKKSLQMASELAPPLPTPAPL
ASLLPPPPGPPPLLPVPLA.LSRSGILVPPNSGFSLSCHSW.PLR.LR.SPGLLWVSTST
SLLGSAAAAVVARAEF

FIG. 25

```
FDTSCGAGHGGEPEPERASAARGLRAGGHREVPDRLGSLYL.RQQQ.HPRGWHR
GGWPGGDGGGAQQREGDVRLLQSEGP
QLWTAQICPHQLDRRGRERCAEGSLCQPRQHHGQLPEGGPCDHQRTGRGGCGA
VHHGEGGQGFRCQLQLSQGEWPLPGR
GTPGPSGLCVPEDQCRD.D.KGW.RQLLGQSREGGGEPSAGGKAAGRGGTAAAG
AGAPGA.AA.GCTPGAALSGAGWRGQ
PPEQDVGAAARSGFKEPK.AGVCRAPEGDFQAEGEGHVHHLHLQSSAWQAEEPL
PAEAAHPTRDPLWQRASCCHLKAQGR
SPC.GAGAQHSSMSGAGRRGGCV.GTSRAGDLLRAAPTGAAARCWL.AH.PPHSG
PGAQWARALCPCPVRLPGSRRHRDL
L.PREPHHGHRGDRRRLVAWLWAGWPFWHVPCQLRGAH.VRLRAHLALPLSDM
ASLLLEEEAWELTFSTLPGIGPPVRMR
PQGSLRLGRLSLSPQMQQWPGDSHTSFLHPP
RHELRGGPWRRT.AGTGQRCKRPTCGWSPRSPRPTGLSLPMKATAMTSAWLAQ
GRVAWRRWWRSSTAGR.CTPSAE.RTP
TLDCPNLSSSTGQARA.TMCGREPVPATSAPWPAS.RGPM.PSTHGPRRMWSLSAS
WRRWPRLQVPTTAFTRRVAASRTW
DPRPQWALCTRRPMPCLRLKGLVKTASGPKQRRRRRTVGWRKSGGPRRHSGSW
SRSAGSVSCVRLHAGSSAIRSRVARPA
PRAGRGSSSKKWFQGTEMSRSLPCTRGRFSSRRRGPCPPPPSPVLSLAS.GAPSCRS
SSPNQRPTLAESQLLPSQGPGQI
SLLRSRRPALLHVWCRQKRRLCMRNLQSRRPSTSSPHWCSSKVLALSTLTTTFRA
RGSVGKGSVPVPCTTTRQPTTQRSP
LTPRTSSRASR.STKAGGVAMGRMAILACSLPTTWSSLSEAEGTSCPSPLRHGFLI
AGRGGLGVDIQHSSRNRTPSEDEA
SGLPPAWQTQPVTPNAAMAW.FPHILPASPD
VGGCRKDVWESPGHCCIWGDRLSLPSRREP.GLILTGGPIPGRVLNVNSQASSSSN
KEAMSERGRARCALSLTQ.APRSW
QGTCQNGHPAHSHATSLRRSPRCP.GSRGQRRSLCRRLPGSRTGHGHRALAH.AP
GPECGGQCAQSQHLAAAPVGAARR
RSPALEVPHTQPPLLPAPDMEECWAPAPQQGDLPWALRWQQLALCQSGSLVG.A
ASAGRGSSACQAEDWRWRWWTWPSPS
A.KSPSGARQTPAHFGSLKPLLAAAPTSCSGGWPRHPAPDSAAPGVQPHAAHAPG
APAPAAAYPPRPAAFPPADGSPPPS
LLWPRSCLYQPF.SQTRHWSSGTQSPLGPGVPRPGSGHSPCESCSWHLKPWPPSP.
CTQAPHPPRPVR.WSHGPPSGSWP
WC.RGWHRLPSAHRSRPRLSS..GQIWAVQSWGPSLCRRRTSPSRC.APPPSPPGHP
PLCQPRGCHCCCLHR.REPSRSG
TSR.PPARRPLAALARSGSGSPPWPAPQLVS
SGDAGRMCGNHQAIAAFGVTG.VCQAGGSPEASSSLGVLFLEEC.MSTPRPPLPAI
RKPCLRGEGQDVPSASLNELHVVG
REHAKMAIRPIATPPAFVDHLDARDEVLGVKGDLCVVGCLVVVQGTGTEPLPTE
PLALNVVVNVLRASTLLLHQWGLLVE
GLLLWRFLIHSLLFCLHQTWRSAGRRLLSREICPGP.DGSSWLSAKVGLWLGELL
LQEGAPQLARLRTGDGGGGHGPLLL
LENLPRVHGRLLLISVP.NHFLLLLPRPALGAGLATLLLIALLPACSLTQLTLPALL
LQLPLCLLGPPLFLQPTVLLLLL
CFGPEAVFTNPFNLRHGIGLLVHRAHWGLGSHVLEAATLLVKAVVGT.SLGHLL
HDALRLHILLGPCVDGHMGPLQEAGH
GADVAGTGSLPHIVHALACPVDEDKFGQSRVGVLHSAEGVHHLPAVELLHHLLQ
ATLPCASHADVIAVAFIGKESPVGRG
LLGDHPHVGLLQRWPVPAQVRRHGPPRSSCR
RGMQEGCVGITRPLLHLG.QAESAKPEGALRPHPHWGSYSWKSAECQLPGLLFQ
Q.GSHV.EGKGKMCPQPHSMSST.LA
GNMPKWPSGP.PRHQPSSITSMPVMRFSGSKEISVSSAAW.SYRARAQSPCPLSPW
P.MWWSMCSEPACCCTSGGCS.K
VSCSGGSSYTASSSACTRHGGVLGAGSSAGRSALGLEMAAAGSLPKWVSGWVS
CFCRKGLLSLPG.GLEMEVVDMALSFC
LKISLGCTADSCSFRFLETTSCCCSHVLLWGLASPPCS..RCSRRAASRSSRSRRSCS
SCRCASSARRFSSSRRFSSSFS
ALAQKLSLPTLLISDTALVFWYTEPTGAWGPTSWKRPLSL.KL.LAPEALATFSMM
HSGSTSSSARALMVTWAPFRKLAM
VLTWLAQAPFRTSFTPSPVQLMRTNLGSPELGSFTLQKAYITFPLLSSSTISSRPPSP
VPATRMSLLLPS.VKRAQSVGD
FSVTTRT.ASCSAGPFRLRFAAMARPAARVE
```

FIG. 26A

SRRRRSLAVPGARAHPTAPGTCWGLARTVVEGSRSATPDVPRPARRSLKWPNQP
DEPNSPGLPAAAGGPVLPGRALRPAA
LRSPLGRPRQAGWRRMGTERSWPGCAQSSPPATRTARGAWSARSSGHCARSCG
CGRPTPRQYSSGWTPTVTAPSPSRSSR
VASSGPSAGGGAGTGVLWIPRPPCLRRGRRHTTARRTKATRTRRRRWPPRAARR
VPAGLGRISRRDLGTKPSSFPEKSKL
VPCTKTSTLWSQD.FSHMNML.RTSSVRSDFKAQKWKIWPLR.REPRTRQLCS.VS
WKRKWIRGFRLQNIRHGKTKNAKL
RKPSVTSDVSMKLK.EICR.PLKS.ESSKNNQNA.VKRKMWLK.KNKFMIYQWKTR
KLRKTF.KHRQT.PFFRVS.ML.K
VIMLIRV.ILKGIWK.SEHTQKIEIVLRGKLKYSKQLTGSYMTVMMALEVPLKTVI
ASSTDLCI.IISIIQGIQFLEAVPN
SLVIPLNL.AMTGHPALPMWMRTVTPWPSVILCRGQIVKLTACLKAASTAACLP.E
IPMSMTQKWNTSTRGDFRGHTGCR
RALEVMLQTQMFLT.GMKRHLV.KMWLPS.TGSPKGLLVKAALLVHQESPSQHSR
PRQTW.MTTLNLLAHRRLTRLYLLG
TLQWGSLVSS.DFARMNFEKI.APPWELISK.KPSLWMENEQFCSSGIQLVRRDSEV
LPSLTSERQMVFCCCMMLHVRKA
FLTYENG.I.LRMQPMRLFPLCW.ETRLTFVTLLLQRDKNVSQGTLERNWP.RMGH
YSVKQVPKMVLT.WRLFCTLLEK.
KRELTRMTADPLPI.PGPIPKSHHR.RIVAMAKSQTSLACEVFISRILNLCDLFGS.QS
GTSY.HCPMESLQCRET.TQL
SGPSGTLALLCFVSVSDLGPLAK.TSHVLTGLKR.HVNVFKMVKKKKK
VAGGAPWRCLEPGRTPPLPGPVGGWPEPSSKGAARPPPTFLAPPDVPSSGRTSRT
SQTRRASRRQQVAPSFQGGPCAPRR
SGALSAAPARRDGGGWGRRGAGPAALSLRRLRREPLGAPGARGVPGTVHGAAG
AAGRRRGSIPAAGRRP.RRHHLPGVRA
WLPRVPPRGAAPGLGSSGSRARRV.GGAGDTRQRGGRRRRGRGGGAGHLVRPG
ESRPGLAGFPGATWGRSQVHSQRRAS.
YLVPKHQPCGAKINSAI.TCYKELHP.DQTSKHRNGKFGHCGEESPGQGSYAVE.V
GRGNGSEDSGCRT.DTERRKTQS.
GSPQ.PQTSV.N.SRRSAGDH.KAKKARRTIKTRKSKGRCGCIEKTNL.FINGKPES.E
RPFRSTDKHSLSSE.VRCFEK
.LC.SESEY.KGSGNNPSIHRRSK.S.EAN.NTPNS.PEAT.Q..WP.KCP.KQL.QVQQIFA
YK.YLTREYNF.KQSQI
HWSFPSTSRL.QVIPLFLCG.GL.LPGPL.SSAEDKL.S.QPA.KLLRQRLVYLERSQ.V.
LRSGIQAPEGISEVTRGAG
ELWR.CFRHRCS.HKG.RDIWFRRCGFRLRLEAPRVC..RQHC.FIKKAHLSTLAPDR
PGR.QR.IF.LTEGLQDCTCWG
RCSGEV.FPHETLQE.ISRKYKRHPGS.FPNENPHCGWRTNSSAALGYSWSGEIQKY
CQVLLQKGRWCFAAV.CYM.EKL
S.HTRMGRYD.GCSP.DCSHYAGRKQG.HS.HCCYRGTKMCPRALWRETGHDVWG
IIL.NKCQRWF.HSGGCSAPCSRSE
KEN.QG.QQIHYQSNRDQFQKVTTDEELLQWLNPKHPWPVKSSFPEY.ICVTYLAL
NRVAHPTDTVLWRVYSAGKPEPSS
QVPLELWLFFVLSQ.VIWALWLNRLVMSLQVLKDNM.MFLKW.KKKKK
FFFFFFTILKTFTCYLLRPVRT.LVYLARGPKSLTETKQRRAKVPEGPESWVQVSL
HCKLSIGQCQ.DVPLC.EPNKSHK
FSILEMKTSQAKDVWDLAIATILHLW.LFGIGPG.IGNGSAVILVSSLFHFSSKVQNS
LHYVRTIFGTCFTE.CPIRHGQ
FLSKVPWDTFLSLCSSSVTNVSLVSYQHNGNSLMGCILNHIYPFSYVKKAFLTCNI
IQQQNTICLSEVRLGNTSESLLTS
CIPELQNCSFSIHNEGFHLEINSQGGAYIFSKFILAKSHEETRLPHCSVPSKYNLVSL
L.AKRFSVVIYQVCLGREC.DG
LS..TNNAAFTNRPLGLPV.DGSHIF.TKCLFIPYVRNICV.SITSKALLHPV.PLKSPLV
LVFHF.VILIGISQGRQAA
VEAAFRQAVNFTICPLQRITEGQGVTVLIHIGRAG.PVIA.RLRGMTNEFGTASRNC
IPW.DIIYMQRSVELAITVFKGT

To FIG. 26B        To FIG. 26B

From FIG. 26A            From FIG. 26A

SKAIITVM.LPVSCLEYFNLPLKTISIFCVCSDYFQIPFSIQTLISIITFQSI.LTLKKGY
VCLCF.KVFLNFLVFH..I
INLFFQCSHIFLLTYAF.LFFELS.LFNGHLQISYFSFILTSEVTEGFLSFAFFVFPCLM
FCSLNPLIHFLFQLTQLHSC
LVLGSLHRNGQIFHFCALKSDLTDEVLYNMFIWLN.SWLHKVDVLVQGTNLLFS
GNELGFVPKSRLEILPSPAGTRRAAR
GGQRRRVLVAFVLLAVVCLRPRLRHGGRGIQRTPVPAPPPAEGPEEATRELLEG
DGAVTVGVQPLEYCLGVGRPHPQLR
AQCPELLALQAPRAVRVAGGED.AQPGQLLSVPIRLHPAWRGRPRGLRSAAGRR
ALPGRTGPPAAAGRPGEFGSSGWFGH
LRERRAGRGTSGVAERLPSTTVRASPQQVPGAVGCARAPGTAKERLLRL
FFFFFLPF.KHLHVIF.DL.GHD.SI.PEGPNHSLRQNKEEPKFQRDLRAGFRFPCTVNS
P.DSVSRMCHSVKSQISHTN
SVFWK.RLHRPRMFGI.PLQQFFICGDFLELVPVRLVMDLLSSLSVLFFTSRARCRT
ASTMLEPSLALVSQNNAPYVMAS
FSPKCPGTHFCPSVAAVSRMSALFPTSIMGTVSWAASSIISTHSRMLRKLFSHVTS
YSSKTPSAFLK.DLAILLNLS.PA
VSQSCRTVRSPSTMRVFIWKSTPRVALIFSRNSFLQSLMRKLDFPTAASPASTIL.A
FCELKDLALSSTRSVWGESAEMG
FLDELTMLPSLTDPWGFQSKTEATSSKPNVSSSLMSGTSVSEASPPKLSCTPCDL.
NPLWCLYSTSESYSLGSLKVDKPL
SKQLSGRLSTSQFVLCRGSQRARESQSSST.EERDDLS.PRG.GE.PMNLGLLLEIVFP
GEILFICKDLLNLL.LLFSRAL
LRPSLLSCSFRLAVWSISICLSRLFRSSVYARIISRSLSVFRL.SA.SLFKASNSL.RKA
MFVCASKRSFLTFWFSIDKS
.ICFFNAATSSF.LTRFDCSSSFLSFLMVTCRSPTSVSY.RLRSLRASSALRFSSFRVL
CSAA.IL.SISSSNSLNCIAA
LSWALFTAMAKFSISVL.SLISRMKFFITCSYG.INLGSTRLMFWYKVLTCSSLGMN
LASSPSRAWKSCQARPGLAGPHE
VASAAAASSSPSSSSLSCVSGPASDTAGAGSRGPQSRRRPPRRDPRKPRANSWKV
MAPSRSASSRWNTASASAGRTRSSV
HSARNSSRSRRPERFASQAAKTERSRASSSPSPSASIPPGGGGREGSGAPRGAGPS
LEGRGHLLPPGGPASLARPAGSAT
.GNVGRGEERRGWPSGSLRRRFGPAPNRSRERWGAPGLQAPPRSASCD
FFFFFYHFKNIYMLSFKTCKDMTSLFSQRAQITH.DKTKKSQSSRGT.ELGSGFPAL.
TLHRTVSVGCATLLRAK.VTQI
QYSGNEDFTGQGCLGFSHCNNSSSVVTFWNWSRLDW.WICCHPCQFSFSLLEQG
AEQPPLC.NHLWHLFHRIMPHTSWPV
SLQSALGHIFVPL.QQCHECQPCFLPA.WEQSHGLHPQSYLPILVC.ESFSHM.HHTA
AKHHLPF.SKTWQYF.ISPDQL
YPRAAELFVLHPQ.GFSFGNQLPGWRLYFLEIHSCKVS.GN.TSPLQRPQQVQSCKP
SVS.KI.RCHLPGLSGARVLRWA
FLMN.QCCLH.QTLGASSLRRKPHLLNQMSLHPLCQEHLCLKHHLQSSPAPRVTSE
IPSGACIPLLSHTHWDLSR.TSRC
RSSFQAGCQLHNLSSAEDHRGPGSHSPHPHRKSGMTCHSLEVEGNDQ.IWDCF.K
LYSLVRYYLYAKIC.TCYNCFQGIIF
.GHHYCHVASG.LFGVFQFASQDYFDLLCMLGLFPDPFQYSDSDQHNHFSKHLTH
SEERLCLSVLLKGLS.LSGFPLINH
KFVFSMQPHLPFDLRVLIVLRAFLAF.WSPADLLLQFHTDV.GH.GLPQLCVFRLSV
SYVLQPESSDPFPLPTHSTA.LP
CPGLSSPQWPNFPFLCFEV.SHG.SSL.HVHMAELILAPQG.CFGTRY.LALLWE.TW
LRPQVAPGNPAKPGRDSPGRTR
WPAPPPRPRRLRPPRCRVSPAPPQTRRARDPEDPSPGAAPRGGTRGSHARTPGR.
WRRHGRRPAAGILPRRRPAAPAAPC
TVPGTPRAPGAPSGSRRRRRRLSAAGPAPLRPHPPPSRLAGAAERAPERRGAQGP
PWKDGATCCRREARRVWLVRLVRPL
EGTSGGARNVGGGRAAPFDDGSGQPPTGPSGGVRPGSRHRQGAPPAT

FIG. 26B

TYROSINE KINASE SUBSTRATE(TKS) PROTEINS

This application claims the benefit of U.S. provisional application No. 60/128,492 filed on Apr. 9, 1999.

FIELD OF THE INVENTION

The present invention relates to novel polypeptides, nucleotide sequences encoding the novel polypeptides, as well as various products and methods useful for the diagnosis and treatment of various diseases and conditions.

BACKGROUND OF THE INVENTION

The following description of the background of the invention is provided to aid in understanding the invention, but is not admitted to be or to describe prior art to the invention.

Cellular signal transduction is a fundamental mechanism whereby external stimuli that regulate diverse cellular processes are relayed to the interior of cells. One of the key biochemical mechanisms of signal transduction involves the reversible phosphorylation through kinases of proteins, which enables regulation of the activity of mature proteins by altering their structure and function.

The best characterized protein kinases in eukaryotes phosphorylate proteins on the hydroxyl substituent of serine, threonine and tyrosine residues. These kinases largely fall into two groups, those specific for phosphorylating serines and threonines, and those specific for phosphorylating tyrosines. Some kinases, referred to as "dual specificity" kinases, are able to phosphorylate on tyrosine as well as serine/threonine residues.

Many kinases are involved in regulatory cascades wherein their substrates may include other kinases whose activities are regulated by their phosphorylation state. Ultimately the activity of some downstream effector is modulated by phosphorylation resulting from activation of such a pathway.

Non-receptor tyrosine kinases may be recruited to the plasma membrane where they mediate cellular signaling by cell surface receptors lacking intrinsic protein tyrosine kinase activities. For instance, members of the Src family of protein tyrosine kinases are activated in response to stimulation of growth factor receptors and G-protein coupled receptors, as well as many other extracellular stimuli (Thomas, er al., 1997. Annu. Rev. Cell. Dev. Biol. 13:513–609).

Src family kinases have been found associated with coated membrane regions in platelets (Stenberg, et al., 1997. Blood 89:2384–93). Src copurifies with synaptic vesicles in PC12 cells (Linstedt, et al., 1992. J. Cell Biol. 117:1077–84). Src associates with and phosphorylates several proteins involved in membrane trafficking, such as the neuronal synaptic vesicle associated protein synapsin I, synaptophysin and synaptogyrin (Barnekow, et al., 1990. Oncogene 5:1019–24; Foster-Barber, et al., 1998. Proc. Natl. Acad. Sci. USA 95:4673–7; Janz, et al., 1998. J. Biol. Chem. 273:2851–7).

Small GTPases represent a large family of proteins that act as molecular switches that control diverse biological functions, including cell proliferation and differentiation, cytoskeletal organization, protein transport, cell cycle and free radical production (Bourne, H. R. et. al., Nature, 348 (6297):125–32, 1990. Bourne, H. R. et. al., Nature, 349 (6305):117–27, 1991). That GTPases modulate these central cellular pathways suggest that both GTPases and their regulators are of critical importance.

The dbl homology region (DH domain) is a region of approximately 250 amino acids initially found in the Dbl and Cdc24 proteins. Many proteins have been found to contain DH domains. Many DH containing proteins exhibit cellular transformation activity upon N-terminal truncation. (Reviewed in Quilliam, L. A., et. al. BioEssays, 17:395–404, 1995. Whitehead, I. P., et. al., Biochemica et Biophysica Acta, 1332:F1–F23, 1997. Cerione, R. A. and Zheng, Y. Curr. Opin. Cell. Biol. 8:216–222, 1996).

The DH/PH modules of many Dbl family proteins have been shown to regulate the activity of various Rho subfamily small GTPases by serving as Guanine Exchange Factors (GEF) (Whitehead, I. P., et. al., Biochimica et Biophysica Acta, 1332:F1–F23, 1997. Cerione, R. A. and Zheng, Y. Curr. Opin. Cell Biol. 8:216–222, 1996). Many Rho family GTPases have been shown to regulate the assembly of actin structures and may also regulate gene transcription through various kinase pathways (Hall, A. Science, 279:509–514, 1998).

SUMMARY OF THE INVENTION

The present invention relates to novel substrates of the cytoplasmic tyrosine kinase Src, Tks 107, Tks 113, Tks 118 and Tks 202.

A first aspect of the invention features an isolated, enriched or purified nucleic acid molecule encoding a polypeptide selected from the group consisting of Tks 107, Tks 113, Tks 118 and Tks 202.

By "isolated" in reference to nucleic acid is meant a polymer of nucleotides conjugated to each other, including DNA and RNA, that is isolated from a natural source or that is synthesized. The isolated nucleic acid of the present invention is unique in the sense that it is not found in a pure or separated state in nature. Use of the term "isolated" indicates that a naturally occurring sequence has been removed from its normal cellular (i.e., chromosomal) environment. Thus, the sequence may be in a cell-free solution or placed in a different cellular environment. The term does not imply that the sequence is the only nucleotide chain present, but that it is essentially free (about 90–95% pure at least) of non-nucleotide material naturally associated with it, and thus is distinguished from isolated chromosomes.

By the use of the term "enriched" in reference to nucleic acid is meant that the specific DNA or RNA sequence constitutes a significantly higher fraction (2–5 fold) of the total DNA or RNA present in the cells or solution of interest than in normal or diseased cells or in the cells from which the sequence was taken. This could be caused by a person by preferential reduction in the amount of other DNA or RNA present or by a preferential increase in the amount of the specific DNA or RNA sequence or by a combination of the two. However, it should be noted that enriched does not imply that there are no other DNA or RNA sequences present, just that the relative amount of the sequence of interest has been significantly increased. The term "significant" is used to indicate that the level of increase is useful to the person making such an increase, and generally means an increase relative to other nucleic acids of about at least 2 fold, more preferably at least 5 to 10 fold or even more. The term also does not imply that there is no DNA or RNA from other sources. The other source DNA may, for example, comprise DNA from a yeast or bacterial genome, or a cloning vector such as pUC19. This term distinguishes from naturally occurring events, such as viral infection, or tumor type growths, in which the level of one mRNA may be naturally increased relative to other species of mRNA. That is, the term is meant to cover only those situations in which a person has intervened to elevate the proportion of the desired nucleic acid.

It is also advantageous for some purposes that a nucleotide sequence be in purified form. The term "purified" in reference to nucleic acid does not require absolute purity (such as a homogeneous preparation). Instead, it represents an indication that the sequence is relatively more pure than in the natural environment (compared to the natural level this level should be at least 2–5 fold greater, e.g., in terms of mg/mL). Individual clones isolated from a cDNA library may be purified to electrophoretic homogeneity. The claimed DNA molecules obtained from these clones could be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^6$-fold purification of the native message. Thus, purification of at least one order of magnitude, preferably two or three orders, and more preferably four or five orders of magnitude is expressly contemplated.

By a polypeptide is meant at least 108, 93, 60 or 203 or more contiguous amino acids set forth in the amino acid sequence of SEQ ID NO:5, SEQ ID NO:6, SEQ ID NO:7 or SEQ ID NO:8, respectively, or the corresponding full-length amino acid sequence; or a functional derivative thereof as described herein. For sequences for which the full-length sequence is not given, the remaining sequences can be determined using methods well-known to those in the art and are intended to be included in the invention. The polypeptide can be encoded by a full-length nucleic acid sequence or any portion of the full-length nucleic acid sequence, so long as a functional activity of the polypeptide is retained.

The amino acid sequence will be substantially similar to the sequence shown in SEQ ID NO:5, SEQ ID NO:6, SEQ ID NO:7 or SEQ ID NO:8, or the corresponding full-length amino acid sequence, or fragments thereof. A sequence that is substantially similar to the sequence of SEQ ID NO:5, SEQ ID NO:6, SEQ ID NO:7 or SEQ ID NO:8 will preferably have at least 90% identity (more preferably at least 95% and most preferably 99–100%) to the respective sequence.

By "identity" is meant a property of sequences that measures their similarity or relationship. Identity is measured by dividing the number of identical residues by the total number of residues and gaps and multiplying the product by 100. "Gaps" are spaces in an alignment that are the result of additons or deletions of amino acids. Thus, two copies of exactly the same sequence have 100% identity, but sequences that are less highly conserved, and have deletions, additions, or replacements, may have a lower degree of identity. Those skilled in the art will recognize that several computer programs are available for determining sequence identity using standard parameters as default settings. Examples of such programs are Gapped BLAST or PSI-BLAST (Altschul, et al. (1997) Nucleic Acids Res. 25:3389–3402), BLAST (Altschul, et al. (1990) J. Mol. Biol. 215:403–410), and Smith-Waterman (Smith, et al. (1981) J. Mol. Biol. 147:195–197). Preferably, the default settings of these programs will be employed, but those skilled in the art recognize whether these settings need to be changed and know how to make the changes.

In preferred embodiments, the invention features isolated, enriched or purified nucleic acid molecules encoding a polypeptide comprising a nucleotide sequence that: (a) encodes a polypeptide having the amino acid sequence set forth in SEQ ID NO:5, SEQ ID NO:6, SEQ ID NO:7 or SEQ ID NO:8; (b) is the complement of the nucleotide sequence of (a); (c) hybridizes under highly stringent conditions to the nucleotide molecule of (a) of (b) and encodes a naturally occurring polypeptide; (d) differs from a polypeptide having the amino acid sequence of SEQ ID NO:5, SEQ ID NO:6, SEQ ID NO:7 or SEQ ID NO:8 by lacking one or more, but not all, of the following segments of amino acid residues: 1–1082, 1083–1257, 1258–1264, 1265–1372 or 1373–1519 of SEQ ID NO:5; 1–383 or 384–476 of SEQ ID NO:6; 1–227, 228–371 or 372–431 of SEQ ID NO:7; or 1–629 or 630–832 of SEQ ID NO:8; (e) is the complement of the nucleotide sequence of (d); (f) encodes a polypeptide having the amino acid sequence set forth in amino acid residues: 1–1082, 1083–1257, 1258–1264, 1265–1372 or 1373–1519 of SEQ ID NO:5; 1–383 or 384–476 of SEQ ID NO:6; 1–227, 228–371 or 372–431 of SEQ ID NO:7; or 1–629 or 630–832 of SEQ ID NO:8; (g) is the complement of the nucleotide sequence of (f); (h) differs from a polypeptide having the amino acid sequence set forth in SEQ ID NO:5, SEQ ID NO:6, SEQ ID NO:7 or SEQ ID NO:8 by lacking one or more of the domains selected from the group consisting of an N-terminal domain, a DH domain, a C-terminal domain, a PH domain, a spacer region, an SH3 domain, a GTPase domain and a proline-rich region; or (i) is the complement of the nucleotide sequence of (h).

The term "complement" refers to two nucleotides that can form multiple favorable interactions with one another. For example, adenine is complementary to thymine as they can form two hydrogen bonds. Similarly, guanine and cytosine are complementary since they can form three hydrogen bonds. A nucleotide sequence is the complement of another nucleotide sequence if all of the nucleotides of the first sequence are complementary to all of the nucleotides of the second sequence.

The term "domain" refers to a region of a polypeptide which contains a particular function. For instance, N-terminal or C-terminal domains of signal transduction proteins can serve functions including, but not limited to, binding molecules that localize the signal transduction molecule to different regions of the cell or binding other signaling molecules directly responsible for propagating a particular cellular signal. Some domains can be expressed separately from the rest of the protein and function by themselves, while others must remain part of the intact protein to retain function. The latter are termed functional regions of proteins and also relate to domains.

The term "N-terminal domain" refers to the extracatalytic region located between the initiator methionine and the subsequent domain of the protein. The N-terminal domain can be identified following a Smith-Waterman alignment of the protein sequence against the non-redundant protein database to define the N-terminal boundary of the catalytic domain. Depending on its length, the N-terminal domain may or may not play a regulatory role in kinase function. An example of a protein kinase whose N-terminal domain has been shown to play a regulatory role is p65PAK, which contains a CRIB motif used for Cdc42 and rac binding (Burbelo, P. D. et al. (1995) J. Biol. Chem. 270, 29071–29074).

The N-terminal domain spans amino acid residues 1–1082 of SEQ ID NO:5, 1–383 of SEQ ID NO:6, 1–227 of SEQ ID NO:7 and 1–629 of SEQ ID NO:8.

The term "substrate" as used herein refers to a molecule phosphorylated by a protein of the invention.

The term "C-terminal domain" refers to the region located between the last (located closest to the C-terminus) functional domain and the carboxy-terminal amino acid residue of the preceding domain. By "functional" domain is meant any region of the polypeptide that may play a regulatory or catalytic role as predicted from amino acid sequence homology to other proteins or by the presence of amino acid sequences that may give rise to specifc structural conformations. The C-terminal domain can be identified by using a Smith-Waterman alignment of the protein sequence against the non-redundant protein database to define the C-terminal boundary of the catalytic domain or of any functional C-terminal extracatalytic domain.

The C-terminal domain spans amino acid residues 1373–1519 of SEQ ID NO:5.

The term "dbl homology domain (DH domain)" refers to a domain composed essentially of α-helices, several of which correspond to previously defined conserved regions (Soisson, S. M., et. al., Cell, 95:259–268), as identified by a hidden Markov model (http:/hmmer.wustl.edu).

The DH domain spans amino acid residues 1083–1257 of SEQ ID NO:5.

By "PH domain" is meant a polypeptide having homology to an approximately 100 amino acid region of pleckstrin. The total number of proposed PH domains now exceeds 70. Recent structural studies have demonstrated that PH domains are distinct structural modules. The fold is best described as a seven-stranded sandwich of two orthogonal b sheets that is closed at one corner by a C-terminal helix. A polarization of the domain is evident, with the three most variable loops forming a positively charged surface at the corner of the sandwich opposite from that closed off by the helix. Ferguson, K. M. et al., *Cell,* 79, 199–209, 1994, incorporated herein by reference in its entirety, including any drawings. Examples of various PH domains are provided in Musacchio, A., et al., *TIBS,* 18:343–348, 1993 and Gibson, T. J., et al., *TIBS,* 19:349–353, 1994, both of which are incorporated herein by reference in their entirety, including any drawings. Other PH domains may be identified using the sequence alignment techniques and three dimensional structure comparisons described in those publications. PH domains include those in serine/threonine as well as tyrosine kinases; regulators of small GTP-binding proteins; cytoskeletal proteins; and putative signaling adapter molecules. PH domains are also those from dynamin, proteins involved in cellular membrane transport and phospholipase C isoforms. The cloning and sequence of multiple forms of phospholipase C is described in Suh, et al., Cell, 54:161–169, 1988, icorporated herein by reference in its entirety, including any drawings.

The PH domain spans amino acids 1265–1372 of SEQ ID NO:5.

The terms "SH3" domain and GTPase domain are well-known terms and the meaning is defined as known to one skilled in the art.

The SH3 domain spans amino acids 372–431 of SEQ ID NO:9. The GTPase domain spans amino acids 630–832 of SEQ ID NO:8.

The term "signal transduction pathway" refers to the molecules that propagate an extracellular signal through the cell membrane to become an intracellular signal. This signal can then stimulate a cellular response. The polypeptide molecules involved in signal transduction processes are typically receptor and non-receptor protein tyrosine kinases, receptor and non-receptor protein phosphatases, SRC homology 2 and 3 domains, phosphotyrosine binding proteins (SRC homology 2 (SH2) and phosphotyrosine binding (PTB and PH) domain containing proteins), proline-rich binding proteins (SH3 domain containing proteins), nucleotide exchange factors, and transcription factors.

The term "proline-rich region" as used herein, refers to a region of a protein whose proline content over a given amino acid length is higher than the average content of this amino acid found in proteins (i.e., >10%). Proline-rich regions are easily discernable by visual inspection of amino acid sequences and quantitated by standard computer sequence analysis programs such as the DNAStar program EditSeq. Proline-rich regions have been demonstrated to participate in regulatory protein—protein interactions. (see for example Galisteo, M. L. et al. (1996) J. Biol. Chem. 271:20997–21000 and Sudol, M. (1996) Prog. Biochys. Mol. Bio. 65:113–132).

The proline-rich region spans amino acid residues 384–476 of SEQ ID NO:5.

The term "spacer region" as used herein, refers to a region of the protein located between predicted functional domains. The spacer region has no detectable homology to any amino acid sequence in the database and can be identified by using a Smith-Waterman alignment of the protein sequence against the non-redundant protein database to define the C- and N-terminal boundaries of the flanking functional domains. Spacer regions may or may not play a fundamental role in protein kinase function. Precedence for the regulatory role of spacer regions in kinase function is provided by the role of the src kinase spacer in inter-domain interactions (Xu, W. et al. (1997) Nature 385:595–602).

The spacer region spans amino acid residues 1258–1264 of SEQ ID NO:5.

Various low or high stringency hybridization conditions may be used depending upon the specificity and selectivity desired. These conditions are well-known to those skilled in the art. Under stringent hybridization conditions only highly complementary nucleic acid sequences hybridize. Preferably, such conditions prevent hybridization of nucleic acids having more than 1 or 2 mismatches out of 20 contiguous nucleotides, more preferably, such conditions prevent hybridization of nucleic acids having more than 1 or 2 mismatches out of 50 contiguous nucleotides, most preferably, such conditions prevent hybridization of nucleic acids having more than 1 or 2 mismatches out of 100 contiguous nucleotides. In some instances, the conditions may prevent hybridization of nucleic acids having more than 5 mismatches in the full-length sequence.

By stringent hybridization assay conditions is meant hybridization assay conditions at least as stringent as the following: hybridization in 50% formamide, 5×SSC, 50 mM NaH2PO4, pH 6.8, 0.5% SDS, 0.1 mg/mL sonicated salmon sperm DNA, and 5× Denhart solution at 42° C. overnight; washing with 2×SSC, 0.1% SDS at 45° C.; and washing with 0.2×SSC, 0.1% SDS at 45° C. More stringent conditions include 0.1×SSC, 0.05% SDS and 55° C. for the second wash. Under some of the most stringent hybridization assay conditions, the second wash can also be done with 0.1×SSC at a temperature up to 70° C. (Berger et al. (1987) *Guide to Molecular Cloning Techniques* pg 421, hereby incorporated by reference herein in its entirety including any figures, tables or drawings.). However, other applications may require the use of conditions falling between these sets of conditions. Methods of determining the conditions required to achieve desired hybridizations are well known to those with ordinary skill in the art and are based on several factors, including but not limited to, the sequences to be hybridized and the samples to be tested. Washing conditions of lower stringency frequently utilize a lower temperature during the washing steps, such as 65° C., 60° C., 55° C., 50° C. or 42° C.

In other preferred embodiments, the invention features isolated, enriched or purified nucleic acid molecules encoding polypeptides, further comprising a vector or promoter effective to initiate transcription in a host cell. The invention also features a recombinant nucleic acid, preferably in a cell or an organism. The recombinant nucleic acid may contain a sequence set forth in SEQ ID NO:1, SEQ ID NO:2, SEQ ID NO:3 or SEQ ID NO:4, a nucleic aicd encoding the polypeptide set forth in SEQ ID NO:5, SEQ ID NO:6, SEQ ID NO:7, or SEQ ID NO:8, or a functional derivative thereof and a vector or a promoter effective to initiate transcription in a host cell. The recombinant nucleic acid can alternatively contain a transcriptional initiation region functional in a cell, a sequence complementary to an RNA sequence encoding a polypeptide and a transcriptional termination region functional in a cell.

The term "vector" relates to a single or double-stranded circular nucleic acid molecule that can be transfected into cells and replicated within or independently of a cell genome. A circular double-stranded nucleic acid molecule can be cut and thereby linearized upon treatment with restriction enzymes. An assortment of nucleic acid vectors, restriction enzymes and the knowledge of the nucleotide sequences cut by restriction enzymes are readily available to those skilled in the art. A nucleic acid molecule encoding a kinase can be inserted into a vector by cutting the vector with restriction enzymes and ligating the two pieces together.

The term "transfecting" defines a number of methods to insert a nucleic acid vector or other nucleic acid molecules into a cellular organism. These methods involve a variety of techniques, such as treating the cells with high concentrations of salt, an electric field, detergent or DMSO to render the outer membrane or wall of the cells permeable to nucleic acid molecules of interest or use of various viral transduction strategies.

The term "promoter" as used herein, refers to nucleic acid sequencer(s) needed for gene sequence expression. Promoter regions vary from organism to organism, but are well known to persons skilled in the art for different organisms. For example, in prokaryotes, the promoter region contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence and the like.

In preferred embodiments, the isolated nucleic acid comprises, consists essentially of, or consists of a nucleic acid sequence set forth in SEQ ID NO:1, SEQ ID NO:2, SEQ ID NO:3 or SEQ ID NO:4, or the corresponding full-length sequence, encodes the amino acid sequence of SEQ ID NO:5, SEQ ID NO:6, SEQ ID NO:7 or SEQ ID NO:8, or the corresponding full-length amino acid sequence, a functional derivative thereof, or at least 108, 93, 60 or 203 contiguous amino acids of SEQ ID NO:5, SEQ ID NO:6, or SEQ ID NO:7 or SEQ ID NO:8, respectively, or of the corresponding full-length amino acid sequence. The nucleic acid may be isolated from a natural source by cDNA cloning or by subtractive hybridization. The natural source may be mammalian, preferably human, blood, semen, or tissue, and the nucleic acid may be synthesized by the triester method or by using an automated DNA synthesizer.

The term "mammal" refers preferably to such organisms as mice, rats, rabbits, guinea pigs, sheep, and goats, more preferably to cats, dogs, monkeys, and apes, and most preferably to humans.

In yet other preferred embodiments, the nucleic acid is a conserved or unique region, for example those useful for: the design of hybridization probes to facilitate identification and cloning of additional polypeptides, the design of PCR probes to facilitate cloning of additional polypeptides, obtaining antibodies to polypeptide regions, and designing antisense oligonucleotides.

By "conserved nucleic acid regions" are meant regions present on two or more nucleic acids encoding a polypeptide, to which a particular nucleic acid sequence can hybridize under lower stringency conditions. Examples of lower stringency conditions suitable for screening for nucleic acid encoding kinase polypeptides are provided in Berger et al. (1987) *Guide to Molecular Cloning Techniques* pg 421 (hereby incorporated by reference herein in its entirety including any figures, tables or drawings). Preferably, conserved regions differ by no more than 7 out of 20 nucleotides.

By "unique nucleic acid region" is meant a sequence present in a nucleic acid coding for a polypeptide that is not present in a sequence coding for any other naturally occurring polypeptide. Such regions preferably encode 108, 93, 60 or 203 or more contiguous amino acids set forth in the amino acid sequence of SEQ ID NO:5, SEQ ID NO:6, or SEQ ID NO:7 or SEQ ID NO:8, respectively, or the corresponding full-length amino acid sequence or functional derivatives thereof. In particular, a unique nucleic acid region is preferably of mammalian origin.

Another aspect of the invention features a nucleic acid probe for the detection of nucleic acid encoding a polypeptide in a sample, wherein said polypeptide is selected from the group consisting of Tks 107, Tks 113, Tks 118 and Tks 202. The nucleic acid probe may encode a polypeptide that is a fragment of the protein encoded by the amino acid sequence set forth in SEQ ID NO:5, SEQ ID NO:6, SEQ ID NO:7 or SEQ ID NO:8, or the corresponding full-length amino acid sequences or a complement thereof. The nucleic acid probe contains a nucleotide base sequence that will hybridize to a sequence set forth in SEQ ID NO:1, SEQ ID NO:2, SEQ ID NO:3 or SEQ ID NO:4, or the corresponding full-length sequence, or a functional derivative thereof.

Methods for using the probes include detecting the presence or amount of RNA in a sample by contacting the sample with a nucleic acid probe under conditions such that hybridization occurs and detecting the presence or amount of the probe bound to RNA. The nucleic acid duplex formed between the probe and a nucleic acid sequence coding for a polypeptide may be used in the identification of the sequence of the nucleic acid detected (Nelson et al., in Nonisotopic DNA Probe Techniques, Academic Press, San Diego, Kricka, ed., p. 275, 1992, hereby incorporated by reference herein in its entirety, including any drawings, figures, or tables). Kits for performing such methods may be constructed to include a container means having disposed therein a nucleic acid probe.

In another aspect, the invention describes recombinant DNA molecules or a cell or tissue comprising a recombinant nucleic acid molecule encoding a polypeptide selected from the group consisting of Tks 107, Tks 113, Tks 118 and Tks 202. In such cells, the nucleic acid may be under the control of the genomic regulatory elements, or may be under the control of exogenous regulatory elements including an exogenous promoter. By "exogenous" it is meant a promoter that is not normally coupled in vivo transcriptionally to the coding sequence for the polypeptides.

The polypeptide is preferably a fragment of the protein encoded by the amino acid sequence set forth in SEQ ID NO:5, SEQ ID NO:6, SEQ ID NO:7 or SEQ ID NO:8 or full-length sequence thereof. By "fragment," is meant an amino acid sequence present in a polypeptide. Preferably, such a sequence comprises at least 108, 93, 60 or 203 contiguous amino acids of SEQ ID NO:5, SEQ ID NO:6, SEQ ID NO:7 or SEQ ID NO:8, respectively.

In another aspect, the invention features an isolated, enriched or purified polypeptide selected from the group consisting of Tks 107, Tks 113, Tks 118 and Tks 202.

By "isolated" in reference to a polypeptide is meant a polymer of amino acids (2 or more amino acids) conjugated to each other, including polypeptides that are isolated from a natural source or that are synthesized. The isolated polypeptides of the present invention are unique in the sense that they are not found in a pure or separated state in nature. Use of the term "isolated" indicates that a naturally occurring sequence has been removed from its normal cellular environment. Thus, the sequence may be in a cell-free solution or placed in a different cellular environment. The term does not imply that the sequence is the only amino acid chain present, but that it is essentially free (about 90–95% pure at least) of non-amino acid material naturally associated with it.

By the use of the term "enriched" in reference to a polypeptide is meant that the specific amino acid sequence constitutes a significantly higher fraction (2–5 fold) of the total amino acid sequences present in the cells or solution of interest than in normal or diseased cells or in the cells from which the sequence was taken. This could be caused by a person by preferential reduction in the amount of other amino acid sequences present, or by a preferential increase in the amount of the specific amino acid sequence of interest, or by a combination of the two. However, it should be noted that enriched does not imply that there are no other amino acid sequences present, just that the relative amount of the sequence of interest has been significantly increased. The term significant here is used to indicate that the level of increase is useful to the person making such an increase, and generally means an increase relative to other amino acid sequences of about at least 2-fold, more preferably at least 5- to 10-fold or even more. The term also does not imply that there is no amino acid sequence from other sources. The other source of amino acid sequences may, for example, comprise amino acid sequence encoded by a yeast or bacterial genome, or a cloning vector such as pUC19. The term is meant to cover only those situations in which one has intervened to increase the proportion of the desired amino acid sequence.

It is also advantageous for some purposes that an amino acid sequence be in purified form. The term "purified" in reference to a polypeptide does not require absolute purity (such as a homogeneous preparation); instead, it represents an indication that the sequence is relatively purer than in the natural environment. Compared to the natural level this level should be at least 2–5 fold greater (e.g., in terms of mg/mL). Purification of at least one order of magnitude, preferably two or three orders, and more preferably four or five orders of magnitude is expressly contemplated. The substance is preferably free of contamination at a functionally significant level, for example 90%, 95%, or 99% pure.

In preferred embodiments, the polypeptide is a fragment of the protein encoded by the amino acid sequence set forth in SEQ D NO:5, SEQ ID NO:6, SEQ ID NO:7 or SEQ ID NO:8, or the corresponding full-length amino acid sequences. Preferably, the polypeptide contains at least 108, 93, 60 or 203 contiguous amino acids of SEQ ID NO:5, SEQ ID NO:6, or SEQ ID NO:7 or SEQ ID NO:8, respectively.

In preferred embodiments, the polypeptide comprises an amino acid sequence having (a) the amino acid sequence set forth in SEQ ID NO:5, SEQ ID NO:6, SEQ ID NO:7 or SEQ ID NO:8; (b) an amino acid sequence differing from that set forth in SEQ ID NO:5, SEQ ID NO:6, SEQ ID NO:7 or SEQ ID NO:8 by lacking one or more, but not all, of the following segments of amino acid residues: 1–1082, 1083–1257, 1258–1264, 1265–1372 or 1373–1519 of SEQ ID NO:5; 1–383 or 384–476 of SEQ ID NO:6; 1–227, 228–371 or 372–431 or SEQ D NO:7 or 1–629 or 630–832 or SEQ ID NO:8; (c) the amino acid sequence set forth in SEQ ID NO:5, SEQ ID NO:6, SEQ ID NO:7 or SEQ ID NO:8 from amino acid residues 1–1082, 1083–1257, 1258–1264, 1265–1372 or 1373–1519 of SEQ ID NO:5; 1–383 or 384–476 of SEQ ID NO:6; 1–227, 228–371 or 372–431 or SEQ ID NO:7 or 1–629 or 630–832 or SEQ ID NO:8; or (d) an amino acid sequence differing from that set forth in SEQ ID NO:5, SEQ ID NO:6, SEQ ID NO:7 or SEQ ID NO:8 by lacking one or more, but not all, of the domains selected from the group consisting of a C-terminal domain, a PH domain, a DH domain, an N-terminal domain, an SH3 domain, a spacer region, a proline-rich region and a GTPase domain.

The polypeptide can be isolated from a natural source by methods well-known in the art. The natural source may be mammalian, preferably human, blood, semen or tissue, and the polypeptide may be synthesized using an automated polypeptide synthesizer. The isolated, enriched, or purified polypeptide is preferably: a Tks 107, Tks 113, Tks 118 or Tks 202 polypeptide.

In some embodiments the invention includes a recombinant polypeptide selected from the group consisting of Tks 107, Tks 113, Tks 118 and Tks 202. By "recombinant polypeptide" is meant a polypeptide produced by recombinant DNA techniques such that it is distinct from a naturally occurring polypeptide either in its location (e.g., present in a different cell or tissue than found in nature), purity or structure. Generally, such a recombinant polypeptide will be present in a cell in an amount different from that normally observed in nature.

In other aspects, the invention features an antibody (e.g., a monoclonal or polyclonal antibody) having specific binding affinity to a polypeptide or a polypeptide domain or fragment where the polypeptide is selected from the group consisting of Tks 107, Tks 113, Tks 118 and Tks 202. By "specific binding affinity" is meant that the antibody binds to the target polypeptide with greater affinity than it binds to other polypeptides under specified conditions. Antibodies or antibody fragments are polypeptides that contain regions that can bind other polypeptides. The term "specific binding affinity" describes an antibody that binds to a polypeptide with greater affinity than it binds to other polypeptides under specified conditions.

The term "polyclonal" refers to antibodies that are heterogenous populations of antibody molecules derived from the sera of animals immunized with an antigen or an antigenic functional derivative thereof. For the production of polyclonal antibodies, various host animals may be immunized by injection with the antigen. Various adjuvants may be used to increase the immunological response, depending on the host species.

"Monoclonal antibodies" are substantially homogenous populations of antibodies to a particular antigen. They may be obtained by any technique which provides for the production of antibody molecules by continuous cell lines in culture. Monoclonal antibodies may be obtained by methods known to those skilled in the art (Kohler et al., Nature 256:495–497, 1975, and U.S. Pat. No. 4,376,110, both of which are hereby incorporated by reference herein in their entirety including any figures, tables, or drawings).

The term "antibody fragment" refers to a portion of an antibody, often the hyper variable region and portions of the surrounding heavy and light chains, that displays specific binding affinity for a particular molecule. A hyper variable region is a portion of an antibody that physically binds to the polypeptide target.

Antibodies or antibody fragments having specific binding affinity to a polypeptide of the invention may be used in methods for detecting the presence and/or amount of polypeptide in a sample by probing the sample with the antibody under conditions suitable for polypeptide-antibody immunocomplex formation and detecting the presence and/or amount of the antibody conjugated to the polypeptide. Diagnostic kits for performing such methods may be constructed to include antibodies or antibody fragments specific for the polypeptide as well as a conjugate of a binding partner of the antibodies or the antibodies themselves.

An antibody or antibody fragment with specific binding affinity to a polypeptide of the invention can be isolated, enriched or purified from a prokaryotic or eukaryotic organism. Routine methods known to those skilled in the art enable production of antibodies or antibody fragments, in both prokaryotic and eukaryotic organisms. Purification, enrichment, and isolation of antibodies, which are polypeptide molecules, are described above.

Antibodies having specific binding affinity to a polypeptide of the invention may be used in methods for detecting the presence and/or amount of polypeptide in a sample by contacting the sample with the antibody under conditions such that an immunocomplex forms and detecting the presence and/or amount of the antibody conjugated to the polypeptide. Diagnostic kits for performing such methods may be constructed to include a first container containing the antibody and a second container having a conjugate of a binding partner of the antibody and a label, such as, for example, a radioisotope. The diagnostic kit may also include notification of an FDA approved use and instructions therefor.

Further aspects of the invention feature a hybridoma which produces an antibody having specific binding affinity to a polypeptide or a polypeptide domain, where the polypeptide is selected from the group consisting of Tks 107, Tks 113, Tks 118 and Tks 202. By "hybridoma" is meant an immortalized cell line that is capable of secreting an antibody, for example an antibody to a polypeptide of the invention. In preferred embodiments, the antibody to the polypeptide comprises a sequence of amino acids that is able to specifically bind a polypeptide of the invention.

In another aspect, the invention features a polypeptide binding agent able to bind to a polypeptide selected from the group consisting of Tks 107, Tks 113, Tks 118 and Tks 202. The binding agent is preferably a purified antibody that recognizes an epitope present on a polypeptide of the invention. Other binding agents include molecules that bind to polypeptides and analogous molecules that bind to a polypeptide. Such binding agents may be identified by using assays that measure binding partner activity.

The invention also features a method for screening for human cells containing a polypeptide of the invention or an equivalent sequence. The method involves identifying the novel polypeptide in human cells using techniques that are routine and standard in the art, such as those described herein for identifying the polypeptides of the invention (e.g., cloning, Southern or Northern blot analysis, in situ hybridization, PCR amplification, etc.).

In yet another aspect, the invention features methods for identifying a substance that modulates polypeptide activity comprising the steps of: (a) contacting a polypeptide selected from the group consisting of Tks 107, Tks 113, Tks 118 and Tks 202 with a test substance; (b) measuring the activity of said polypeptide; and (c) determining whether said substance modulates the activity of said polypeptide.

The term "modulates" refers to the ability of a compound to alter the function of a polypeptide of the invention. A modulator preferably activates or inhibits the activity of a polypeptide of the invention depending on the concentration of the compound exposed to the polypeptide.

The term "activates" refers to increasing the cellular activity of the polypeptide. The term "inhibit" refers to decreasing the cellular activity of the peptide. Activity preferably affects the interaction with a natural binding partner, such as src.

The term "modulates" also refers to altering the function of polypeptides of the invention by increasing or decreasing the probability that a complex forms between the polypeptide and a natural binding partner. A modulator preferably increases the probability that such a complex forms between the polypeptide and the natural binding partner, more preferably increases or decreases the probability that a complex forms depending on the concentration of the compound exposed, and most preferably decreases the probability that a complex forms.

The term "complex" refers to an assembly of at least two molecules bound to one another. Signal transduction complexes often contain at least two protein molecules bound to one another.

The term "natural binding partner" refers to polypeptides, lipids, small molecules or nucleic acids that bind to polypeptides in cells. A change in the interaction between a polypeptide and a natural binding partner can manifest itself as an increased or decreased probability that the interaction forms or an increased or decreased concentration of polypeptide/natural binding partner complex.

The term "contacting" as used herein refers to mixing a solution comprising the test compound with a liquid medium bathing the cells of the methods. The solution comprising the compound may also comprise another component, such as dimethyl sulfoxide (DMSO), which facilitates the uptake of the test compound or compounds into the cells of the methods. The solution comprising the test compound may be added to the medium bathing the cells by utilizing a delivery apparatus, such as a pipet-based device or syringe-based device.

Other aspects of the invention feature methods for identifying a substance that modulates polypeptide activity in a cell comprising the steps of: (a) expressing a polypeptide in a cell, wherein said polypeptide is selected from the group consisting of Tks 107, Tks 113, Tks 118 and Tks 202; (b) adding a test substance to said cell; and (c) monitoring a change in cell phenotype or the interaction between said polypeptide and a natural binding partner.

The term "expressing" as used herein refers to the production of polypeptide of the invention from a nucleic acid vector within a cell. The nucleic acid vector is transfected into cells using well known techniques in the art as described herein.

Another aspect of the invention provides methods for treating a disease by administering to a patient in need of such treatment a substance that modulates the activity of a polypeptide selected from the group consisting of Tks 107, Tks 113, Tks 118 and Tks 202. Preferably, the disease is selected from the group consisting of rheumatoid arthritis, artherosclerosis, autoimmune disorders, organ transplantation, myocardial infarction, cardiomyopathies, stroke, renal failure, oxidative stress-related neurodegenerative disorders and cancer.

Substances useful for treatment of disorders or diseases preferably show positive results in one or more in vitro assays for an activity corresponding to treatment of the disease or disorder in question. Substances that modulate the activity of the polypeptides preferably include, but are not limited to, antisense oligonucleotides and inhibitors of protein kinases.

The term "preventing" refers to decreasing the probability that an organism contracts or develops an abnormal condition.

The term "treating" refers to having a therapeutic effect and at least partially alleviating or abrogating an abnormal condition in the organism.

The term "therapeutic effect" refers to the inhibition or activation factors causing or contributing to the abnormal condition. A therapeutic effect relieves to some extent one or more of the symptoms of the abnormal condition. In reference to the treatment of abnormal conditions, a therapeutic effect can refer to one or more of the following: (a) an increase or decrease in the proliferation, growth, and/or differentiation of cells; (b) inhibition (i.e., slowing or stopping) or acceleration of cell death; (c) inhibition or acceleration of degeneration; (d) relieving to some extent one or more of the symptoms associated with the abnormal condition; and (e) enhancing the function of the affected population of cells. Compounds demonstrating efficacy against abnormal conditions can be identified as described herein.

The term "abnormal condition" refers to a function in the cells or tissues of an organism that deviates from their normal functions in that organism. An abnormal condition can relate to cell proliferation, cell differentiation or cell survival.

Abnormal cell proliferative conditions include cancers such as fibrotic and mesangial disorders, abnormal angiogenesis and vasculogenesis, wound healing, psoriasis, diabetes mellitus and inflammation.

Abnormal differentiation conditions include, but are not limited to, neurodegenerative disorders, slow wound healing rates and slow tissue grafting healing rates.

Abnormal cell survival conditions relate to conditions in which programmed cell death (apoptosis) pathways are activated or abrogated. A number of protein kinases are associated with the apoptosis pathways. Aberrations in the function of any one of the protein kinases could lead to cell immortality or premature cell death.

The term "aberration", in conjunction with the function of a kinase in a signal transduction process, refers to a kinase that is over- or under-expressed in an organism, mutated such that its catalytic activity is lower or higher than wild-type protein kinase activity, mutated such that it can no longer interact with a natural binding partner, is no longer modified by another protein kinase or protein phosphatase, or no longer interacts with a natural binding partner.

The term "administering" relates to a method of incorporating a compound into cells or tissues of an organism. The abnormal condition can be prevented or treated when the cells or tissues of the organism exist within the organism or outside of the organism. Cells existing outside the organism can be maintained or grown in cell culture dishes. For cells harbored within the organism, many techniques exist in the art to administer compounds, including (but not limited to) oral, parenteral, dermal, injection, and aerosol applications. For cells outside of the organism, multiple techniques exist in the art to administer the compounds, including (but not limited to) cell microinjection techniques, transformation techniques and carrier techniques.

The abnormal condition can also be prevented or treated by administering a compound to a group of cells having an aberration in a signal transduction pathway to an organism. The effect of administering a compound on organism function can then be monitored. The organism is preferably a mouse, rat, rabbit, guinea pig or goat, more preferably a monkey or ape, and most preferably a human.

Another aspect of the invention features methods for detection of a polypeptide (or nucleic acid that encodes a polypeptide) in a sample as a diagnostic tool for diseases or disorders, wherein the method comprises the steps of: (a) contacting the sample with a nucleic acid probe which hybridizes under hybridization assay conditions to a nucleic acid target region of a polypeptide selected from the group consisting of Tks 107, Tks 113, Tks 118 and Tks 202, said probe comprising the nucleic acid sequence encoding the polypeptide, fragments thereof, and the complements of the sequences and fragments; and (b) detecting the presence or amount of the probe:target region hybrid as an indication of the disease.

In preferred embodiments of the invention, the diseases or disorders are selected from the group consisting of rheumatoid arthritis, artherosclerosis, autoimmune disorders, organ transplantation, myocardial infarction, cardiomyopathies, stroke, renal failure, oxidative stress-related neurodegenerative disorders and cancer.

Hybridization conditions should be such that hybridization occurs only with the genes in the presence of other nucleic acid molecules. Under stringent hybridization conditions only highly complementary nucleic acid sequences hybridize. Preferably, such conditions prevent hybridization of nucleic acids having 1 or 2 mismatches out of 20 contiguous nucleotides. Such conditions are defined supra.

The diseases for which detection of genes in a sample could be diagnostic include diseases in which nucleic acid (DNA and/or RNA) is amplified in comparison to normal cells. By "amplification" is meant increased numbers of DNA or RNA in a cell compared with normal cells.

"Amplification" as it refers to RNA can be an increase in nucleic acid to indicate a detectable presence of RNA in cells, since in some normal cells there is no basal expression of RNA. In other normal cells, a basal level of expression exists, therefore in these cases amplification is an increase in nucleic acid to indicate an increase in detectable presence of at least 1–2-fold, and preferably more, compared to the basal level.

Diseases that could be diagnosed by detection of nucleic acid in a sample preferably include cancers. The test samples suitable for nucleic acid probing methods of the present invention include, for example, cells or nucleic acid extracts of cells, or biological fluids. The samples used in the above-described methods will vary based on the assay format, the detection method and the nature of the tissues, cells or extracts to be assayed. Methods for preparing nucleic acid extracts of cells are well known in the art and can be readily adapted in order to obtain a sample that is compatible with the method utilized.

Finally, the invention is drawn to transgenic animals and gene therapy using tks 107, tks 113, tks 118 and tks 202.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

The summary of the invention described above is not limiting and other features and advantages of the invention will be apparent from the following detailed description of the invention, and from the claims.

BRIEF DESCRIPTION OF THE FIGURES

FIG. 1 shows the nucleotide sequence for tks 107 (SEQ ID NO:1);

FIG. 2 shows the nucleotide sequence for tks 113 (SEQ. ID NO:2);

FIG. 3 shows the nucleotide sequence for tks 118 (SEQ ID NO:3);

FIG. 4 shows the nucleotide sequence for tks 202 (SEQ ID NO:4);

FIG. 5 shows the purported translated amino acid sequence for tks 107 (SEQ ID NO:5);

FIG. 6 shows the purported translated amino acid sequence for tks 113 (SEQ ID NO:6);

FIG. 7 shows the purported translated amino acid sequence for tks 118 (SEQ ID NO:7);

FIG. 8 shows the purported translated amino acid sequence for tks 202 (SEQ ID NO:8);

FIG. 9 (SEQ ID NOS 39–44, respectively, in order of appearance) shows a Hidden Markov Model (HMM) alignment of the dbl homology (DH) domains of dbl, cdc24, vav, tiam, fgdl and Grub; the bars above the sequence represent important α-helices as predicted from crystal structure of the DH/PH domain of h-sos (H1–H8) or conserved regions (CR1–CR3); the few well conserved amino acids are shaded (Soisson, S., et al. (1988) Cell 95:259–268);

FIG. 10 (SEQ ID NOS 45–48, respectively, in order of appearance) shows a Hidden Markov Model (HMM) alignment of the Grub Pleckstrin Homology (PH) domain with the PH domains of dbl, tiam, and fgdl; the shaded amino acids represent the few well conserved amino acids found in PH domains (Shaw, G. (1996) BioEssays 18:35–46);

FIG. 14 shows expression of Tks113 in various tissues; a 1.5 kb EcoRI fragment from Tks113 was used to probe Multiple Tissue Northerns (Clontech);

FIG. 16 (SEQ ID NOS 49–52, respectively, in order of appearance) shows amino acid sequence alignment (MegAlign using the J. Hein method) of Tks 118 with mSH3P7, Drebrin E and the SH3 domain of Src;

FIG. 21 (SEQ ID NOS 53–55, respectively, in order of appearance) shows Alignment of the C-terminal of Tks 202 with c-mel and rab8 (MegAlign using Clustal method);

FIG. 22 shows Expression of Tks202 in various tissues; the 5' 500 b.p. of the original Tks202 clone was used to probe Multiple Tissue Northerns (Clontech);

FIGS. 23A–23D (SEQ ID NOS. 19–23, respectively, in order of appearance) show translations in 5 other reading frames for Grub;

FIG. 24 (SEQ ID NOS 24–28, respectively, in order of appearance) shows translation in 5 other reading frames for Tks 113;

FIG. 25 (SEQ ID NOS 29–33, respectively, in order of appearance) shows translation in 5 other reading frames for Tks 118; and FIGS. 26A–26B (SEQ ID NOS. 34–38, respectively, in order of appearance) show translation in 5 other reading frames for Tks 202.

DETAILED DESCRIPTION OF THE INVENTION

Figure 11:
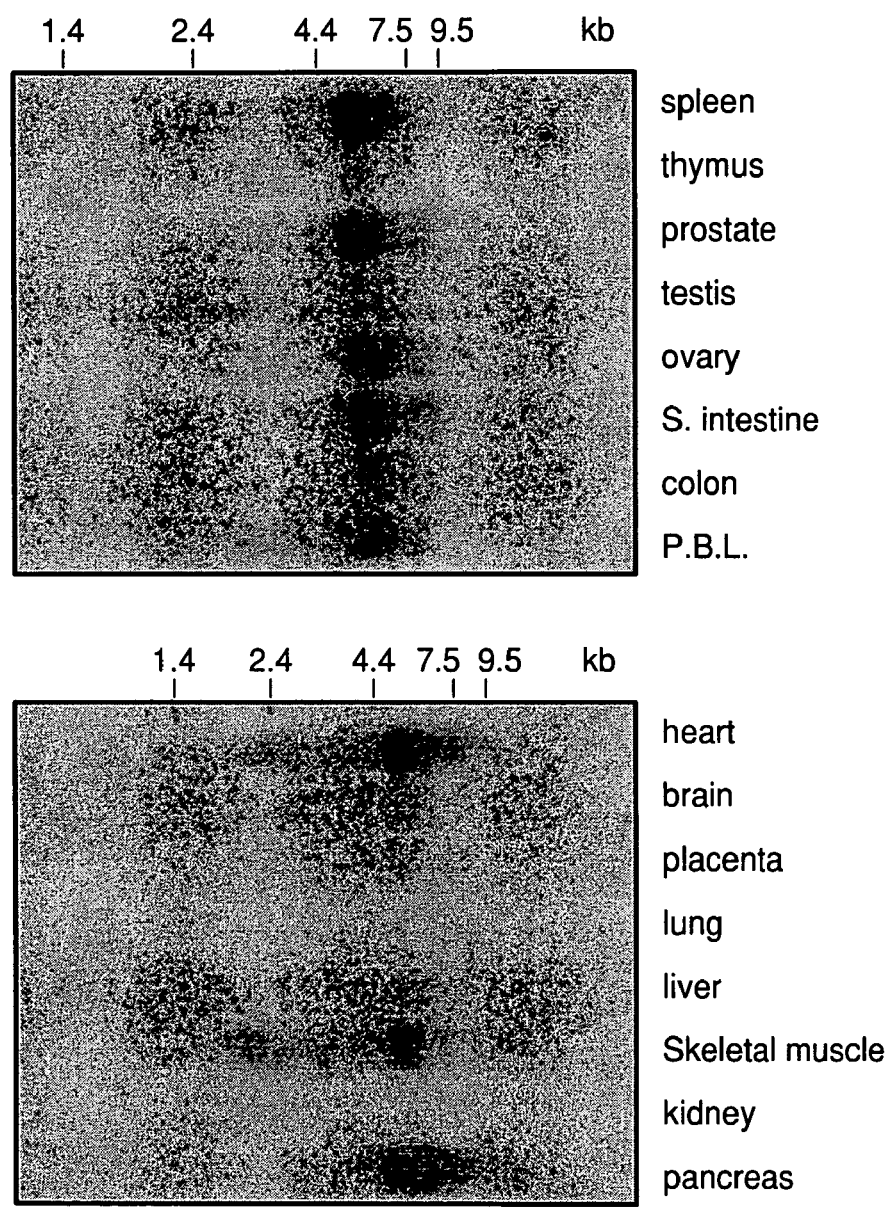
FIG. 11 shows expression of Grub in various tissues, where the original Tks 107 clone was used to probe Multiple Tissue Northern Blots.

The present invention relates in part to the polypeptides, nucleic acids encoding such polypeptides, cells containing such nucleic acids, antibodies to such polypeptides, assays utilizing such polypeptides, and methods relating to all of the foregoing with respect to the novel substrates of the invention, Tks 107, Tks 113, Tks 118 and Tks 202. The polypeptides and nucleic acids may be produced using well-known and standard synthesis techniques when given the sequences presented herein. The examples below demonstrate the isolation and characterization of the proteins tks 107/Grub, tks 113, tks 118/Dresh and tks 202 (tyrosine kinase substrate).

Protein tyrosine kinases comprise a large superfamily of related proteins that function to transduce signals from the extracellular environment to the interior of the cell. These signals direct all aspects of cellular functions, including growth, differentiation, and death. For any particular kinase, identification of the relevant substrates is an important step in elucidation of its function.

We set out to identify novel substrates of the cytoplasmic tyrosine kinase Src. We employed a screening strategy based on the in vitro phosphorylation of lambda expression libraries immobilized on nitrocellulose filters by Src containing Sf9 lysates (Lock, P. et. al. EMBO J. 17(15):4346–4357, 1998). Lambda clones encoding 4 Src substrates were identified in this manner, tks 107, 113, 118 and tks 202.

I. The Nucleic Acids of the Invention

Included within the scope of this invention are the functional equivalents of the herein-described isolated nucleic acid molecules. The degeneracy of the genetic code permits substitution of certain codons by other codons that specify the same amino acid and hence would give rise to the same protein. The nucleic acid sequence can vary substantially since, with the exception of methionine and tryptophan, the known amino acids can be coded for by more than one codon. Thus, portions or all of the genes of the invention could be synthesized to give a nucleic acid sequence significantly different from that shown in SEQ ID NO:1, SEQ ID NO:2, SEQ ID NO:3 and SEQ ID NO:4. The encoded amino acid sequence thereof would, however, be preserved.

In addition, the nucleic acid sequence may comprise a nucleotide sequence which results from the addition, deletion or substitution of at least one nucleotide to the 5'-end and/or the 3'-end of the nucleic acid formula shown in SEQ ID NO:1, SEQ ID NO:2, SEQ ID NO:3 or SEQ ID NO:4, or a derivative thereof. Any nucleotide or polynucleotide may be used in this regard, provided that its addition, deletion or substitution does not alter the amino acid sequence of SEQ ID NO:5, SEQ ID NO:6, SEQ ID NO:7 or SEQ ID NO:8, which is encoded by the nucleotide sequence. For example, the present invention is intended to include any nucleic acid sequence resulting from the addition of ATG as an initiation codon at the 5'-end of the inventive nucleic acid sequence or its derivative, or from the addition of ITA, TAG or TGA as a termination codon at the 3'-end of the inventive nucleotide sequence or its derivative. Moreover, the nucleic acid molecule of the present invention may, as necessary, have restriction endonuclease recognition sites added to its 5'-end and/or 3'-end.

Such functional alterations of a given nucleic acid sequence afford an opportunity to promote secretion and/or processing of heterologous proteins encoded by foreign nucleic acid sequences fused thereto. All variations of the nucleotide sequence of the genes of the invention and fragments thereof permitted by the genetic code are, therefore, included in this invention.

Further, it is possible to delete codons or to substitute one or more codons with codons other than degenerate codons to produce a structurally modified polypeptide, but one which has substantially the same utility or activity as the polypeptide produced by the unmodified nucleic acid molecule. As recognized in the art, the two polypeptides are functionally equivalent, as are the two nucleic acid molecules that give rise to their production, even though the differences between the nucleic acid molecules are not related to the degeneracy of the genetic code.

To isolate the Src substrates of the invention, a screening strategy based on the in vitro phosphorylation of lambda expression libraries immobilized on nitrocellulose filters by Src containing Sf9 lysates was employed to isolate Src substrates, as in Lock, P. et. al. EMBO J. 17(15):4346–4357, 1998, which is incorporated in its entirety, including any drawings. Lambda clones encoding 4 Src substrates were identified in this manner, tks 107, 113, 118 and tks 202.

Tks 107 (Grub)

The lambda clone tks 107 was isolated from a λZap cDNA library constructed with cDNA from the human lung tumor cell line NCI-H460. The DNA fragment encoding tks 107 was used to isolate various overlapping clones of tks 107 from the same library. One of these clones (tks 107-4) contains a large open reading frame (ORF) with an in frame stop codon upstream of a putative initiating methionine. This ORF is predicted to encode a protein of 1511 amino acids and has been renamed Grub. Computer searches of public sequence data bases with this sequence as a query revealed that this ORF contains a dbl homology domain (DH) followed by a pleckstrin homology domain (PH) in its C-terminus.

The dbl homology domain (DH domain) is a region of approximately 250 amino acids intially found in Dbl and the Cdc24 protein. Subsequently, a growing list (>20) of proteins have been found to contain DH domains. DH domains of different proteins share about 30% amino acid identity to each other. Proteins containing DH domains have been shown to act as Guanine Exchange Factors (GEF's) for the Rho members of small GTPases. Many DH containing proteins exhibit cellular transformation activity upon N-terminal truncation (where the DH domain is left unmutated). (Reviewed in Quilliam, L. A., et. al. BioEssays, 17:395–404, 1995. Whitehead, I. P., et. al., Biochimica et Biophysica Acta, 1332:F1–F23, 1997. Cerione, R. A. and Zheng, Y. Curr. Opin. Cell Biol. 8:216–222, 1996). Recently, the 3 dimensional structure of the DH domain of human Sos was elucidated (Soisson, S. M., et. al., Cell, 95:259–268). It was shown to be composed of α-helixes, several of which correspond well to previously defined conserved regions (CR) of DH domains (Whitehead, I. P., et. al., Biochimica et Biophysica Acta, 1332:F1–F23, 1997, and figure Grub GEF align). A hidden Markov model (HMM) for DH domain was built using HMMER (http://hmmer.wustl.edu). Input to HMMER was a multiple-sequence alignment generated by CLUSTALW (Thmpson, J D, Higgins D G, Gibson, T J, Nucleic Acid Research, 1994). Secondary structural information from (Soisson, S. M., et. al., Cell, 95: 259–268) was incorporated into CLUSTALW alignment. The amino acid region from 1083–1257 of Seq I.D. NO: 5 (Tks107/Grub) aligned well with this Hidden Markov Model, exhibiting both conserved α-helical motifs as well as conserved amino acid residues (Grub GEF align figure).

In addition, two EST's (AA778210 and AA829341) were found which overlapped the 3' sequence of tks 107-4 and extended the 3' untranslated sequence to the poly-adenylation tail. The sequence compiled from tks 107, tks 107-4 and the two EST's is shown in SEQ ID NO:1 and was renamed Grub. Proposed relevant features of this sequence include:

| nucleotide(s) | Comments |
|---|---|
| 155–1778 | sequence of original tks 107 |
| 1–5107 | sequence of tks 107-4 |
| 208–4764 | putative coding region of Grub |
| 3454–3978 | Dbl homology domain |
| 4000–4323 | Pleckstrin homology domain |
| 4164–5335 | EST AA778210 |
| ?–5332 | EST AA829341 (5' limit is unknown) |
| 5305–5315 | Not present in AA829341 |
| 4897 | T instead of G in the EST's |
| 5005 | T instead of G in the EST's |
| 5010 | T instead of G in the EST's |
| 5072 | T instead of C in the EST's |
| 5103 | T instead of C in the EST's |

The tandem array of DH/PH domains in the C-terminus of Grub is a hallmark of the Dbl family of proteins. Many members of this family exhibit cellular transformation activity upon N-terminal truncations. Cellular transformation requires that the DH/PH modules be intact. The DH/PH modules of many Dbl family proteins have been shown to regulate the activity of various Rho sub-family small GTPases by serving as Guanine Exchange Factors (GEF). Many Rho family GTPases have been shown to regulate the assembly of actin structures and may also regulate gene transcription through activation of various kinase pathways such as Jnk (Hall, A. Science, 279:509–514, 1998).

Grub mRNA is expressed in all human tissues examined, with particularly high expression in the pancreas and spleen. The expression level of Grub was determined for 60 tumor cell lines and was found to be significantly elevated in 13 (~21%) cell lines and may be slightly elevated in 10 or more cell lines. Deletion analyses show that Grub is phosphorylated on the N-terminus by Src when both are co-expressed in 293 cells. Recombinant Grub expressed in 293 cells migrates with an apparent Mr of ~190,000. Although this is larger than its predicted Mr of 164,701 (based on the primary amino acid sequence), it is often difficult to accurately determine Mr for proteins in this size range and it is unknown whether Grub contains any post-translational modifications that may alter its Mr.

NIH 3T3 clones stably expressing full length, N-terminus or C-terminus of Grub have been generated. These clones do not show enhanced growth rates, exhibit growth in soft agar, nor demonstrate altered morphologies (data not shown). However co-expression of the N or C terminus of Grub in 293 cells with HA-JNK activate Jnk activity 4–6× over that of vector alone. Co-expression of wild type Grub with HA-Jnk stimulates Jnk activity about 2.5×, despite the fact that wild type Grub is expressed at a level much lower (approximately 1/10) than either the N or C terminus of Grub. In contrast, excessive overexpression of another heterologous protein (SH3P7ΔSH3) only activates Jnk expression weakly. These data suggest that the C-term of Grub can activate Jnk activity possibly by acting as a guanine exchange factor for an unknown Rho family GTPase. It is interesting to note that the DH/PH or DH domain of Grub by themselves do not activate Jnk activity strongly. This is consistent with anecdotal evidence that the DH domains of some dbl family members require flanking region to exhibit full activity (perhaps due to additional structural stability conferred by the flanking sequences). The N-term is also capable of activating Jnk. While the mechanism by which the N-term activates Jnk is currently unknown, it is possible that the N-term contain domain or domains with enzymatic (i.e. a cryptic GEF activity) or binding activities toward proteins capable of activating Jnk.

To further our understanding of possible Grub function, the N-terminus of Grub was used as bait in a yeast 2-hybrid screen in order to isolate Grub interacting proteins. Approximately $1.8 \times 10^6$ transformants of a Hela cDNA library were isolated. 6 independent cDNA's encoding the protein snapin and 2 independent cDNA's encoding the human homologue of the rat RACK1 were isolated in this assay.

Snapin is a small neuron specific protein, localized on synaptic vesicles which serves as a bridge between the SNARE complex and synaptotagmin (Ilardi, J., et. al., Nature Neuro. 1999, 2:119–124). Synaptotagmin is the calcium sensor that triggers the final fusion of ynaptic vesicles with the plasma membrane. Small GTPases of the Rab subfamily of GTPases also play a role in efficient synaptic transport (Sudhof, T. C., Nature 1996, 375: 645–653). It is tempting to hypothesize that Grub could act as a GEF for these small GTPases. Alternatively, Grub may act in a more traditional manner as a GEF for a Rho family GTPase, but by binding to snapin, links vesicular transport to the actin cycle by regulating Rho family members.

RACK1 was initially cloned as an intracellular receptor for activated Protein Kinase C (Ron, D., et. al., P.N.A.S. 1994, 91:839–843). Since then, RACK1 has been shown to bind to a variety of signalling molecules, including Src, and may act as a molecular scaffold on which signalling complexes may assemble (Rodriguez MM, et al. Biochemistry. 1999 38: 13787–94. Liliental, J. and Chang, D. D. IBC 1998 273: 2379–2383. Chang, B., et al., MCB 1998 18:32453256.).

Tks 113

The lambda clone tks 113 was isolated from a λZap cDNA library constructed with cDNA from the human lung tumor cell line NCI-H460. Tks contains a 1430 nucleotide EcoRIXhoI fragment. This fragment encodes an ORF of 476 amino acids with no significant homologies to any publicly available sequence. However, tks 113 contains several PXXP motifs in a C terminal proline rich domain (26% prolines), suggesting that it may be a binding partner for signalling molecules with SH3 domains. Proteins serving as scaffolds, anchors or adaptors for signalling complexes often display multiple motifs (such as PXXP) for protein/protein interactions (Pawson, T. and Scott, J. D., Science 278: 2075–2080, 1997).

The sequence of Tks113 is shown in SEQ ID NO:2. The relevant features of this sequence include: Tks 113 mRNA is expressed in all human tissues examined and is most highly expressed in testis, heart and skeletal muscle. The apparent size of tks 113's mRNA in these experiments is approximately 2.4 kb. In addition, an antibody raised against the N-terminus of tks 113 identifies a protein of approximately 77 kDa in NIH 3T3 cells. Therefore, based on these data, tks 113 is unlikely to be a full length clone. Isolation of a full length clone is neccessary to allow generation of reagents such as expression constructs in order to elucidate the function of tks 113.

Tks 118

Tks 118 was isolated from a λZap cDNA library constructed with cDNA from the human lung tumor cell line NCI-H460. Tks 118 is a clone of 1532 nucleotides with a large ORF of 430 amino acids (starting at the putative initiating methionine). An independent clone (tks 109), indentical to the first 1115 nucleotides of tks 118, was also isolated in the same screen. Searches of the public data base with these sequences revealed that tks 118 is 86% identical to a previously cloned murine sequence SH3P7, suggesting that tks 118 is likely to be the human orthologue of mSH3P7 (Sparks, et. al., Nature Biotech. 14:741–744, 1996). Furthermore, the N-terminal 240 amino acids of tks 118 is 44% identical to the chicken protein, Drebrin. Drebrin has been reported to bind and alter actin structures (Shirao, T., J. Biochem., 117:231–236, 1995). In addition, hSH3P7 also contains an SH3 domain in the C-terminal 62 amino acids. The sequence of tks 118 is shown in SEQ ID NO:3. The relevant features of this sequence include:

| nucleotides | comments |
| --- | --- |
| 1–1535 | Tks118 sequence |
| 1–1115 | tks 109 sequence |
| 26–1319 | Tks 118 coding sequence |
| 1–720 | Drebrin homology domain |
| 1130–1319 | SH3 domain |
| 966 | T instead of C in tks 109 |
| 969 | T instead of C in tks 109 |
| 1023 | T instead of C in tks 109 |

Tks118 mRNA is expressed in all tissues examined, with highest expression in spleen, thymus, prostate and peripheral blood leukocytes. Tks118 mRNA is overexpressed in >40% of tumor cell lines tested. Tks118 is phosphorylated by Src upon co-expression in 293 cells. Overexpression of Tks118 in NIH 3T3 and Src transformed NIH 3T3 cells leads to localization at actin like structures. Noteably, Tks118 localizes to podosomes in Src transformed cells. This localization depends on the Drebrin homology domain and is consistent with previous reports that Drebrin binds and alter actin structures. Recently, it has been shown that m-SH3P7 is tyrosine phosphorylated in antigen receptor stimulated lymphocytes and co-localizes with actin structures in NIH 3T3 cells (Larbolette, O., MCB. 19:1539–1546, 1999).

Presently, we will determine if Tks118 binds and/or affect actin structures in vitro and in vivo. Overexpression of various Tks118 constructs in cell lines will be carried out to determine Tks118's effects on cell growth, transformation, and motility.

Tks 202

The lambda clone tks 202 was isolated from a λZap cDNA library constructed with cDNA from the human colon tumor cell line Colo 205 (Stratagene). The DNA sequence encoding tks 202 was used to query public data bases to uncover any informative homologies. This search revealed that the 3' end of tks 202 encodes an amino acid sequence homologous to proteins of the small GTPase family. In addition, 2 EST's (AA470519 and r78655) were also found that overlapped with the 3' sequence of tks 202. Sequences from these ESTs were used to extend the tks 202 sequence to the poly-adenylation site. A 5' ~500 nucleotide RI/XbaI fragment from Tks 202 was used to probe a Trip;Ex Prostate library (Clontech) to isolate additional Tks 202 clones. One of these clones, Tks 202-17 extended the 5' sequence by 933 nucleotides. An additional 370 nucleotides of 5' sequences was obtained by a modification of 5' RACE as described below. This 5' RACE product revealed a stop codon at nucleotide 170, 5' of a putative starting methionine at nucleotide 647. The sequence compiled from Tks202, Tks202-17, the two EST's, and the 5' RACE product is shown in SEQ ID NO:4. The relevant features of this sequence include:

| nucleotides | Comments |
| --- | --- |
| 1305–3155 | Tks202 |
| 371–1798 | Tks202-17 |
| 647–2866 | Putative Tks202 coding region |
| 2258–2866 | GTPase domain |
| 1–532 5' | RACE product |
| 1788–3155 | EST AA470519 |
| 2544–3155 | EST r78655 |

DNA fragments of tks 202 were used to probe multiple tissue northern blots (Clontech). This revealed that the endogeneous tks 202 mRNA is approximately 5 kb and is expressed at very low or undetectable levels in most tissues tested with the exception of prostate and pancreas.

Small GTPases represent a large family of proteins that act as molecular switches that control diverse biological functions, including cell proliferation and differentiation, cytoskeletal organization, protein transport, cell cycle and free radical production (Bourne, H. R. et. al., Nature, 348 (6297):125–32, 1990. Bourne, H. R. et. al., Nature, 349 (6305):117–27, 1991). That GTPases modulate these central cellular pathways suggest that both GTPases and their regulators are of critical importance.

Small GTPases are typically about 200 amino acids, almost all of which is folded into a single GTPase domain. As such, tks 202 is unusual in that it contains a significant extension N-terminal to its GTPase domain. One could speculate that the presence of this extension may implicate tks 202 (and as yet undiscovered GTPases of similar structures) in cellular roles previously unsuspected for GTPases or may represent a novel mechanism for regulating GTPase activity.

II. Nucleic Acid Probes, Methods, and Kits for Detection of the Proteins of the Invention.

A nucleic acid probe of the present invention may be used to probe an appropriate chromosomal or cDNA library by usual hybridization methods to obtain other nucleic acid molecules of the present invention. A chromosomal DNA or cDNA library may be prepared from appropriate cells according to recognized methods in the art (cf. "Molecular Cloning: A Laboratory Manual", second edition, Cold Spring Harbor Laboratory, Sambrook, Fritsch, & Maniatis, eds., 1989).

In the alternative, chemical synthesis can be carried out in order to obtain nucleic acid probes having nucleotide sequences which correspond to N-terminal and C-terminal portions of the amino acid sequence of the polypeptide of interest. The synthesized nucleic acid probes may be used as primers in a polymerase chain reaction (PCR) carried out in accordance with recognized PCR techniques, essentially according to PCR Protocols, "A Guide to Methods and Applications", Academic Press, Michael, et al., eds., 1990, utilizing the appropriate chromosomal or cDNA library to obtain the fragment of the present invention.

One skilled in the art can readily design such probes based on the sequence disclosed herein using methods of computer alignment and sequence analysis known in the art ("Molecular Cloning: A Laboratory Manual", 1989, supra). The hybridization probes of the present invention can be labeled by standard labeling techniques such as with a radiolabel, enzyme label, fluorescent label, biotin-avidin label, chemiluminescence, and the like. After hybridization, the probes may be visualized using known methods.

The nucleic acid probes of the present invention include RNA, as well as DNA probes, such probes being generated using techniques known in the art. The nucleic acid probe may be immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling nucleic acid probes to such solid supports are well known in the art.

The test samples suitable for nucleic acid probing methods of the present invention include, for example, cells or nucleic acid extracts of cells, or biological fluids. The samples used in the above-described methods will vary based on the assay format, the detection method and the nature of the tissues, cells or extracts to be assayed. Methods for preparing nucleic acid extracts of cells are well known in the art and can be readily adapted in order to obtain a sample which is compatible with the method utilized.

One method of detecting the presence of nucleic acids of the invention in a sample comprises (a) contacting said sample with the above-described nucleic acid probe under conditions such that hybridization occurs and (b) detecting the presence of said probe bound to said nucleic acid molecule. One skilled in the art would select the nucleic acid probe according to techniques known in the art as described above. Samples to be tested include but should not be limited to RNA samples of human tissue.

A kit for detecting the presence of nucleic acids of the invention in a sample comprises at least one container means having disposed therein the above-described nucleic acid probe. The kit may further comprise other containers comprising one or more of the following: wash reagents and reagents capable of detecting the presence of bound nucleic acid probe. Examples of detection reagents include, but are not limited to radiolabelled probes, enzymatic labeled probes (horseradish peroxidase, alkaline phosphatase), and affinity labeled probes (biotin, avidin, or steptavidin).

In detail, a compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (such as phosphate buffered saline, Tris-buffers, and the like), and containers which contain the reagents used to detect the hybridized probe, bound antibody, amplified product, or the like. One skilled in the art will readily recognize that the nucleic acid probes described in the present invention can readily be incorporated into one of the established kit formats which are well known in the art.

III. DNA Constructs Comprising a Tks 107, Tks 113, Tks 118 and Tks 202 Related Nucleic Acid Molecule and Cells Containing these Constructs.

The present invention also relates to a recombinant DNA molecule comprising, 5' to 3', a promoter effective to initiate transcription in a host cell and the above-described nucleic acid molecules. In addition, the present invention relates to a recombinant DNA molecule comprising a vector and an above-described nucleic acid molecule. The present invention also relates to a nucleic acid molecule comprising a transcriptional region functional in a cell, a sequence complementary to an RNA sequence encoding an amino acid sequence corresponding to the above-described polypeptide, and a transcriptional termination region functional in said cell. The above-described molecules may be isolated and/or purified DNA molecules.

The present invention also relates to a cell or organism that contains an above-described nucleic acid molecule and thereby is capable of expressing a polypeptide. The polypeptide may be purified from cells which have been altered to express the polypeptide. A cell is said to be "altered to express a desired polypeptide" when the cell, through genetic manipulation, is made to produce a protein which it normally does not produce or which the cell normally produces at lower levels. One skilled in the art can readily adapt procedures for introducing and expressing either genomic, cDNA, or synthetic sequences into either eukaryotic or prokaryotic cells.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression may vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

If desired, the non-coding region 3' to the sequence encoding a polypeptide of the invention may be obtained by the above-described methods. This region may be retained for its transcriptional termination regulatory sequences, such as termination and polyadenylation. Thus, by retaining the 3'-region naturally contiguous to the DNA sequence encoding a polypeptide of the invention, the transcriptional termination signals may be provided. Where the transcriptional termination signals are not satisfactorily functional in the expression host cell, then a 3' region functional in the host cell may be substituted.

Two DNA sequences (such as a promoter region sequence and a sequence encoding a polypeptide of the invention) are said to be operably linked if the nature of the linkage between the two DNA sequences does not (1) result in the introduction of a frame-shift mutation, (2) interfere with the ability of the promoter region sequence to direct the transcription of a gene sequence encoding a polypeptide of the invention or (3) interfere with the ability of the gene sequence of a polypeptide of the invention to be transcribed by the promoter region sequence. Thus, a promoter region would be operably linked to a DNA sequence if the promoter were capable of effecting transcription of that DNA sequence. Thus, to express a gene encoding a polypeptide of the invention, transcriptional and translational signals recognized by an appropriate host are necessary.

The present invention encompasses the expression of a gene encoding a polypeptide of the invention (or a functional derivative thereof) in either prokaryotic or eukaryotic cells. Prokaryotic hosts are, generally, very efficient and convenient for the production of recombinant proteins and are, therefore, one type of preferred expression system for polypeptides of the invention. Prokaryotes most frequently are represented by various strains of *E. coli*. However, other microbial strains may also be used, including other bacterial strains.

In prokaryotic systems, plasmid vectors that contain replication sites and control sequences derived from a species compatible with the host may be used. Examples of suitable plasmid vectors may include pBR322, pUC118, pUC119 and the like; suitable phage or bacteriophage vectors may include γgt10, γgt11 and the like; and suitable virus vectors may include pMAM-neo, pKRC and the like. Preferably, the selected vector of the present invention has the capacity to replicate in the selected host cell.

Recognized prokaryotic hosts include bacteria such as *E. coli, Bacillus, Streptomyces, Pseudomonas, Salmonella, Serratia*, and the like. However, under such conditions, the polypeptide will not be glycosylated. The prokaryotic host must be compatible with the replicon and control sequences in the expression plasmid.

To express a polypeptide of the invention (or a functional derivative thereof) in a prokaryotic cell, it is necessary to operably link the sequence encoding the polypeptide of the invention to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene sequence of pBR322, and the cat promoter of the chloramphenicol acetyl transferase gene sequence of pPR325, and the like. Examples of inducible prokaryotic promoters include the major right and left promoters of bacteriophage λ ($P_L$ and $P_R$), the trp, recA, λacZ, λacI, and gal promoters of *E. coli*, the α-amylase (Ulmanen et al., J. Bacteriol. 162:176–182, 1985) and the ξ-28-specific promoters of *B. subtilis* (Gilman et al., Gene Sequence 32:11–20, 1984), the promoters of the bacteriophages of *Bacillus* (Gryczan, In: The Molecular Biology of the Bacilli, Academic Press, Inc., NY, 1982), and *Streptomyces* promoters (Ward et al., Mol. Gen. Genet. 203:468–478, 1986). Prokaryotic promoters are reviewed by Glick (Ind. Microbiot. 1:277–282, 1987), Cenatiempo (Biochimie 68:505–516, 1986), and Gottesman (Ann. Rev. Genet. 18:415–442, 1984).

Proper expression in a prokaryotic cell also requires the presence of a ribosome-binding site upstream of the gene sequence-encoding sequence. Such ribosome-binding sites are disclosed, for example, by Gold et al. (Ann. Rev. Microbiol. 35:365–404, 1981). The selection of control sequences, expression vectors, transformation methods, and the like, are dependent on the type of host cell used to express the gene. As used herein, "cell", "cell line", and "cell culture" may be used interchangeably and all such designations include progeny. Thus, the words "transformants" or "transformed cells" include the primary subject cell and cultures derived therefrom, without regard to the number of transfers. It is also understood that all progeny may not be precisely identical in DNA content, due to deliberate or inadvertent mutations. However, as defined, mutant progeny have the same functionality as that of the originally transformed cell.

Host cells which may be used in the expression systems of the present invention are not strictly limited, provided that they are suitable for use in the expression of the polypeptide of interest. Suitable hosts may often include eukaryotic cells. Preferred eukaryotic hosts include, for example, yeast, fungi, insect cells, mammalian cells either in vivo, or in tissue culture. Mammalian cells which may be useful as hosts include HeLa cells, cells of fibroblast origin such as VERO or CHO-K1, or cells of lymphoid origin and their derivatives. Preferred mammalian host cells include SP2/0 and J558L, as well as neuroblastoma cell lines such as IMR 332, which may provide better capacities for correct post-translational processing.

In addition, plant cells are also available as hosts, and control sequences compatible with plant cells are available, such as the cauliflower mosaic virus 35S and 19S, and nopaline synthase promoter and polyadenylation signal sequences. Another preferred host is an insect cell, for example the *Drosophila* larvae. Using insect cells as hosts, the *Drosophila* alcohol dehydrogenase promoter can be used (Rubin, Science 240:1453–1459, 1988). Alternatively, baculovirus vectors can be engineered to express large amounts of polypeptides of the invention in insect cells (Jasny, Science 238:1653, 1987; Miller et al., In: Genetic Engineering, Vol. 8, Plenum, Setlow et al., eds., pp. 277–297, 1986).

Any of a series of yeast expression systems can be utilized which incorporate promoter and termination elements from the actively expressed sequences coding for glycolytic enzymes that are produced in large quantities when yeast are grown in mediums rich in glucose. Known glycolytic gene sequences can also provide very efficient transcriptional control signals. Yeast provides substantial advantages in that it can also carry out post-translational modifications. A number of recombinant DNA strategies exist utilizing strong promoter sequences and high copy number plasmids which can be utilized for production of the desired proteins in yeast. Yeast recognizes leader sequences on cloned mammalian genes and secretes peptides bearing leader sequences (i.e., pre-peptides). Several possible vector systems are available for the expression of polypeptides of the invention in a mammalian host.

A wide variety of transcriptional and translational regulatory sequences may be employed, depending upon the nature of the host. The transcriptional and translational regulatory signals may be derived from viral sources, such as adenovirus, bovine papilloma virus, cytomegalovirus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

Expression of polypeptides of the invention in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., J. Mol. Appl. Gen. 1:273–288, 1982); the TK promoter of Herpes virus (McKnight, Cell 31:355–365, 1982); the SV40 early promoter (Benoist et al., Nature (London) 290:304–31, 1981); and the yeast gal4 gene sequence promoter (Johnston et al., Proc. Natl. Acad. Sci. (USA) 79:6971–6975, 1982; Silver et al., Proc. Natl. Acad. Sci. (USA) 81:5951–5955, 1984).

Translation of eukaryotic mRNA is initiated at the codon which encodes the first methionine. For this reason, it is preferable to ensure that the linkage between a eukaryotic promoter and a DNA sequence which encodes a polypeptide of the invention (or a functional derivative thereof) does not contain any intervening codons which are capable of encoding a methionine (i.e., AUG). The presence of such codons results either in the formation of a fusion protein (if the AUG codon is in the same reading frame as the polypeptide of the invention coding sequence) or a frame-shift mutation (if the AUG codon is not in the same reading frame as the polypeptide of the invention coding sequence).

A nucleic acid molecule encoding a polypeptide of the invention and an operably linked promoter may be introduced into a recipient prokaryotic or eukaryotic cell either as a nonreplicating DNA or RNA molecule, which may either be a linear molecule or, more preferably, a closed covalent circular molecule. Since such molecules are incapable of autonomous replication, the expression of the gene may occur through the transient expression of the introduced sequence. Alternatively, permanent expression may occur through the integration of the introduced DNA sequence into the host chromosome.

A vector may be employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of mRNA. These elements may include splice signals, as well as transcription promoters, enhancers, and termination signals. cDNA expression vectors incorporating such elements include those described by Qkayama (Mol. Cell. Biol. 3:280-, 1983).

The introduced nucleic acid molecule can be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids such as those capable of replication in *E. coli* (such as, for example, pBR322, ColEl, pSC101, pACYC 184, πVX; "Molecular Cloning: A Laboratory Manual", 1989, supra). *Bacillus* plasmids include pC194, pC221, pT127, and the like (Gryczan, In: The Molecular Biology of the Bacilli, Academic Press, NY, pp. 307–329, 1982). Suitable *Streptomyces* plasmids include plJ101 (Kendall et al., J. Bacteriol. 169: 4177–4183, 1987), and *streptomyces* bacteriophages such as φC31 (Chater et al., In: Sixth International Symposium on Actinomycetales Biology, Akademiai Kaido, Budapest, Hungary, pp. 45–54, 1986). *Pseudomonas* plasmids are reviewed by John et al. (Rev. Infect. Dis. 8:693–704, 1986), and Izaki (Jpn. J. Bacteriol. 33:729–742, 1978).

Preferred eukaryotic plasmids include, for example, BPV, vaccinia, SV40, 2-micron circle, and the like, or their derivatives. Such plasmids are well known in the art (Botstein et al., Miami Wntr. Symp. 19:265–274, 1982; Broach, In: "The Molecular Biology of the Yeast *Saccharomyces*: Life Cycle and Inheritance", Cold Spring Harbor Laboratory, Cold Spring Harbor, N.Y., p. 445–470, 1981; Broach, Cell 28:203–204, 1982; Bollon et al., J. Clin. Hematol. Oncol. 10:39–48, 1980; Maniatis, In: Cell Biology: A Comprehensive Treatise, Vol. 3, Gene Sequence Expression, Academic Press, NY, pp. 563–608, 1980).

Once the vector or nucleic acid molecule containing the construct(s) has been prepared for expression, the DNA construct(s) may be introduced into an appropriate host cell by any of a variety of suitable means, i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene(s) results in the production of a polypeptide of the invention, or fragments thereof. This can take place in the transformed cells as such, or following the induction of these cells to differentiate (for example, by administration of bromodeoxyuracil to neuroblastoma cells or the like). A variety of incubation conditions can be used to form the peptide of the present invention. The most preferred conditions are those which mimic physiological conditions.

IV. The Proteins of the Invention and their Expression Patterns

A variety of methodologies known in the art can be utilized to obtain the polypeptides of the present invention. The polypeptides may be purified from tissues or cells that naturally produce the polypeptides. Alternatively, the above-described isolated nucleic acid fragments could be used to express the polypeptides of the invention in any organism. The samples of the present invention include cells, protein extracts or membrane extracts of cells, or biological fluids. The samples will vary based on the assay format, the detection method, and the nature of the tissues, cells or extracts used as the sample.

Any eukaryotic organism can be used as a source for the polypeptides of the invention, as long as the source organism naturally contains such polypeptides. As used herein, "source organism" refers to the original organism from which the amino acid sequence of the subunit is derived, regardless of the organism the subunit is expressed in and ultimately isolated from.

One skilled in the art can readily follow known methods for isolating proteins in order to obtain the polypeptides free of natural contaminants. These include, but are not limited to: size-exclusion chromatography, HPLC, ion-exchange chromatography, and immuno-affinity chromatography.

Tks 107 (Grub)

The tandem array of DH/PH domains in the C-terminus of Grub is a hallmark of the Dbl family of proteins. Many members of this family exhibit cellular transformation activity upon N-terminal truncations. Cellular transformation requires that the DH/PH modules be intact.

Figure 12:
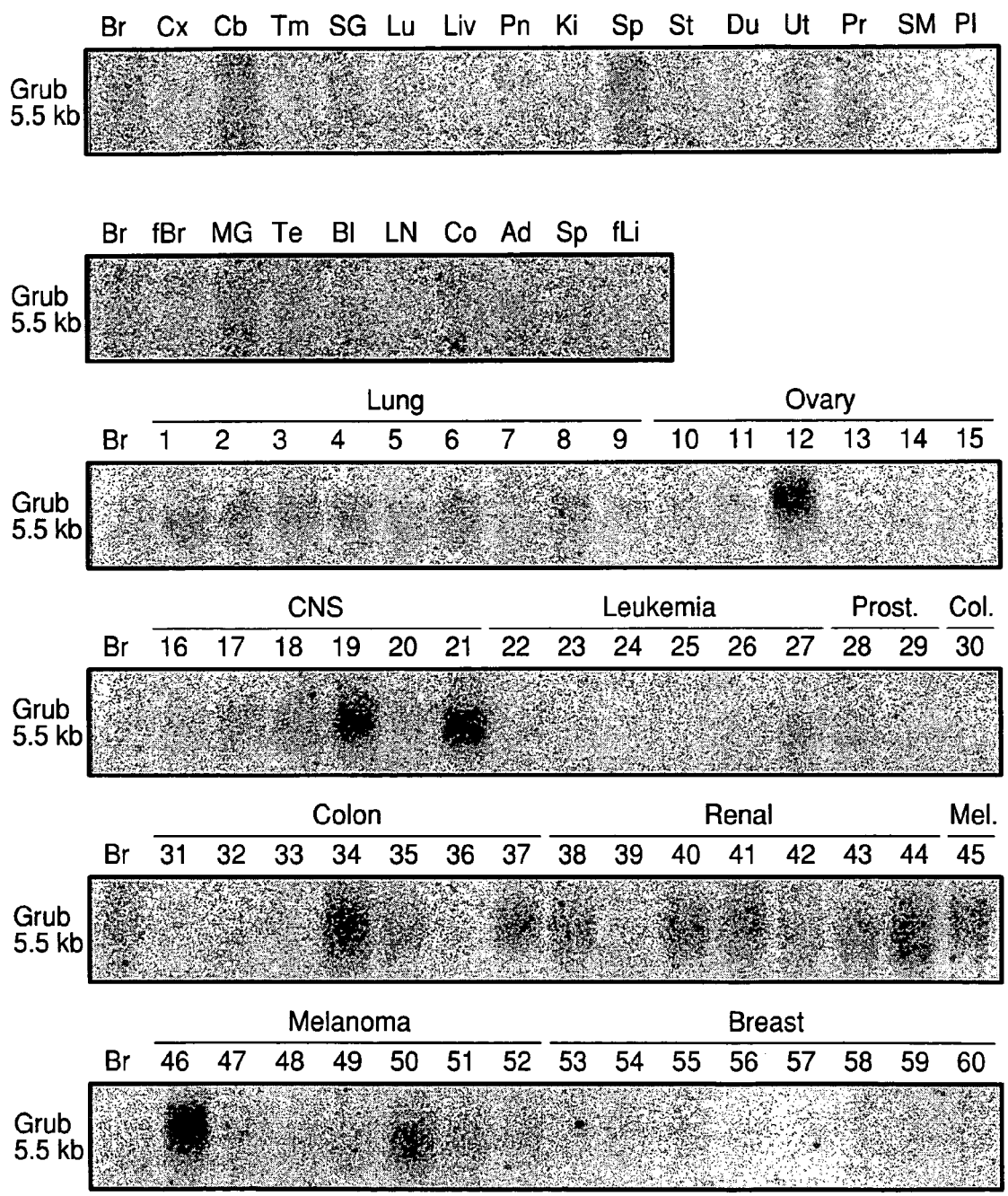
FIG. 12 shows Grub expression in normal tissues and NCI tumor cells, where the original Tks 107 clone was use to probe total RNA from various sources; the top 2 panels contain RNA from normal tissues and the remaining panels contain RNA from various tumor cell lines.
Figure 13:
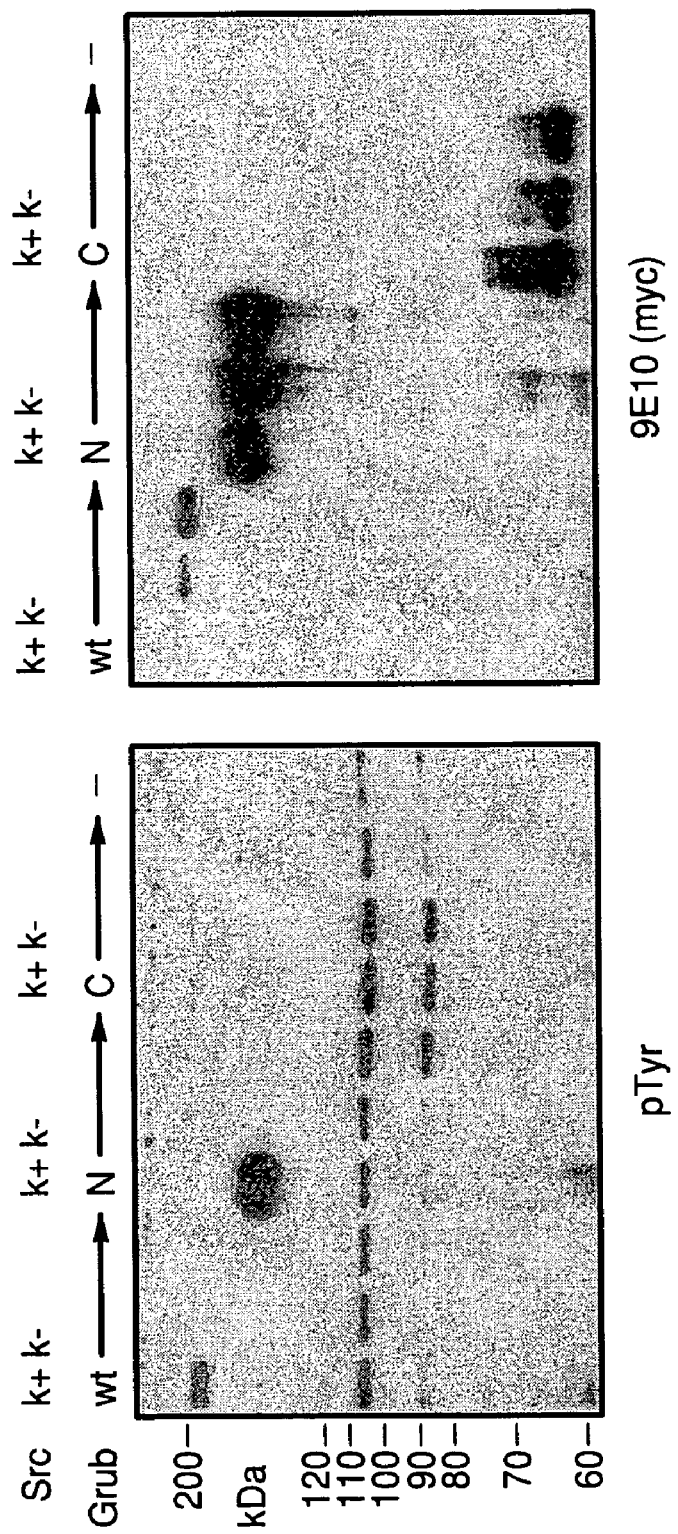
FIG. 13 shows coexpression of Grub with Src in 293 cells. Constructs expressing myc tagged, full length (wt), N-terminal (N), or C-terminal (C); of Grub were co-expressed in 293 cells with activated Src (k+), kinase dead Src (k−), or no Src; lysates were immunoprecipitated with α-myc antibodies (9E10) and western blotted with 9E10 or with α-phosphotyrosine antibodies (pTyr); only the full length or N terminal Grub is phosphorylated by activated Src; no phosphorylation is observed when C terminal Grub is co-expressed with activated Src or when any Grub constructs are co-expressed with kinase dead Src.

Grub mRNA is expressed in all human tissues examined, with particularly high expression in the pancreas and spleen (FIG. 11). The expression level of Grub was determined for 60 tumor cell lines and was found to be significantly elevated in 13 (~21%) cell lines and may be slightly elevated in 10 or more cell lines (FIG. 12). Deletion analyses show that Grub is phosphorylated on the N-terminus by Src when both are co-expressed in 293 cells (FIG. 13). Recombinant Grub expressed in 293 cells migrates with an apparent Mr of ~190,000 (FIG. 13). Although this is larger than its predicted Mr of 164,701 (based on the primary amino acid sequence), it is often difficult to accurately determine Mr for proteins in this size range and it is unknown whether Grub contains any post-translational modifications that may alter its Mr.

Characterization of the consequences of overexpression of normal and truncation mutants of Grub are underway, focusing particularly on whether they induce or reverse cellular transformation. Recombinantly expressed full length and truncated versions of Grub will be tested for their possible GEF activity toward various members of small GTPases. Stable clones will be isolated that express these recombinant proteins. They will be characterized for growth rate, DNA synthesis, cell-contact inhibition (foci formation), anchorage-independent growth (soft agar assays), and tumorigenicity in nude mice.

Tks 113

Figure 15:
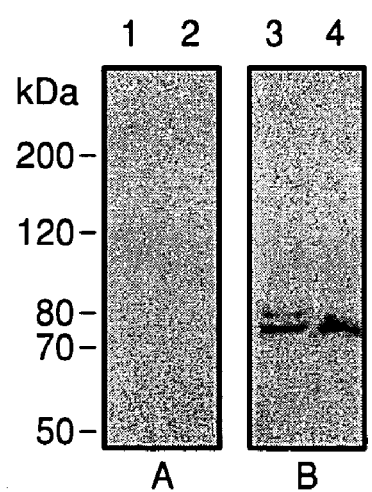
FIG. 15 shows Tks 113 specific antibodies. Lanes 1 and 3 contain cell lysates from NIH3T3 cells and lanes 2 and 4 contain cell lysates from NCI H460 cells; panel A was immunoblotted with rabbit preimmune serum; panel B was immunoblotted with serum from a rabbit immunized with Gst-Tks113.

Tks 113 mRNA is expressed in all human tissues examined and is most highly expressed in testis, heart and skeletal muscle (FIG. 14). The apparent size of tks 113's mRNA in these experiments is approximately 2.4 kb. In addition, an antibody raised against the N-terminus of tks 113 identifies a protein of approximately 77 kDa in NIH 3T3 cells. Based on these data, tks 113 is unlikely to be a full length clone (FIG. 15).

Tks 118

Figure 17:
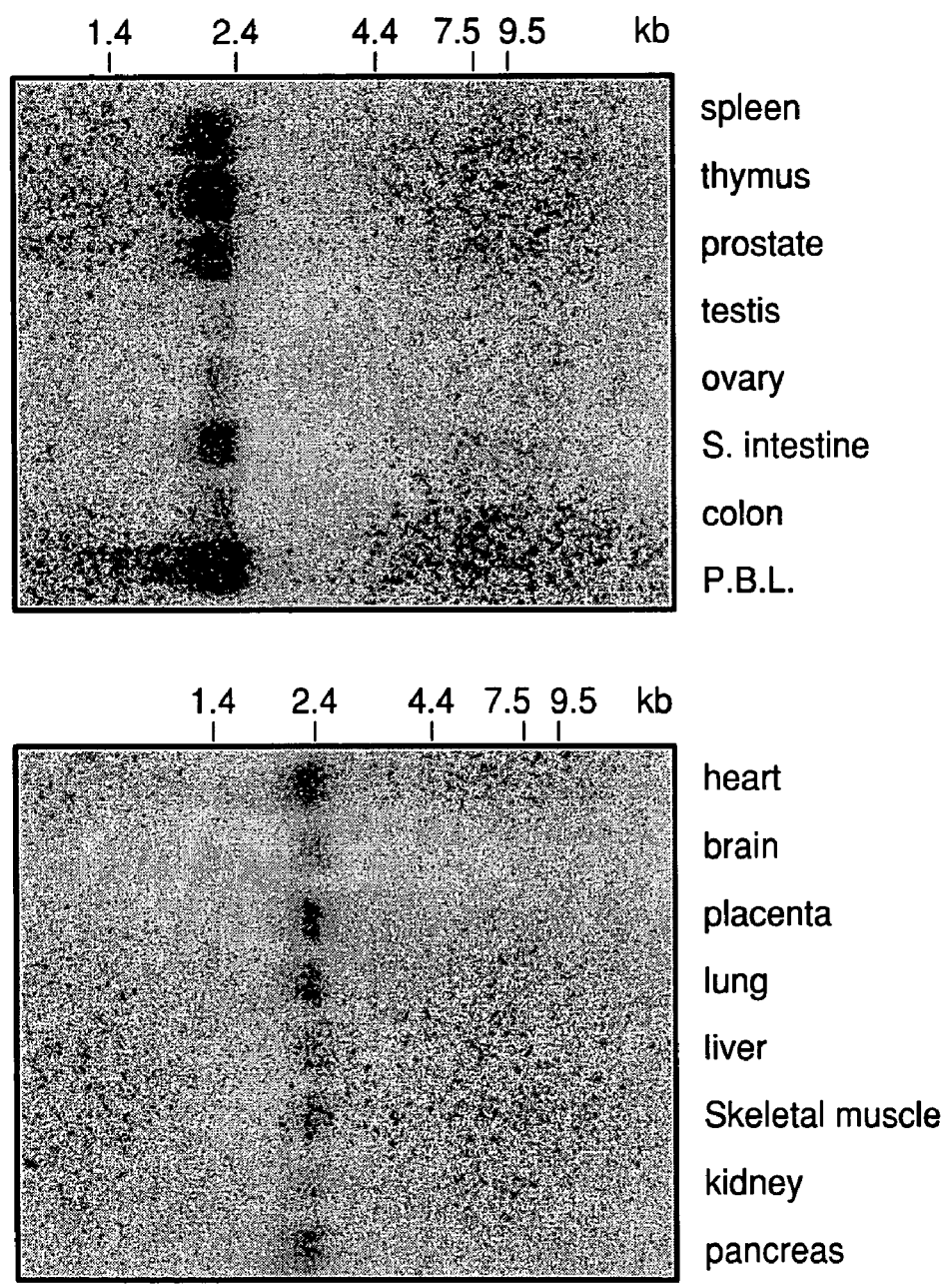
FIG. 17 shows expression of Tks118 in various tissues, where a 1.6 kb EcoRI/XhoI fragment from Tks118 was used to probe Multiple Tissue Northerns (Clontech)
Figure 18:
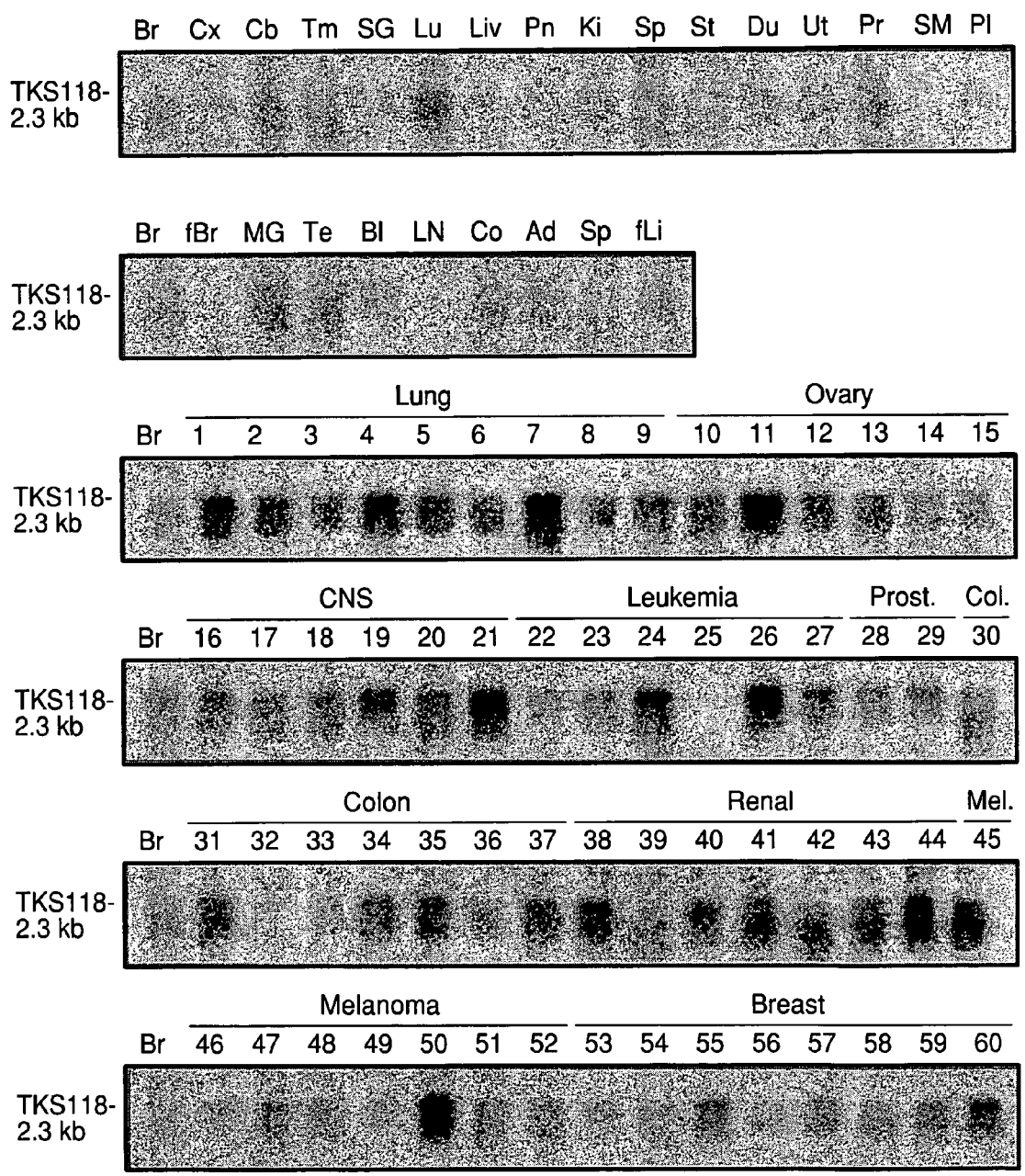
FIG. 18 shows Tks118 expression in normal tissues and NCI tumor cells; the original Tks118 clone was used to probe total RNA from various sources; the top 2 panels contain RNA from normal tissues; the remaining panels contain RNA from various tumor cell lines.
Figure 19:
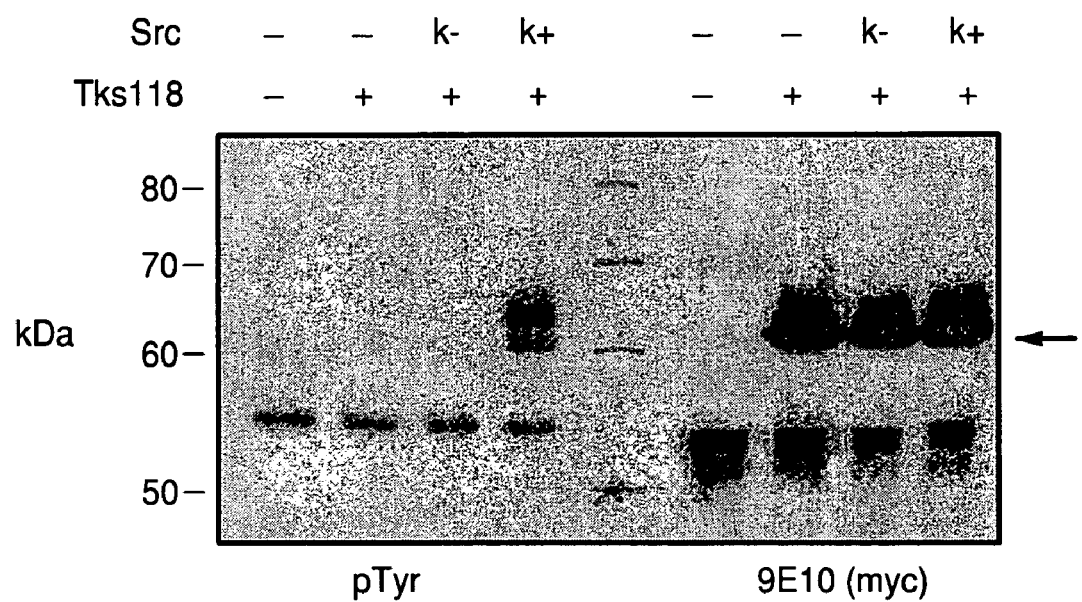
FIG. 19 shows coexpression of Tks118 with Src in 293 cells; constructs expressing myc tagged Tks119 was co-expressed in 293 cells with activated Src (k+), kinase dead Src (k−) or empty vector control (−); lysates were immunoprecipitated with a -myc antibodies (9E10) and western blotted with 9E10 or with α-phosphotyrosine antibodies; note that Tks118 is only phosphorylated when it is coexpressed with activated (but not kinase dead) Src.
Figure 20:
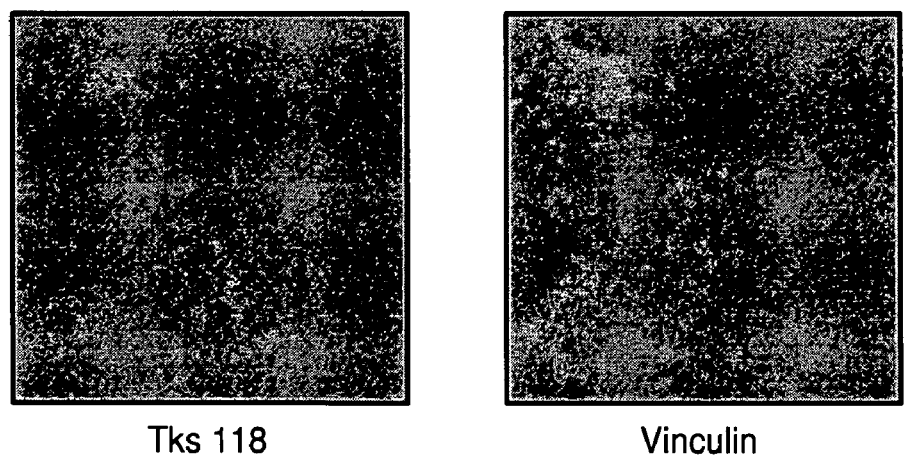
FIG. 20 shows co-staining of NIH3T3-Y527F cells with α-Tks118 (α-5033) and α-Vinculin (Upstate Biotechnology); the stain shows that Tks118 staining co-localizes with Vinculin, which stains the round podosomal structures at the ends of cell projections seen in these cells.

Tks mRNA is expressed in all tissues examined, with highest expression in spleen, thymus, prostate and peripheral blood leukocytes (FIG. 17). Tks 118 mRNA is overexpressed in >40% of tumor cell lines tested (FIG. 18). Tks 118 is phosphorylated by Src upon co-expression in 293 cells (FIG. 19). Overexpression of Tks 118 in NIH 3T3 and Src transformed NIH 3T3 cells leads to localization at actin like structures (FIG. 20). Noteably, Tks 118 localizes to podosomes in Src transformed cells (FIG. 20). This localization depends on the Drebrin homology domain and is consistent with previous reports that Drebrin binds and alter actin structures. Recently, it has been shown that m-SH3P7 is tyrosine phosphorylated in antigen receptor stimulated lymphocytes and co-localizes with actin structures in NIH 3T3 cells (Larbolette, O., MCB. 19:1539–1546, 1999).

Presently, we will determine if Tks 118 binds and/or affect actin structures in vitro and in vivo. Overexpression of various Tks 118 constructs in cell lines will be carried out to determine Tks 118 effects on cell growth, transformation and motility.

Tks 202

DNA fragments of tKs 202 were used to probe multiple tissue northern blots (Clontech). This revealed that the endogeneous tks 202 mRNA is approximately 5 kb and is expressed at very low or undetectable levels in most tissues tested with the exception of prostate and pancreas (FIG. 22).

Small GTPases are typically about 200 amino acids, almost all of which is folded into a single GTPase domain. As such, tks 202 is unusual in that it contains a significant extension N-terminal to its GTPase domain. One could speculate that the presence of this extension may implicate Tks 202 (and as yet undiscovered GTPases of similar structures) in cellular roles previously unsuspected for GTPases or may represent a novel mechanism for regulating GTPase activity.

V. Antibodies, Hybridomas, Methods of Use and Kits for Detection of Tks 107, Tks 113, Tks 118 or Tks 202

The present invention also relates to an antibody having specific binding affinity to a full or partial polypeptide of the invention. Such an antibody may be isolated by comparing its binding affinity to a polypetide of the invention with its binding affinity to other polypeptides. Those which bind selectively to a polypeptide of the invention would be chosen for use in methods requiring a distinction between a polypeptide of the invention and other polypeptides. Such methods could include, but should not be limited to, the analysis of altered expression in tissue containing other polypeptides.

The polypeptides of the present invention can be used in a variety of procedures and methods, such as for the generation of antibodies, for use in identifying pharmaceutical compositions, and for studying DNA/protein interaction.

The polypeptides of the present invention can be used to produce antibodies or hybridomas. One skilled in the art will recognize that if an antibody is desired, such a peptide could be generated as described herein and used as an immunogen. The antibodies of the present invention include monoclonal and polyclonal antibodies, as well fragments of these antibodies, and humanized forms. Humanized forms of the antibodies of the present invention may be generated using one of the procedures known in the art such as chimerization or CDR grafting.

The present invention also relates to a hybridoma which produces the above-described monoclonal antibody, or binding fragment thereof. A hybridoma is an immortalized cell line which is capable of secreting a specific monoclonal antibody.

In general, techniques for preparing monoclonal antibodies and hybridomas are well known in the art (Campbell, "Monoclonal Antibody Technology: Laboratory Techniques in Biochemistry and Molecular Biology," Elsevier Science Publishers, Amsterdam, The Netherlands, 1984; St. Groth et al., J. Immunol. Methods 35:1–21, 1980). Any animal (mouse, rabbit, and the like) which is known to produce antibodies can be immunized with the selected polypeptide. Methods for immunization are well known in the art. Such methods include subcutaneous or intraperitoneal injection of the polypeptide. One skilled in the art will recognize that the amount of polypeptide used for immunization will vary based on the animal which is immunized, the antigenicity of the polypeptide and the site of injection.

The polypeptide may be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells. Any one of a number of methods well known in the art can be used to identify the hybridoma cell which produces an antibody with the desired characteristics. These include screening the hybridomas with an ELISA assay, western blot analysis, or radioimmunoassay (Lutz et al., Exp. Cell Res. 175:109–124, 1988). Hybridomas secreting the desired antibodies are cloned and the class and subclass are determined using procedures known in the art (Campbell, "Monoclonal Antibody Technology: Laboratory Techniques in Biochemistry and Molecular Biology", supra, 1984).

For polyclonal antibodies, antibody-containing antisera is isolated from the immunized animal and is screened for the presence of antibodies with the desired specificity using one of the above-described procedures. The above-described antibodies may be detectably labeled. Antibodies can be detectably labeled through the use of radioisotopes, affinity labels (such as biotin, avidin, and the like), enzymatic labels (such as horse radish peroxidase, alkaline phosphatase, and the like) fluorescent labels (such as FITC or rhodamine, and the like), paramagnetic atoms, and the like. Procedures for accomplishing such labeling are well-known in the art, for example, see Stemberger et al., J. Histochem. Cytochem. 18:315, 1970; Bayer et al., Meth. Enzym. 62:308-, 1979; Engval et al., Inmunol. 109:129-, 1972; Goding, J. Immunol. Meth. 13:215-, 1976. The labeled antibodies of the present invention can be used for in vitro, in vivo and in situ assays to identify cells or tissues which express a specific peptide.

The above-described antibodies may also be immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "Handbook of Experimental Immunology" 4th Ed., Blackwell Scientific Publications, Oxford, England, Chapter 10, 1986; Jacoby et al., Meth. Enzym. 34, Academic Press, N.Y., 1974). The immobilized antibodies of the present invention can be used for in vitro, in vivo and in situ assays as well as in immunochromotography.

Furthermore, one skilled in the art can readily adapt currently available procedures, as well as the techniques, methods and kits disclosed herein with regard to antibodies, to generate peptides capable of binding to a specific peptide sequence in order to generate rationally designed antipeptide peptides (Hurby et al., "Application of Synthetic Peptides: Antisense Peptides", In Synthetic Peptides, A User's Guide, W.H. Freeman, N.Y., pp. 289–307, 1992; Kaspczak et al., Biochemistry 28:9230–9238, 1989).

Anti-peptide peptides can be generated by replacing the basic amino acid residues found in the peptide sequences of the polypeptides of the invention with acidic residues, while maintaining hydrophobic and uncharged polar groups. For example, lysine, arginine, and/or histidine residues are replaced with aspartic acid or glutamic acid and glutamic acid residues are replaced by lysine, arginine or histidine.

The present invention also encompasses a method of detecting a Tks 107, Tks 113, Tks 118 or Tks 202 polypeptide in a sample, comprising: (a) contacting the sample with an above-described antibody, under conditions such that immunocomplexes form, and (b) detecting the presence of said antibody bound to the polypeptide. In detail, the methods comprise incubating a test sample with one or more of the antibodies of the present invention and assaying whether the antibody binds to the test sample. Altered levels of a polypeptide of the invention in a sample as compared to normal levels may indicate disease.

Conditions for incubating an antibody with a test sample vary. Incubation conditions depend on the format employed in the assay, the detection methods employed and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard ("An Introduction to Radioimmunoassay and Related Techniques" Elsevier Science Publishers, Amsterdam, The Netherlands, 1986), Bullock et al. ("Techniques in Immunocytochemistry," Academic Press, Orlando, Fla. Vol. 1, 1982; Vol. 2, 1983; Vol. 3, 1985), Tijssen ("Practice and Theory of Enzyme Immunoassays: Laboratory Techniques in Biochemistry and Molecular Biology," Elsevier Science Publishers, Amsterdam, The Netherlands, 1985).

The immunological assay test samples of the present invention include cells, protein or membrane extracts of cells, or biological fluids such as blood, serum, plasma or urine. The test samples used in the above-described method will vary based on the assay format, nature of the detection method and the tissues, cells or extracts used as the sample to be assayed. Methods for preparing protein extracts or membrane extracts of cells are well known in the art and can be readily adapted in order to obtain a sample which is testable with the system utilized.

A kit contains all the necessary reagents to carry out the previously described methods of detection. The kit may comprise: (i) a first container means containing an above-described antibody, and (ii) second container means containing a conjugate comprising a binding partner of the antibody and a label. In another preferred embodiment, the kit further comprises one or more other containers comprising one or more of the following: wash reagents and reagents capable of detecting the presence of bound antibodies.

Examples of detection reagents include, but are not limited to, labeled secondary antibodies, or in the alternative, if the primary antibody is labeled, the chromophoric, enzymatic, or antibody binding reagents which are capable of reacting with the labeled antibody. The compartmentalized kit may be as described above for nucleic acid probe kits. One skilled in the art will readily recognize that the antibodies described in the present invention can readily be incorporated into one of the established kit formats which are well known in the art.

VI. Isolation of Compounds which Interact with the Polypeptides of the Invention The present invention also relates to a method of detecting a compound capable of binding to a Tks 107, Tks 113, Tks 118 or Tks 202 of the invention comprising incubating the compound with a Tks 107, Tks 113, Tks 118 or Tks 202 of the invention and detecting the presence of the compound bound to the Tks 107, Tks 113, Tks 118 or Tks 202. The compound may be present within a complex mixture, for example, serum, body fluid or cell extracts.

The present invention also relates to a method of detecting an agonist or antagonist of Tks 107, Tks 113, Tks 118 or Tks 202 activity or binding partner, such as src, activity comprising incubating cells that produce a polypeptide of the invention in the presence of a compound and detecting changes in the level of polypeptide activity or polypeptide binding partner activity. The compounds thus identified would produce a change in activity indicative of the presence of the compound. The compound may be present within a complex mixture, for example, serum, body fluid, or cell extracts. Once the compound is identified it can be isolated using techniques well known in the art.

The present invention also encompasses a method of agonizing (stimulating) or antagonizing a src-binding partner associated activity in a mammal comprising administering to said mammal an agonist or antagonist to a Tks 107, Tks 113, Tks 118 and Tks 202 polypeptide in an amount sufficient to effect said agonism or antagonism. A method of treating diseases in a mammal with an agonist or antagonist of Tks 107, Tks 113, Tks 118 or Tks 202 activity comprising administering the agonist or antagonist to a mammal in an amount sufficient to agonize or antagonize Tks 107, Tks 113, Tks 118 or Tks 202 associated functions is also encompassed in the present application.

In an effort to discover novel treatments for diseases, biomedical researchers and chemists have designed, synthesized, and tested molecules that inhibit the function of protein polypeptides. Some small organic molecules form a class of compounds that modulate the function of protein polypeptides. Examples of molecules that have been reported to inhibit the function of protein kinases include, but are not limited to, bis monocyclic, bicyclic or heterocyclic aryl compounds (PCT WO 92/20642, published Nov. 26, 1992 by Maguire et al.), vinylene-azaindole derivatives (PCT WO 94/14808, published Jul. 7, 1994 by Ballinari et al.), 1-cyclopropyl-4-pyridyl-quinolones (U.S. Pat. No. 5,330,992), styryl compounds (U.S. Pat. No. 5,217,999), styryl-substituted pyridyl compounds (U.S. Pat. No. 5,302, 606), certain quinazoline derivatives (EP Application No. 0 566 266 A1), seleoindoles and selenides (PCT WO 94/03427, published Feb. 17, 1994 by Denny et al.), tricyclic polyhydroxylic compounds (PCT WO 92/21660, published Dec. 10, 1992 by Dow), and benzylphosphonic acid compounds (PCT WO 91/15495, published Oct. 17, 1991 by Dow et al), all of which are incorporated by reference herein, including any drawings.

Compounds that can traverse cell membranes and are resistant to acid hydrolysis are potentially advantageous as therapeutics as they can become highly bioavailable after being administered orally to patients. However, many of these protein inhibitors only weakly inhibit protein function. In addition, many inhibit a variety of protein kinases and will therefore cause multiple side-effects as therapeutics for diseases.

Some indolinone compounds, however, form classes of acid resistant and membrane permeable organic molecules. WO 96/22976 (published Aug. 1, 1996 by Ballinari et al.) describes hydrosoluble indolinone compounds that harbor tetralin, naphthalene, quinoline, and indole substituents fused to the oxindole ring. These bicyclic substituents are in turn substituted with polar groups including hydroxylated alkyl, phosphate, and ether substituents. U.S. patent application Ser. No. 08/702,232, filed Aug. 23, 1996, entitled "Indolinone Combinatorial Libraries and Related Products and Methods for the Treatment of Disease" by Tang et al. and Ser. No. 08/485,323, filed Jun. 7, 1995, entitled "Benzylidene-Z-Indoline Compounds for the Treatment of Disease" by Tang et al. and International Patent Publication WO 96/22976, published Aug. 1, 1996 by Ballinari et al., all of which are incorporated herein by reference in their entirety, including any drawings, describe indolinone chemical libraries of indolinone compounds harboring other bicyclic moieties as well as monocyclic moieties fused to the oxindole ring. Application Ser. No. 08/702,232, filed Aug. 23, 1996, entitled "Indolinone Combinatorial Libraries and Related Products and Methods for the Treatment of Disease" by Tang et al., Ser. No. 08/485,323, filed Jun. 7, 1995, entitled "Benzylidene-Z-Indoline Compounds for the Treatment of Disease" by Tang et al., and WO 96/22976, published Aug. 1, 1996 by Ballinari et al. teach methods of indolinone synthesis, methods of testing the biological activity of indolinone compounds in cells, and inhibition patterns of indolinone derivatives, both of which are incorporated by reference herein, including any drawings.

Other examples of substances capable of modulating kinase activity include, but are not limited to, tyrphostins, quinazolines, quinoxalines, and quinolines. The quinazolines, tyrphostins, quinolines, and quinoxalines referred to above include well known compounds such as those described in the literature. For example, representative publications describing quinazolines include Barker et al., EPO Publication No. 0 520 722 A1; Jones et al., U.S. Pat. No. 4,447,608; Kabbe et al., U.S. Pat. No. 4,757,072; Kaul and Vougioukas, U.S. Pat. No. 5,316,553; Kreighbaum and Comer, U.S. Pat. No. 4,343,940; Pegg and Wardleworth, EPO Publication No. 0 562 734 A1; Barker et al., *Proc. of Am. Assoc. for Cancer Research* 32:327 (1991); Bertino, J. R., *Cancer Research* 3:293–304 (1979); Bertino, J. R., *Cancer Research* 9(2 part 1):293–304 (1979); Curtin et al., *Br. J. Cancer* 53:361–368 (1986); Fernandes et al., *Cancer Research* 43:1117–1123 (1983); Ferris et al. *J. Org. Chem.* 44(2):173–178; Fry et al., Science 265:1093–1095 (1994); Jackman et al., Cancer Research 51:5579–5586 (1981); Jones et al. J. Med. Chem. 29(6):1114–1118; Lee and Skibo, Biochemistry 26(23):7355–7362 (1987); Lemus et al., J. Org. Chem. 54:3511–3518 (1989); Ley and Seng, Synthesis 1975:415–522 (1975); Maxwell et al., *Magnetic Resonance in Medicine* 17:189–196 (1991); Mini et al., *Cancer Research* 45:325–330 (1985); Phillips and Castle, *J. Heterocyclic Chem.* 17(19):1489–1596 (1980); Reece et al., Cancer Research 47(11):2996–2999 (1977); Sculier et al., *Cancer Immunol. and Immunother.* 23:A65 (1986); Sikora et al., *Cancer Letters* 23:289–295 (1984); and Sikora et al., *Analytical Biochem.* 172:344–355 (1988), all of which are incorporated herein by reference in their entirety, including any drawings.

Quinoxaline is described in Kaul and Vougioukas, U.S. Pat. No. 5,316,553, incorporated herein by reference in its entirety, including any drawings.

Quinolines are described in Dolle et al., J. Med. Chem. 37:2627–2629 (1994); MaGuire, J. Med. Chem. 37:2129–2131 (1994); Burke et al., J. Med. Chem. 36:425–432 (1993); and Burke et al. BioOrganic Med. Chem. Letters 2:1771–1774 (1992), all of which are incorporated by reference in their entirety, including any drawings.

Tyrphostins are described in Allen et al., *Clin. Exp. Immunol.* 91:141–156 (1993); Anafi et al., *Blood* 82:12: 3524–3529 (1993); Baker et al., *J. Cell Sci.* 102:543–555 (1992); Bilder et al., *Amer. Physiol. Soc.* pp. 6363–6143: C721–C730 (1991); Brunton et al., *Proceedings of Amer. Assoc. Cancer Rsch.* 33:558 (1992); Bryckaert et al., *Experimental Cell Research* 199:255–261 (1992); Dong et al., *J. Leukocyte Biology* 53:53–60 (1993); Dong et al., *J. Immunol.* 151(5):2717–2724 (1993); Gazit et al., *J. Med. Chem.* 32:2344–2352 (1989); Gazit et al., "*J. Med. Chem.* 36:3556–3564 (1993); Kaur et al., *Anti-Cancer Drugs* 5:213–222 (1994); Kaur et al., King et al., *Biochem. J.* 275:413–418 (1991); Kuo et al., *Cancer Letters* 74:197–202 (1993); Levitzki, A., *The FASEB J.* 6:3275–3282 (1992); Lyall et al., *J. Biol. Chem.* 264:14503–14509 (1989); Peterson et al., *The Prostate* 22:335–345 (1993); Pillemer et al., *Int. J. Cancer* 50:80–85 (1992); Posner et al., *Molecular Pharmacology* 45:673–683 (1993); Rendu et al., *Biol. Pharmacology* 44(5):881–888 (1992); Sauro and Thomas, Life Sciences 53:371–376 (1993); Sauro and Thomas, *J. Pharm. and Experimental Therapeutics* 267(3):119–1125 (1993); Wolbring et al., J. Biol. Chem. 269(36):22470–22472 (1994); and Yoneda et al., *Cancer Research* 51:4430–4435 (1991); all of which are incorporated herein by reference in their entirety, including any drawings.

Other compounds that could be used as modulators include oxindolinones such as those described in U.S. patent application Ser. No. 08/702,232 filed Aug. 23, 1996, incorporated herein by reference in its entirety, including any drawings.

VIII. Transgenic Animals.

A variety of methods are available for the production of transgenic animals associated with this invention. DNA can be injected into the pronucleus of a fertilized egg before fusion of the male and female pronuclei or injected into the nucleus of an embryonic cell (e.g., the nucleus of a two-cell embryo) following the initiation of cell division (Brinster et al., Proc. Nat. Acad. Sci. USA 82: 4438–4442, 1985). Embryos can be infected with viruses, especially retroviruses, modified to carry inorganic-ion receptor nucleotide sequences of the invention.

Pluripotent stem cells derived from the inner cell mass of the embryo and stabilized in culture can be manipulated in culture to incorporate nucleotide sequences of the invention. A transgenic animal can be produced from such cells through implantation into a blastocyst that is implanted into a foster mother and allowed to come to term. Animals suitable for transgenic experiments can be obtained from standard commercial sources such as Charles River (Wilmington, Mass.), Taconic (Germantown, N.Y.), Harlan Sprague Dawley (Indianapolis, Ind.), etc.

The procedures for manipulation of the rodent embryo and for microinjection of DNA into the pronucleus of the zygote are well known to those of ordinary skill in the art (Hogan et al., supra). Microinjection procedures for fish, amphibian eggs and birds are detailed in Houdebine and Chourrout (Experientia 47: 897–905, 1991). Other procedures for introduction of DNA into tissues of animals are described in U.S. Pat. No. 4,945,050 (Sandford et al., Jul. 30, 1990).

By way of example only, to prepare a transgenic mouse, female mice are induced to superovulate. Females are placed with males, and the mated females are sacrificed by CO2 asphyxiation or cervical dislocation and embryos are recovered from excised oviducts. Surrounding cumulus cells are removed. Pronuclear embryos are then washed and stored until the time of injection. Randomly cycling adult female mice are paired with vasectomized males. Recipient females are mated at the same time as donor females. Embryos then are transferred surgically. The procedure for generating transgenic rats is similar to that of mice (Hammer et al., Cell 63:1099–1112, 1990).

Methods for the culturing of embryonic stem (ES) cells and the subsequent production of transgenic animals by the introduction of DNA into ES cells using methods such as electroporation, calcium phosphate/DNA precipitation and direct injection also are well known to those of ordinary skill in the art (Teratocarcinomas and Embryonic Stem Cells, A Practical Approach, E. J. Robertson, ed., IRL Press, 1987).

In cases involving random gene integration, a clone containing the sequence(s) of the invention is co-transfected with a gene encoding resistance. Alternatively, the gene encoding neomycin resistance is physically linked to the sequence(s) of the invention. Transfection and isolation of desired clones are carried out by any one of several methods well known to those of ordinary skill in the art (E. J. Robertson, supra).

DNA molecules introduced into ES cells can also be integrated into the chromosome through the process of homologous recombination (Capecchi, Science 244: 1288–1292, 1989). Methods for positive selection of the recombination event (i.e., neo resistance) and dual positive-negative selection (i.e., neo resistance and gancyclovir resistance) and the subsequent identification of the desired clones by PCR have been described by Capecchi, supra and Joyner et al. (Nature 338: 153–156, 1989), the teachings of which are incorporated herein in their entirety including any drawings. The final phase of the procedure is to inject targeted ES cells into blastocysts and to transfer the blastocysts into pseudopregnant females. The resulting chimeric animals are bred and the offspring are analyzed by Southern blotting to identify individuals that carry the transgene. Procedures for the production of non-rodent mammals and other animals have been discussed by others (Houdebine and Chourrout, supra; Pursel et al., Science 244:1281–1288, 1989; and Simms et al., Bio/Technology 6:179–183, 1988).

The invention provides transgenic, nonhuman mammals containing a transgene encoding a polypeptide of the invention or a gene effecting the expression of the polypeptide. Such transgenic nonhuman mammals are particularly useful as an in vivo test system for studying the effects of introduction of a polypeptide, or regulating the expression of a polypeptide (i.e., through the introduction of additional genes, antisense nucleic acids, or ribozymes).

All of the above references are incorporated by reference herein, including any drawings.

A "transgenic animal" is an animal having cells that contain DNA which has been artificially inserted into a cell, which DNA becomes part of the genome of the animal which develops from that cell. Preferred transgenic animals are primates, mice, rats, cows, pigs, horses, goats, sheep, dogs and cats. The transgenic DNA may encode human Tks 107, Tks 113, Tks 118 or Tks 202. Native expression in an animal may be reduced by providing an amount of anti-sense RNA or DNA effective to reduce expression of the receptor.

IX. Gene Therapy

Tks 107, Tks 113, Tks. 118 or Tks 202 genes or their genetic sequences will also be useful in gene therapy (reviewed in Miller, Nature 357:455–460, 1992). Miller states that advances have resulted in practical approaches to human gene therapy that have demonstrated positive initial results. The basic science of gene therapy is described in Mulligan (Science 260:926–931, 1993).

In one preferred embodiment, an expression vector containing a Tks 107, Tks 113, Tks 118 or Tks 202 coding sequence is inserted into cells, the cells are grown in vitro and then infused in large numbers into patients. In another preferred embodiment, a DNA segment containing a promoter of choice (for example a strong promoter) is transferred into cells containing an endogenous gene of the invention in such a manner that the promoter segment enhances expression of the endogenous gene (for example, the promoter segment is transferred to the cell such that it becomes directly linked to the endogenous gene).

The gene therapy may involve the use of an adenovirus containing polypeptide cDNA targeted to a tumor, systemic polypeptide increase by implantation of engineered cells, injection with polypeptide-encoding virus, or injection of naked DNA into appropriate tissues.

Target cell populations may be modified by introducing altered forms of one or more components of the protein complexes in order to modulate the activity of such complexes. For example, by reducing or inhibit-ing a complex component activity within target cells, an abnormal signal transduction event(s) leading to a condition may be decreased, inhibited, or reversed. Deletion or missense mutants of a component, that retain the ability to interact with other components of the protein complexes but cannot function in signal transduction may be used to inhibit an abnormal, deleterious signal transduction event.

Expression vectors derived from viruses such as retroviruses, vaccinia virus, adenovirus, adeno-associ-ated virus, herpes viruses, several RNA viruses or bovine papilloma virus, may be used for delivery of nucleotide sequences (e.g., cDNA) encoding recom-binant polypeptide of the invention protein into the targeted cell population (e.g., tumor cells). Methods which are well known to those skilled in the art can be used to construct recombinant viral vectors contain-ing coding sequences (Maniatis et al., Molecu-lar Cloning: A Laboratory Manual, Cold Spring Harbor Laboratory, N.Y., 1989; Ausubel et al., Current Proto-cols in Molecular Biology, Greene Publishing Associates and Wiley Interscience, N.Y., 1989). Alter-natively, recombinant nucleic acid molecules encoding protein sequences can be used as naked DNA or in a recon-stituted system e.g., liposomes or other lipid systems for delivery to target cells (e.g., Feigner et al., Nature 337:387–8, 1989). Several other methods for the direct transfer of plasmid DNA into cells exist for use in human gene therapy and involve targeting the DNA to receptors on cells by complexing the plasmid DNA to proteins (Miller, supra).

In its simplest form, gene transfer can be performed by simply injecting minute amounts of DNA into the nucleus of a cell, through a process of microinjection (Capecchi, Cell 22:479–88, 1980). Once recombinant genes are introduced into a cell, they can be recognized by the cell's normal mechanisms for transcription and translation, and a gene product will be expressed. Other methods have also been attempted for introducing DNA into larger numbers of cells. These methods include: transfection, wherein DNA is pre-cipitated with CaPO4 and taken into cells by pinocytosis (Chen et al., Mol. Cell Biol. 7:2745–52, 1987); electropo-ration, wherein cells are exposed to large voltage pulses to introduce holes into the membrane (Chu et al., Nucleic Acids Res. 15:1311–26, 1987); lipofection/liposome fusion, wherein DNA is packaged into lipophilic vesicles which fuse with a target cell (Felgner et al., Proc. Natl. Acad. Sci. USA. 84:7413–7417, 1987); and particle bombardment using DNA bound to small projectiles (Yang et al., Proc. Natl. Acad. Sci. 87:9568–9572, 1990). Another method for introducing DNA into cells is to couple the DNA to chemi-cally modified proteins.

It has also been shown that adenovirus proteins are capable of destabilizing endosomes and enhancing the uptake of DNA into cells. The admixture of adenovirus to solutions containing DNA complexes, or the binding of DNA to polylysine covalently attached to adenovirus using protein crosslinking agents substantially improves the uptake and expression of the recombinant gene (Curiel et al., Am. J. Respir. Cell. Mol. Biol., 6:247–52, 1992).

As used herein "gene transfer" means the process of introducing a foreign nucleic acid molecule into a cell. Gene transfer is commonly performed to enable the expression of a particular product encoded by the gene. The product may include a protein, polypeptide, anti-sense DNA or RNA, or enzymatically active RNA. Gene transfer can be performed in cultured cells or by direct administration in to animals. Generally gene transfer involves the process of nucleic acid contact with a target cell by non-specific or receptor medi-ated interactions, uptake of nucleic acid into the cell through the membrane or by endocytosis and release of nucleic acid into the cytoplasm from the plasma membrane or endosome. Expression may require, in addition, movement of the nucleic acid into the nucleus of the cell and binding to appropriate nuclear factors for transcription.

As used herein "gene therapy" is a form of gene transfer and is included within the definition of gene transfer as used herein and specifically refers to gene transfer to express a therapeutic product from a cell in vivo or in vitro. Gene transfer can be performed ex vivo on cells which are then transplanted into a patient, or can be performed by direct administration of the nucleic acid or nucleic acid-protein complex into the patient.

In another preferred embodiment, a vector having nucleic acid sequences encoding a Tks 107, Tks 113, Tks 118 or Tks 202 polypeptide is provided in which the nucleic acid sequence is expressed only in specific tissue. Methods of achieving tissue-specific gene expres-sion are set forth in International Publication No. WO 93/09236, filed Nov. 3, 1992 and published May 13, 1993.

All of the above-mentioned references are incorporated by reference herein, including any drawings.

In all of the preceding vectors set forth above, a further aspect of the invention is that the nucleic acid sequence contained in the vector may include additions, deletions or modifications to some or all of the sequence of the nucleic acid, as defined above.

In another preferred embodiment, a method of gene replacement is set forth. "Gene replacement" as used herein means supplying a nucleic acid sequence which is capable of being expressed in vivo in an animal and thereby providing or augmenting the function of an endogenous gene which is missing or defective in the animal.

X. Administration of Substances

Methods of determining the dosages of compounds to be administered to a patient and modes of administering com-pounds to an organism are disclosed in U.S. application Ser. No. 08/702,282, filed Aug. 23, 1996 and International patent publication number WO 96/22976, published Aug. 1, 1996, both of which are incorporated herein by reference in their entirety, including any drawings, figures or tables. Those skilled in the art will appreciate that such descriptions are applicable to the present invention and can be easily adapted to it.

The proper dosage depends on various factors such as the type of disease being treated, the particular composi-tion being used and the size and physiological condition of the patient. Therapeutically effective doses for the compounds described herein can be estimated initially from cell culture and animal models. For example, a dose can be formulated in animal models to achieve a circulating concentration range that initially takes into account the $IC_{50}$ as determined in cell culture assays. The animal model data can be used to more accurately determine useful doses in humans.

Plasma half-life and biodistribution of the drug and metabolites in the plasma, tumors and major organs can also be determined to facilitate the selection of drugs most appropriate to inhibit a disorder. Such measurements can be carried out. For example, HPLC analysis can be performed on the plasma of animals treated with the drug and the location of radiolabeled compounds can be deter-mined using detection methods such as X-ray, CAT scan and MRI. Compounds that show potent inhibitory activity in the screening assays, but have poor pharmacokinetic character-istics, can be optimized by altering the chemical structure and retesting. In this regard, compounds displaying good pharmacokinetic characteristics can be used as a model.

Toxicity studies can also be carried out by measuring the blood cell composition. For example, toxicity studies can be carried out in a suitable animal model as follows: 1) the compound is administered to mice (an untreated control mouse should also be used); 2) blood samples are periodi-cally obtained via the tail vein from one mouse in each treatment group; and 3) the samples are analyzed for red and white blood cell counts, blood cell composition and the percent of lymphocytes versus polymorphonuclear cells. A comparison of results for each dosing regime with the controls indicates if toxicity is present.

At the termination of each toxicity study, further studies can be carried out by sacrificing the animals (preferably, in accordance with the American Veterinary Medical Association guidelines Report of the American Veterinary Medical Assoc. Panel on Euthanasia, *Journal of American Veterinary Medical Assoc.*, 202:229–249, 1993). Representative animals from each treatment group can then be examined by gross necropsy for immediate evidence of metastasis, unusual illness or toxicity. Gross abnormalities in tissue are noted and tissues are examined histologically. Compounds causing a reduction in body weight or blood components are less preferred, as are compounds having an adverse effect on major organs. In general, the greater the adverse effect the less preferred the compound.

For the treatment of cancers the expected daily dose of a hydrophobic pharmaceutical agent is between 1 to 500 mg/day, preferably 1 to 250 mg/day, and most preferably 1 to 50 mg/day. Drugs can be delivered less frequently provided plasma levels of the active moiety are sufficient to maintain therapeutic effectiveness.

Plasma levels should reflect the potency of the drug. Generally, the more potent the compound the lower the plasma levels necessary to achieve efficacy.

EXAMPLES

The examples below are not limiting and are merely representative of various aspects and features of the present invention.

Phosphorylation Screening

The phosphorylation screening method we used to identify Src substrates was previously reported in Lock, P., et. al. EMBO J. 17(15):4346–4357, 1998). Approximately $1.2 \times 10^6$ plaques from an NCI H460 λZAP library and $\sim 4.9 \times 10^5$ plaques from a Colo205 λZAPII library (Stratagene) were plated on 150 mm petri dishes. Plates were overlaid with nitrocellulose filters impregnated with 10 mM isopropyl-β-D-thiogalactopyranoside (IPTG) and incubated at 37° C. for 16 hours to induce expression of recombinant lacZ fusion proteins. Replica filters were washed extensively in TBST (10 mM Tris-HCl pH7.4, 150 mM NaCl, 0.1% Triton X-100) then equilibrated for one hour in kinase buffer (TBST containing 10 mM $MgCl_2$ and 2 mM $MnCl_2$). Filters were blocked for 1 hour at room temperature in kinase buffer containing 3% bovine serum albumin (BSA). Recombinant proteins were phosphorylated by incubating filters at 30° C. for 60 minutes in kinase buffer supplemented with 1/10 or 1/20 volume of an Sf9 extract containing baculovirus-derived human Src, 250 μM ATP and 100 μM sodium orthovanadate. Filters were washed briefly with kinase buffer alone then incubated in stripping buffer (62.5 mM Tris-HCl pH7.0, 2% SDS, 100 mM 2-β-mercaptoethanol) at 50° C. for 30 minutes to remove possible associated phosphoproteins, including Src itself or Sf9 cell derived proteins, which might interfere with the screening. Tyrosine phosphorylated proteins were detected with an anti-phosphotyrosine monoclonal antibody, 4G10, using standard immunoblotting methodology. Positive primary clones were isolated, eluted into SM buffer (0.1 M NaCl, 8 mM MgSO4.7H20, 50 mM Tris 7.5, 0.01% gelatin) and purified through 2 additional rounds of phosphorylation screening. pBluescript phagemids of purified clones were excised from the λZAP clones into SOLR cells using ExAssist helper phage according to the manufacturer's instructions (Stratagene).

Lambda Plague Screening and Northern Hybridization

~360,000 NCI H460 λZAP library plaques were plated onto NCZYM plates and lifted onto nitrocellulose filters. Filters were denatured (0.5M NaOH, 1.5M NaCl), neutralized (0.5M Tris 7.4, 1.5M NaCl), baked at 80C and prehybridized in hybridization buffer (5×SSPE, 10× Denhardts, 2% SDS, 50% Form amide, 0.1 mg/mL Salmon Sperm DNA) for 3–6 hours. The original 1.6 kb RI/XhoI tks 107 fragment (from excised phagemid) was purified and labelled with Boehringer Mannheim's Random Primed DNA Labelling Kit and purified with Qiagen's QiaQuick PCR purification kit. Filters were probed with this labelled fragment during an overnight hybridization in fresh hybridization buffer at 42° C. followed by 3×10 minutes washes at room temperature with 2×SSC, 0.05% SDS and 2×20' with 0.1× SSC, 0.1% SDS at 50° C. The filters were air dried and expose to X-OMAT-AR film (Kodak) overnight with 1 intensifying screen at −80° C. Positive plaques were isolated and purified to homogeneity through subsequent rounds of hybridization screening. pBluescript phagemids of purified clones were exised from the λZAP clones into SOLR cells as described above.

Approximately 270,000 TriplEX-Prostate library plaques (Clontech) were similarly probed with a ~500 b.p. EcoRI/XbaI fragment obtained from the original tks 202 clone. This fragment was random prime labelled using the Ready to Go DNA Labelling Beads and purified with Probe Quant G-50 Micro columns (Pharmacia).

Human Multiple Tissue Northern Blots I and II (Clontech) were hybridized with the 1.6 kb EcoRI/XhoI fragment from tks 107, a 1.5 kb EcoRI fragment from tks 113, the 1.6 kb EcoRI/XhoI fragment from tks 118, and 500 b.p. EcoRI/XbaI fragment from tks 202 clone using the same labelling, hybridization and wash protocols as above. The blots were stripped by boiling in 0.5% SDS for 10 minutes and washed with 2×SSC between probes.

All molecular biology techniques and buffers were performed and prepared as described in Sambrook, et. al. 1989.

Constructs

PCnM-107 was constructed by cloning the 4.65 kb NarI/PvuI fragment (containing the entire open reading frame [ORF] of tks 107 with about 90 n.t. of 3' untranslated region [UTR] into the EcoRV site of pCMV neoMyc2. This creates an N-term Myc tagged, full length tks 107 under transcriptional regulation of the CMV promoter. PCnM-107N, which contains an in frame 466 amino acids deletion of the C-term of pCnM-107, was created by digestion of pCnM-107 with BstEII/XhoI, filling in with dNTP's and T4 polymerase, and reclosing with T4 DNA ligase. PCnM-107C, consisting of the C-term 477 a.a. of tks 107 fused to the Myc tag of pCnM2, was created by an in frame deletion of the BamHI/BstEII fragment of pCnM-107. PCANMyc-GrubDH/PH was generated by cloning a BamHI/XhoI PCR fragment encoding just the DH/PH domains of Grub into the BamHI/XhoI sites of pCAN-MycA. PCAN-MycA is a pCDNA3 (Invitrogen) derivative with a Myc tag inserted into the polylinker. The primers used for the PCR were CCCCG-GATCCGAGCGCAAGCGAAGCAT and AACTCCTC-GAGCTAGGCTGCCTGTCTCCAC (italicized nucleotides represent the BamHI or XhoI sites; underlined CTA is an engineered stop codon). PCAN-Myc-GrubDH was generated by cloning a BamHI/XhoI PCR fragment encoding just the DH domain of Grub into pCANMycA. The primers used for the PCR were CCCCGGATCCGAGCGCAAGCGAAG-CAT (SEQ ID NO: 13); and AACTCCTCGAGCTAGGCT-GCCTGTCTCCAC (SEQ ID NO: 14); (italicized nucleotides represent the BamHI or XhoI sites; underlined CTA is an engineered stop codon). PCAN-Myc-GrubDH was generated by cloning a BamHI/XhoI PCR fragment encoding just the DH domain of Grub into pCANMycA. The primers used for the PCR were CCCCGGATCCGAGCGCAAGC-GAAGCAT (SEQ ID NO: 15); and CACCTCGAGC-TACGCTTCCACGGCCAGCAGGTC (SEQ ID NO: 16) (italicized nucleotides represent the BamHI or XhoI sites; underlined CTA is an engineered stop codon).

A ~330 n.t. BamHI/NcoI PCR fragment of tks 118 was generated which fused the 5' coding region of tks118 with a BamI site. The NcoI site is naturally found in tks 118. Primers used were: 5' primer, GCTGGGATCCGATC TATGCGCGCGAACCTG (SEQ ID NO:9) (italicized nucleotides represent the BamHI site; underlined ATG is tks 118's initiating methionine); 3' primer, TGAAAGCTG-TAGTTGGCACCTGA (SEQ ID NO:10). This PCR product was used to replace the BanHI/NcoI fragment in tks 118. This effectively deletes all 5' UTR. The BamHI/HindII fragment from the resultant construct (encoding full length tks 118) was cloned into the BamI/EcoRV site of pCnM2 to yield pCnM-118. An expression construct missing the SH3 domain of Dresh, pCnM-118ΔSH3, was created by cloning the BamHI/XcmI fragment of pCnM-118 into the BamHI/EcoRV sites of pCnM2. A construct expressing just the SH3 domain of tks118, pCnM-118SH3, was created by cloning the XcmI/Asp718 fragment of pCnM-118 into the StuI/Asp718 sites of pCnM2.

A construct expressing the SH3 domain of tks118 fused to glutathione-S-transferase (GST) was created by PCR amplification of the SH3 domain using the primers 5'CGCGAAT-TCCGGGCTCAGTGGGCAAGGG (SEQ ID NO:11) and GGGCTCGAGTCACTCAATGAGCTCCAC (SEQ ID NO:12) 3', digesting with EcoRI/XhoI and cloning into the same sites of pGEX-4T-3 (Pharmacia), resulting in the plasmid pGEX-118SH3.

A construct expressing the N-term of tks 113 fused to GST was created by cloning the EcoRI tks 113 fragment into pGEX4T-3, resulting in pGEX-113a. An Asp718/XhoI fragment, encoding the C-term of tks113, was deleted from pGEX-113a to yield pGEX-113c.

5' RACE-PCR

A modification of 5' RACE PCR was carried out in order to extend the 5' end of Tks202. First strand cDNA was made from human pancreas mRNA by Oligo DT primed reverse transcription. Second strand was primed by the oligo (ML2G) AAGTGGCAACAGAGATAACGCGTACCGGG. (SEQ ID NO: 17) The 3 G's at the 3' end of ML2G base pairs with runs of non-specific C's added by reverse transcriptase at the end of transcripts. Tks 202 5' RACE PCR reaction was performed with a tks202 specific primer of sequence GGCTGGTTCGGCCACTTGAGGG (SEQ ID NO: 18) and ML2G using the GC-Rich PCR kit (Roche Molecular Biochemicals). The PCR reaction was separated on an agarose gel, transferred to nitrocellulose, and hybridized (as described above) with a random primed (Ready to Go Beads from Pharmacia) labelled 550 nt DNA fragment from the 5' end of tks202-17. An approximately 500 bp labelled band was excised and cloned into pCR 2.1 Topo using the Topo TA cloning kit (Invitrogen). Colonies with the desired inserts were identified by colony hybridization using the same tks202-17 probe. DNA from these colonies were prepared and sequenced.

Cell Cultures, and DNA Transfection

293, NIH3T3, and an NIH3T3 cell line stably expressing the activated chicken Src allele Y527F (NIH3T3-Y527F) were grown in Dulbecco's modified Eagle's Medium (DMEM) containing 10% FCS and antibiotics. Confluent 293 cells were split 1:10 or NIH3T3's were split 1:5 the day prior to DNA transfection. Cells were transfected with 0.1–5 μg of DNA for 4–20 hrs using Lipofectamine (Gibco) or Effectene (Qiagen) according to manufacturers' instructions. Transfected cells were recovered overnight in DMEM, 10% FCS, and antibiotics.

Antibodies

Production of GST-DreshSH3 and GST-113c fusion proteins were induced in bacteria and purified over Glutathione-agarose beads (Pharmacia). Cell pellets from a 400 mL induction were resuspended in 30 mL 10 mM Tris 8.0, 150 mM NaCl, 1 mM EDTA (STE) with 100 mg/mL lysozyme, 10 μg/mL aprotinin, 20 μM leupeptin and 100 μM (PMSF) and sonicated to lyse cells. Lysates were centrifuged for 15' at 17K g's. 10 mL of PBS was added to the supernatant and Tween 20 was added to a final concentration of 0.1%. This was applied onto a Glutathione-agarose column and washed extensively with PBS with 0.1% Tween 20. Fusion proteins were eluted with 75 mM Hepes 7.5, 150 mM NaCl, 200 mM glutathione, 5 mM DTT and 0.1% octylglucoside. Eluate was dialyzed against PBS.

Polyclonal antibodies were raised by immunizing rabbits with the two fusion proteins (Animal Pharm). Antibodies were precipitated with $(NH_4)_2SO_4$, resuspended in PBS and passed over a column with coupled GST to remove GST specific antibodies. The resultant eluate were affinity purified by passing over columns containing the GST fusion proteins coupled to CN—Br activated Sepharose 4B (Pharmacia).

Cell Lysis, Immunoprecipitation, Immunoblotting

Cells destined for lysis were washed in (PBS+Na3VO4) and lysed in RIPA lysis buffer (20 mM Tris 7.5, 150 mM NaCl, 1% TX100, 1% Deoxycholate, 0.1% SDS) or HNTG (1.5 mM $MgCl_2$, 150 mM NaCl, 50 mM Hepes 7.5, 10% glycerol, 1% TX100, 1 mM EGTA) containing 100 μM $Na_3VO_4$, 10 mM NaF, 0.5–2.0 mM DTT, 10 μg/ml aprotinin, 20 μM leupeptin and 100 μM phenylmethylsulfonylflouride (PMSF). Extracts were clarified by centrifugation at 16,000 g's for 10 minutes.

Approximately 0.2–5.0 mg of total proteins were immunoprecipitated by incubation with 2–20 μg of 9E10 antibody or 12CA5 and 20 μL of Protein A/G (Santa Cruz Biotechnology) at 4° C. for 4 hours. Immunocomplexes were washed 4× with lysis buffer, resuspended in 45 uL SDS sample buffer (80 mM Tris 6.8, 2% SDS, 10% glycerol, 1.25% bromophenol blue and 280 mM B-mercaptoethanol), and heated at 95° C. for 3–5 minutes. Samples were subjected to SDS-PAGE and immunoblotted onto nitrocellulose membranes (MSI) using a Millipore semi-dry blotting apparatus.

Filters were blocked in TBST (25 mMTris 7.5, 150 mM NaCl and 0.1% Tween 20) with 3% BSA or 2% non-fat dry milk for 1 hour at room temperature. Filters were incubated in blocking buffer with primary antibodies for 1 hours using the following dilutions: 12CA5, 9E10, and 4G10 1:5000; α-cst1, 1:200; α-118SH3 (α5033) and α-tks 118 (α5029), 1:1000. Filters were washed 3×10 minutes with TBST and incubated in donkey anti-rabbit HRP (Amersham) or sheep anti-mouse HRP (Amersham) at 1:10000 in blocking buffer for 1 hour. Filters were washed as previous and the protein bands detected using enhanced chemiluminescence (SuperSignal, Pierce) in conjunction with Fuji RX, Film.

Cell Staining

NIH3T3 or NIH3T3-Y527F cells were split 1:5 from a confluent dish onto coverslips. Cells were transfected with various plasmids as described above and in the main text. Cells on coverslips were fixed with 3% para-formaldehyde in PBS and permeabilized with 0.2% TX100 in PBS. Cells were stained with various combinations of antibodies diluted in 0.2% TX100, 0.2% BSA in PBST. Primary antibodies used were diluted 1/50. Secondary antibodies were also diluted 1:50 and were Rabbit-TexRed (Immuno Research) and Mouse-Oregon-Green (Molecular Probes). Cells were also stained with Bis-benzimide to stain the nucleus.

JNK Kinase Assay 293 cells were transfected with pCAN-HA-JNK and various expression plasmids. Cells were lysed in BNTG and 0.2 mg were immunoprecipitated with 12CA5 for 4 hrs. Immunoprecipitates were washed 3× with lysis buffer and 2× with Kinase Buffer (25 mM Hepes7.6, 20 mM $MgCl_2$, 2 mM DTT, 100% $Na_3VO_4$, 1 mM PMSF). ½ of each immunoprecipitate was run on acrylamide gel and Western blotted for HA-JNK expression level. The remainder was resuspended in 30 μL kinase buffer with 20 μM ATP, 5 μCi $\gamma P^{32}ATP$, and 5 μg GST-Jun 1–223 and incubated at 30° C. for 30 minutes. Reactions were stopped with 7, 5× Laemmli sample buffer, boiled, separated on a 10% SDS-PAGE gel, dried, and exposed to film. The GST-Jun bands were excised and counted on a Scintillation counter.

2-Hybrid Screen

The BamHI fragment encoding the N-term domain of Grub from pCnM-107N was cloned into the BamHI site of pEG202 to produce pEG-107N. This plasmid encodes the N-term of Grub fused to the DNA binding domain LexA. This bait construct was introduced into the S. cervisiae strain EGY48 producing a resulting strain. EGY48 contains the LEU2 and β-galactosidase genes under the control of a synthetic promoter with LexA binding sites. A Hela cDNA expression library in the yeast expression vector pJG45 was transformed into the resultant strain (Gyuris, J., Golemis, E., Chertkov, H., and Brent, R. (1993) Cell 75, 791–803). Approximately 1.8×106 transformants were screened for interacting clones. 6 independent cDNA's were found to be identical to a previously isolated gene Snapin (Ilardi, et. al. Nature Neuro. (1999) 2, 119–124). 2 independent overlapping clones were found to be the human orthologue of the rat RACK1 (Ron, D., et. al. P.N.A.S. (1994) 91, 839–843).

CONCLUSION

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

In view of the degeneracy of the genetic code, other combinations of nucleic acids also encode the claimed peptides and proteins of the invention. For example, all four nucleic acid sequences GCT, GCC, GCA, and GCG encode the amino acide alanine. Therefore, if for an amino acid there exists an average of three codons, a polypeptide of 100 amino acids in length will, on average, be encoded by 3100, or 5×1047, nucleic acid sequences. Thus, a nucleic acid sequence can be modified to form a second nucleic acid sequence, encoding the same polypeptide as endoded by the first nucleic acid sequences, using routine procedures and without undue experimentation. Thus, all possible nucleic acids that encode the claimed peptides and proteins are also fully described herein, as if all were written out in full taking into account the codon usage, especially that preferred in humans. Furthermore, changes in the amino acid sequences of polypeptides, or in the corresponding nucleic acid sequence encoding such polypeptide, may be designed or selected to take place in an area of the sequence where the significant activity of the polypeptide remains unchanged. For example, an amino acid change may take place within a β-turn, away from the active site of the polypeptide. Also changes such as deletions (e.g. removal of a segment of the polypeptide, or in the corresponding nucleic acid sequence encoding such polypeptide, which does not affect the active site) and additions (e.g. addition of more amino acids to the polypeptide sequence without affecting the function of the active site, such as the formation of GST-fusion proteins, or additions in the corresponding nucleic acid sequence encoding such polypeptide without affecting the function of the active site) are also within the scope of the present invention. Such changes to the polypeptides can be performed by those with ordinary skill in the art using routine procedures and without undue experimentation. Thus, all possible nucleic and/or amino acid sequences that can readily be determined not to affect a significant activity of the peptide or protein of the invention are also fully described herein.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims.

What is claimed is:

1. An isolated, enriched, or purified nucleic acid molecule of SEQ ID NO: 1.

2. An isolated, enriched or purified nucleic acid molecule, encodes a polypeptide sharing at least 95% sequence identity to SEQ ID NO: 5 and wherein said polypeptide comprises src tyrosine kinase substrate activity.

3. The nucleic acid molecule of claim 1, further comprising a vector or promoter effective to initiate transcription in a host cell.

4. The nucleic acid molecule of claim 1, wherein said nucleic acid molecule is isolated, enriched or purified from a mammal.

5. The nucleic acid molecule of claim 4, wherein said mammal is a human.

6. A recombinant cell comprising the nucleic acid molecule of claim 1.

7. The nucleic acid molecule of claim 2, wherein the nucleic acid molecule encodes a polypeptide sharing at least 99% sequence identity to SEQ ID NO: 5 and wherein said polypeptide comprises src tyrosine kinase substrate activity.

8. The nucleic acid molecule of claim 2, wherein the nucleic acid molecule encodes the polypeptide of SEQ ID NO: 5.

9. The nucleic acid molecule of claim 2, her comprising a vector or promoter effective to initiate transcription in a host cell.

10. The nucleic acid molecule of claim 2, wherein said nucleic acid molecule is isolated, enriched or purified from a mammal.

11. The nucleic acid molecule of claim 10, wherein said mammal is a human.

12. A recombinant cell comprising the nucleic acid molecule of claim 2.

13. The nucleic acid molecule of claim 7, further comprising a vector or promoter effective to initiate transcription in a host cell.

14. The nucleic acid molecule of claim 7, wherein said nucleic acid molecule is isolated, enriched or purified from a mammal.

15. The nucleic acid molecule of claim 14, wherein said mammal is a human.

16. A recombinant cell comprising the nucleic acid molecule of claim 7.

17. The nucleic acid molecule of claim 8, further comprising a vector or promoter effective to initiate transcription in a host cell.

18. The nucleic acid molecule of claim 8, wherein said nucleic acid molecule is isolated, enriched or purified from a mammal.

19. The nucleic acid molecule of claim 18, wherein said mammal is a human.

20. A recombinant cell comprising the nucleic acid molecule of claim 8.

* * * * *

```
                              SEQUENCE LISTING

<160> NUMBER OF SEQ ID NOS: 55

<210> SEQ ID NO 1
<211> LENGTH: 5335
<212> TYPE: DNA
<213> ORGANISM: Unknown Organism
<220> FEATURE:
<223> OTHER INFORMATION: Description of Unknown Organism: Tks 107

<400> SEQUENCE: 1
cgctgaaggg cggggcgggg aggggcggcc gtctcggccc tccctggcgg ggccccgcgg      60
cctggaagcc ggagcgggcc gagccgccac cgcggccgga gctgtccctt agccagaccc     120
ggcgagacac gagcggcggg agggaggcgg tggcgcgccc ggccccgccc gcccgaccaa     180
gcgtcggacg cggcccggcg ccgagccatg gagcctgagc cagtggagga ctgtgtgcag     240
agcactctcg ccgccctgta tccacccttt gaggcaacag cccccaccct gttgggccag     300
gtgttccagg tggtggagag gacttatcgg gaggacgcac tgaggtacac gctggacttc     360
ctggtaccag ccaagcacct gcttgccaag gtccagcagg aagcctgtgc ccaatacagt     420
ggattcctct tcttccatga ggggtggccg ctctgcctgc atgaacaggt ggtggtgcag     480
ctagcagccc taccctggca actgctgcgc ccaggagact tctatctgca ggtggtgccc     540
tcagctgccc aagcaccccg actagcactc aagtgtctgg cccctggggg tgggcgggtg     600
caggaggttc ctgtgcccaa tgaggcttgt gcctacctat tcacacctga gtggctacaa     660
ggcatcaaca aggaccggcc aacaggtcgc ctcagtacct gctactgtc tgcgccctct      720 gggattcagc ggctgccctg ggctgagctc atctgtccac gatttgtgca caaagagggc     780
ctcatggttg gacatcagcc aagtacactg cccccagaac tgccctctgg acctccaggg     840
cttcccagcc ctccacttcc tgaggaggcg ctgggtaccc ggagtcctgg ggatgggcac     900
aatgcccctg tggaaggacc tgagggcgag tatgtggagc tgttagaggt gacgctgccc     960
gtgaggggga gcccaacaga tgctgaaggc tccccaggcc tctccagagt ccggacggta    1020
cccacccgca agggcgctgg agggaagggc cgccaccgga gacaccgggc gtggatgcac    1080
cagaagggcc tggggcctcg ggccaggat ggagcacgcc caccggcga ggggagcagc      1140 accggagcct cccctgagtc tcccccagga gctgaggctg tccagaggc agcagtcttg     1200 gaggtgtttg agcccccagc agaggctgtg ggagaagcct ccggatcttg cccctgagg     1260 ccaggggagc ttagaggagg aggaggagga ggccaggggg ctgaaggacc acctggtacc    1320
cctcggagaa caggcaaagg aaacagaaga aagaagcgag ctgcaggtcg agggctctt     1380 agccgaggag gggacagtgc cccactgagc cctggggaca aggaagatgc cagccaccaa    1440
gaagcccttg gcaatctgcc ctcaccaagt gagcacaagc ttccagaatg ccacctggtt    1500
aaggaggaat atgaaggctc agggaagcca gaatctgagc caaagagct caaaacagca     1560 ggcgagaaag agcctcagct ctctgaagcc tgtgggccta cagaagaggg ggccggagag    1620
agagagctgg aggggccagg cctgctgtgt atggcaggac acacaggccc agaaggcccc    1680
ctgtctgaca ctccaacacc tccgctggag actgtgcagg aaggaaaagg ggacaacatt    1740
ccagaagagg cccttgcagt ctccgtctct gatcaccctg atgtagcttg ggacttgatg    1800
```

-continued

```
gcatctggat tcctcatcct gacgggaggg gtggaccaga gtgggcgagc tctgctgacc    1860 attacccccac cgtgccctcc tgaggagccc ccaccctccc gagacacgct gaacacaact    1920
cttcattacc tccactcact gctcaggcct gatctacaga cactggggct gtccgtcctg    1980
ctggaccttc gtcaggcacc tccactgcct ccagcactca ttcctgcctt gagccaactt    2040
caggactcag gagatcctcc ccttgttcag cggctgctga ttctcattca tgatgacctt    2100
ccaactgaac tctgtggatt tcaggttgct gaggtgctgt cagagaatga tctgaaaaga    2160
gtggccaagc cagaggagct gcagtgggag ttaggaggtc acagggaccc ctctcccagt    2220
cactgggtag agatacacca ggaagtggta aggctatgtc gcctgtgcca aggtgtgctg    2280
ggctcggtac ggcaggccat tgaggagctg gagggagcag cagagccaga ggaagaggag    2340
gcagtgggaa tgcccaagcc actgcagaag gtgctggcag atccccggct gacggcactg    2400
cagagggatg gggggccat cctgatgagg ctgcgctcca ctcccagcag caagctggag    2460
ggccaaggcc cagctacact gtatcaggaa gtggacgagg ccattcacca gcttgtgcgc    2520
ctctccaacc tgcacgtgca gcagcaagag cagcggcagt gcctgcggcg actccagcag    2580
gtgttgcagt ggctctcggg cccaggggag gagcagctgg caagctttgc tatgcctggg    2640
gacaccttgt ctgccctgca ggagacagag ctgcgattcc gtgctttcag cgctgaggtc    2700
caggagcgcc tggcccaggc acgggaggcc ctggctctgg aggagaatgc cacctcccag    2760
aaggtgctgg atatctttga acagcggctg gagcaggttg agagtggcct ccatcgggcc    2820
ctgcggctac agcgcttctt ccagcaggca catgaatggg tggatgaggg cttttgctcgg    2880 ctggcaggag ctgggccggg tcgggaggct gtgctggctg cactggccct gcggcgggcc    2940
ccagagccca gtgccggcac cttccaggag atgcgggccc tggccctgga cctgggcagc    3000
ccagcagccc tgcgagaatg gggccgctgc caggccccgct gccaagagct agagaggagg    3060
atccagcaac acctgggaga ggaggcgagc ccacggggct accgacgacg gcgggcagac    3120
ggtgccagca gtggaggggc ccagtggggg ccccgcagcc cctcgcccag cctcagctcc    3180
ttgctgctcc ccagcagccc tgggccacgg ccagccccat cccattgctc cctggcccca    3240
tgtggagagg actatgagga agagggccct gagctggctc cagaagcaga gggcaggccc    3300
ccaagagctg tgctgatccg aggcctggag gtcaccagca ctgaggtggt agacaggacg    3360
tgctcaccac gggaacacgt gctgctgggc cgggctaggg ggccagacgg accctgggga    3420
gtaggcgccc cccggatgga gcgcaagcga agcatcagtg cccagcagcg gctggtgtct    3480
gagctgattg cctgtgaaca agattacgtg gccaccttga gtgagccagt gccacccct    3540 gggcctgagc tgacgcctga acttcggggc acctggctg ctgccctgag tgcccgggaa    3600
aggcttcgca gcttccaccg gacacacttt ctgcgggagc ttcagggctg cgccacccac    3660
cccctacgca ttggggcctg cttccttcgc cacgggacc agttcagcct ttatgcacag    3720
tacgtgaagc accgacacaa actggagaat ggtctggctg cgctcagtcc cttaagcaag    3780
ggctccatgg aggctggccc ttacctgccc cgagccctgc agcagcctct ggaacagctg    3840
actcggtatg ggcggctcct ggaggagctc ctgagggaag ctgggcctga gctcagttct    3900
gagtgccggg cccttgggg ctgctgtacag ctgctccggg aacaagaggc ccgtggcaga    3960
gacctgctgg ccgtggaggc ggtgcgtggc tgtgagatag atctgaagga gcagggacag    4020
ctcttgcatc gagacccctt cactgtcatc tgtggccgaa agaagtgcct tcgccatgtc    4080
tttctcttcg agcatctcct cctgttcagc aagctcaagg gccctgaagg gggtcagag    4140 atgtttgttt acaagcaggc ctttaagact gctgatatgg ggctgacaga aaacatcggg    4200
```

-continued

```
gacagcggac tctgctttga gttgtggttt cggcggcggc gtgcacgaga ggcatacact   4260
ctgcaggcaa cctcaccaga gatcaaactc aagtggacaa gttctattgc ccagctgctg   4320
tggagacagg cagcccacaa caaggagctc cgagtgcagc agatggtgtc catgggcatt   4380
gggaataaac ccttcctgga catcaaagcc cttggggagc ggacgctgag tgccctgctc   4440
actggaagag ccgcccgcac ccgggcctcc gtggccgtgt catcctttga gcatgccggc   4500
ccctcccttc ccggccttc gccgggagcc tgctccctgc ctgcccgcgt cgaggaggag   4560
gcctgggatc tggacgtcaa gcaaatttcc ctggccccag aaacacttga ctcttctgga   4620
gatgtgtccc caggaccaag aaacagcccc agcctgcaac cccccacccc tgggagcagc   4680 actcccacccc tggccagtcg agggatctta gggctatccc gacagagtca tgctcgagcc   4740
ctgagtgacc ccaccacgcc tctgtgacct ggagaagatc cagaacttgc gtgcagcttc   4800
tcctctcagc acactttggg ctgggatggc agtgggcat aatggagccc tgggcgatcg   4860
ctgaatttct tccctctgct tcctggacac agaggaggtc taacgaccag agtattgccc   4920
tgccaccact atctctagtc tccctagctt ggtgccttct cctgcaggag tcagagcagc   4980
cacattgctt gccttcatac cctggaggtg gggaagttat ccctcttccg gtgctttccc   5040
atcctgggcc actgtatcca ggacatcact cccatgccag ccctccctgg cagcccatgt   5100
tcccctcttt tctcacccc tgactttccc tgagaagaat catctctgcc aggtcaactg   5160
gagtccctgg tgactccatt ctgaggtgtc acaagcaatg aagctatgca acaatagga   5220 gggtgtgaca ggggaaccgt agactttata tatgtaatta ctgttattat aatactattg   5280
ttatattaaa tgtatttact cacactttgc ctctaaaaaa aaaaaaaaaa aaaaa         5335
```

<210> SEQ ID NO 2
<211> LENGTH: 1430
<212> TYPE: DNA
<213> ORGANISM: Unknown Organism
<220> FEATURE:
<223> OTHER INFORMATION: Description of Unknown Organism: Tks 113

<400> SEQUENCE: 2

```
gaattcggca cgagcaacta cggcggcggc ggcagaaccc agcagtgatg tggaggtgga     60
gacccacagg agccccggac ttcacctgag ctacctcagt ggtcaccaag agtggcaaga    120
taaagaaaac cctgagttgg gcgggaccag gatgcctgac cgggacagct atgccaacgg    180
taccgggagc agcggtggag gccctggagg tggtggcagc aaggaggcca gtggggcagg    240
ggtaggcagt ggcggggcca gctcagatgc catctgtaga gacttcttga ggaatgtgtg    300
caagcgaggc aagcgttgcc gatatcgcca cccagacatg agcgaggtgt ccaacttggg    360
ggtgagcaaa aacgagttca tcttctgcca tgacttccag aacaaggagt gtagccgccc    420
aaattgccgt tcatccatg gctccaagga ggatgaggat ggctataaga agacaggaga    480 gcttcccca cggctgaggc agaaagtagc agctggcctt ggcctttcac cggctgacct    540
accaaatggc aaggaggagg tccctatctg ccgtgacttt ctcaagggtg actgtcagag    600
aggagccaag tgcaagttcc gtcacctgca acgggatttt gagtttgatg ctcggggtgg    660
aggaggcact ggtgggggct caacaggctc agtcctccca ggacgacgtc atgatctcta    720
tgatatctat gaccttcctg acaggggctt tgaggaccat gagccaggcc caaaacgccg    780
gcgaggtgga tgctgccccc ctgatggccc tcattttgag tcatatgaat atagtttggc    840
tccaccgcga ggggtggagt gcagactgct agaggaggag aatgccatgc tcaggaagcg    900
```

-continued

| | |
|---|---|
| ggtagaggag ttaaagaagc aggtcagcaa cctgctggcc accaatgagg tactactgga | 960 |
| acaaaatgct cagttccgca atcaggccaa ggtcataacc ctgagctcca ctgcaccagc | 1020 |
| gactgagcag actctggccc ccactgtggg cactgttgcc acttttaacc atggcattgc | 1080 |
| ccagactcac actactctca gcagccaggc tctacagcct cgtccagtgt cccagcaaga | 1140 |
| actggtggcc cctgctggag ctccagctgc tcccccaact aatgctgcac ctcctgctgc | 1200 |
| tccaccaccc ccaccccac acttgacccc agagatcacg ccactgtcag ctgccctggc | 1260 |
| tcaaacaatt gcccagggaa tggcacctcc acctgtctcc atggctcctg tggctgtatc | 1320 |
| tgtggctcct gtgcccctg tggctgtatc gatggcccaa cccttggcag gaatcacaat | 1380 |
| gagccacacc accactccca tggtgactta ccctatcgct cccctcgag | 1430 |

<210> SEQ ID NO 3
<211> LENGTH: 1535
<212> TYPE: DNA
<213> ORGANISM: Unknown Organism
<220> FEATURE:
<223> OTHER INFORMATION: Description of Unknown Organism: Tks 118

<400> SEQUENCE: 3

| | |
|---|---|
| ttcgacacga gctgcggggc gggccatggc ggcgaacctg agccggaacg ggccagcgct | 60 |
| gcaagaggcc tacgtgcggg tggtcaccga gaagtcccg accgactggg ctctctttac | 120 |
| ctatgaaggc aacagcaatg acatccgcgt ggctggcaca ggggagggtg gcctggagga | 180 |
| gatggtggag gagctcaaca gcgggaaggt gatgtacgcc ttctgcagag tgaaggaccc | 240 |
| caactctgga ctgcccaaat ttgtcctcat caactggaca ggcgagggcg tgaacgatgt | 300 |
| gcggaaggga gcctgtgcca gccacgtcag caccatggcc agcttcctga ggggggccca | 360 |
| tgtgaccatc aacgcacggg ccgaggagga tgtggagcct gagtgcatca tggagaaggt | 420 |
| ggccaaggct tcaggtgcca actacagctt tcacaaggag agtggccgct tccaggacgt | 480 |
| gggacccag gccccagtgg gctctgtgta ccagaagacc aatgccgtgt ctgagattaa | 540 |
| aagggttggt aaagacagct ctgggccaa agcagagaag gaggaggaga accgtcggct | 600 |
| ggaggaaaag cggcgggccg aggaggcaca gcggcagctg gagcaggagc gccgggagcg | 660 |
| tgagctgcgt gaggctgcac gccgggagca gcgctatcag gagcagggtg gcgaggccag | 720 |
| cccccagagc aggacgtggg agcagcagca agaagtggtt tcaaggaacc gaaatgagca | 780 |
| ggagtctgcc gtgcacccga gggagatttt caagcagaag gagagggcca tgtccaccac | 840 |
| ctccatctcc agtcctcagc ctggcaagct gaggagcccc ttcctgcaga agcagctcac | 900 |
| ccaaccagag acccactttg gcagagagcc agctgctgcc atctcaaggc cagggcaga | 960 |
| tctccctgct gaggagccgg cgcccagcac tcctccatgt ctggtgcagg cagaagagga | 1020 |
| ggctgtgtat gaggaacctc cagagcagga gaccttctac gagcagcccc cactggtgca | 1080 |
| gcagcaaggt gctggctctg agcacattga ccaccacatt cagggccagg gctcagtgg | 1140 |
| gcaagggctc tgtgcccgtg ccctgtacga ctaccaggca gccgacgaca cagagatctc | 1200 |
| cttttgacccc gagaacctca tcacgggcat cgaggtgatc gacgaaggct ggtggcgtgg | 1260 |
| ctatgggccg gatggccatt ttggcatgtt ccctgccaac tacgtggagc tcattgagtg | 1320 |
| aggctgaggg cacatcttgc ccttcccctc tcagacatgg cttccttatt gctgaagag | 1380 |
| gaggcctggg agttgacatt cagcactctt ccaggaatag gaccccagt gaggatgagg | 1440 |
| cctcagggct ccctccggct tggcagactc agcctgtcac cccaaatgca gcaatggcct | 1500 |
| ggtgattccc acacatcctt cctgcatccc ccgac | 1535 |

<210> SEQ ID NO 4
<211> LENGTH: 2787
<212> TYPE: DNA
<213> ORGANISM: Unknown Organism
<220> FEATURE:
<223> OTHER INFORMATION: Description of Unknown Organism: Tks 202

<400> SEQUENCE: 4

```
cagtcgcagg aggcgctcct tggcggtgcc tggagcccgg gcgcacccca ccgctcccgg      60
gacctgttgg gggctggccc gaaccgtcgt cgaagggagc cgctcggcca ccccgacgt      120
tcctcgcccc gcccgacgtt ccctcaagtg gccgaaccag ccggacgagc caaactcgcc     180
gggcctccg cgcggcagcag gtggcccgt ccttccaggg agggccctgc gccccgcggc      240
gctccggagc cctctcggcc gccccgcca ggcgggatgg aggcggatgg ggacggagag      300
gagctggccc ggctgcgctc agtcttcgcc gcctgcgacg cgaaccgctc ggggcgcctg     360
gagcgcgagg agttccgggc actgtgcacg gagctgcggg tgcggccggc cgacgccgag     420
gcagtattcc agcggctgga cgccgaccgt gacggcgcca tcaccttcca ggagttcgcg     480
cgtggcttcc tcgggtccct ccgcgggggg cggcgccggg actgggtgtcc tctggatccc    540
gcgcccgccg tgtctgaggc ggggccggag acacacgaca gcgaggagga cgaaggcgac     600
gaggacgcgc cggcggcgct ggccacctcg tgcggcccgg cgagtcccgg ccgggcttgg     660
caggatttcc aggcgcgact tggggacgaa gccaagttca ttcccagaga gagcaagtt      720
agtaccttgt accaaaacat caaccttgtg gagccaagat taattcagcc atatgaacat     780
gttataaaga acttcatccg tgagatcaga cttcaaagca cagaaatgga aaatttggcc     840
attgcggtga gagagccca ggacaaggca gctatgcagt tgagtgagtt ggaagaggaa      900
atggatcaga ggattcaggc tgcagaacat aagcacgga aagacgaaaa acgcaaagct      960
gaggaagccc tcagtgacct cagacgtcag tatgaaactg aagtaggaga tctgcaggtg     1020
accattaaaa agctaagaaa gctcgaagaa caatcaaaac gcgtaagtca aaaggaagat    1080
gtggctgcat tgaaaaaaca aatttatgat ttatcaatgg aaaaccagaa agttaagaaa    1140
gaccttttag aagcacagac aaacatagcc tttcttcaga gtgagttaga tgctttgaaa    1200
agtgattatg ctgatcagag tctgaatact gaaagggatc tggaaataat ccagagcatac   1260
acagaagatc gaaatagtct tgagaggcaa attgaaatac tccaaacagc taaccggaag    1320
ctacatgaca gtaatgatgg ccttagaagt gcccttgaaa acagttatag caagttcaac    1380
agatctttgc atataaataa tatctcacca gggaatacaa tttctagaag cagtcccaaa    1440
ttcattggtc attcccctca acctctaggc tatgacaggt catcccgctc ttcctatgtg    1500
gatgaggact gtgactccct ggccctctgt gatcctctgc agaggacaaa ttgtgaagtt    1560
gacagcctgc ctgaaagctg cttcgacagc ggcttgtcta ccttgagaga tcccaatgag    1620
tatgactcag aagtggaata caagcaccag aggggatttc agaggtcaca cggggtgcag    1680
gagagctttg gaggtgatgc ttcagacaca gatgttcctg acataaggga tgaagagaca    1740
tttggtttag aagatgtggc ttccgtctta gactggaagc cccaagggtc tgttagtgaa    1800
ggcagcattg ttagttcatc aagaaagccc atctcagcac tctcgcccca gacagacctg    1860
gtagatgaca acgctaaatc ttttagctca cagaaggctt acaagattgt acttgctggg    1920
gacgctgcag tggggaagtc tagtttcctc atgagacttt gcaagaatga atttcgagaa    1980
aatataagcg ccaccctggg agttgatttc caaatgaaaa ccctcattgt ggatggagaa    2040
```

-continued

```
cgaacagttc tgcagctctg ggatacagct ggtcaggaga gattcagaag tattgccaag    2100
tcttacttca gaaaggcaga tggtgttttg ctgctgtatg atgttacatg tgagaaaagc    2160
tttcttaaca tacgagaatg ggtagatatg attgaggatg cagcccatga gactgttccc    2220
attatgctgg taggaaacaa ggctgacatt cgtgacactg ctgctacaga gggacaaaaa    2280
tgtgtcccag gcactttgg agagaaactg gccatgacgt atgggcatt attctgtgaa      2340 acaagtgcca aagatggttc taacatagtg gaggctgttc tgcaccttgc tcgagaagtg    2400
aaaaagagaa ctgacaagga tgacagcaga tccattacca atctaaccgg gaccaattcc    2460
aaaaagtcac cacagatgaa gaattgttgc aatggctaaa tcccaaacat ccttggcctg    2520
tgaagtcttc atttccagaa tactgaattt gtgtgactta tttggctctt aacagagtgg    2580
cacatcctac tgacactgtc ctatggagag tttacagtgc agggaaacct gaacccagct    2640
ctcaggtccc tctggaactt tggctcttct ttgttttgtc tcagtgagtg atttgggccc    2700
tctggctaaa tagactagtc atgtccttac aggtcttaaa agataacatg taaatgtttt    2760
taaaatggta aaaaaaaaa aaaaaaa                                         2787
```

<210> SEQ ID NO 5
<211> LENGTH: 1519
<212> TYPE: PRT
<213> ORGANISM: Unknown Organism
<220> FEATURE:
<223> OTHER INFORMATION: Description of Unknown Organism: Tks 107

<400> SEQUENCE: 5

```
Met Glu Pro Glu Pro Val Glu Asp Cys Val Gln Ser Thr Leu Ala Ala
  1               5                  10                  15

Leu Tyr Pro Pro Phe Glu Ala Thr Ala Pro Thr Leu Leu Gly Gln Val
                 20                  25                  30

Phe Gln Val Val Glu Arg Thr Tyr Arg Glu Asp Ala Leu Arg Tyr Thr
             35                  40                  45

Leu Asp Phe Leu Val Pro Ala Lys His Leu Leu Ala Lys Val Gln Gln
         50                  55                  60

Glu Ala Cys Ala Gln Tyr Ser Gly Phe Leu Phe His Glu Gly Trp
 65                  70                  75                  80

Pro Leu Cys Leu His Glu Gln Val Val Gln Leu Ala Ala Leu Pro
                 85                  90                  95

Trp Gln Leu Leu Arg Pro Gly Asp Phe Tyr Leu Gln Val Val Pro Ser
            100                 105                 110

Ala Ala Gln Ala Pro Arg Leu Ala Leu Lys Cys Leu Ala Pro Gly Gly
        115                 120                 125

Gly Arg Val Gln Glu Val Pro Val Pro Asn Glu Ala Cys Ala Tyr Leu
    130                 135                 140

Phe Thr Pro Glu Trp Leu Gln Gly Ile Asn Lys Asp Arg Pro Thr Gly
145                 150                 155                 160

Arg Leu Ser Thr Cys Leu Leu Ser Ala Pro Ser Gly Ile Gln Arg Leu
                165                 170                 175

Pro Trp Ala Glu Leu Ile Cys Pro Arg Phe Val His Lys Glu Gly Leu
            180                 185                 190

Met Val Gly His Gln Pro Ser Thr Leu Pro Pro Glu Leu Pro Ser Gly
        195                 200                 205

Pro Pro Gly Leu Pro Ser Pro Pro Leu Pro Glu Glu Ala Leu Gly Thr
    210                 215                 220

Arg Ser Pro Gly Asp Gly His Asn Ala Pro Val Glu Gly Pro Glu Gly
```

```
                225                 230                 235                 240
Glu Tyr Val Glu Leu Leu Glu Val Thr Leu Pro Val Arg Gly Ser Pro
                    245                 250                 255
Thr Asp Ala Glu Gly Ser Pro Gly Leu Ser Arg Val Arg Thr Val Pro
                260                 265                 270
Thr Arg Lys Gly Ala Gly Gly Lys Gly Arg His Arg Arg His Arg Ala
            275                 280                 285
Trp Met His Gln Lys Gly Leu Gly Pro Arg Gly Gln Asp Gly Ala Arg
        290                 295                 300
Pro Pro Gly Glu Gly Ser Ser Thr Gly Ala Ser Pro Glu Ser Pro Pro
305                 310                 315                 320
Gly Ala Glu Ala Val Pro Glu Ala Ala Val Leu Glu Val Phe Glu Pro
                    325                 330                 335
Pro Ala Glu Ala Val Gly Glu Ala Ser Gly Ser Cys Pro Leu Arg Pro
                340                 345                 350
Gly Glu Leu Arg Gly Gly Gly Gly Gln Gly Ala Glu Gly Pro
            355                 360                 365
Pro Gly Thr Pro Arg Arg Thr Gly Lys Gly Asn Arg Arg Lys Lys Arg
        370                 375                 380
Ala Ala Gly Arg Gly Ala Leu Ser Arg Gly Gly Asp Ser Ala Pro Leu
385                 390                 395                 400
Ser Pro Gly Asp Lys Glu Asp Ala Ser His Gln Glu Ala Leu Gly Asn
                    405                 410                 415
Leu Pro Ser Pro Ser Glu His Lys Leu Pro Glu Cys His Leu Val Lys
                420                 425                 430
Glu Glu Tyr Glu Gly Ser Gly Lys Pro Glu Ser Glu Pro Lys Glu Leu
            435                 440                 445
Lys Thr Ala Gly Glu Lys Glu Pro Gln Leu Ser Glu Ala Cys Gly Pro
        450                 455                 460
Thr Glu Glu Gly Ala Gly Glu Arg Glu Leu Glu Gly Pro Gly Leu Leu
465                 470                 475                 480
Cys Met Ala Gly His Thr Gly Pro Glu Gly Pro Leu Ser Asp Thr Pro
                    485                 490                 495
Thr Pro Pro Leu Glu Thr Val Gln Glu Gly Lys Gly Asp Asn Ile Pro
                500                 505                 510
Glu Glu Ala Leu Ala Val Ser Val Ser Asp His Pro Asp Val Ala Trp
            515                 520                 525
Asp Leu Met Ala Ser Gly Phe Leu Ile Leu Thr Gly Gly Val Asp Gln
        530                 535                 540
Ser Gly Arg Ala Leu Leu Thr Thr Pro Pro Cys Pro Pro Glu Glu
545                 550                 555                 560
Pro Pro Pro Ser Arg Asp Thr Leu Asn Thr Thr Leu His Tyr Leu His
                    565                 570                 575
Ser Leu Leu Arg Pro Asp Leu Gln Thr Leu Gly Leu Ser Val Leu Leu
                580                 585                 590
Asp Leu Arg Gln Ala Pro Pro Leu Pro Ala Leu Ile Pro Ala Leu
            595                 600                 605
Ser Gln Leu Gln Asp Ser Gly Asp Pro Pro Leu Val Gln Arg Leu Leu
        610                 615                 620
Ile Leu Ile His Asp Asp Leu Pro Thr Glu Leu Cys Gly Phe Gln Gly
625                 630                 635                 640
Ala Glu Val Leu Ser Glu Asn Asp Leu Lys Arg Val Ala Lys Pro Glu
                    645                 650                 655
```

```
Glu Leu Gln Trp Glu Leu Gly Gly His Arg Asp Pro Ser Pro Ser His
            660                 665                 670

Trp Val Glu Ile His Gln Glu Val Val Arg Leu Cys Arg Leu Cys Gln
            675                 680                 685

Gly Val Leu Gly Ser Val Arg Gln Ala Ile Glu Glu Leu Glu Gly Ala
            690                 695                 700

Ala Glu Pro Glu Glu Glu Ala Val Gly Met Pro Lys Pro Leu Gln
705                 710                 715                 720

Lys Val Leu Ala Asp Pro Arg Leu Thr Ala Leu Gln Arg Asp Gly Gly
                725                 730                 735

Ala Ile Leu Met Arg Leu Arg Ser Thr Pro Ser Ser Lys Leu Glu Gly
                740                 745                 750

Gln Gly Pro Ala Thr Leu Tyr Gln Glu Val Asp Glu Ala Ile His Gln
                755                 760                 765

Leu Val Arg Leu Ser Asn Leu His Val Gln Gln Glu Gln Arg Gln
            770                 775                 780

Cys Leu Arg Arg Leu Gln Gln Val Leu Gln Trp Leu Ser Gly Pro Gly
785                 790                 795                 800

Glu Glu Gln Leu Ala Ser Phe Ala Met Pro Gly Asp Thr Leu Ser Ala
                805                 810                 815

Leu Gln Glu Thr Glu Leu Arg Phe Arg Ala Phe Ser Ala Glu Val Gln
            820                 825                 830

Glu Arg Leu Ala Gln Ala Arg Glu Ala Leu Ala Leu Glu Glu Asn Ala
            835                 840                 845

Thr Ser Gln Lys Val Leu Asp Ile Phe Glu Gln Arg Leu Glu Gln Val
850                 855                 860

Glu Ser Gly Leu His Arg Ala Leu Arg Leu Gln Arg Phe Phe Gln Gln
865                 870                 875                 880

Ala His Glu Trp Val Asp Glu Gly Phe Ala Arg Leu Ala Gly Ala Gly
                885                 890                 895

Pro Gly Arg Glu Ala Val Leu Ala Ala Leu Ala Leu Arg Arg Ala Pro
                900                 905                 910

Glu Pro Ser Ala Gly Thr Phe Gln Glu Met Arg Ala Leu Ala Leu Asp
            915                 920                 925

Leu Gly Ser Pro Ala Ala Leu Arg Glu Trp Gly Arg Cys Gln Ala Arg
930                 935                 940

Cys Gln Glu Leu Glu Arg Arg Ile Gln Gln His Leu Gly Glu Ala
945                 950                 955                 960

Ser Pro Arg Gly Tyr Arg Arg Arg Ala Asp Gly Ala Ser Ser Gly
                965                 970                 975

Gly Ala Gln Trp Gly Pro Arg Ser Pro Ser Pro Ser Leu Ser Ser Leu
            980                 985                 990

Leu Leu Pro Ser Ser Pro Gly Pro Arg Pro Ala Pro Ser His Cys Ser
            995                 1000                1005

Leu Ala Pro Cys Gly Glu Asp Tyr Glu Glu Gly Pro Glu Leu Ala
    1010                1015                1020

Pro Glu Ala Glu Gly Arg Pro Pro Arg Ala Val Leu Ile Arg Gly Leu
1025                1030                1035                1040

Glu Val Thr Ser Thr Glu Val Val Asp Arg Thr Cys Ser Pro Arg Glu
                1045                1050                1055

His Val Leu Leu Gly Arg Ala Arg Gly Pro Asp Gly Pro Trp Gly Val
            1060                1065                1070
```

-continued

Gly Ala Pro Arg Met Glu Arg Lys Arg Ser Ile Ser Ala Gln Gln Arg
    1075                1080                1085

Leu Val Ser Glu Leu Ile Ala Cys Glu Gln Asp Tyr Val Ala Thr Leu
1090                1095                1100

Ser Glu Pro Val Pro Pro Gly Pro Glu Leu Thr Pro Glu Leu Arg
1105                1110                1115                1120

Gly Thr Trp Ala Ala Ala Leu Ser Ala Arg Glu Arg Leu Arg Ser Phe
        1125                1130                1135

His Arg Thr His Phe Leu Arg Glu Leu Gln Gly Cys Ala Thr His Pro
            1140                1145                1150

Leu Arg Ile Gly Ala Cys Phe Leu Arg His Gly Asp Gln Phe Ser Leu
    1155                1160                1165

Tyr Ala Gln Tyr Val Lys His Arg His Lys Leu Glu Asn Gly Leu Ala
1170                1175                1180

Ala Leu Ser Pro Leu Ser Lys Gly Ser Met Glu Ala Gly Pro Tyr Leu
1185                1190                1195                1200

Pro Arg Ala Leu Gln Gln Pro Leu Glu Gln Leu Thr Arg Tyr Gly Arg
        1205                1210                1215

Leu Leu Glu Glu Leu Leu Arg Glu Ala Gly Pro Glu Leu Ser Ser Glu
        1220                1225                1230

Cys Arg Ala Leu Gly Ala Ala Val Gln Leu Leu Arg Glu Gln Glu Ala
        1235                1240                1245

Arg Gly Arg Asp Leu Leu Ala Val Glu Ala Val Arg Gly Cys Glu Ile
    1250                1255                1260

Asp Leu Lys Glu Gln Gly Gln Leu Leu His Arg Asp Pro Phe Thr Val
1265                1270                1275                1280

Ile Cys Gly Arg Lys Lys Cys Leu Arg His Val Phe Leu Phe Glu His
            1285                1290                1295

Leu Leu Leu Phe Ser Lys Leu Lys Gly Pro Glu Gly Gly Ser Glu Met
        1300                1305                1310

Phe Val Tyr Lys Gln Ala Phe Lys Thr Ala Asp Met Gly Leu Thr Glu
    1315                1320                1325

Asn Ile Gly Asp Ser Gly Leu Cys Phe Glu Leu Trp Phe Arg Arg Arg
1330                1335                1340

Arg Ala Arg Glu Ala Tyr Thr Leu Gln Ala Thr Ser Pro Glu Ile Lys
1345                1350                1355                1360

Leu Lys Trp Thr Ser Ser Ile Ala Gln Leu Leu Trp Arg Gln Ala Ala
        1365                1370                1375

His Asn Lys Glu Leu Arg Val Gln Gln Met Val Ser Met Gly Ile Gly
            1380                1385                1390

Asn Lys Pro Phe Leu Asp Ile Lys Ala Leu Gly Glu Arg Thr Leu Ser
    1395                1400                1405

Ala Leu Leu Thr Gly Arg Ala Ala Arg Thr Arg Ala Ser Val Ala Val
1410                1415                1420

Ser Ser Phe Glu His Ala Gly Pro Ser Leu Pro Gly Leu Ser Pro Gly
1425                1430                1435                1440

Ala Cys Ser Leu Pro Ala Arg Val Glu Glu Glu Ala Trp Asp Leu Asp
        1445                1450                1455

Val Lys Gln Ile Ser Leu Ala Pro Glu Thr Leu Asp Ser Ser Gly Asp
            1460                1465                1470

Val Ser Pro Gly Pro Arg Asn Ser Pro Ser Leu Gln Pro Pro His Pro
    1475                1480                1485

Gly Ser Ser Thr Pro Thr Leu Ala Ser Arg Gly Ile Leu Gly Leu Ser

-continued

```
          1490                1495                1500
Arg Gln Ser His Ala Arg Ala Leu Ser Asp Pro Thr Thr Pro Leu
1505                1510                1515

<210> SEQ ID NO 6
<211> LENGTH: 476
<212> TYPE: PRT
<213> ORGANISM: Unknown Organism
<220> FEATURE:
<223> OTHER INFORMATION: Description of Unknown Organism: Tks 113

<400> SEQUENCE: 6

Asn Ser Ala Arg Ala Thr Thr Ala Ala Ala Glu Pro Ser Ser Asp
 1               5                  10                  15

Val Glu Val Glu Thr His Arg Ser Pro Gly Leu His Leu Ser Tyr Leu
                20                  25                  30

Ser Gly His Gln Glu Trp Gln Asp Lys Glu Asn Pro Glu Leu Gly Gly
            35                  40                  45

Thr Arg Met Pro Asp Arg Asp Ser Tyr Ala Asn Gly Thr Gly Ser Ser
        50                  55                  60

Gly Gly Gly Pro Gly Gly Gly Ser Lys Glu Ala Ser Gly Ala Gly
65                  70                  75                  80

Val Gly Ser Gly Gly Ala Ser Ser Asp Ala Ile Cys Arg Asp Phe Leu
                85                  90                  95

Arg Asn Val Cys Lys Arg Gly Lys Arg Cys Arg Tyr Arg His Pro Asp
            100                 105                 110

Met Ser Glu Val Ser Asn Leu Gly Val Ser Lys Asn Glu Phe Ile Phe
        115                 120                 125

Cys His Asp Phe Gln Asn Lys Glu Cys Ser Arg Pro Asn Cys Arg Phe
    130                 135                 140

Ile His Gly Ser Lys Glu Asp Glu Asp Gly Tyr Lys Lys Thr Gly Glu
145                 150                 155                 160

Leu Pro Pro Arg Leu Arg Gln Lys Val Ala Ala Gly Leu Gly Leu Ser
                165                 170                 175

Pro Ala Asp Leu Pro Asn Gly Lys Glu Val Pro Ile Cys Arg Asp
            180                 185                 190

Phe Leu Lys Gly Asp Cys Gln Arg Gly Ala Lys Cys Lys Phe Arg His
        195                 200                 205

Leu Gln Arg Asp Phe Glu Phe Asp Ala Arg Gly Gly Gly Gly Thr Gly
    210                 215                 220

Gly Gly Ser Thr Gly Ser Val Leu Pro Gly Arg Arg His Asp Leu Tyr
225                 230                 235                 240

Asp Ile Tyr Asp Leu Pro Asp Arg Gly Phe Glu Asp His Glu Pro Gly
                245                 250                 255

Pro Lys Arg Arg Arg Gly Gly Cys Cys Pro Pro Asp Gly Pro His Phe
            260                 265                 270

Glu Ser Tyr Glu Tyr Ser Leu Ala Pro Pro Arg Gly Val Glu Cys Arg
        275                 280                 285

Leu Leu Glu Glu Glu Asn Ala Met Leu Arg Lys Arg Val Glu Glu Leu
    290                 295                 300

Lys Lys Gln Val Ser Asn Leu Leu Ala Thr Asn Glu Val Leu Leu Glu
305                 310                 315                 320

Gln Asn Ala Gln Phe Arg Asn Gln Ala Lys Val Ile Thr Leu Ser Ser
                325                 330                 335

Thr Ala Pro Ala Thr Glu Gln Thr Leu Ala Pro Thr Val Gly Thr Val
```

-continued

```
                340                 345                 350
Ala Thr Phe Asn His Gly Ile Ala Gln Thr His Thr Leu Ser Ser
            355                 360                 365

Gln Ala Leu Gln Pro Arg Pro Val Ser Gln Gln Glu Leu Val Ala Pro
    370                 375                 380

Ala Gly Ala Pro Ala Pro Pro Thr Asn Ala Ala Pro Pro Ala Ala
385                 390                 395                 400

Pro Pro Pro Pro Pro His Leu Thr Pro Glu Ile Thr Pro Leu Ser
                405                 410                 415

Ala Ala Leu Ala Gln Thr Ile Ala Gln Gly Met Ala Pro Pro Val
            420                 425                 430

Ser Met Ala Pro Val Ala Val Ser Val Ala Pro Val Ala Pro Val Ala
            435                 440                 445

Val Ser Met Ala Gln Pro Leu Ala Gly Ile Thr Met Ser His Thr Thr
    450                 455                 460

Thr Pro Met Val Thr Tyr Pro Ile Ala Pro Pro Arg
465                 470                 475

<210> SEQ ID NO 7
<211> LENGTH: 431
<212> TYPE: PRT
<213> ORGANISM: Unknown Organism
<220> FEATURE:
<223> OTHER INFORMATION: Description of Unknown Organism: Tks 118

<400> SEQUENCE: 7

Met Ala Ala Asn Leu Ser Arg Asn Gly Pro Ala Leu Gln Glu Ala Tyr
  1               5                  10                  15

Val Arg Val Val Thr Glu Lys Ser Pro Thr Asp Trp Ala Leu Phe Thr
             20                  25                  30

Tyr Glu Gly Asn Ser Asn Asp Ile Arg Val Ala Gly Thr Gly Glu Gly
         35                  40                  45

Gly Leu Glu Glu Met Val Glu Leu Asn Ser Gly Lys Val Met Tyr
     50                  55                  60

Ala Phe Cys Arg Val Lys Asp Pro Asn Ser Gly Leu Pro Lys Phe Val
 65                  70                  75                  80

Leu Ile Asn Trp Thr Gly Glu Gly Val Asn Asp Val Arg Lys Gly Ala
                 85                  90                  95

Cys Ala Ser His Val Ser Thr Met Ala Ser Phe Leu Lys Gly Ala His
            100                 105                 110

Val Thr Ile Asn Ala Arg Ala Glu Glu Asp Val Glu Pro Glu Cys Ile
        115                 120                 125

Met Glu Lys Val Ala Lys Ala Ser Gly Ala Asn Tyr Ser Phe His Lys
130                 135                 140

Glu Ser Gly Arg Phe Gln Asp Val Gly Pro Gln Ala Pro Val Gly Ser
145                 150                 155                 160

Val Tyr Gln Lys Thr Asn Ala Val Ser Glu Ile Lys Arg Val Gly Lys
                165                 170                 175

Asp Ser Phe Trp Ala Lys Ala Glu Lys Glu Glu Asn Arg Arg Leu
            180                 185                 190

Glu Glu Lys Arg Arg Ala Glu Glu Ala Gln Arg Gln Leu Glu Gln Glu
        195                 200                 205

Arg Arg Glu Arg Glu Leu Arg Glu Ala Ala Arg Glu Gln Arg Tyr
    210                 215                 220

Gln Glu Gln Gly Gly Glu Ala Ser Pro Gln Ser Arg Thr Trp Glu Gln
```

-continued

```
               225                 230                 235                 240
Gln Gln Glu Val Val Ser Arg Asn Arg Asn Glu Gln Glu Ser Ala Val
                245                 250                 255
His Pro Arg Glu Ile Phe Lys Gln Lys Glu Arg Ala Met Ser Thr Thr
            260                 265                 270
Ser Ile Ser Ser Pro Gln Pro Gly Lys Leu Arg Ser Pro Phe Leu Gln
        275                 280                 285
Lys Gln Leu Thr Gln Pro Glu Thr His Phe Gly Arg Glu Pro Ala Ala
    290                 295                 300
Ala Ile Ser Arg Pro Arg Ala Asp Leu Pro Ala Glu Glu Pro Ala Pro
305                 310                 315                 320
Ser Thr Pro Pro Cys Leu Val Gln Ala Glu Glu Ala Val Tyr Glu
                325                 330                 335
Glu Pro Pro Glu Gln Glu Thr Phe Tyr Glu Gln Pro Pro Leu Val Gln
            340                 345                 350
Gln Gln Gly Ala Gly Ser Glu His Ile Asp His His Ile Gln Gly Gln
        355                 360                 365
Gly Leu Ser Gly Gln Gly Leu Cys Ala Arg Ala Leu Tyr Asp Tyr Gln
    370                 375                 380
Ala Ala Asp Asp Thr Glu Ile Ser Phe Asp Pro Glu Asn Leu Ile Thr
385                 390                 395                 400
Gly Ile Glu Val Ile Asp Glu Gly Trp Trp Arg Gly Tyr Gly Pro Asp
                405                 410                 415
Gly His Phe Gly Met Phe Pro Ala Asn Tyr Val Glu Leu Ile Glu
            420                 425                 430

<210> SEQ ID NO 8
<211> LENGTH: 832
<212> TYPE: PRT
<213> ORGANISM: Unknown Organism
<220> FEATURE:
<223> OTHER INFORMATION: Description of Unknown Organism: Tks 202

<400> SEQUENCE: 8

Gln Ser Gln Glu Ala Leu Leu Gly Gly Ala Trp Ser Pro Gly Ala Pro
1               5                   10                  15
His Arg Ser Arg Asp Leu Leu Gly Ala Gly Pro Asn Arg Arg Arg
            20                  25                  30
Glu Pro Leu Gly His Pro Arg Arg Ser Ser Pro Arg Pro Thr Phe Pro
        35                  40                  45
Gln Val Ala Glu Pro Ala Gly Arg Ala Lys Leu Ala Gly Pro Pro Gly
    50                  55                  60
Gly Ser Arg Trp Pro Arg Pro Ser Arg Glu Gly Pro Ala Pro Arg Gly
65                  70                  75                  80
Ala Pro Glu Pro Ser Arg Pro Pro Pro Gly Gly Met Glu Ala Asp
                85                  90                  95
Gly Asp Gly Glu Glu Leu Ala Arg Leu Arg Ser Val Phe Ala Ala Cys
            100                 105                 110
Asp Ala Asn Arg Ser Gly Arg Leu Glu Arg Glu Phe Arg Ala Leu
        115                 120                 125
Cys Thr Glu Leu Arg Val Arg Pro Ala Asp Ala Glu Ala Val Phe Gln
    130                 135                 140
Arg Leu Asp Ala Asp Arg Asp Gly Ala Ile Thr Phe Gln Glu Phe Ala
145                 150                 155                 160
Arg Gly Phe Leu Gly Ser Leu Arg Gly Gly Arg Arg Arg Asp Trp Gly
```

-continued

```
            165                 170                 175
Pro Leu Asp Pro Ala Pro Ala Val Ser Glu Ala Gly Pro Glu Thr His
            180                 185                 190
Asp Ser Glu Glu Asp Glu Gly Asp Glu Asp Ala Ala Ala Leu Ala
            195                 200                 205
Thr Ser Cys Gly Pro Ala Ser Pro Gly Arg Ala Trp Gln Asp Phe Gln
            210                 215                 220
Ala Arg Leu Gly Asp Glu Ala Lys Phe Ile Pro Arg Glu Glu Gln Val
225                 230                 235                 240
Ser Thr Leu Tyr Gln Asn Ile Asn Leu Val Glu Pro Arg Leu Ile Gln
                245                 250                 255
Pro Tyr Glu His Val Ile Lys Asn Phe Ile Arg Glu Ile Arg Leu Gln
            260                 265                 270
Ser Thr Glu Met Glu Asn Leu Ala Ile Ala Val Lys Arg Ala Gln Asp
            275                 280                 285
Lys Ala Met Gln Leu Ser Glu Leu Glu Glu Met Asp Gln Arg
            290                 295                 300
Ile Gln Ala Ala Glu His Lys Thr Arg Lys Asp Glu Lys Arg Lys Ala
305                 310                 315                 320
Glu Glu Ala Leu Ser Asp Leu Arg Arg Gln Tyr Glu Thr Glu Val Gly
                325                 330                 335
Asp Leu Gln Val Thr Ile Lys Lys Leu Arg Lys Leu Glu Glu Gln Ser
            340                 345                 350
Lys Arg Val Ser Gln Lys Glu Asp Val Ala Ala Leu Lys Lys Gln Ile
            355                 360                 365
Tyr Asp Leu Ser Met Glu Asn Gln Lys Val Lys Lys Asp Leu Leu Glu
            370                 375                 380
Ala Gln Thr Asn Ile Ala Phe Leu Gln Ser Glu Leu Asp Ala Leu Lys
385                 390                 395                 400
Ser Asp Tyr Ala Asp Gln Ser Leu Asn Thr Glu Arg Asp Leu Glu Ile
                405                 410                 415
Ile Arg Ala Tyr Thr Glu Asp Arg Asn Ser Leu Glu Arg Gln Ile Glu
            420                 425                 430
Ile Leu Gln Thr Ala Asn Arg Lys Leu His Asp Ser Asn Asp Gly Leu
            435                 440                 445
Arg Ser Ala Leu Glu Asn Ser Tyr Ser Lys Phe Asn Arg Ser Leu His
450                 455                 460
Ile Asn Asn Ile Ser Pro Gly Asn Thr Ile Ser Arg Ser Ser Pro Lys
465                 470                 475                 480
Phe Ile Gly His Ser Pro Gln Pro Leu Gly Tyr Asp Arg Ser Ser Arg
                485                 490                 495
Ser Ser Tyr Val Asp Glu Asp Cys Asp Ser Leu Ala Leu Cys Asp Pro
            500                 505                 510
Leu Gln Arg Thr Asn Cys Glu Val Asp Ser Leu Pro Glu Ser Cys Phe
            515                 520                 525
Asp Ser Gly Leu Ser Thr Leu Arg Asp Pro Asn Glu Tyr Asp Ser Glu
            530                 535                 540
Val Glu Tyr Lys His Gln Arg Gly Phe Gln Arg Ser His Gly Val Gln
545                 550                 555                 560
Glu Ser Phe Gly Gly Asp Ala Ser Asp Thr Asp Val Pro Asp Ile Arg
                565                 570                 575
Asp Glu Glu Thr Phe Gly Leu Glu Asp Val Ala Ser Val Leu Asp Trp
            580                 585                 590
```

```
Lys Pro Gln Gly Ser Val Ser Glu Gly Ser Ile Val Ser Ser Arg
            595                 600                 605
Lys Pro Ile Ser Ala Leu Ser Pro Gln Thr Asp Leu Val Asp Asp Asn
            610                 615                 620
Ala Lys Ser Phe Ser Ser Gln Lys Ala Tyr Lys Ile Val Leu Ala Gly
625                 630                 635                 640
Asp Ala Ala Val Gly Lys Ser Ser Phe Leu Met Arg Leu Cys Lys Asn
                645                 650                 655
Glu Phe Arg Glu Asn Ile Ser Ala Thr Leu Gly Val Asp Phe Gln Met
            660                 665                 670
Lys Thr Leu Ile Val Asp Gly Glu Arg Thr Val Leu Gln Leu Trp Asp
            675                 680                 685
Thr Ala Gly Gln Glu Arg Phe Arg Ser Ile Ala Lys Ser Tyr Phe Arg
            690                 695                 700
Lys Ala Asp Gly Val Leu Leu Leu Tyr Asp Val Thr Cys Glu Lys Ser
705                 710                 715                 720
Phe Leu Asn Ile Arg Glu Trp Val Asp Met Ile Glu Asp Ala Ala His
                725                 730                 735
Glu Thr Val Pro Ile Met Leu Val Gly Asn Lys Ala Asp Ile Arg Asp
            740                 745                 750
Thr Ala Thr Glu Gly Gln Lys Cys Val Pro Gly His Phe Gly Glu
            755                 760                 765
Lys Leu Ala Met Thr Tyr Gly Ala Leu Phe Cys Glu Thr Ser Ala Lys
            770                 775                 780
Asp Gly Ser Asn Ile Val Glu Ala Val Leu His Leu Ala Arg Glu Val
785                 790                 795                 800
Lys Lys Arg Thr Asp Lys Asp Ser Arg Ser Ile Thr Asn Leu Thr
                805                 810                 815
Gly Thr Asn Ser Lys Lys Ser Pro Gln Met Lys Asn Cys Cys Asn Gly
            820                 825                 830
```

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 9
gctgggatcc gatctatgcg cgcgaacctg                                        30

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 10
tgaaagctgt agttggcacc tga                                               23

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 11

```
cgcgaattcc gggctcagtg ggcaaggg                                    28

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 12
gggctcgagt cactcaatga gctccac                                     27

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 13
ccccggatcc gagcgcaagc gaagcat                                     27

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 14
aactcctcga gctaggctgc ctgtctccac                                  30

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 15
ccccggatcc gagcgcaagc gaagcat                                     27

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 16
cacctcgagc tacgcttcca cggccagcag gtc                              33

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 17
aagtggcaac agagataacg cgtaccggg                                   29

<210> SEQ ID NO 18
<211> LENGTH: 22
```

-continued

```
<212> TYPE: DNA
<213> ORGANISM: Artificial Sequence
<220> FEATURE:
<223> OTHER INFORMATION: Description of Artificial Sequence: Primer

<400> SEQUENCE: 18
ggctggttcg gccacttgag gg                                              22

<210> SEQ ID NO 19
<211> LENGTH: 1730
<212> TYPE: PRT
<213> ORGANISM: Unknown Organism
<220> FEATURE:
<223> OTHER INFORMATION: Description of Unknown Organism: Grub

<400> SEQUENCE: 19
```

Ala Glu Gly Arg Gly Gly Glu Gly Arg Pro Ser Arg Pro Ser Leu Ala
 1               5                  10                  15

Gly Pro Arg Gly Leu Glu Ala Gly Ala Gly Arg Ala Ala Thr Ala Ala
            20                  25                  30

Gly Ala Val Pro Pro Asp Pro Ala Arg His Glu Arg Glu Gly Gly
        35                  40                  45

Gly Gly Ala Pro Gly Pro Ala Arg Pro Thr Lys Arg Arg Thr Arg Pro
    50                  55                  60

Gly Ala Glu Pro Trp Ser Leu Ser Gln Trp Arg Thr Val Cys Arg Ala
65                  70                  75                  80

Leu Ser Pro Pro Cys Ile His Pro Leu Arg Gln Gln Pro Pro Cys
                85                  90                  95

Trp Ala Arg Cys Ser Arg Trp Trp Arg Gly Leu Ile Gly Arg Thr His
            100                 105                 110

Gly Thr Arg Trp Thr Ser Trp Tyr Gln Pro Ser Thr Cys Leu Pro Arg
        115                 120                 125

Ser Ser Arg Lys Pro Val Pro Asn Thr Val Asp Ser Ser Ser Met
    130                 135                 140

Arg Gly Gly Arg Ser Ala Cys Met Asn Arg Trp Trp Cys Ser Gln Pro
145                 150                 155                 160

Tyr Pro Gly Asn Cys Cys Ala Gln Glu Thr Ser Ile Cys Arg Trp Cys
                165                 170                 175

Pro Gln Leu Pro Lys His Pro Asp His Ser Ser Val Trp Pro Leu Gly
            180                 185                 190

Val Gly Gly Cys Arg Arg Phe Leu Cys Pro Met Arg Leu Val Pro Thr
        195                 200                 205

Tyr Ser His Leu Ser Gly Tyr Lys Ala Ser Thr Arg Thr Gly Gln Gln
    210                 215                 220

Val Ala Ser Val Pro Ala Tyr Cys Leu Arg Pro Leu Gly Phe Ser Gly
225                 230                 235                 240

Cys Pro Gly Leu Ser Ser Val His Asp Leu Cys Thr Lys Arg Ala
                245                 250                 255

Ser Trp Leu Asp Ile Ser Gln Val His Cys Pro Gln Asn Cys Pro Leu
            260                 265                 270

Asp Leu Gln Gly Phe Pro Ala Leu His Phe Leu Arg Arg Arg Trp Val
        275                 280                 285

Pro Gly Val Leu Gly Met Gly Thr Met Pro Leu Trp Lys Asp Leu Arg
    290                 295                 300

Ala Ser Met Trp Ser Cys Arg Arg Cys Pro Gly Gly Ala Gln Gln Met
305                 310                 315                 320

-continued

```
Leu Lys Ala Pro Gln Ala Ser Pro Glu Ser Gly Arg Tyr Pro Pro Ala
            325                 330                 335
Arg Ala Leu Glu Gly Arg Ala Ala Thr Gly Asp Thr Gly Arg Gly Cys
        340                 345                 350
Thr Arg Arg Ala Trp Gly Leu Gly Ala Arg Met Glu His Ala His Pro
    355                 360                 365
Ala Arg Gly Ala Ala Pro Glu Pro Pro Leu Ser Leu Pro Gln Glu Leu
370                 375                 380
Arg Leu Ser Gln Arg Gln Gln Ser Trp Arg Cys Leu Ser Pro Gln Gln
385                 390                 395                 400
Arg Leu Trp Glu Lys Pro Pro Asp Leu Ala Pro Gly Gln Gly Ser Leu
                405                 410                 415
Glu Glu Glu Glu Glu Ala Arg Gly Leu Lys Asp His Leu Val Pro
            420                 425                 430
Leu Gly Glu Gln Ala Lys Glu Thr Glu Glu Arg Ser Glu Leu Gln Val
        435                 440                 445
Glu Gly Leu Leu Ala Glu Gly Thr Val Pro His Ala Leu Gly Thr
    450                 455                 460
Arg Lys Met Pro Ala Thr Lys Lys Pro Leu Ala Ile Cys Pro His Gln
465                 470                 475                 480
Val Ser Thr Ser Phe Gln Asn Ala Thr Trp Leu Arg Arg Asn Met Lys
                485                 490                 495
Ala Gln Gly Ser Gln Asn Leu Ser Gln Lys Ser Ser Lys Gln Gln Ala
            500                 505                 510
Arg Lys Ser Leu Ser Ser Leu Lys Pro Val Gly Leu Gln Lys Arg Gly
        515                 520                 525
Pro Glu Arg Glu Ser Trp Arg Gly Gln Ala Cys Cys Val Trp Gln Asp
    530                 535                 540
Thr Gln Ala Gln Lys Ala Pro Cys Leu Thr Leu Gln His Leu Arg Trp
545                 550                 555                 560
Arg Leu Cys Arg Lys Glu Lys Gly Thr Thr Phe Gln Lys Arg Pro Leu
                565                 570                 575
Gln Ser Pro Ser Leu Ile Thr Leu Met Leu Gly Thr Trp His Leu Asp
            580                 585                 590
Ser Ser Ser Arg Glu Gly Trp Thr Arg Val Gly Glu Leu Cys Pro Leu
        595                 600                 605
Pro His Arg Ala Leu Leu Arg Ser Pro His Pro Glu Thr Arg Thr
    610                 615                 620
Gln Leu Phe Ile Thr Ser Thr His Cys Ser Gly Leu Ile Tyr Arg His
625                 630                 635                 640
Trp Gly Cys Pro Ser Cys Trp Thr Phe Val Arg His Leu His Cys Leu
                645                 650                 655
Gln His Ser Phe Leu Pro Ala Asn Phe Arg Thr Gln Glu Ile Leu Pro
            660                 665                 670
Leu Phe Ser Gly Cys Phe Ser Phe Met Met Thr Phe Gln Leu Asn Ser
        675                 680                 685
Val Asp Phe Arg Val Leu Arg Cys Cys Gln Arg Met Ile Lys Glu Trp
    690                 695                 700
Pro Ser Gln Arg Ser Cys Ser Gly Ser Glu Val Thr Gly Thr Pro Leu
705                 710                 715                 720
Pro Val Thr Gly Arg Tyr Thr Arg Lys Trp Gly Tyr Val Ala Cys Ala
                725                 730                 735
Lys Val Cys Trp Ala Arg Tyr Gly Arg Pro Leu Arg Ser Trp Arg Glu
```

```
                    740                 745                 750
        Gln Gln Ser Gln Arg Lys Arg Gln Trp Glu Cys Pro Ser His Cys
                755                 760                 765
        Arg Arg Cys Trp Gln Ile Pro Gly Arg His Cys Arg Gly Met Gly Gly
                770                 775                 780
        Pro Ser Gly Cys Ala Pro Leu Pro Ala Ala Ser Trp Arg Ala Lys Ala
        785                 790                 795                 800
        Gln Leu His Cys Ile Arg Lys Trp Thr Arg Pro Phe Thr Ser Leu Cys
                        805                 810                 815
        Ala Ser Pro Thr Cys Thr Cys Ser Ser Lys Ser Ser Gly Ser Ala Cys
                    820                 825                 830
        Gly Asp Ser Ser Arg Cys Cys Ser Gly Ser Arg Ala Gln Gly Arg Ser
                    835                 840                 845
        Ser Trp Gln Ala Leu Leu Cys Leu Gly Thr Pro Cys Leu Pro Cys Arg
                850                 855                 860
        Arg Gln Ser Cys Asp Ser Val Leu Ser Ala Leu Arg Ser Arg Ser Ala
        865                 870                 875                 880
        Trp Pro Arg His Gly Arg Pro Trp Leu Trp Arg Arg Met Pro Pro Pro
                        885                 890                 895
        Arg Arg Cys Trp Ile Ser Leu Asn Ser Gly Trp Ser Arg Leu Arg Val
                    900                 905                 910
        Ala Ser Ile Gly Pro Cys Gly Tyr Ser Ala Ser Ser Arg His Met
                    915                 920                 925
        Asn Gly Trp Met Arg Ala Leu Leu Gly Trp Gln Glu Leu Gly Arg Val
                930                 935                 940
        Gly Arg Leu Cys Trp Leu His Trp Pro Cys Gly Gly Pro Gln Ser Pro
        945                 950                 955                 960
        Val Pro Ala Pro Ser Arg Arg Cys Gly Pro Trp Thr Trp Ala
                        965                 970                 975
        Ala Gln Gln Pro Cys Glu Asn Gly Ala Ala Arg Pro Ala Ala Lys
                    980                 985                 990
        Ser Arg Gly Gly Ser Ser Asn Thr Trp Glu Arg Arg Ala His Gly
                    995                 1000                1005
        Ala Thr Asp Asp Gly Gly Gln Thr Val Pro Ala Val Glu Gly Pro Ser
            1010                1015                1020
        Gly Gly Pro Ala Ala Pro Arg Pro Ala Ser Ala Pro Cys Cys Ser Pro
        1025                1030                1035                1040
        Ala Ala Leu Gly His Gly Gln Pro His Pro Ile Ala Pro Trp Pro His
                        1045                1050                1055
        Val Glu Arg Thr Met Arg Lys Arg Ala Leu Ser Trp Leu Gln Lys Gln
                    1060                1065                1070
        Arg Ala Gly Pro Gln Glu Leu Cys Ser Glu Ala Trp Arg Ser Pro Ala
                    1075                1080                1085
        Leu Arg Trp Thr Gly Arg Ala His His Gly Asn Thr Cys Cys Trp Ala
                    1090                1095                1100
        Gly Leu Gly Gly Gln Thr Asp Pro Gly Glu Ala Pro Pro Gly Trp Ser
        1105                1110                1115                1120
        Ala Ser Glu Ala Ser Val Pro Ser Ser Gly Trp Cys Leu Ser Leu Pro
                        1125                1130                1135
        Val Asn Lys Ile Thr Trp Pro Pro Val Ser Gln Cys His Pro Leu Gly
                    1140                1145                1150
        Leu Ser Arg Leu Asn Phe Gly Ala Pro Gly Leu Leu Pro Val Pro Gly
                    1155                1160                1165
```

-continued

```
Lys Gly Phe Ala Ala Ser Thr Gly His Thr Phe Cys Gly Ser Phe Arg
    1170                1175                1180

Ala Ala Pro Pro Thr Pro Tyr Ala Leu Gly Pro Ala Ser Phe Ala Thr
1185                1190                1195                1200

Gly Thr Ser Ser Ala Phe Met His Ser Thr Ser Thr Asp Thr Asn Trp
                1205                1210                1215

Arg Met Val Trp Leu Arg Ser Val Pro Ala Arg Ala Pro Trp Arg Leu
            1220                1225                1230

Ala Leu Thr Cys Pro Glu Pro Cys Ser Ser Leu Trp Asn Ser Leu Gly
        1235                1240                1245

Met Gly Gly Ser Trp Arg Ser Ser Gly Lys Leu Gly Leu Ser Ser Val
    1250                1255                1260

Leu Ser Ala Gly Pro Leu Gly Leu Leu Tyr Ser Cys Ser Gly Asn Lys
1265                1270                1275                1280

Arg Pro Val Ala Glu Thr Cys Trp Pro Trp Arg Arg Cys Val Ala Val
                1285                1290                1295

Arg Ile Arg Ser Arg Asp Ser Ser Cys Ile Glu Thr Pro Ser Leu Ser
            1300                1305                1310

Ser Val Ala Glu Arg Ser Ala Phe Ala Met Ser Phe Ser Ser Ser Ile
        1315                1320                1325

Ser Ser Cys Ser Ala Ser Ser Arg Ala Leu Lys Gly Gly Gln Arg Cys
    1330                1335                1340

Leu Phe Thr Ser Arg Pro Leu Arg Leu Leu Ile Trp Gly Gln Lys Thr
1345                1350                1355                1360

Ser Gly Thr Ala Asp Ser Ala Leu Ser Cys Gly Phe Gly Gly Gly Val
                1365                1370                1375

His Glu Arg His Thr Leu Cys Arg Gln Pro His Gln Arg Ser Asn Ser
            1380                1385                1390

Ser Gly Gln Val Leu Leu Pro Ser Cys Cys Gly Asp Arg Gln Pro Thr
        1395                1400                1405

Thr Arg Ser Ser Glu Cys Ser Arg Trp Cys Pro Trp Ala Leu Gly Ile
    1410                1415                1420

Asn Pro Ser Trp Thr Ser Lys Pro Leu Gly Ser Gly Arg Val Pro Cys
1425                1430                1435                1440

Ser Leu Glu Glu Pro Pro Ala Pro Gly Pro Pro Trp Pro Cys His Pro
                1445                1450                1455

Leu Ser Met Pro Ala Pro Pro Phe Pro Ala Phe Arg Arg Glu Pro Ala
            1460                1465                1470

Pro Cys Leu Pro Ala Ser Arg Arg Pro Gly Ile Trp Thr Ser Ser
        1475                1480                1485

Lys Phe Pro Trp Pro Gln Lys His Leu Thr Leu Leu Glu Met Cys Pro
    1490                1495                1500

Gln Asp Gln Glu Thr Ala Pro Ala Cys Asn Pro Pro Thr Leu Gly Ala
1505                1510                1515                1520

Ala Leu Pro Pro Trp Pro Val Glu Gly Ser Gly Tyr Pro Asp Arg Val
                1525                1530                1535

Met Leu Glu Pro Val Thr Pro Pro Arg Leu Cys Asp Leu Glu Lys Ile
            1540                1545                1550

Gln Asn Leu Arg Ala Ala Ser Pro Leu Ser Thr Leu Trp Ala Gly Met
        1555                1560                1565

Ala Val Gly His Asn Gly Ala Leu Gly Asp Arg Ile Ser Ser Leu Cys
    1570                1575                1580
```

```
Phe Leu Asp Thr Glu Glu Val Arg Pro Glu Tyr Cys Pro Ala Thr Thr
1585                1590                1595                1600

Ile Ser Ser Leu Pro Ser Leu Val Pro Ser Pro Ala Gly Val Arg Ala
            1605                1610                1615

Ala Thr Leu Leu Ala Phe Ile Pro Trp Arg Trp Gly Ser Tyr Pro Ser
            1620                1625                1630

Ser Gly Ala Phe Pro Ser Trp Ala Thr Val Ser Arg Thr Ser Leu Pro
            1635                1640                1645

Cys Gln Pro Ser Leu Ala Ala His Val Pro Leu Phe Ser His Pro Leu
            1650                1655                1660

Thr Phe Pro Glu Lys Asn His Leu Cys Gln Val Asn Trp Ser Pro Trp
1665                1670                1675                1680

Leu His Ser Glu Val Ser Gln Ala Met Lys Leu Cys Lys Gln Glu Gly
            1685                1690                1695

Val Thr Gly Glu Pro Thr Leu Tyr Met Leu Leu Leu Tyr Tyr Cys
            1700                1705                1710

Tyr Ile Lys Cys Ile Tyr Ser His Phe Ala Ser Lys Lys Lys Lys
            1715                1720                1725

Lys Lys
   1730

<210> SEQ ID NO 20
<211> LENGTH: 1717
<212> TYPE: PRT
<213> ORGANISM: Unknown Organism
<220> FEATURE:
<223> OTHER INFORMATION: Description of Unknown Organism: Grub

<400> SEQUENCE: 20

Leu Lys Gly Gly Ala Gly Arg Gly Gly Arg Leu Gly Pro Pro Trp Arg
  1               5                  10                  15

Gly Pro Ala Ala Trp Lys Pro Glu Arg Ala Glu Pro Pro Arg Pro
             20                  25                  30

Glu Leu Ser Leu Ser Gln Thr Arg Arg Asp Thr Ser Gly Gly Arg Glu
         35                  40                  45

Ala Val Ala Arg Pro Ala Pro Pro Ala Arg Pro Ser Val Gly Arg Gly
     50                  55                  60

Pro Ala Pro Ser His Gly Ala Ala Ser Gly Gly Leu Cys Ala Glu His
 65                  70                  75                  80

Ser Arg Arg Pro Val Ser Thr Leu Gly Asn Ser Pro His Pro Val Gly
             85                  90                  95

Pro Gly Val Pro Gly Gly Gly Glu Asp Leu Ser Gly Gly Arg Thr Glu
            100                 105                 110

Val His Ala Gly Leu Pro Gly Thr Ser Gln Ala Pro Ala Cys Gln Gly
        115                 120                 125

Pro Ala Gly Ser Leu Cys Pro Ile Gln Trp Ile Pro Leu Leu Pro Gly
    130                 135                 140

Val Ala Ala Leu Pro Ala Thr Gly Gly Gly Ala Ala Ser Ser Pro Thr
145                 150                 155                 160

Leu Ala Thr Ala Ala Pro Arg Arg Leu Leu Ser Ala Gly Ala Leu
                165                 170                 175

Ser Cys Pro Ser Thr Pro Thr Ser Thr Gln Val Ser Gly Pro Trp Gly
            180                 185                 190

Trp Ala Gly Ala Gly Gly Ser Cys Ala Gln Gly Leu Cys Leu Pro Ile
        195                 200                 205
```

-continued

```
His Thr Val Ala Thr Arg His Gln Gln Gly Pro Ala Asn Arg Ser Pro
    210                 215                 220
Gln Tyr Leu Pro Thr Val Cys Ala Leu Trp Asp Ser Ala Ala Ala Leu
225                 230                 235                 240
Gly Ala His Leu Ser Thr Ile Cys Ala Gln Arg Gly Pro His Gly Trp
                245                 250                 255
Thr Ser Ala Lys Tyr Thr Ala Pro Arg Thr Ala Leu Trp Thr Ser Arg
            260                 265                 270
Ala Ser Gln Pro Ser Thr Ser Gly Ala Gly Tyr Pro Glu Ser Trp
        275                 280                 285
Gly Trp Ala Gln Cys Pro Cys Gly Arg Thr Gly Arg Val Cys Gly Ala
    290                 295                 300
Val Arg Gly Asp Ala Ala Arg Glu Gly Glu Pro Asn Arg Cys Arg Leu
305                 310                 315                 320
Pro Arg Pro Leu Gln Ser Pro Asp Gly Thr His Pro Gln Gly Arg Trp
                325                 330                 335
Arg Glu Gly Pro Pro Pro Glu Thr Pro Gly Val Asp Ala Pro Glu Gly
            340                 345                 350
Pro Gly Ala Ser Gly Pro Gly Trp Ser Thr Pro Thr Arg Arg Gly Glu
        355                 360                 365
Gln His Arg Ser Leu Pro Val Ser Pro Arg Ser Gly Cys Pro Arg Gly
    370                 375                 380
Ser Ser Leu Gly Gly Val Ala Pro Ser Arg Gly Cys Gly Arg Ser Leu
385                 390                 395                 400
Arg Ile Leu Pro Pro Glu Ala Arg Gly Ala Arg Arg Arg Arg Arg Arg
                405                 410                 415
Pro Gly Gly Arg Thr Thr Trp Tyr Pro Ser Glu Asn Arg Gln Arg Lys
            420                 425                 430
Gln Lys Lys Glu Ala Ser Cys Arg Ser Arg Gly Ser Pro Arg Arg Gly
        435                 440                 445
Gln Cys Pro Thr Glu Pro Trp Gly Gln Gly Arg Cys Gln Pro Pro Arg
    450                 455                 460
Ser Pro Trp Gln Ser Ala Leu Thr Lys Ala Gln Ala Ser Arg Met Pro
465                 470                 475                 480
Pro Gly Gly Gly Ile Arg Leu Arg Glu Ala Arg Ile Ala Lys Arg Ala
                485                 490                 495
Gln Asn Ser Arg Arg Glu Arg Ala Ser Ala Leu Ser Leu Trp Ala Tyr
            500                 505                 510
Arg Arg Gly Gly Arg Arg Glu Arg Ala Gly Gly Ala Arg Pro Ala Val
        515                 520                 525
Tyr Gly Arg Thr His Arg Pro Arg Arg Pro Val His Ser Asn Thr
    530                 535                 540
Ser Ala Gly Asp Cys Ala Gly Arg Lys Arg Gly Gln His Ser Arg Arg
545                 550                 555                 560
Gly Pro Cys Ser Leu Arg Leu Ser Pro Cys Ser Leu Gly Leu Asp Gly
                565                 570                 575
Ile Trp Ile Pro His Pro Asp Gly Arg Gly Gly Pro Glu Trp Ala Ser
            580                 585                 590
Ser Ala Asp His Tyr Pro Thr Val Pro Ser Gly Ala Pro Thr Leu Pro
        595                 600                 605
Arg His Ala Glu His Asn Ser Ser Leu Pro Pro Leu Thr Ala Gln Ala
    610                 615                 620
Ser Thr Asp Thr Gly Ala Val Arg Pro Ala Gly Pro Ser Ser Gly Thr
```

```
                    625             630             635             640
Ser Thr Ala Ser Ser Thr His Ser Cys Leu Glu Pro Thr Ser Gly Leu
                645             650             655
Arg Arg Ser Ser Pro Cys Ser Ala Ala Asp Ser His Ser Pro Ser
            660             665             670
Asn Thr Leu Trp Ile Ser Gly Cys Gly Ala Val Arg Glu Ser Glu Lys
            675             680             685
Ser Gly Gln Ala Arg Gly Ala Ala Val Gly Val Arg Arg Ser Gln Gly
    690             695             700
Pro Leu Ser Gln Ser Leu Gly Arg Asp Thr Pro Gly Ser Gly Lys Ala
705             710             715             720
Met Ser Pro Val Pro Arg Cys Ala Gly Leu Gly Thr Ala Gly His Gly
                725             730             735
Ala Gly Gly Ser Ser Arg Ala Arg Gly Arg Gly Gly Ser Gly Asn Ala
                740             745             750
Gln Ala Thr Ala Glu Gly Ala Gly Arg Ser Pro Ala Asp Gly Thr Ala
                755             760             765
Glu Gly Trp Gly Gly His Pro Asp Glu Ala Ala Leu His Ser Gln Gln
    770             775             780
Gln Ala Gly Gly Pro Arg Pro Ser Tyr Thr Val Ser Gly Ser Gly Arg
785             790             795             800
Gly His Ser Pro Ala Cys Ala Pro Leu Gln Pro Ala Arg Ala Ala Ala
                805             810             815
Arg Ala Ala Ala Val Pro Ala Ala Thr Pro Ala Gly Val Ala Val Ala
            820             825             830
Leu Gly Pro Arg Gly Gly Ala Ala Gly Lys Leu Cys Tyr Ala Trp Gly
            835             840             845
His Leu Val Cys Pro Ala Gly Asp Arg Ala Ala Ile Pro Cys Phe Gln
    850             855             860
Arg Gly Pro Gly Ala Pro Gly Pro Gly Thr Gly Gly Pro Gly Ser Gly
865             870             875             880
Gly Glu Cys His Leu Pro Glu Gly Ala Gly Tyr Leu Thr Ala Ala Gly
                885             890             895
Ala Gly Glu Trp Pro Pro Ser Gly Pro Ala Ala Thr Ala Leu Leu Pro
                900             905             910
Ala Gly Thr Met Gly Gly Leu Cys Ser Ala Gly Arg Ser Trp Ala
            915             920             925
Gly Ser Gly Gly Cys Ala Gly Cys Thr Gly Pro Ala Ala Gly Pro Arg
    930             935             940
Ala Gln Cys Arg His Leu Pro Gly Asp Ala Gly Pro Gly Pro Gly Pro
945             950             955             960
Gly Gln Pro Ser Ser Pro Ala Arg Met Gly Pro Leu Gly Pro Leu
                965             970             975
Pro Arg Ala Arg Glu Glu Asp Pro Ala Thr Pro Gly Arg Gly Gly Glu
            980             985             990
Pro Thr Gly Leu Pro Thr Thr Ala Gly Arg Arg Cys Gln Gln Trp Arg
            995             1000            1005
Gly Pro Val Gly Ala Pro Gln Pro Leu Ala Gln Pro Gln Leu Leu Ala
    1010            1015            1020
Ala Pro Gln Gln Pro Trp Ala Thr Ala Ser Pro Ile Pro Leu Leu Pro
1025            1030            1035            1040
Gly Pro Met Trp Arg Gly Leu Gly Arg Gly Pro Ala Gly Ser Arg Ser
                1045            1050            1055
```

-continued

Arg Gly Gln Ala Pro Lys Ser Cys Ala Asp Pro Arg Pro Gly His
          1060                1065                1070

Gln His Gly Gly Arg Gln Asp Val Leu Thr Thr Gly Thr Arg Ala Ala
     1075                1080                1085

Gly Pro Gly Gly Ala Arg Arg Thr Leu Gly Ser Arg Arg Pro Pro Asp
1090                1095                1100

Gly Ala Gln Ala Lys His Gln Cys Pro Ala Ala Ala Gly Val Ala Asp
1105                1110                1115                1120

Cys Leu Thr Arg Leu Arg Gly His Leu Glu Ala Ser Ala Thr Pro Trp
          1125                1130                1135

Ala Ala Asp Ala Thr Ser Gly His Leu Gly Cys Cys Pro Glu Cys Pro
     1140                1145                1150

Gly Lys Ala Ser Gln Leu Pro Pro Asp Thr Leu Ser Ala Gly Ala Ser
1155                1160                1165

Gly Leu Arg His Pro Pro Pro Thr His Trp Gly Leu Leu Pro Ser Pro
     1170                1175                1180

Arg Gly Pro Val Gln Pro Leu Cys Thr Val Arg Glu Ala Pro Thr Gln
1185                1190                1195                1200

Thr Gly Glu Trp Ser Gly Cys Ala Gln Ser Leu Lys Gln Gly Leu His
          1205                1210                1215

Gly Gly Trp Pro Leu Pro Ala Pro Ser Pro Ala Ala Ala Ser Gly Thr
          1220                1225                1230

Ala Asp Ser Val Trp Ala Ala Pro Gly Gly Ala Pro Glu Gly Ser Trp
     1235                1240                1245

Ala Ala Gln Phe Val Pro Gly Pro Trp Gly Cys Cys Thr Ala Ala Pro
     1250                1255                1260

Gly Thr Arg Gly Pro Trp Gln Arg Pro Ala Gly Arg Gly Gly Gly Ala
1265                1270                1275                1280

Trp Leu Asp Arg Ser Glu Gly Ala Gly Thr Ala Leu Ala Ser Arg Pro
          1285                1290                1295

Leu His Cys His Leu Trp Pro Lys Glu Val Pro Ser Pro Cys Leu Ser
          1300                1305                1310

Leu Arg Ala Ser Pro Pro Val Gln Gln Ala Gln Gly Pro Arg Gly Val
     1315                1320                1325

Arg Asp Val Cys Leu Gln Ala Gly Leu Asp Cys Tyr Gly Ala Asp Arg
1330                1335                1340

Lys His Arg Gly Gln Arg Thr Leu Leu Val Val Val Ser Ala Ala Ala
1345                1350                1355                1360

Cys Thr Arg Gly Ile His Ser Ala Gly Asn Leu Thr Arg Asp Gln Thr
          1365                1370                1375

Gln Val Asp Lys Phe Tyr Cys Pro Ala Ala Val Glu Thr Gly Ser Pro
     1380                1385                1390

Gln Gln Gly Ala Pro Ser Ala Ala Asp Gly Val His Gly His Trp Glu
     1395                1400                1405

Thr Leu Pro Gly His Gln Ser Pro Trp Gly Ala Asp Ala Glu Cys Pro
     1410                1415                1420

Ala His Trp Lys Ser Arg Pro His Pro Gly Leu Arg Gly Arg Val Ile
1425                1430                1435                1440

Leu Ala Cys Arg Pro Leu Pro Ser Arg Pro Phe Ala Gly Ser Leu Leu
          1445                1450                1455

Pro Ala Cys Pro Arg Arg Gly Gly Gly Leu Gly Ser Gly Arg Gln Ala
     1460                1465                1470

```
Asn Phe Pro Gly Pro Arg Asn Thr Leu Phe Trp Arg Cys Val Pro Arg
        1475                1480                1485

Thr Lys Lys Gln Pro Gln Pro Ala Thr Pro Pro Trp Glu Gln His
    1490                1495                1500

Ser His Pro Gly Gln Ser Arg Asp Leu Arg Ala Ile Pro Thr Glu Ser
1505                1510                1515                1520

Cys Ser Ser Pro Glu Pro His His Ala Ser Val Thr Trp Arg Arg Ser
            1525                1530                1535

Arg Thr Cys Val Gln Leu Leu Leu Ser Ala His Phe Gly Leu Gly Trp
        1540                1545                1550

Gln Trp Gly Ile Met Glu Pro Trp Ala Ile Ala Glu Phe Leu Pro Ser
    1555                1560                1565

Ala Ser Trp Thr Gln Arg Arg Ser Asn Asp Gln Ser Ile Ala Leu Pro
1570                1575                1580

Pro Leu Ser Leu Val Ser Leu Ala Trp Cys Leu Leu Leu Gln Glu Ser
            1585                1590                1595                1600

Glu Gln Pro His Cys Leu Pro Ser Tyr Pro Gly Gly Glu Val Ile
        1605                1610                1615

Pro Leu Pro Val Leu Ser His Pro Gly Pro Leu Tyr Pro Gly His His
    1620                1625                1630

Ser His Ala Ser Pro Pro Trp Gln Pro Met Phe Pro Ser Phe Leu Thr
1635                1640                1645

Pro Leu Ser Leu Arg Arg Ile Ile Ser Ala Arg Ser Thr Gly Val Pro
            1650                1655                1660

Gly Asp Ser Ile Leu Arg Cys His Lys Gln Ser Tyr Ala Asn Asn Arg
1665                1670                1675                1680

Arg Val Gln Gly Asn Arg Arg Leu Tyr Ile Cys Asn Tyr Cys Tyr Tyr
            1685                1690                1695

Asn Thr Ile Val Ile Leu Asn Val Phe Thr His Thr Leu Pro Leu Lys
        1700                1705                1710

Lys Lys Lys Lys Lys
        1715

<210> SEQ ID NO 21
<211> LENGTH: 1733
<212> TYPE: PRT
<213> ORGANISM: Unknown Organism
<220> FEATURE:
<223> OTHER INFORMATION: Description of Unknown Organism: Grub

<400> SEQUENCE: 21

Phe Phe Phe Phe Phe Phe Phe Arg Gly Lys Val Val Asn Thr Phe Asn
  1               5                  10                  15

Ile Thr Ile Val Leu Gln Leu His Ile Ser Leu Arg Phe Pro Cys His
             20                  25                  30

Thr Leu Leu Leu Phe Ala Leu His Cys Leu His Leu Arg Met Glu Ser
         35                  40                  45

Pro Gly Thr Pro Val Asp Leu Ala Glu Met Ile Leu Leu Arg Glu Ser
     50                  55                  60

Gln Gly Val Arg Lys Glu Gly Asn Met Gly Cys Gln Gly Gly Leu Ala
 65                  70                  75                  80

Trp Glu Cys Pro Gly Tyr Ser Gly Pro Gly Trp Glu Ser Thr Gly Arg
                 85                  90                  95

Gly Ile Thr Ser Pro Pro Pro Gly Tyr Glu Gly Lys Gln Cys Gly Cys
            100                 105                 110
```

-continued

```
Ser Asp Ser Cys Arg Arg His Gln Ala Arg Glu Thr Arg Asp Ser
        115                 120                 125

Gly Gly Arg Ala Ile Leu Trp Ser Leu Asp Leu Leu Cys Val Gln Glu
130                 135                 140

Ala Glu Gly Arg Asn Ser Ala Ile Ala Gln Gly Ser Ile Met Pro His
145                 150                 155                 160

Cys His Pro Ser Pro Lys Cys Ala Glu Arg Arg Ser Cys Thr Gln Val
                165                 170                 175

Leu Asp Leu Leu Gln Val Thr Glu Ala Trp Trp Gly His Ser Gly Leu
            180                 185                 190

Glu His Asp Ser Val Gly Ile Ala Leu Arg Ser Leu Asp Trp Pro Gly
        195                 200                 205

Trp Glu Cys Cys Ser Gln Gly Gly Val Ala Gly Trp Gly Cys Phe
210                 215                 220

Leu Val Leu Gly Thr His Leu Gln Lys Ser Gln Val Phe Leu Gly Pro
225                 230                 235                 240

Gly Lys Phe Ala Arg Pro Asp Pro Arg Pro Pro Arg Arg Gly Gln
                245                 250                 255

Ala Gly Ser Arg Leu Pro Ala Lys Gly Arg Glu Gly Arg Gly Arg His
            260                 265                 270

Ala Gln Arg Met Thr Arg Pro Arg Arg Pro Gly Cys Gly Arg Leu Phe
        275                 280                 285

Gln Ala Gly His Ser Ala Ser Ala Pro Gln Gly Leu Cys Pro Gly Arg
        290                 295                 300

Val Tyr Ser Gln Cys Pro Trp Thr Pro Ser Ala Ala Leu Gly Ala Pro
305                 310                 315                 320

Cys Cys Gly Leu Pro Val Ser Thr Ala Ala Gly Gln Asn Leu Ser Thr
                325                 330                 335

Val Ser Leu Val Arg Leu Pro Ala Glu Cys Met Pro Leu Val His Ala
            340                 345                 350

Ala Ala Glu Thr Thr Thr Gln Ser Arg Val Arg Cys Pro Arg Cys Phe
        355                 360                 365

Leu Ser Ala Pro Tyr Gln Gln Ser Arg Pro Ala Cys Lys Gln Thr Ser
370                 375                 380

Leu Thr Pro Leu Gln Gly Pro Ala Cys Thr Gly Gly Asp Ala Arg Arg
385                 390                 395                 400

Glu Arg His Gly Glu Gly Thr Ser Phe Gly His Arg Gln Arg Gly Leu
                405                 410                 415

Asp Ala Arg Ala Val Pro Ala Pro Ser Asp Leu Ser His Ser His Ala
            420                 425                 430

Pro Pro Pro Arg Pro Ala Gly Leu Cys His Gly Pro Leu Val Pro Gly
        435                 440                 445

Ala Ala Val Gln Gln Pro Gln Gly Pro Gly Thr Gln Asn Ala Gln Ala
450                 455                 460

Gln Leu Pro Ser Gly Ala Pro Pro Gly Ala Ala His Thr Glu Ser Ala
465                 470                 475                 480

Val Pro Glu Ala Ala Ala Gly Leu Gly Ala Gly Lys Gly Gln Pro Pro
                485                 490                 495

Trp Ser Pro Cys Leu Arg Asp Ala Gln Pro Asp His Ser Pro Val Cys
            500                 505                 510

Val Gly Ala Ser Arg Thr Val His Lys Gly Thr Gly Pro Arg Gly Glu
        515                 520                 525

Gly Ser Arg Pro Gln Cys Val Gly Gly Gly Trp Arg Ser Pro Glu Ala
```

```
                530                 535                 540
Pro Ala Glu Ser Val Ser Gly Gly Ser Cys Glu Ala Phe Pro Gly His
545                 550                 555                 560

Ser Gly Gln Gln Pro Arg Cys Pro Glu Val Gln Ala Ser Ala Gln Ala
                565                 570                 575

Gln Gly Val Ala Leu Ala His Ser Arg Trp Pro Arg Asn Leu Val His
                580                 585                 590

Arg Gln Ser Ala Gln Thr Pro Ala Ala Gly His Cys Phe Ala Cys
            595                 600                 605

Ala Pro Ser Gly Gly Arg Leu Leu Pro Arg Val Arg Leu Ala Pro Pro
610                 615                 620

Gly Pro Ala Ala Arg Val Pro Val Ser Thr Ser Cys Leu Pro Pro
625                 630                 635                 640

Gln Cys Trp Pro Pro Gly Leu Gly Ser Ala Gln Leu Leu Gly Ala Cys
                645                 650                 655

Pro Leu Leu Leu Glu Pro Ala Gln Gly Pro Leu Pro His Ser Pro Leu
                660                 665                 670

His Met Gly Pro Gly Ser Asn Gly Met Gly Leu Ala Val Ala Gln Gly
            675                 680                 685

Cys Trp Gly Ala Ala Arg Ser Gly Trp Ala Arg Gly Cys Gly Ala Pro
690                 695                 700

Thr Gly Pro Leu His Cys Trp His Arg Leu Pro Ala Val Val Gly Ser
705                 710                 715                 720

Pro Val Gly Ser Pro Leu Pro Gly Val Ala Gly Ser Ser Ser Leu
                725                 730                 735

Ala Leu Gly Ser Gly Pro Gly Ser Gly Pro Ile Leu Ala Gly Leu Leu
            740                 745                 750

Gly Cys Pro Gly Pro Gly Pro Ala Ser Pro Gly Arg Cys Arg
            755                 760                 765

His Trp Ala Leu Gly Pro Ala Ala Gly Pro Val Gln Pro Ala Gln Pro
770                 775                 780

Pro Asp Pro Ala Gln Leu Leu Pro Ala Glu Gln Ser Pro His Pro Pro
785                 790                 795                 800

Ile His Val Pro Ala Gly Arg Ser Ala Val Ala Gly Pro Asp Gly
                805                 810                 815

Gly His Ser Gln Pro Ala Pro Ala Ala Val Gln Arg Tyr Pro Ala Pro
            820                 825                 830

Ser Gly Arg Trp His Ser Pro Glu Pro Gly Pro Val Pro Gly
            835                 840                 845

Pro Gly Ala Pro Gly Pro Gln Arg Lys His Gly Ile Ala Ala Leu Ser
850                 855                 860

Pro Ala Gly Gln Thr Arg Cys Pro Gln Ala Gln Ser Leu Pro Ala Ala
865                 870                 875                 880

Pro Pro Leu Gly Pro Arg Ala Thr Ala Pro Ala Gly Val Ala Ala
                885                 890                 895

Gly Thr Ala Ala Ala Leu Ala Ala Ala Arg Ala Gly Trp Arg Gly Ala
            900                 905                 910

Gln Ala Gly Glu Trp Pro Arg Pro Leu Pro Asp Thr Val Leu Gly Leu
            915                 920                 925

Gly Pro Pro Ala Cys Cys Trp Glu Trp Ser Ala Ala Ser Ser Gly Trp
            930                 935                 940

Pro Pro His Pro Ser Ala Val Pro Ser Ala Gly Asp Leu Pro Ala Pro
945                 950                 955                 960
```

-continued

```
Ser Ala Val Ala Trp Ala Phe Pro Leu Pro Pro Leu Ala Leu
            965                 970                 975

Leu Leu Pro Pro Ala Pro Gln Trp Pro Ala Val Pro Ser Ala His
        980                 985                 990

Leu Gly Thr Gly Asp Ile Ala Leu Pro Leu Pro Gly Val Ser Leu Pro
            995                1000                1005

Ser Asp Trp Glu Arg Gly Pro Cys Asp Leu Leu Thr Pro Thr Ala Ala
1010                1015                1020

Pro Leu Ala Trp Pro Leu Phe Ser Asp His Ser Leu Thr Ala Pro Gln
1025                1030                1035                1040

His Pro Glu Ile His Arg Val Gln Leu Glu Gly His His Glu Glu Ser
            1045                1050                1055

Ala Ala Ala Glu Gln Gly Glu Asp Leu Leu Ser Pro Glu Val Gly Ser
                1060                1065                1070

Arg Gln Glu Val Leu Glu Ala Val Glu Val Pro Asp Glu Gly Pro Ala
            1075                1080                1085

Gly Arg Thr Ala Pro Val Ser Val Asp Gln Ala Ala Val Ser Gly Gly
            1090                1095                1100

Asn Glu Glu Leu Cys Ser Ala Cys Leu Gly Arg Val Gly Ala Pro Gln
1105                1110                1115                1120

Glu Gly Thr Val Gly Trp Ser Ala Glu Leu Ala His Ser Gly Pro Pro
            1125                1130                1135

Leu Pro Ser Gly Gly Ile Gln Met Pro Ser Ser Pro Lys Leu His Gln
            1140                1145                1150

Gly Asp Gln Arg Arg Arg Leu Gln Gly Pro Leu Leu Glu Cys Cys Pro
            1155                1160                1165

Leu Phe Leu Pro Ala Gln Ser Pro Ala Glu Val Leu Glu Cys Gln Thr
1170                1175                1180

Gly Gly Leu Leu Gly Leu Cys Val Leu Pro Tyr Thr Ala Gly Leu Ala
1185                1190                1195                1200

Pro Pro Ala Leu Ser Leu Arg Pro Pro Leu Leu Ala His Arg Leu Gln
                1205                1210                1215

Arg Ala Glu Ala Leu Ser Arg Leu Leu Phe Ala Leu Leu Ala Gln Ile
            1220                1225                1230

Leu Ala Ser Leu Ser Leu His Ile Pro Pro Gly Gly Ile Leu Glu
            1235                1240                1245

Ala Cys Ala His Leu Val Arg Ala Asp Cys Gln Gly Leu Leu Gly Gly
            1250                1255                1260

Trp His Leu Pro Cys Pro Gln Gly Ser Val Gly His Cys Pro Leu Leu
1265                1270                1275                1280

Gly Glu Pro Leu Asp Leu Gln Leu Ala Ser Phe Cys Phe Leu Cys
                1285                1290                1295

Leu Phe Ser Glu Gly Tyr Gln Val Val Leu Gln Pro Gly Leu Leu
            1300                1305                1310

Leu Leu Leu Leu Ala Pro Leu Ala Ser Gly Gly Lys Ile Arg Arg Leu
            1315                1320                1325

Leu Pro Gln Pro Leu Leu Gly Ala Gln Thr Pro Pro Arg Leu Leu Pro
1330                1335                1340

Leu Gly Gln Pro Gln Leu Leu Gly Glu Thr Gln Gly Arg Leu Arg Cys
1345                1350                1355                1360

Cys Ser Pro Arg Arg Val Gly Val Leu His Pro Gly Pro Glu Ala Pro
            1365                1370                1375
```

```
Gly Pro Ser Gly Ala Ser Thr Pro Gly Val Ser Gly Gly Pro Ser
        1380                1385                1390

Leu Gln Arg Pro Cys Gly Trp Val Pro Ser Gly Leu Trp Arg Gly Leu
        1395                1400                1405

Gly Ser Leu Gln His Leu Leu Gly Ser Pro Ser Arg Ala Ala Ser Pro
    1410                1415                1420

Leu Thr Ala Pro His Thr Arg Pro Gln Val Leu Pro Gln Gly His Cys
1425                1430                1435                1440

Ala His Pro Gln Asp Ser Gly Tyr Pro Ala Pro Pro Gln Glu Val Glu
            1445                1450                1455

Gly Trp Glu Ala Leu Glu Val Gln Arg Ala Val Leu Gly Ala Val Tyr
        1460                1465                1470

Leu Ala Asp Val Gln Pro Gly Pro Leu Cys Ala Gln Ile Val Asp Arg
    1475                1480                1485

Ala Gln Pro Arg Ala Ala Ala Glu Ser Gln Arg Ala Gln Thr Val Gly
    1490                1495                1500

Arg Tyr Gly Asp Leu Leu Ala Gly Pro Cys Cys Leu Val Ala Thr Gln
1505                1510                1515                1520

Val Ile Gly Arg His Lys Pro His Trp Ala Gln Glu Pro Pro Ala Pro
        1525                1530                1535

Ala His Pro Gln Gly Pro Asp Thr Val Leu Val Gly Val Leu Gly Gln
        1540                1545                1550

Leu Arg Ala Pro Pro Ala Asp Arg Ser Leu Leu Gly Ala Ala Val Ala
        1555                1560                1565

Arg Val Gly Leu Leu Ala Ala Pro Pro Val His Ala Gly Arg Ala
    1570                1575                1580

Ala Thr Pro His Gly Arg Arg Gly Ile His Cys Ile Gly His Arg Leu
1585                1590                1595                1600

Pro Ala Gly Pro Trp Gln Ala Gly Ala Trp Leu Val Pro Gly Ser Pro
        1605                1610                1615

Ala Cys Thr Ser Val Arg Pro Pro Asp Lys Ser Ser Pro Pro Pro Gly
        1620                1625                1630

Thr Pro Gly Pro Thr Gly Trp Gly Leu Leu Pro Gln Arg Val Asp Thr
        1635                1640                1645

Gly Arg Arg Glu Cys Ser Ala His Ser Pro Leu Ala Gln Ala Pro
    1650                1655                1660

Trp Leu Gly Ala Gly Pro Arg Pro Thr Leu Gly Arg Ala Gly Ala
1665                1670                1675                1680

Gly Arg Ala Thr Ala Ser Leu Pro Pro Leu Val Ser Arg Arg Val Trp
            1685                1690                1695

Leu Arg Asp Ser Ser Gly Arg Gly Gly Gly Ser Ala Arg Ser Gly Phe
        1700                1705                1710

Gln Ala Ala Gly Pro Arg Gln Gly Gly Pro Arg Arg Pro Pro Leu Pro
    1715                1720                1725

Ala Pro Pro Phe Ser
    1730

<210> SEQ ID NO 22
<211> LENGTH: 1744
<212> TYPE: PRT
<213> ORGANISM: Unknown Organism
<220> FEATURE:
<223> OTHER INFORMATION: Description of Unknown Organism: Grub

<400> SEQUENCE: 22
```

-continued

```
Phe Phe Phe Phe Phe Phe Leu Glu Ala Lys Cys Glu Ile His Leu Ile
 1               5                  10                  15

Gln Tyr Tyr Asn Asn Ser Asn Tyr Ile Tyr Lys Val Tyr Gly Ser Pro
                 20                  25                  30

Val Thr Pro Ser Tyr Cys Leu His Ser Phe Ile Ala Cys Asp Thr Ser
             35                  40                  45

Glu Trp Ser His Gln Gly Leu Gln Leu Thr Trp Gln Arg Phe Phe Ser
         50                  55                  60

Gly Lys Val Arg Gly Glu Lys Arg Gly Thr Trp Ala Ala Arg Glu Gly
 65                  70                  75                  80

Trp His Gly Ser Asp Val Leu Asp Thr Val Ala Gln Asp Gly Lys Ala
                 85                  90                  95

Pro Glu Glu Gly Leu Pro His Leu Gln Gly Met Lys Ala Ser Asn Val
             100                 105                 110

Ala Ala Leu Thr Pro Ala Gly Glu Gly Thr Lys Leu Gly Arg Leu Glu
             115                 120                 125

Ile Val Val Ala Gly Gln Tyr Ser Gly Arg Thr Ser Ser Val Ser Arg
 130                 135                 140

Lys Gln Arg Glu Glu Ile Gln Arg Ser Pro Arg Ala Pro Leu Cys Pro
145                 150                 155                 160

Thr Ala Ile Pro Ala Gln Ser Val Leu Arg Gly Glu Ala Ala Arg Lys
                 165                 170                 175

Phe Trp Ile Phe Ser Arg Ser Gln Arg Arg Gly Gly Val Thr Gln Gly
             180                 185                 190

Ser Ser Met Thr Leu Ser Gly Pro Asp Pro Ser Thr Gly Gln Gly Gly
             195                 200                 205

Ser Ala Ala Pro Arg Val Gly Leu Gln Ala Gly Ala Val Ser Trp
 210                 215                 220

Ser Trp Gly His Ile Ser Arg Arg Val Lys Cys Phe Trp Gly Gln Gly
225                 230                 235                 240

Asn Leu Leu Asp Val Gln Ile Pro Gly Leu Leu Asp Ala Gly Arg
                 245                 250                 255

Gln Gly Ala Gly Ser Arg Arg Lys Ala Gly Lys Gly Gly Ala Gly Met
             260                 265                 270

Leu Lys Gly His Gly His Gly Gly Pro Gly Ala Gly Gly Ser Ser Ser
             275                 280                 285

Glu Gln Gly Thr Gln Arg Pro Leu Pro Lys Gly Phe Asp Val Gln Glu
             290                 295                 300

Gly Phe Ile Pro Asn Ala His Gly His His Leu Leu His Ser Glu Leu
305                 310                 315                 320

Leu Val Val Gly Cys Leu Ser Pro Gln Leu Gly Asn Arg Thr Cys
                 325                 330                 335

Pro Leu Glu Phe Asp Leu Trp Gly Cys Leu Gln Ser Val Cys Leu Ser
             340                 345                 350

Cys Thr Pro Pro Lys Pro Gln Leu Lys Ala Glu Ser Ala Val Pro
             355                 360                 365

Asp Val Phe Cys Gln Pro His Ile Ser Ser Leu Lys Gly Leu Leu Val
             370                 375                 380

Asn Lys His Leu Pro Pro Phe Arg Ala Leu Glu Leu Ala Glu Gln Glu
385                 390                 395                 400

Glu Met Leu Glu Glu Lys Asp Met Ala Lys Ala Leu Leu Ser Ala Thr
             405                 410                 415

Asp Asp Ser Glu Gly Val Ser Met Gln Glu Leu Ser Leu Leu Leu Gln
```

```
                   420              425              430
Ile Tyr Leu Thr Ala Thr His Arg Leu His Gly Gln Gln Val Ser Ala
        435              440              445

Thr Gly Leu Leu Phe Pro Glu Gln Leu Tyr Ser Ser Pro Lys Gly Pro
        450              455              460

Ala Leu Arg Thr Glu Leu Arg Pro Ser Phe Pro Gln Glu Leu Leu Gln
465              470              475              480

Glu Pro Pro Ile Pro Ser Gln Leu Phe Gln Arg Leu Leu Gln Gly Ser
                 485              490              495

Gly Gln Val Arg Ala Ser Leu His Gly Ala Leu Ala Gly Thr Glu Arg
            500              505              510

Ser Gln Thr Ile Leu Gln Phe Val Ser Val Leu His Val Leu Cys Ile
        515              520              525

Lys Ala Glu Leu Val Pro Val Ala Lys Glu Ala Gly Pro Asn Ala Gly
        530              535              540

Val Gly Gly Ala Ala Leu Lys Leu Pro Gln Lys Val Cys Pro Val Glu
545              550              555              560

Ala Ala Lys Pro Phe Pro Gly Thr Gln Gly Ser Ser Pro Gly Ala Pro
                 565              570              575

Lys Phe Arg Arg Gln Leu Arg Pro Arg Gly Trp His Trp Leu Thr Gln
            580              585              590

Gly Gly His Val Ile Leu Phe Thr Gly Asn Gln Leu Arg His Gln Pro
        595              600              605

Leu Leu Gly Thr Asp Ala Ser Leu Ala Leu His Pro Gly Gly Ala Tyr
        610              615              620

Ser Pro Gly Ser Val Trp Pro Pro Ser Pro Ala Gln Gln His Val Phe
625              630              635              640

Pro Trp Ala Arg Pro Val Tyr His Leu Ser Ala Gly Asp Leu Gln Ala
                 645              650              655

Ser Asp Gln His Ser Ser Trp Gly Pro Ala Leu Cys Phe Trp Ser Gln
            660              665              670

Leu Arg Ala Leu Phe Leu Ile Val Leu Ser Thr Trp Gly Gln Gly Ala
        675              680              685

Met Gly Trp Gly Trp Pro Trp Pro Arg Ala Ala Gly Glu Gln Gln Gly
        690              695              700

Ala Glu Ala Gly Arg Gly Ala Ala Gly Pro Pro Leu Gly Pro Ser Thr
705              710              715              720

Ala Gly Thr Val Cys Pro Pro Ser Ser Val Ala Pro Trp Ala Arg Leu
                 725              730              735

Leu Ser Gln Val Leu Leu Asp Pro Pro Leu Leu Leu Ala Ala Gly Leu
            740              745              750

Ala Ala Ala Pro Phe Ser Gln Gly Cys Trp Ala Ala Gln Val Gln Gly
        755              760              765

Gln Gly Pro His Leu Leu Glu Gly Ala Gly Thr Gly Leu Trp Gly Pro
        770              775              780

Pro Gln Gly Gln Cys Ser Gln His Ser Leu Pro Thr Arg Pro Ser Ser
785              790              795              800

Cys Gln Pro Ser Lys Ala Leu Ile His Pro Phe Met Cys Leu Leu Glu
                 805              810              815

Glu Ala Leu Pro Gln Gly Pro Met Glu Ala Thr Leu Asn Leu Leu Gln
            820              825              830

Pro Leu Phe Lys Asp Ile Gln His Leu Leu Gly Gly Ile Leu Leu
        835              840              845
```

```
Gln Ser Gln Gly Leu Pro Cys Leu Gly Gln Ala Leu Leu Asp Leu Ser
    850                 855                 860

Ala Glu Ser Thr Glu Ser Gln Leu Cys Leu Leu Gln Gly Arg Gln Gly
865                 870                 875                 880

Val Pro Arg His Ser Lys Ala Cys Gln Leu Leu Leu Pro Trp Ala Arg
                885                 890                 895

Glu Pro Leu Gln His Leu Leu Ser Pro Gln Ala Leu Pro Leu Leu
            900                 905                 910

Leu Leu Leu His Val Gln Val Gly Glu Ala His Lys Leu Val Asn Gly
            915                 920                 925

Leu Val His Phe Leu Ile Gln Cys Ser Trp Ala Leu Ala Leu Gln Leu
    930                 935                 940

Ala Ala Gly Ser Gly Ala Gln Pro His Gln Asp Gly Pro Pro Ile Pro
945                 950                 955                 960

Leu Gln Cys Arg Gln Pro Gly Ile Cys Gln His Leu Leu Gln Trp Leu
                965                 970                 975

Gly His Ser His Cys Leu Leu Phe Leu Trp Leu Cys Cys Ser Leu Gln
            980                 985                 990

Leu Leu Asn Gly Leu Pro Tyr Arg Ala Gln His Thr Leu Ala Gln Ala
        995                 1000                1005

Thr Pro Tyr His Phe Leu Val Tyr Leu Tyr Pro Val Thr Gly Arg Gly
    1010                1015                1020

Val Pro Val Thr Ser Leu Pro Leu Gln Leu Leu Trp Leu Gly His Ser
1025                1030                1035                1040

Phe Gln Ile Ile Leu Gln His Leu Ser Thr Leu Lys Ser Thr Glu Phe
                1045                1050                1055

Ser Trp Lys Val Ile Met Asn Glu Asn Gln Gln Pro Leu Asn Lys Gly
            1060                1065                1070

Arg Ile Ser Val Leu Lys Leu Ala Gln Gly Arg Asn Glu Cys Trp Arg
        1075                1080                1085

Gln Trp Arg Cys Leu Thr Lys Val Gln Gln Asp Gly Gln Pro Gln Cys
    1090                1095                1100

Leu Ile Arg Pro Glu Gln Val Glu Val Met Lys Ser Cys Val Gln Arg
1105                1110                1115                1120

Val Ser Gly Gly Trp Gly Leu Leu Arg Arg Ala Arg Trp Gly Asn Gly
                1125                1130                1135

Gln Gln Ser Ser Pro Thr Leu Val His Pro Ser Arg Gln Asp Glu Glu
            1140                1145                1150

Ser Arg Cys His Gln Val Pro Ser Tyr Ile Arg Val Ile Arg Asp Gly
        1155                1160                1165

Asp Cys Lys Gly Leu Phe Trp Asn Val Val Pro Phe Ser Phe Leu His
    1170                1175                1180

Ser Leu Gln Arg Arg Cys Trp Ser Val Arg Gln Gly Ala Phe Trp Ala
1185                1190                1195                1200

Cys Val Ser Cys His Thr Gln Gln Ala Trp Pro Leu Gln Leu Ser Leu
                1205                1210                1215

Ser Gly Pro Leu Phe Cys Arg Pro Thr Gly Phe Arg Glu Leu Arg Leu
            1220                1225                1230

Phe Leu Ala Cys Cys Phe Glu Leu Phe Trp Leu Arg Phe Trp Leu Pro
        1235                1240                1245

Ala Phe Ile Phe Leu Leu Asn Gln Val Ala Phe Trp Lys Leu Val Leu
    1250                1255                1260
```

```
                            -continued

Thr Trp Gly Gln Ile Ala Lys Gly Phe Leu Val Ala Gly Ile Phe Leu
1265                1270                1275                1280

Val Pro Arg Ala Gln Trp Gly Thr Val Pro Ser Ser Ala Lys Ser Pro
                1285                1290                1295

Ser Thr Cys Ser Ser Leu Leu Ser Ser Val Ser Phe Ala Cys Ser Pro
            1300                1305                1310

Arg Gly Thr Arg Trp Ser Phe Ser Pro Leu Ala Ser Ser Ser Ser Ser
        1315                1320                1325

Ser Lys Leu Pro Trp Pro Gln Gly Ala Arg Ser Gly Gly Phe Ser His
    1330                1335                1340

Ser Leu Cys Trp Gly Leu Lys His Leu Gln Asp Cys Cys Leu Trp Asp
1345                1350                1355                1360

Ser Leu Ser Ser Trp Gly Arg Leu Arg Gly Gly Ser Gly Ala Ala Pro
                1365                1370                1375

Leu Ala Gly Trp Ala Cys Ser Ile Leu Ala Pro Arg Pro Gln Ala Leu
            1380                1385                1390

Leu Val His Pro Arg Pro Val Ser Pro Val Ala Ala Leu Pro Ser Ser
        1395                1400                1405

Ala Leu Ala Gly Gly Tyr Arg Pro Asp Ser Gly Glu Ala Trp Gly Ala
    1410                1415                1420

Phe Ser Ile Cys Trp Ala Pro Pro His Gly Gln Arg His Leu Gln Leu
1425                1430                1435                1440

His Ile Leu Ala Leu Arg Ser Phe His Arg Gly Ile Val Pro Ile Pro
                1445                1450                1455

Arg Thr Pro Gly Thr Gln Arg Leu Leu Arg Lys Trp Arg Ala Gly Lys
            1460                1465                1470

Pro Trp Arg Ser Arg Gly Gln Phe Trp Gly Gln Cys Thr Trp Leu Met
        1475                1480                1485

Ser Asn His Glu Ala Leu Phe Val His Lys Ser Trp Thr Asp Glu Leu
    1490                1495                1500

Ser Pro Gly Gln Pro Leu Asn Pro Arg Gly Arg Gln Ala Gly Thr
1505                1510                1515                1520

Glu Ala Thr Cys Trp Pro Val Leu Val Asp Ala Leu Pro Leu Arg Cys
                1525                1530                1535

Glu Val Gly Thr Ser Leu Ile Gly His Arg Asn Leu Leu His Pro Pro
            1540                1545                1550

Thr Pro Arg Gly Gln Thr Leu Glu Cys Ser Gly Cys Leu Gly Ser Gly
        1555                1560                1565

His His Leu Gln Ile Glu Val Ser Trp Ala Gln Gln Leu Pro Gly Gly
    1570                1575                1580

Cys Leu His His His Leu Phe Met Gln Ala Glu Arg Pro Pro Leu Met
1585                1590                1595                1600

Glu Glu Glu Glu Ser Thr Val Leu Gly Thr Gly Phe Leu Leu Asp Leu
                1605                1610                1615

Gly Lys Gln Val Leu Gly Trp Tyr Gln Glu Val Gln Arg Val Pro Gln
            1620                1625                1630

Cys Val Leu Pro Ile Ser Pro Leu His His Leu Glu His Leu Ala Gln
        1635                1640                1645

Gln Gly Gly Gly Cys Cys Leu Lys Gly Trp Ile Gln Gly Gly Glu Ser
    1650                1655                1660

Ala Leu His Thr Val Leu His Trp Leu Arg Leu His Gly Ser Ala Pro
1665                1670                1675                1680

Gly Arg Val Arg Arg Leu Val Gly Arg Ala Gly Pro Gly Ala Pro Pro
```

-continued

```
                   1685                1690                1695
Pro Pro Ser Arg Arg Ser Cys Leu Ala Gly Ser Gly Gly Thr Ala Pro
            1700                1705                1710

Ala Ala Val Ala Ala Arg Pro Ala Pro Ala Ser Arg Pro Arg Gly Pro
        1715                1720                1725

Ala Arg Glu Gly Arg Asp Gly Arg Pro Ser Pro Pro Arg Pro Ser Ala
    1730                1735                1740

<210> SEQ ID NO 23
<211> LENGTH: 1742
<212> TYPE: PRT
<213> ORGANISM: Unknown Organism
<220> FEATURE:
<223> OTHER INFORMATION: Description of Unknown Organism: Grub

<400> SEQUENCE: 23

Phe Phe Phe Phe Phe Phe Arg Gln Ser Val Ser Lys Tyr Ile Tyr Asn
  1               5                  10                  15

Asn Ser Ile Ile Ile Thr Val Ile Thr Tyr Ile Lys Ser Thr Val Pro
             20                  25                  30

Leu Ser His Pro Pro Ile Val Cys Ile Ala Ser Leu Leu Val Thr Pro
         35                  40                  45

Gln Asn Gly Val Thr Arg Asp Ser Ser Pro Gly Arg Asp Asp Ser Ser
     50                  55                  60

Gln Gly Lys Ser Gly Gly Glu Lys Arg Gly Glu His Gly Leu Pro Gly
 65                  70                  75                  80

Arg Ala Gly Met Gly Val Met Ser Trp Ile Gln Trp Pro Arg Met Gly
                 85                  90                  95

Lys His Arg Lys Arg Asp Asn Phe Pro Thr Ser Arg Val Arg Gln Ala
            100                 105                 110

Met Trp Leu Leu Leu Leu Gln Glu Lys Ala Pro Ser Gly Asp Arg Trp
        115                 120                 125

Trp Gln Gly Asn Thr Leu Val Val Arg Pro Leu Cys Pro Gly Ser
    130                 135                 140

Arg Gly Lys Lys Phe Ser Asp Arg Pro Gly Leu His Tyr Ala Pro Leu
145                 150                 155                 160

Pro Ser Gln Pro Lys Val Cys Glu Glu Lys Leu His Ala Ser Ser Gly
                165                 170                 175

Ser Ser Pro Gly His Arg Gly Val Val Gly Ser Leu Arg Ala Arg Ala
            180                 185                 190

Leu Cys Arg Asp Ser Pro Lys Ile Pro Arg Leu Ala Arg Val Gly Val
        195                 200                 205

Leu Leu Pro Gly Trp Gly Gly Cys Arg Leu Gly Leu Phe Leu Gly Pro
    210                 215                 220

Gly Asp Thr Ser Pro Glu Glu Ser Ser Val Ser Gly Ala Arg Glu Ile
225                 230                 235                 240

Cys Leu Thr Ser Arg Ser Gln Ala Ser Ser Thr Arg Ala Gly Arg
                245                 250                 255

Glu Gln Ala Pro Gly Glu Arg Pro Arg Glu Gly Pro Ala Cys Ser
            260                 265                 270

Lys Asp Asp Thr Ala Thr Glu Ala Arg Val Arg Ala Ala Leu Pro Val
        275                 280                 285

Ser Arg Ala Leu Ser Val Arg Ser Pro Arg Ala Leu Met Ser Arg Lys
    290                 295                 300

Gly Leu Phe Pro Met Pro Met Asp Thr Ile Cys Cys Thr Arg Ser Ser
```

-continued

```
            305                 310                 315                 320
Leu Leu Trp Ala Ala Cys Leu His Ser Ser Trp Ala Ile Glu Leu Val
                325                 330                 335
His Leu Ser Leu Ile Ser Gly Glu Val Ala Cys Arg Val Tyr Ala Ser
                340                 345                 350
Arg Ala Arg Arg Arg Asn His Asn Ser Lys Gln Ser Pro Leu Ser
                355                 360                 365
Pro Met Phe Ser Val Ser Pro Ile Ser Ala Val Leu Lys Ala Cys Leu
        370                 375                 380
Thr Asn Ile Ser Asp Pro Pro Ser Gly Pro Leu Ser Leu Leu Asn Arg
385                 390                 395                 400
Arg Arg Cys Ser Lys Arg Lys Thr Trp Arg Arg His Phe Phe Arg Pro
                405                 410                 415
Gln Met Thr Val Lys Gly Ser Arg Cys Lys Ser Cys Pro Cys Ser Phe
                420                 425                 430
Arg Ser Ile Ser Gln Pro Arg Thr Ala Ser Thr Ala Ser Arg Ser Leu
                435                 440                 445
Pro Arg Ala Ser Cys Ser Arg Ser Ser Cys Thr Ala Ala Pro Arg Ala
        450                 455                 460
Arg His Ser Glu Leu Ser Ser Gly Pro Ala Ser Leu Arg Ser Ser Ser
465                 470                 475                 480
Arg Ser Arg Pro Tyr Arg Val Ser Cys Ser Arg Gly Cys Cys Arg Ala
                485                 490                 495
Arg Gly Arg Gly Pro Ala Ser Met Glu Pro Leu Leu Lys Gly Leu Ser
                500                 505                 510
Ala Ala Arg Pro Phe Ser Ser Leu Cys Arg Cys Phe Thr Tyr Cys Ala
                515                 520                 525
Arg Leu Asn Trp Ser Pro Trp Arg Lys Gln Ala Pro Met Arg Arg
        530                 535                 540
Gly Trp Val Ala Gln Pro Ser Ser Arg Arg Lys Cys Val Arg Trp Lys
545                 550                 555                 560
Leu Arg Ser Leu Ser Arg Ala Leu Arg Ala Ala Gln Val Pro Arg
                565                 570                 575
Ser Ser Gly Val Ser Ser Gly Pro Gly Gly Thr Gly Ser Leu Lys
                580                 585                 590
Val Ala Thr Ser Cys Ser Gln Ala Ile Ser Ser Asp Thr Ser Arg Cys
                595                 600                 605
Trp Ala Leu Met Leu Arg Leu Arg Ser Ile Arg Gly Ala Pro Thr Pro
        610                 615                 620
Gln Gly Pro Ser Gly Pro Leu Ala Arg Pro Ser Ser Thr Cys Ser Arg
625                 630                 635                 640
Gly Glu His Val Leu Ser Thr Thr Ser Val Leu Val Thr Ser Arg Pro
                645                 650                 655
Arg Ile Ser Thr Ala Leu Gly Gly Leu Pro Ser Ala Ser Gly Ala Ser
                660                 665                 670
Ser Gly Pro Ser Ser Ser Ser Pro His Gly Ala Arg Glu Gln Trp
                675                 680                 685
Asp Gly Ala Gly Arg Gly Pro Gly Leu Leu Gly Ser Ser Lys Glu Leu
        690                 695                 700
Arg Leu Gly Glu Gly Leu Arg Gly Pro His Trp Ala Pro Pro Leu Leu
705                 710                 715                 720
Ala Pro Ser Ala Arg Arg Arg Arg Pro Arg Gly Leu Ala Ser Ser Pro
                725                 730                 735
```

-continued

```
Arg Cys Cys Trp Ile Leu Leu Ser Ser Ser Trp Gln Arg Ala Trp Gln
            740                 745                 750

Arg Pro His Ser Arg Arg Ala Ala Gly Leu Pro Arg Ser Arg Ala Arg
            755                 760                 765

Ala Arg Ile Ser Trp Lys Val Pro Ala Leu Gly Ser Gly Ala Arg Arg
            770                 775                 780

Arg Ala Ser Ala Ala Ser Thr Ala Ser Arg Pro Gly Pro Ala Pro Ala
785                 790                 795                 800

Ser Arg Ala Lys Pro Ser Ser Thr His Ser Cys Ala Cys Trp Lys Lys
                    805                 810                 815

Arg Cys Ser Arg Arg Ala Arg Trp Arg Pro Leu Ser Thr Cys Ser Ser
            820                 825                 830

Arg Cys Ser Lys Ile Ser Ser Thr Phe Trp Glu Val Ala Phe Ser Ser
            835                 840                 845

Arg Ala Arg Ala Ser Arg Ala Trp Ala Arg Arg Ser Trp Thr Ser Ala
850                 855                 860

Leu Lys Ala Arg Asn Arg Ser Ser Val Ser Cys Arg Ala Asp Lys Val
865                 870                 875                 880

Ser Pro Gly Ile Ala Lys Leu Ala Ser Cys Ser Ser Pro Gly Pro Glu
                    885                 890                 895

Ser His Cys Asn Thr Cys Trp Ser Arg Arg His Cys Arg Cys Ser
            900                 905                 910

Cys Cys Cys Thr Cys Arg Leu Glu Arg Arg Thr Ser Trp Met Ala Ser
            915                 920                 925

Ser Thr Ser Tyr Ser Val Ala Gly Pro Trp Pro Ser Ser Leu Leu Leu
        930                 935                 940

Gly Val Glu Arg Ser Leu Ile Arg Met Ala Pro Pro Ser Leu Cys Ser
945                 950                 955                 960

Ala Val Ser Arg Gly Ser Ala Ser Thr Phe Cys Ser Gly Leu Gly Ile
                965                 970                 975

Pro Thr Ala Ser Ser Ser Ser Gly Ser Ala Ala Pro Ser Ser Ser Ser
            980                 985                 990

Met Ala Cys Arg Thr Glu Pro Ser Thr Pro Trp His Arg Arg His Ser
            995                 1000                1005

Leu Thr Thr Ser Trp Cys Ile Ser Thr Gln Leu Gly Glu Gly Ser Leu
        1010                1015                1020

Pro Pro Asn Ser His Cys Ser Ser Ser Gly Leu Ala Thr Leu Phe Arg
1025                1030                1035                1040

Ser Phe Ser Asp Ser Thr Ser Ala Pro Asn Pro Gln Ser Ser Val Gly
                1045                1050                1055

Arg Ser Ser Met Arg Ile Ser Ser Arg Thr Arg Gly Ser Pro Glu
            1060                1065                1070

Ser Ser Trp Leu Lys Ala Gly Met Ser Ala Gly Gly Ser Gly Gly Ala
            1075                1080                1085

Arg Arg Ser Ser Arg Thr Asp Ser Pro Ser Val Cys Arg Ser Gly Leu
        1090                1095                1100

Ser Ser Glu Trp Arg Arg Val Val Phe Ser Val Ser Arg Glu Gly Gly
1105                1110                1115                1120

Gly Ser Ser Gly Gly His Gly Gly Val Met Val Ser Arg Ala Arg Pro
                1125                1130                1135

Leu Trp Ser Thr Pro Pro Val Arg Met Arg Asn Pro Asp Ala Ile Lys
            1140                1145                1150
```

```
Ser Gln Ala Thr Ser Gly Ser Glu Thr Glu Thr Ala Arg Ala Ser Ser
        1155                1160                1165

Gly Met Leu Ser Pro Phe Pro Ser Cys Thr Val Ser Ser Gly Gly Val
    1170                1175                1180

Gly Val Ser Asp Arg Gly Pro Ser Gly Pro Val Cys Pro Ala Ile His
1185                1190                1195                1200

Ser Arg Pro Gly Pro Ser Ser Ser Leu Ser Pro Ala Pro Ser Ser Val
            1205                1210                1215

Gly Pro Gln Ala Ser Glu Ser Gly Ser Phe Ser Pro Ala Val Leu Ser
        1220                1225                1230

Ser Phe Gly Ser Asp Ser Gly Phe Pro Glu Pro Ser Tyr Ser Ser Leu
    1235                1240                1245

Thr Arg Trp His Ser Gly Ser Leu Cys Ser Leu Gly Glu Gly Arg Leu
1250                1255                1260

Pro Arg Ala Ser Trp Trp Leu Ala Ser Ser Leu Ser Pro Gly Leu Ser
1265                1270                1275                1280

Gly Ala Leu Ser Pro Pro Arg Leu Arg Ala Pro Arg Pro Ala Ala Arg
            1285                1290                1295

Phe Phe Leu Leu Phe Pro Leu Pro Val Leu Arg Gly Val Pro Gly Gly
        1300                1305                1310

Pro Ser Ala Pro Trp Pro Pro Pro Pro Pro Leu Ser Ser Pro Gly
    1315                1320                1325

Leu Arg Gly Gln Asp Pro Glu Ala Ser Pro Thr Ala Ser Ala Gly Gly
1330                1335                1340

Ser Asn Thr Ser Lys Thr Ala Ala Ser Gly Thr Ala Ser Ala Pro Gly
1345                1350                1355                1360

Gly Asp Ser Gly Glu Ala Pro Val Leu Leu Pro Ser Pro Gly Gly Arg
            1365                1370                1375

Ala Pro Ser Trp Pro Arg Gly Pro Arg Pro Phe Trp Cys Ile His Ala
        1380                1385                1390

Arg Cys Leu Arg Trp Arg Pro Phe Pro Pro Ala Pro Leu Arg Val Gly
    1395                1400                1405

Thr Val Arg Thr Leu Glu Arg Pro Gly Glu Pro Ser Ala Ser Val Gly
    1410                1415                1420

Leu Pro Leu Thr Gly Ser Val Thr Ser Asn Ser Ser Thr Tyr Ser Pro
1425                1430                1435                1440

Ser Gly Pro Ser Thr Gly Ala Leu Cys Pro Ser Pro Gly Leu Arg Val
            1445                1450                1455

Pro Ser Ala Ser Ser Gly Ser Gly Gly Leu Gly Ser Pro Gly Gly Pro
        1460                1465                1470

Glu Gly Ser Ser Gly Gly Ser Val Leu Gly Cys Pro Thr Met Arg Pro
    1475                1480                1485

Ser Leu Cys Thr Asn Arg Gly Gln Met Ser Ser Ala Gln Gly Ser Arg
    1490                1495                1500

Ile Pro Glu Gly Ala Asp Ser Arg Gln Val Leu Arg Arg Pro Val Gly
1505                1510                1515                1520

Arg Ser Leu Leu Met Pro Cys Ser His Ser Gly Val Asn Arg Ala Gln
            1525                1530                1535

Ala Ser Leu Gly Thr Gly Thr Ser Cys Thr Arg Pro Pro Gly Ala
        1540                1545                1550

Arg His Leu Ser Ala Ser Arg Gly Ala Trp Ala Ala Glu Gly Thr Thr
    1555                1560                1565

Cys Arg Lys Ser Pro Gly Arg Ser Ser Cys Gln Gly Arg Ala Ala Ser
```

-continued

```
             1570                1575                1580
Cys Thr Thr Cys Ser Cys Arg Gln Ser Gly His Pro Ser Trp Lys
1585                1590                1595                1600

Lys Arg Asn Pro Leu Tyr Trp Ala Gln Ala Ser Cys Trp Thr Leu Ala
                1605                1610                1615

Ser Arg Cys Leu Ala Gly Thr Arg Lys Ser Ser Val Tyr Leu Ser Ala
            1620                1625                1630

Ser Ser Arg Val Leu Ser Thr Thr Trp Asn Thr Trp Pro Asn Arg Val
        1635                1640                1645

Gly Ala Val Ala Ser Lys Gly Gly Tyr Arg Ala Ala Arg Val Leu Cys
    1650                1655                1660

Thr Gln Ser Ser Thr Gly Ser Gly Ser Met Ala Arg Arg Ala Ala
1665                1670                1675                1680

Ser Asp Ala Trp Ser Gly Gly Arg Gly Arg Ala Arg His Arg Leu Pro
                1685                1690                1695

Pro Ala Ala Arg Val Ser Pro Gly Leu Ala Lys Gly Gln Leu Arg Pro
            1700                1705                1710

Arg Trp Arg Leu Gly Pro Leu Arg Leu Pro Gly Arg Gly Ala Pro Pro
        1715                1720                1725

Gly Arg Ala Glu Thr Ala Ala Pro Pro Arg Pro Ala Leu Gln
    1730                1735                1740

<210> SEQ ID NO 24
<211> LENGTH: 448
<212> TYPE: PRT
<213> ORGANISM: Unknown Organism
<220> FEATURE:
<223> OTHER INFORMATION: Description of Unknown Organism: Tks 113

<400> SEQUENCE: 24

Glu Phe Gly Thr Ser Asn Tyr Gly Gly Gly Arg Thr Gln Gln Cys
 1               5                  10                  15

Gly Gly Gly Asp Pro Gln Glu Pro Arg Thr Ser Pro Glu Leu Pro Gln
                20                  25                  30

Trp Ser Pro Arg Val Ala Arg Arg Lys Pro Val Gly Arg Asp Gln Asp
            35                  40                  45

Ala Pro Gly Gln Leu Cys Gln Arg Tyr Arg Glu Gln Arg Trp Arg Pro
        50                  55                  60

Trp Arg Trp Trp Gln Gln Gly Gly Gln Trp Gly Arg Gly Arg Gln Trp
65                  70                  75                  80

Arg Gly Gln Leu Arg Cys His Leu Arg Leu Leu Glu Glu Cys Val Gln
                85                  90                  95

Ala Arg Gln Ala Leu Pro Ile Ser Pro Pro Arg His Glu Arg Gly Val
            100                 105                 110

Gln Leu Gly Gly Glu Gln Lys Arg Val His Leu Leu Pro Leu Pro Glu
        115                 120                 125

Gln Gly Val Pro Pro Lys Leu Pro Phe His Pro Trp Leu Gln Gly Gly
    130                 135                 140

Gly Trp Leu Glu Asp Arg Arg Ala Ser Pro Thr Ala Glu Ala Glu Ser
145                 150                 155                 160

Ser Ser Trp Pro Trp Pro Phe Thr Gly Pro Thr Lys Trp Gln Gly Gly
                165                 170                 175

Gly Pro Tyr Leu Pro Leu Ser Gln Gly Leu Ser Glu Arg Ser Gln Val
            180                 185                 190

Gln Val Pro Ser Pro Ala Thr Gly Phe Val Cys Ser Gly Trp Arg Arg
```

```
                  195                 200                 205
His Trp Trp Gly Leu Asn Arg Leu Ser Pro Pro Arg Thr Thr Ser Ser
    210                 215                 220

Leu Tyr Leu Pro Ser Gln Gly Leu Gly Pro Ala Arg Pro Lys Thr Pro
225                 230                 235                 240

Ala Arg Trp Met Leu Pro Pro Trp Pro Ser Phe Val Ile Ile Phe Gly
                245                 250                 255

Ser Thr Ala Arg Gly Gly Val Gln Thr Ala Arg Gly Gly Glu Cys His
            260                 265                 270

Ala Gln Glu Ala Gly Arg Gly Val Lys Glu Ala Gly Gln Gln Pro Ala
        275                 280                 285

Gly His Gln Gly Thr Thr Gly Thr Lys Cys Ser Val Pro Gln Ser Gly
    290                 295                 300

Gln Gly His Asn Pro Glu Leu His Cys Thr Ser Asp Ala Asp Ser Gly
305                 310                 315                 320

Pro His Cys Gly His Cys Cys His Phe Pro Trp His Cys Pro Asp Ser
                325                 330                 335

His Tyr Ser Gln Gln Pro Gly Ser Thr Ala Ser Ser Val Pro Ala
            340                 345                 350

Arg Thr Gly Gly Pro Cys Trp Ser Ser Cys Ser Pro Asn Cys Cys
        355                 360                 365

Thr Ser Cys Cys Ser Thr Thr Pro Thr Pro Thr Leu Asp Pro Arg Asp
    370                 375                 380

His Ala Thr Val Ser Cys Pro Gly Ser Asn Cys Pro Gly Asn Gly
385                 390                 395                 400

Thr Ser Thr Cys Leu His Gly Ser Cys Gly Cys Ile Cys Gly Ser Cys
                405                 410                 415

Gly Pro Cys Gly Cys Ile Asp Gly Pro Thr Leu Gly Arg Asn His Asn
            420                 425                 430

Glu Pro His His His Ser His Gly Asp Leu Pro Tyr Arg Ser Pro Ser
        435                 440                 445

<210> SEQ ID NO 25
<211> LENGTH: 461
<212> TYPE: PRT
<213> ORGANISM: Unknown Organism
<220> FEATURE:
<223> OTHER INFORMATION: Description of Unknown Organism: Tks 113

<400> SEQUENCE: 25

Ile Arg His Glu Gln Leu Arg Arg Arg Gln Asn Pro Ala Val Met
 1               5                  10                  15

Trp Arg Trp Arg Pro Thr Gly Ala Pro Asp Phe Thr Ala Thr Ser Val
            20                  25                  30

Val Thr Lys Ser Gly Lys Ile Lys Lys Thr Leu Ser Trp Ala Gly Pro
        35                  40                  45

Gly Cys Leu Thr Gly Thr Ala Met Pro Thr Val Pro Gly Ala Ala Val
    50                  55                  60

Glu Ala Leu Glu Val Val Ala Ala Arg Arg Pro Val Gly Gln Gly Ala
65                  70                  75                  80

Val Ala Gly Pro Ala Gln Met Pro Ser Val Glu Thr Ser Gly Met Cys
                85                  90                  95

Ala Ser Glu Ala Ser Val Ala Asp Ile Ala Thr Gln Thr Ala Arg Cys
            100                 105                 110

Pro Thr Trp Gly Ala Lys Thr Ser Ser Ser Ser Ala Met Thr Ser Arg
```

-continued

```
            115                 120                 125
Thr Arg Ser Val Ala Ala Gln Ile Ala Val Ser Ser Met Ala Pro Arg
    130                 135                 140

Arg Met Arg Met Ala Ile Arg Arg Gln Glu Ser Phe Pro His Gly Gly
145                 150                 155                 160

Arg Lys Gln Leu Ala Leu Ala Phe His Arg Leu Thr Tyr Gln Met Ala
                165                 170                 175

Arg Arg Arg Ser Leu Ser Ala Val Thr Phe Ser Arg Val Thr Val Arg
                180                 185                 190

Glu Glu Pro Ser Ala Ser Ser Val Thr Cys Asn Gly Ile Leu Ser Leu
                195                 200                 205

Met Leu Gly Val Glu Glu Ala Leu Val Gly Ala Gln Gln Ala Gln Ser
    210                 215                 220

Ser Gln Asp Asp Val Met Ile Ser Met Ile Ser Met Thr Phe Leu Thr
225                 230                 235                 240

Gly Ala Leu Arg Thr Met Ser Gln Ala Gln Asn Ala Gly Glu Val Asp
                245                 250                 255

Ala Ala Pro Leu Met Ala Leu Ile Leu Ser His Met Asn Ile Val Trp
                260                 265                 270

Leu His Arg Glu Gly Trp Ser Ala Asp Cys Arg Arg Met Pro Cys
    275                 280                 285

Ser Gly Ser Gly Arg Ser Arg Ser Arg Ser Ala Thr Cys Trp Pro Pro
    290                 295                 300

Met Arg Tyr Tyr Trp Asn Lys Met Leu Ser Ser Ala Ile Arg Pro Arg
305                 310                 315                 320

Ser Pro Ala Pro Leu His Gln Arg Leu Ser Arg Leu Trp Pro Pro Leu
                325                 330                 335

Trp Ala Leu Leu Pro Leu Leu Thr Met Ala Leu Pro Arg Leu Thr Leu
                340                 345                 350

Leu Ser Ala Ala Arg Leu Tyr Ser Leu Val Gln Cys Pro Ser Lys Asn
    355                 360                 365

Trp Trp Pro Leu Leu Glu Leu Gln Leu Leu Pro Gln Leu Met Leu His
    370                 375                 380

Leu Leu Leu His His Pro His Pro His Thr Pro Gln Arg Ser Arg
385                 390                 395                 400

His Cys Gln Leu Pro Trp Leu Lys Gln Leu Pro Arg Glu Trp His Leu
                405                 410                 415

His Leu Ser Pro Trp Leu Leu Trp Leu Tyr Leu Trp Leu Leu Trp Pro
                420                 425                 430

Leu Trp Leu Tyr Arg Trp Pro Asn Pro Trp Gln Glu Ser Gln Ala Thr
    435                 440                 445

Pro Pro Leu Pro Trp Leu Thr Leu Ser Leu Pro Leu Glu
    450                 455                 460

<210> SEQ ID NO 26
<211> LENGTH: 460
<212> TYPE: PRT
<213> ORGANISM: Unknown Organism
<220> FEATURE:
<223> OTHER INFORMATION: Description of Unknown Organism: Tks 113

<400> SEQUENCE: 26

Leu Glu Gly Glu Arg Gly Lys Ser Pro Trp Glu Trp Cys Gly Ser
1               5                   10                  15

Leu Phe Leu Pro Arg Val Gly Pro Ser Ile Gln Pro Gln Gly Pro Gln
```

-continued

```
                20                  25                  30
Glu Pro Gln Ile Gln Pro Gln Glu Pro Trp Arg Gln Val Glu Val Pro
            35                  40                  45
Phe Pro Gly Gln Leu Phe Glu Pro Gly Gln Leu Thr Val Ala Ser Leu
        50                  55                  60
Gly Ser Ser Val Gly Val Gly Val Val Glu Gln Gln Glu Val Gln His
65                  70                  75                  80
Leu Gly Glu Gln Leu Glu Leu Gln Gln Gly Pro Pro Val Leu Ala Gly
                85                  90                  95
Thr Leu Asp Glu Ala Val Glu Pro Gly Cys Glu Cys Glu Ser Gly Gln
            100                 105                 110
Cys His Gly Lys Trp Gln Gln Cys Pro Gln Trp Gly Pro Glu Ser Ala
        115                 120                 125
Gln Ser Leu Val Gln Trp Ser Ser Gly Leu Pro Trp Pro Asp Cys Gly
    130                 135                 140
Thr Glu His Phe Val Pro Val Val Pro His Trp Trp Pro Ala Gly Cys
145                 150                 155                 160
Pro Ala Ser Leu Thr Pro Leu Pro Ala Ser Ala Trp His Ser Pro Pro
                165                 170                 175
Leu Ala Val Cys Thr Pro Pro Leu Ala Val Glu Pro Asn Tyr Ile His
            180                 185                 190
Met Thr Gln Asn Glu Gly His Gln Gly Gly Ser Ile His Leu Ala Gly
        195                 200                 205
Val Leu Gly Leu Ala His Gly Pro Gln Ser Pro Cys Gln Glu Gly His
    210                 215                 220
Arg Tyr His Arg Asp His Asp Val Val Leu Gly Gly Leu Ser Leu Leu
225                 230                 235                 240
Ser Pro His Gln Cys Leu Leu His Pro Glu His Gln Thr Gln Asn Pro
                245                 250                 255
Val Ala Gly Asp Gly Thr Cys Thr Trp Leu Leu Ser Asp Ser His Pro
            260                 265                 270
Glu Ser His Gly Arg Gly Pro Pro Cys His Leu Val Gly Gln Pro
        275                 280                 285
Val Lys Gly Gln Gly Gln Leu Leu Ser Ala Ser Ala Val Gly Glu
    290                 295                 300
Ala Leu Leu Ser Ser Tyr Ser His Pro His Pro Trp Ser His Gly
305                 310                 315                 320
Asn Gly Asn Leu Gly Gly Tyr Thr Pro Cys Ser Gly Ser His Gly Arg
                325                 330                 335
Arg Thr Arg Phe Cys Ser Pro Pro Ser Trp Thr Pro Arg Ser Cys Leu
            340                 345                 350
Gly Gly Asp Ile Gly Asn Ala Cys Leu Ala Cys Thr His Ser Ser Arg
        355                 360                 365
Ser Leu Tyr Arg Trp His Leu Ser Trp Pro Arg His Cys Leu Pro Leu
    370                 375                 380
Pro His Trp Pro Pro Cys Cys His His Leu Gln Gly Leu His Arg Cys
385                 390                 395                 400
Ser Arg Tyr Arg Trp His Ser Cys Pro Gly Gln Ala Ser Trp Ser Arg
                405                 410                 415
Pro Thr Gln Gly Phe Leu Tyr Leu Ala Thr Leu Gly Asp His Gly Ser
            420                 425                 430
Ser Gly Glu Val Arg Gly Ser Cys Gly Ser Pro Pro His His Cys
        435                 440                 445
```

```
Trp Val Leu Pro Pro Pro Leu Leu Val Pro Asn
    450                 455                 460

<210> SEQ ID NO 27
<211> LENGTH: 465
<212> TYPE: PRT
<213> ORGANISM: Unknown Organism
<220> FEATURE:
<223> OTHER INFORMATION: Description of Unknown Organism: Tks 113

<400> SEQUENCE: 27

Ser Arg Gly Ser Asp Arg Val Ser His His Gly Ser Gly Val Ala
 1               5                  10                  15

His Cys Asp Ser Cys Gln Gly Leu Gly His Arg Tyr Ser His Arg Gly
            20                  25                  30

His Arg Ser His Arg Tyr Ser His Arg Ser His Gly Asp Arg Trp Arg
        35                  40                  45

Cys His Ser Leu Gly Asn Cys Leu Ser Gln Gly Ser Gln Trp Arg Asp
     50                  55                  60

Leu Trp Gly Gln Val Trp Gly Trp Gly Trp Trp Ser Ser Arg Arg Cys
 65                  70                  75                  80

Ser Ile Ser Trp Gly Ser Ser Trp Ser Ser Arg Gly His Gln Phe
                 85                  90                  95

Leu Leu Gly His Trp Thr Arg Leu Ser Leu Ala Ala Glu Ser Ser Val
            100                 105                 110

Ser Leu Gly Asn Ala Met Val Lys Ser Gly Asn Ser Ala His Ser Gly
        115                 120                 125

Gly Gln Ser Leu Leu Ser Arg Trp Cys Ser Gly Ala Gln Gly Tyr Asp
    130                 135                 140

Leu Gly Leu Ile Ala Glu Leu Ser Ile Leu Phe Gln Tyr Leu Ile Gly
145                 150                 155                 160

Gly Gln Gln Val Ala Asp Leu Leu Leu Leu Tyr Pro Leu Pro Glu
                165                 170                 175

His Gly Ile Leu Leu Gln Ser Ala Leu His Pro Ser Arg Trp Ser
            180                 185                 190

Gln Thr Ile Phe Ile Leu Lys Met Arg Ala Ile Arg Gly Ala Ala Ser
        195                 200                 205

Thr Ser Pro Ala Phe Trp Ala Trp Leu Met Val Leu Lys Ala Pro Val
    210                 215                 220

Arg Lys Val Ile Asp Ile Glu Ile Met Thr Ser Ser Trp Glu Asp
225                 230                 235                 240

Ala Cys Ala Pro Thr Ser Ala Ser Ser Thr Pro Ser Ile Lys Leu Lys
                245                 250                 255

Ile Pro Leu Gln Val Thr Glu Leu Ala Leu Gly Ser Ser Leu Thr Val
            260                 265                 270

Thr Leu Glu Lys Val Thr Ala Asp Arg Asp Leu Leu Leu Ala Ile Trp
        275                 280                 285

Val Ser Arg Lys Ala Lys Ala Ser Cys Tyr Phe Leu Pro Gln Pro Trp
    290                 295                 300

Gly Lys Leu Ser Cys Leu Leu Ile Ala Ile Leu Ile Leu Leu Gly Ala
305                 310                 315                 320

Met Asp Glu Thr Ala Ile Trp Ala Ala Thr Leu Leu Val Leu Glu Val
                325                 330                 335

Met Ala Glu Asp Glu Leu Val Phe Ala His Pro Gln Val Gly His Leu
            340                 345                 350
```

```
Ala His Val Trp Val Ala Ile Ser Ala Thr Leu Ala Ser Leu Ala His
            355                 360                 365

Ile Pro Gln Glu Val Ser Thr Asp Gly Ile Ala Gly Pro Ala Thr Ala
        370                 375                 380

Tyr Pro Cys Pro Thr Gly Leu Leu Ala Ala Thr Thr Ser Arg Ala Ser
385                 390                 395                 400

Thr Ala Ala Pro Gly Thr Val Gly Ile Ala Val Pro Val Arg His Pro
                405                 410                 415

Gly Pro Ala Gln Leu Arg Val Phe Phe Ile Leu Pro Leu Leu Val Thr
            420                 425                 430

Thr Glu Val Ala Gln Val Lys Ser Gly Ala Pro Val Gly Leu His Leu
        435                 440                 445

His Ile Thr Ala Gly Phe Cys Arg Arg Arg Ser Cys Ser Cys Arg
    450                 455                 460

Ile
465

<210> SEQ ID NO 28
<211> LENGTH: 460
<212> TYPE: PRT
<213> ORGANISM: Unknown Organism
<220> FEATURE:
<223> OTHER INFORMATION: Description of Unknown Organism: Tks 113

<400> SEQUENCE: 28

Arg Gly Gly Ala Ile Gly Val Thr Met Gly Val Val Val Trp Leu Ile
1               5                   10                  15

Val Ile Pro Ala Lys Gly Trp Ala Ile Asp Thr Ala Thr Gly Ala Thr
            20                  25                  30

Gly Ala Thr Asp Thr Ala Thr Gly Ala Met Glu Thr Gly Gly Gly Ala
        35                  40                  45

Ile Pro Trp Ala Ile Val Ala Arg Ala Ala Asp Ser Gly Val Ile Ser
    50                  55                  60

Gly Val Lys Cys Gly Gly Gly Gly Ala Ala Gly Gly Ala Ala
65                  70                  75                  80

Leu Val Gly Gly Ala Gly Ala Pro Ala Gly Ala Thr Ser Ser Cys
            85                  90                  95

Trp Asp Thr Gly Arg Gly Cys Arg Ala Trp Leu Leu Arg Val Val Val
            100                 105                 110

Trp Ala Met Pro Trp Leu Lys Val Ala Thr Val Pro Thr Val Gly Ala
        115                 120                 125

Arg Val Cys Ser Val Ala Gly Ala Val Glu Leu Arg Val Met Thr Leu
130                 135                 140

Ala Leu Arg Asn Ala Phe Cys Ser Ser Thr Ser Leu Val Ala Ser
145                 150                 155                 160

Arg Leu Leu Thr Cys Phe Asn Ser Ser Thr Arg Phe Leu Ser Met
            165                 170                 175

Ala Phe Ser Ser Ser Ser Leu His Ser Thr Pro Arg Gly Gly Ala
        180                 185                 190

Lys Leu Tyr Ser Tyr Asp Ser Lys Gly Pro Ser Gly Gln His Pro
    195                 200                 205

Pro Arg Arg Phe Gly Pro Gly Ser Trp Ser Lys Pro Leu Ser
    210                 215                 220

Gly Arg Ser Ile Ser Arg Ser Arg Arg Pro Gly Arg Thr Glu Pro Val
225                 230                 235                 240
```

-continued

Glu Pro Pro Pro Val Pro Pro Pro Arg Ala Ser Asn Ser Lys Ser
                245             250             255

Arg Cys Arg Arg Asn Leu His Leu Ala Pro Leu Gln Ser Pro Leu Arg
            260             265             270

Lys Ser Arg Gln Ile Gly Thr Ser Ser Leu Pro Phe Gly Arg Ser Ala
        275             280             285

Gly Glu Arg Pro Arg Pro Ala Ala Thr Phe Cys Leu Ser Arg Gly Gly
    290             295             300

Ser Ser Pro Val Phe Leu Pro Ser Ser Ser Leu Glu Pro Trp Met
305             310             315             320

Lys Arg Gln Phe Gly Arg Leu His Ser Leu Phe Trp Lys Ser Trp Gln
                325             330             335

Lys Met Asn Ser Phe Leu Leu Thr Pro Lys Leu Asp Thr Ser Leu Met
            340             345             350

Ser Gly Trp Arg Tyr Arg Gln Arg Leu Pro Arg Leu His Thr Phe Leu
        355             360             365

Lys Lys Ser Leu Gln Met Ala Ser Glu Leu Ala Pro Pro Leu Pro Thr
    370             375             380

Pro Ala Pro Leu Ala Ser Leu Leu Pro Pro Pro Gly Pro Pro Pro
385             390             395             400

Leu Leu Pro Val Pro Leu Ala Leu Ser Arg Ser Gly Ile Leu Val Pro
                405             410             415

Pro Asn Ser Gly Phe Ser Leu Ser Cys His Ser Trp Pro Leu Arg Leu
            420             425             430

Arg Ser Pro Gly Leu Leu Trp Val Ser Thr Ser Thr Ser Leu Leu Gly
        435             440             445

Ser Ala Ala Ala Val Val Ala Arg Ala Glu Phe
    450             455             460

<210> SEQ ID NO 29
<211> LENGTH: 496
<212> TYPE: PRT
<213> ORGANISM: Unknown Organism
<220> FEATURE:
<223> OTHER INFORMATION: Description of Unknown Organism: Tks 118

<400> SEQUENCE: 29

Phe Asp Thr Ser Cys Gly Ala Gly His Gly Gly Glu Pro Glu Pro Glu
1               5               10              15

Arg Ala Ser Ala Ala Arg Gly Leu Arg Ala Gly Gly His Arg Glu Val
            20              25              30

Pro Asp Arg Leu Gly Ser Leu Tyr Leu Arg Gln Gln His Pro Arg
        35              40              45

Gly Trp His Arg Gly Gly Trp Pro Gly Gly Asp Gly Gly Ala Gln
    50              55              60

Gln Arg Glu Gly Asp Val Arg Leu Leu Gln Ser Glu Gly Pro Gln Leu
65              70              75              80

Trp Thr Ala Gln Ile Cys Pro His Gln Leu Asp Arg Arg Gly Arg Glu
                85              90              95

Arg Cys Ala Glu Gly Ser Leu Cys Gln Pro Arg Gln His His Gly Gln
            100             105             110

Leu Pro Glu Gly Gly Pro Cys Asp His Gln Arg Thr Gly Arg Gly Gly
        115             120             125

Cys Gly Ala Val His His Gly Glu Gly Gly Gln Gly Phe Arg Cys Gln
    130             135             140

```
Leu Gln Leu Ser Gln Gly Glu Trp Pro Leu Pro Gly Arg Gly Thr Pro
145                 150                 155                 160

Gly Pro Ser Gly Leu Cys Val Pro Glu Asp Gln Cys Arg Val Asp Lys
            165                 170                 175

Gly Trp Arg Gln Leu Leu Gly Gln Ser Arg Glu Gly Gly Gly Glu Pro
            180                 185                 190

Ser Ala Gly Gly Lys Ala Ala Gly Arg Gly Thr Ala Ala Ala Gly
            195                 200                 205

Ala Gly Ala Pro Gly Ala Ala Gly Cys Thr Pro Gly Ala Ala Leu
210                 215                 220

Ser Gly Ala Gly Trp Arg Gly Gln Pro Pro Glu Gln Asp Val Gly Ala
225                 230                 235                 240

Ala Ala Arg Ser Gly Phe Lys Glu Pro Lys Ala Gly Val Cys Arg Ala
            245                 250                 255

Pro Glu Gly Asp Phe Gln Ala Glu Gly Glu Gly His Val His His Leu
            260                 265                 270

His Leu Gln Ser Ser Ala Trp Gln Ala Glu Glu Pro Leu Pro Ala Glu
            275                 280                 285

Ala Ala His Pro Thr Arg Asp Pro Leu Trp Gln Arg Ala Ser Cys Cys
290                 295                 300

His Leu Lys Ala Gln Gly Arg Ser Pro Cys Gly Ala Gly Ala Gln His
305                 310                 315                 320

Ser Ser Met Ser Gly Ala Gly Arg Arg Gly Gly Cys Val Gly Thr Ser
            325                 330                 335

Arg Ala Gly Asp Leu Leu Arg Ala Ala Pro Thr Gly Ala Ala Ala Arg
            340                 345                 350

Cys Trp Leu Ala His Pro Pro His Ser Gly Pro Gly Ala Gln Trp Ala
            355                 360                 365

Arg Ala Leu Cys Pro Cys Pro Val Arg Leu Pro Gly Ser Arg Arg His
370                 375                 380

Arg Asp Leu Leu Pro Arg Glu Pro His His Gly His Arg Gly Asp Arg
385                 390                 395                 400

Arg Arg Leu Val Ala Trp Leu Trp Ala Gly Trp Pro Phe Trp His Val
            405                 410                 415

Pro Cys Gln Leu Arg Gly Ala His Val Arg Leu Arg Ala His Leu Ala
            420                 425                 430

Leu Pro Leu Ser Asp Met Ala Ser Leu Leu Glu Glu Ala Trp
            435                 440                 445

Glu Leu Thr Phe Ser Thr Leu Pro Gly Ile Gly Pro Pro Val Arg Met
450                 455                 460

Arg Pro Gln Gly Ser Leu Arg Leu Gly Arg Leu Ser Leu Ser Pro Gln
465                 470                 475                 480

Met Gln Gln Trp Pro Gly Asp Ser His Thr Ser Phe Leu His Pro Pro
            485                 490                 495

<210> SEQ ID NO 30
<211> LENGTH: 502
<212> TYPE: PRT
<213> ORGANISM: Unknown Organism
<220> FEATURE:
<223> OTHER INFORMATION: Description of Unknown Organism: Tks 118

<400> SEQUENCE: 30

Arg His Glu Leu Arg Gly Gly Pro Trp Arg Arg Thr Ala Gly Thr Gly
1               5                   10                  15
```

```
Gln Arg Cys Lys Arg Pro Thr Cys Gly Trp Ser Pro Arg Ser Pro Arg
                 20                  25                  30

Pro Thr Gly Leu Ser Leu Pro Met Lys Ala Thr Ala Met Thr Ser Ala
             35                  40                  45

Trp Leu Ala Gln Gly Arg Val Ala Trp Arg Arg Trp Arg Ser Ser
         50                  55                  60

Thr Ala Gly Arg Cys Thr Pro Ser Ala Glu Arg Thr Pro Thr Leu Asp
 65                  70                  75                  80

Cys Pro Asn Leu Ser Ser Ser Thr Gly Gln Ala Arg Ala Thr Met Cys
                 85                  90                  95

Gly Arg Glu Pro Val Pro Ala Thr Ser Ala Pro Trp Pro Ala Ser Arg
            100                 105                 110

Gly Pro Met Pro Ser Thr His Gly Pro Arg Met Trp Ser Leu Ser
            115                 120                 125

Ala Ser Trp Arg Arg Trp Pro Arg Leu Gln Val Pro Thr Thr Ala Phe
            130                 135                 140

Thr Arg Val Ala Ala Ser Arg Thr Trp Asp Pro Arg Pro Gln Trp
145                 150                 155                 160

Ala Leu Cys Thr Arg Arg Pro Met Pro Cys Leu Arg Leu Lys Gly Leu
                165                 170                 175

Val Lys Thr Ala Ser Gly Pro Lys Gln Arg Arg Arg Arg Thr Val
            180                 185                 190

Gly Trp Arg Lys Ser Gly Gly Pro Arg Arg His Ser Gly Ser Trp Ser
            195                 200                 205

Arg Ser Ala Gly Ser Val Ser Cys Val Arg Leu His Ala Gly Ser Ser
210                 215                 220

Ala Ile Arg Ser Arg Val Ala Arg Pro Ala Pro Arg Ala Gly Arg Gly
225                 230                 235                 240

Ser Ser Ser Lys Lys Trp Phe Gln Gly Thr Glu Met Ser Arg Ser Leu
                245                 250                 255

Pro Cys Thr Arg Gly Arg Phe Ser Ser Arg Arg Arg Gly Pro Cys Pro
            260                 265                 270

Pro Pro Pro Ser Pro Val Leu Ser Leu Ala Ser Gly Ala Pro Ser Cys
        275                 280                 285

Arg Ser Ser Pro Asn Gln Arg Pro Thr Leu Ala Glu Ser Gln Leu
290                 295                 300

Leu Pro Ser Gln Gly Pro Gly Gln Ile Ser Leu Leu Arg Ser Arg Arg
305                 310                 315                 320

Pro Ala Leu Leu His Val Trp Cys Arg Gln Lys Arg Arg Leu Cys Met
                325                 330                 335

Arg Asn Leu Gln Ser Arg Arg Pro Ser Thr Ser Ser Pro His Trp Cys
                340                 345                 350

Ser Ser Lys Val Leu Ala Leu Ser Thr Leu Thr Thr Thr Phe Arg Ala
            355                 360                 365

Arg Gly Ser Val Gly Lys Gly Ser Val Pro Val Pro Cys Thr Thr Thr
    370                 375                 380

Arg Gln Pro Thr Thr Gln Arg Ser Pro Leu Thr Pro Arg Thr Ser Ser
385                 390                 395                 400

Arg Ala Ser Arg Ser Thr Lys Ala Gly Gly Val Ala Met Gly Arg Met
                405                 410                 415

Ala Ile Leu Ala Cys Ser Leu Pro Thr Thr Trp Ser Ser Leu Ser Glu
            420                 425                 430
```

```
Ala Glu Gly Thr Ser Cys Pro Ser Pro Leu Arg His Gly Phe Leu Ile
        435                 440                 445

Ala Gly Arg Gly Gly Leu Gly Val Asp Ile Gln His Ser Ser Arg Asn
    450                 455                 460

Arg Thr Pro Ser Glu Asp Glu Ala Ser Gly Leu Pro Pro Ala Trp Gln
465                 470                 475                 480

Thr Gln Pro Val Thr Pro Asn Ala Ala Met Ala Trp Phe Pro His Ile
                485                 490                 495

Leu Pro Ala Ser Pro Asp
            500

<210> SEQ ID NO 31
<211> LENGTH: 495
<212> TYPE: PRT
<213> ORGANISM: Unknown Organism
<220> FEATURE:
<223> OTHER INFORMATION: Description of Unknown Organism: Tks 118

<400> SEQUENCE: 31

Val Gly Gly Cys Arg Lys Asp Val Trp Glu Ser Pro Gly His Cys Cys
1               5                   10                  15

Ile Trp Gly Asp Arg Leu Ser Leu Pro Ser Arg Arg Glu Pro Gly Leu
            20                  25                  30

Ile Leu Thr Gly Gly Pro Ile Pro Gly Arg Val Leu Asn Val Asn Ser
        35                  40                  45

Gln Ala Ser Ser Ser Asn Lys Glu Ala Met Ser Glu Arg Gly Arg
    50                  55                  60

Ala Arg Cys Ala Leu Ser Leu Thr Gln Ala Pro Arg Ser Trp Gln Gly
65                  70                  75                  80

Thr Cys Gln Asn Gly His Pro Ala His Ser His Ala Thr Ser Leu Arg
                85                  90                  95

Arg Ser Pro Arg Cys Pro Gly Ser Arg Gly Gln Arg Ser Leu Cys
            100                 105                 110

Arg Arg Leu Pro Gly Ser Arg Thr Gly His Gly His Arg Ala Leu Ala
        115                 120                 125

His Ala Pro Gly Pro Glu Cys Gly Gly Gln Cys Ala Gln Ser Gln His
    130                 135                 140

Leu Ala Ala Ala Pro Val Gly Ala Ala Arg Arg Arg Ser Pro Ala Leu
145                 150                 155                 160

Glu Val Pro His Thr Gln Pro Pro Leu Leu Pro Ala Pro Asp Met Glu
                165                 170                 175

Glu Cys Trp Ala Pro Ala Pro Gln Gln Gly Asp Leu Pro Trp Ala Leu
            180                 185                 190

Arg Trp Gln Gln Leu Ala Leu Cys Gln Ser Gly Ser Leu Val Gly Ala
        195                 200                 205

Ala Ser Ala Gly Arg Gly Ser Ser Ala Cys Gln Ala Glu Asp Trp Arg
    210                 215                 220

Trp Arg Trp Trp Thr Trp Pro Ser Pro Ser Ala Lys Ser Pro Ser Gly
225                 230                 235                 240

Ala Arg Gln Thr Pro Ala His Phe Gly Ser Leu Lys Pro Leu Leu Ala
                245                 250                 255

Ala Ala Pro Thr Ser Cys Ser Gly Gly Trp Pro Arg His Pro Ala Pro
            260                 265                 270

Asp Ser Ala Ala Pro Gly Val Gln Pro His Ala His Ala Pro Gly
    275                 280                 285
```

```
Ala Pro Ala Pro Ala Ala Val Pro Pro Arg Pro Ala Phe Pro
    290                 295                 300

Pro Ala Asp Gly Ser Pro Pro Ser Leu Leu Trp Pro Arg Ser Cys
305                 310                 315                 320

Leu Tyr Gln Pro Phe Ser Gln Thr Arg His Trp Ser Ser Gly Thr Gln
                325                 330                 335

Ser Pro Leu Gly Pro Gly Val Pro Arg Pro Gly Ser Gly His Ser Pro
                340                 345                 350

Cys Glu Ser Cys Ser Trp His Leu Lys Pro Trp Pro Ser Pro Cys
                355                 360                 365

Thr Gln Ala Pro His Pro Pro Arg Pro Val Arg Trp Ser His Gly Pro
    370                 375                 380

Pro Ser Gly Ser Trp Pro Trp Cys Arg Gly Trp His Arg Leu Pro Ser
385                 390                 395                 400

Ala His Arg Ser Arg Pro Arg Leu Ser Ser Gly Gln Ile Trp Ala Val
                405                 410                 415

Gln Ser Trp Gly Pro Ser Leu Cys Arg Arg Thr Ser Pro Ser Arg
                420                 425                 430

Cys Ala Pro Pro Ser Pro Pro Gly His Pro Leu Cys Gln Pro
                435                 440                 445

Arg Gly Cys His Cys Cys Leu His Arg Arg Glu Pro Ser Arg Ser
    450                 455                 460

Gly Thr Ser Arg Pro Pro Ala Arg Arg Pro Leu Ala Ala Leu Ala Arg
465                 470                 475                 480

Ser Gly Ser Gly Ser Pro Pro Trp Pro Ala Pro Gln Leu Val Ser
                485                 490                 495

<210> SEQ ID NO 32
<211> LENGTH: 506
<212> TYPE: PRT
<213> ORGANISM: Unknown Organism
<220> FEATURE:
<223> OTHER INFORMATION: Description of Unknown Organism: Tks 118

<400> SEQUENCE: 32

Ser Gly Asp Ala Gly Arg Met Cys Gly Asn His Gln Ala Ile Ala Ala
1               5                   10                  15

Phe Gly Val Thr Gly Val Cys Gln Ala Gly Gly Ser Pro Glu Ala Ser
                20                  25                  30

Ser Ser Leu Gly Val Leu Phe Leu Glu Glu Cys Met Ser Thr Pro Arg
            35                  40                  45

Pro Pro Leu Pro Ala Ile Arg Lys Pro Cys Leu Arg Gly Glu Gly Gln
        50                  55                  60

Asp Val Pro Ser Ala Ser Leu Asn Glu Leu His Val Val Gly Arg Glu
65                  70                  75                  80

His Ala Lys Met Ala Ile Arg Pro Ile Ala Thr Pro Pro Ala Phe Val
                85                  90                  95

Asp His Leu Asp Ala Arg Asp Glu Val Leu Gly Val Lys Gly Asp Leu
                100                 105                 110

Cys Val Val Gly Cys Leu Val Val Val Gln Gly Thr Gly Thr Glu Pro
            115                 120                 125

Leu Pro Thr Glu Pro Leu Ala Leu Asn Val Val Asn Val Leu Arg
        130                 135                 140

Ala Ser Thr Leu Leu Leu His Gln Trp Gly Leu Leu Val Glu Gly Leu
145                 150                 155                 160
```

```
Leu Leu Trp Arg Phe Leu Ile His Ser Leu Leu Phe Cys Leu His Gln
            165                 170                 175

Thr Trp Arg Ser Ala Gly Arg Arg Leu Leu Ser Arg Glu Ile Cys Pro
        180                 185                 190

Gly Pro Asp Gly Ser Ser Trp Leu Ser Ala Lys Val Gly Leu Trp Leu
            195                 200                 205

Gly Glu Leu Leu Leu Gln Glu Gly Ala Pro Gln Leu Ala Arg Leu Arg
    210                 215                 220

Thr Gly Asp Gly Gly Gly His Gly Pro Leu Leu Leu Glu Asn
225                 230                 235                 240

Leu Pro Arg Val His Gly Arg Leu Leu Ile Ser Val Pro Asn His
                245                 250                 255

Phe Leu Leu Leu Pro Arg Pro Ala Leu Gly Ala Gly Leu Ala Thr
            260                 265                 270

Leu Leu Leu Ile Ala Leu Leu Pro Ala Cys Ser Leu Thr Gln Leu Thr
    275                 280                 285

Leu Pro Ala Leu Leu Leu Gln Leu Pro Leu Cys Leu Leu Gly Pro Pro
    290                 295                 300

Leu Phe Leu Gln Pro Thr Val Leu Leu Leu Leu Leu Cys Phe Gly Pro
305                 310                 315                 320

Glu Ala Val Phe Thr Asn Pro Phe Asn Leu Arg His Gly Ile Gly Leu
            325                 330                 335

Leu Val His Arg Ala His Trp Gly Leu Gly Ser His Val Leu Glu Ala
            340                 345                 350

Ala Thr Leu Leu Val Lys Ala Val Gly Thr Ser Leu Gly His Leu
        355                 360                 365

Leu His Asp Ala Leu Arg Leu His Ile Leu Leu Gly Pro Cys Val Asp
    370                 375                 380

Gly His Met Gly Pro Leu Gln Glu Ala Gly His Gly Ala Asp Val Ala
385                 390                 395                 400

Gly Thr Gly Ser Leu Pro His Ile Val His Ala Leu Ala Cys Pro Val
            405                 410                 415

Asp Glu Asp Lys Phe Gly Gln Ser Arg Val Gly Val Leu His Ser Ala
            420                 425                 430

Glu Gly Val His His Leu Pro Ala Val Glu Leu Leu His His Leu Leu
            435                 440                 445

Gln Ala Thr Leu Pro Cys Ala Ser His Ala Asp Val Ile Ala Val Ala
    450                 455                 460

Phe Ile Gly Lys Glu Ser Pro Val Gly Arg Gly Leu Leu Gly Asp His
465                 470                 475                 480

Pro His Val Gly Leu Leu Gln Arg Trp Pro Val Pro Ala Gln Val Arg
                485                 490                 495

Arg His Gly Pro Pro Arg Ser Ser Cys Arg
            500                 505

<210> SEQ ID NO 33
<211> LENGTH: 496
<212> TYPE: PRT
<213> ORGANISM: Unknown Organism
<220> FEATURE:
<223> OTHER INFORMATION: Description of Unknown Organism: Tks 118

<400> SEQUENCE: 33

Arg Gly Met Gln Glu Gly Cys Val Gly Ile Thr Arg Pro Leu Leu His
 1               5                   10                  15
```

-continued

```
Leu Gly Gln Ala Glu Ser Ala Lys Pro Glu Gly Ala Leu Arg Pro His
             20                  25                  30
Pro His Trp Gly Ser Tyr Ser Trp Lys Ser Ala Glu Cys Gln Leu Pro
         35                  40                  45
Gly Leu Leu Phe Gln Gln Gly Ser His Val Glu Gly Lys Gly Lys Met
     50                  55                  60
Cys Pro Gln Pro His Ser Met Ser Ser Thr Leu Ala Gly Asn Met Pro
 65                  70                  75                  80
Lys Trp Pro Ser Gly Pro Pro Arg His Gln Pro Ser Ser Ile Thr Ser
                 85                  90                  95
Met Pro Val Met Arg Phe Ser Gly Ser Lys Glu Ile Ser Val Ser Ser
            100                 105                 110
Ala Ala Trp Ser Tyr Arg Ala Arg Ala Gln Ser Pro Cys Pro Leu Ser
            115                 120                 125
Pro Trp Pro Met Trp Trp Ser Met Cys Ser Glu Pro Ala Pro Cys Cys
        130                 135                 140
Cys Thr Ser Gly Gly Cys Ser Lys Val Ser Cys Ser Gly Gly Ser Ser
145                 150                 155                 160
Tyr Thr Ala Ser Ser Ala Cys Thr Arg His Gly Gly Val Leu Gly
                165                 170                 175
Ala Gly Ser Ser Ala Gly Arg Ser Ala Leu Gly Leu Glu Met Ala Ala
            180                 185                 190
Ala Gly Ser Leu Pro Lys Trp Val Ser Gly Trp Val Ser Cys Phe Cys
        195                 200                 205
Arg Lys Gly Leu Leu Ser Leu Pro Gly Gly Leu Glu Met Glu Val Val
    210                 215                 220
Asp Met Ala Leu Ser Phe Cys Leu Lys Ile Ser Leu Gly Cys Thr Ala
225                 230                 235                 240
Asp Ser Cys Ser Phe Arg Phe Leu Glu Thr Thr Ser Cys Cys Cys Ser
                245                 250                 255
His Val Leu Leu Trp Gly Leu Ala Ser Pro Pro Cys Ser Arg Cys Ser
            260                 265                 270
Arg Arg Ala Ala Ser Arg Ser Ser Arg Ser Arg Ser Cys Ser Ser
            275                 280                 285
Cys Arg Cys Ala Ser Ser Ala Arg Arg Phe Ser Ser Ser Arg Arg Phe
        290                 295                 300
Ser Ser Ser Phe Ser Ala Leu Ala Gln Lys Leu Ser Leu Pro Thr Leu
305                 310                 315                 320
Leu Ile Ser Asp Thr Ala Leu Val Phe Trp Tyr Thr Glu Pro Thr Gly
                325                 330                 335
Ala Trp Gly Pro Thr Ser Trp Lys Arg Pro Leu Ser Leu Lys Leu Leu
            340                 345                 350
Ala Pro Glu Ala Leu Ala Thr Phe Ser Met Met His Ser Gly Ser Thr
            355                 360                 365
Ser Ser Ser Ala Arg Ala Leu Met Val Thr Trp Ala Pro Phe Arg Lys
        370                 375                 380
Leu Ala Met Val Leu Thr Trp Leu Ala Gln Ala Pro Phe Arg Thr Ser
385                 390                 395                 400
Phe Thr Pro Ser Pro Val Gln Leu Met Arg Thr Asn Leu Gly Ser Pro
                405                 410                 415
Glu Leu Gly Ser Phe Thr Leu Gln Lys Ala Tyr Ile Thr Phe Pro Leu
            420                 425                 430
Leu Ser Ser Thr Ile Ser Ser Arg Pro Pro Ser Pro Val Pro Ala
```

```
                435             440             445
Thr Arg Met Ser Leu Leu Pro Ser Val Lys Arg Ala Gln Ser Val
            450             455             460

Gly Asp Phe Ser Val Thr Thr Arg Thr Ala Ser Cys Ser Ala Gly Pro
465             470             475             480

Phe Arg Leu Arg Phe Ala Ala Met Ala Arg Pro Ala Ala Arg Val Glu
                485             490             495
```

<210> SEQ ID NO 34
<211> LENGTH: 890
<212> TYPE: PRT
<213> ORGANISM: Unknown Organism
<220> FEATURE:
<223> OTHER INFORMATION: Description of Unknown Organism: Tks 202

<400> SEQUENCE: 34

```
Ser Arg Arg Arg Ser Leu Ala Val Pro Gly Ala Arg Ala His Pro
 1               5              10              15

Thr Ala Pro Gly Thr Cys Trp Gly Leu Ala Arg Thr Val Val Glu Gly
                20              25              30

Ser Arg Ser Ala Thr Pro Asp Val Pro Arg Pro Ala Arg Arg Ser Leu
            35              40              45

Lys Trp Pro Asn Gln Pro Asp Glu Pro Asn Ser Pro Gly Leu Pro Ala
     50              55              60

Ala Ala Gly Gly Pro Val Leu Pro Gly Arg Ala Leu Arg Pro Ala Ala
 65              70              75              80

Leu Arg Ser Pro Leu Gly Arg Pro Arg Gln Ala Gly Trp Arg Arg Met
                85              90              95

Gly Thr Glu Arg Ser Trp Pro Gly Cys Ala Gln Ser Ser Pro Pro Ala
                100             105             110

Thr Arg Thr Ala Arg Gly Ala Trp Ser Ala Arg Ser Ser Gly His Cys
            115             120             125

Ala Arg Ser Cys Gly Cys Gly Arg Pro Thr Pro Arg Gln Tyr Ser Ser
    130             135             140

Gly Trp Thr Pro Thr Val Thr Ala Pro Ser Pro Arg Ser Ser Arg
145             150             155             160

Val Ala Ser Ser Gly Pro Ser Ala Gly Gly Ala Gly Thr Gly Val
                165             170             175

Leu Trp Ile Pro Arg Pro Cys Leu Arg Arg Gly Arg Arg His Thr
            180             185             190

Thr Ala Arg Arg Thr Lys Ala Thr Arg Thr Arg Arg Arg Trp Pro
        195             200             205

Pro Arg Ala Ala Arg Arg Val Pro Ala Gly Leu Gly Arg Ile Ser Arg
    210             215             220

Arg Asp Leu Gly Thr Lys Pro Ser Ser Phe Pro Glu Lys Ser Lys Leu
225             230             235             240

Val Pro Cys Thr Lys Thr Ser Thr Leu Trp Ser Gln Asp Phe Ser His
                245             250             255

Met Asn Met Leu Arg Thr Ser Ser Val Arg Ser Asp Phe Lys Ala Gln
                260             265             270

Lys Trp Lys Ile Trp Pro Leu Arg Arg Glu Pro Arg Thr Arg Gln Leu
            275             280             285

Cys Ser Val Ser Trp Lys Arg Lys Trp Ile Arg Gly Phe Arg Leu Gln
    290             295             300

Asn Ile Arg His Gly Lys Thr Lys Asn Ala Lys Leu Arg Lys Pro Ser
```

-continued

```
            305                 310                 315                 320
Val Thr Ser Asp Val Ser Met Lys Leu Lys Glu Ile Cys Arg Pro Leu
                325                 330                 335

Lys Ser Glu Ser Ser Lys Asn Asn Gln Asn Ala Val Lys Arg Lys Met
                340                 345                 350

Trp Leu His Lys Asn Lys Phe Met Ile Tyr Gln Trp Lys Thr Arg Lys
                355                 360                 365

Leu Arg Lys Thr Phe Lys His Arg Gln Thr Pro Phe Phe Arg Val Ser
            370                 375                 380

Met Leu Lys Val Ile Met Leu Ile Arg Val Ile Leu Lys Gly Ile Trp
385                 390                 395                 400

Lys Ser Glu His Thr Gln Lys Ile Glu Ile Val Leu Arg Gly Lys Leu
                405                 410                 415

Lys Tyr Ser Lys Gln Leu Thr Gly Ser Tyr Met Thr Val Met Met Ala
                420                 425                 430

Leu Glu Val Pro Leu Lys Thr Val Ile Ala Ser Ser Thr Asp Leu Cys
            435                 440                 445

Ile Ile Ile Ser His Gln Gly Ile Gln Phe Leu Glu Ala Val Pro Asn
            450                 455                 460

Ser Leu Val Ile Pro Leu Asn Leu Ala Met Thr Gly His Pro Ala Leu
465                 470                 475                 480

Pro Met Trp Met Arg Thr Val Thr Pro Trp Pro Ser Val Ile Leu Cys
                485                 490                 495

Arg Gly Gln Ile Val Lys Leu Thr Ala Cys Leu Lys Ala Ala Ser Thr
                500                 505                 510

Ala Ala Cys Leu Pro Glu Ile Pro Met Ser Met Thr Gln Lys Trp Asn
                515                 520                 525

Thr Ser Thr Arg Gly Asp Phe Arg Gly His Thr Gly Cys Arg Arg Ala
            530                 535                 540

Leu Glu Val Met Leu Gln Thr Gln Met Phe Leu Thr Gly Met Lys Arg
545                 550                 555                 560

His Leu Val Lys Met Trp Leu Pro Ser Thr Gly Ser Pro Lys Gly Leu
                565                 570                 575

Leu Val Lys Ala Ala Leu Leu Val His Gln Glu Ser Pro Ser Gln His
                580                 585                 590

Ser Arg Pro Arg Gln Thr Trp Met Thr Thr Leu Asn Leu Leu Ala His
            595                 600                 605

Arg Arg Leu Thr Arg Leu Tyr Leu Leu Gly Thr Leu Gln Trp Gly Ser
            610                 615                 620

Leu Val Ser Ser Asp Phe Ala Arg Met Asn Phe Glu Lys Ile Ala Pro
625                 630                 635                 640

Pro Trp Glu Leu Ile Ser Lys Lys Pro Ser Leu Trp Met Glu Asn Glu
                645                 650                 655

Gln Phe Cys Ser Ser Gly Ile Gln Leu Val Arg Arg Asp Ser Glu Val
                660                 665                 670

Leu Pro Ser Leu Thr Ser Glu Arg Gln Met Val Phe Cys Cys Cys Met
            675                 680                 685

Met Leu His Val Arg Lys Ala Phe Leu Thr Tyr Glu Asn Gly Ile Leu
            690                 695                 700

Arg Met Gln Pro Met Arg Leu Phe Pro Leu Cys Trp Glu Thr Arg Leu
705                 710                 715                 720

Thr Phe Val Thr Leu Leu Leu Gln Arg Asp Lys Asn Val Ser Gln Gly
                725                 730                 735
```

```
Thr Leu Glu Arg Asn Trp Pro Arg Met Gly His Tyr Ser Val Lys Gln
            740                 745                 750

Val Pro Lys Met Val Leu Thr Trp Arg Leu Phe Cys Thr Leu Leu Glu
        755                 760                 765

Lys Lys Arg Glu Leu Thr Arg Met Thr Ala Asp Pro Leu Pro Ile Pro
    770                 775                 780

Gly Pro Ile Pro Lys Ser His His Arg Arg Ile Val Ala Met Ala Lys
785                 790                 795                 800

Ser Gln Thr Ser Leu Ala Cys Glu Val Phe Ile Ser Arg Ile Leu Asn
                805                 810                 815

Leu Cys Asp Leu Phe Gly Ser Gln Ser Gly Thr Ser Tyr His Cys Pro
            820                 825                 830

Met Glu Ser Leu Gln Cys Arg Glu Thr Thr Gln Leu Ser Gly Pro Ser
        835                 840                 845

Gly Thr Leu Ala Leu Leu Cys Phe Val Ser Val Ser Asp Leu Gly Pro
    850                 855                 860

Leu Ala Lys Thr Ser His Val Leu Thr Gly Leu Lys Arg His Val Asn
865                 870                 875                 880

Val Phe Lys Met Val Lys Lys Lys Lys
                885                 890

<210> SEQ ID NO 35
<211> LENGTH: 862
<212> TYPE: PRT
<213> ORGANISM: Unknown Organism
<220> FEATURE:
<223> OTHER INFORMATION: Description of Unknown Organism: Tks 202

<400> SEQUENCE: 35

Val Ala Gly Gly Ala Pro Trp Arg Cys Leu Glu Pro Gly Arg Thr Pro
1               5                   10                  15

Pro Leu Pro Gly Pro Val Gly Gly Trp Pro Glu Pro Ser Ser Lys Gly
            20                  25                  30

Ala Ala Arg Pro Pro Pro Thr Phe Leu Ala Pro Pro Asp Val Pro Ser
        35                  40                  45

Ser Gly Arg Thr Ser Arg Thr Ser Gln Thr Arg Arg Ala Ser Arg Arg
    50                  55                  60

Gln Gln Val Ala Pro Ser Phe Gln Gly Gly Pro Cys Ala Pro Arg Arg
65                  70                  75                  80

Ser Gly Ala Leu Ser Ala Ala Pro Ala Arg Arg Asp Gly Gly Gly Trp
                85                  90                  95

Gly Arg Arg Gly Ala Gly Pro Ala Ala Leu Ser Leu Arg Arg Leu Arg
            100                 105                 110

Arg Glu Pro Leu Gly Ala Pro Gly Ala Arg Gly Val Pro Gly Thr Val
        115                 120                 125

His Gly Ala Ala Gly Ala Ala Gly Arg Arg Arg Gly Ser Ile Pro Ala
    130                 135                 140

Ala Gly Arg Arg Pro Arg Arg His His Leu Pro Gly Val Arg Ala Trp
145                 150                 155                 160

Leu Pro Arg Val Pro Pro Arg Gly Ala Ala Pro Gly Leu Gly Ser Ser
                165                 170                 175

Gly Ser Arg Ala Arg Arg Val Gly Gly Ala Gly Asp Thr Arg Gln Arg
            180                 185                 190

Gly Gly Arg Arg Arg Gly Arg Gly Gly Ala Gly His Leu Val
        195                 200                 205
```

-continued

```
Arg Pro Gly Glu Ser Arg Pro Gly Leu Ala Gly Phe Pro Gly Ala Thr
    210                 215                 220
Trp Gly Arg Ser Gln Val His Ser Gln Arg Arg Ala Ser Tyr Leu Val
225                 230                 235                 240
Pro Lys His Gln Pro Cys Gly Ala Lys Ile Asn Ser Ala Ile Thr Cys
                245                 250                 255
Tyr Lys Glu Leu His Pro Asp Gln Thr Ser Lys His Arg Asn Gly Lys
            260                 265                 270
Phe Gly His Cys Gly Glu Glu Ser Pro Gly Gln Gly Ser Tyr Ala Val
        275                 280                 285
Glu Val Gly Arg Gly Asn Gly Ser Glu Asp Ser Gly Cys Arg Thr Asp
    290                 295                 300
Thr Glu Arg Arg Lys Thr Gln Ser Gly Ser Pro Gln Pro Gln Thr Ser
305                 310                 315                 320
Val Asn Ser Arg Arg Ser Ala Gly Asp His Lys Ala Lys Lys Ala Arg
                325                 330                 335
Arg Thr Ile Lys Thr Arg Lys Ser Lys Gly Arg Cys Gly Cys Ile Glu
            340                 345                 350
Lys Thr Asn Leu Phe Ile Asn Gly Lys Pro Glu Ser Glu Arg Pro Phe
        355                 360                 365
Arg Ser Thr Asp Lys His Ser Leu Ser Ser Glu Val Arg Cys Phe Glu
    370                 375                 380
Lys Leu Cys Ser Glu Ser Glu Tyr Lys Gly Ser Gly Asn Asn Pro Ser
385                 390                 395                 400
Ile His Arg Arg Ser Lys Ser Glu Ala Asn Asn Thr Pro Asn Ser Pro
                405                 410                 415
Glu Ala Thr Gln Trp Pro Lys Cys Pro Lys Gln Leu Gln Val Gln Gln
            420                 425                 430
Ile Phe Ala Tyr Lys Tyr Leu Thr Arg Glu Tyr Asn Phe Lys Gln Ser
        435                 440                 445
Gln Ile His Trp Ser Phe Pro Ser Thr Ser Arg Leu Gln Val Ile Pro
    450                 455                 460
Leu Phe Leu Cys Gly Gly Leu Leu Pro Gly Pro Leu Ser Ser Ala Glu
465                 470                 475                 480
Asp Lys Leu Ser Gln Pro Ala Lys Leu Leu Arg Gln Arg Leu Val Tyr
                485                 490                 495
Leu Glu Arg Ser Gln Val Leu Arg Ser Gly Ile Gln Ala Pro Glu Gly
            500                 505                 510
Ile Ser Glu Val Thr Arg Gly Ala Gly Glu Leu Trp Arg Cys Phe Arg
        515                 520                 525
His Arg Cys Ser His Lys Gly Arg Asp Ile Trp Phe Arg Arg Cys Gly
    530                 535                 540
Phe Arg Leu Arg Leu Glu Ala Pro Arg Val Cys Arg Gln His Cys Phe
545                 550                 555                 560
Ile Lys Lys Ala His Leu Ser Thr Leu Ala Pro Asp Arg Pro Gly Arg
                565                 570                 575
Gln Arg Ile Phe Leu Thr Glu Gly Leu Gln Asp Cys Thr Cys Trp Gly
            580                 585                 590
Arg Cys Ser Gly Glu Val Phe Pro His Glu Thr Leu Gln Glu Ile Ser
        595                 600                 605
Arg Lys Tyr Lys Arg His Pro Gly Ser Phe Pro Asn Glu Asn Pro His
    610                 615                 620
```

```
Cys Gly Trp Arg Thr Asn Ser Ser Ala Ala Leu Gly Tyr Ser Trp Ser
625                 630                 635                 640

Gly Glu Ile Gln Lys Tyr Cys Gln Val Leu Leu Gln Lys Gly Arg Trp
            645                 650                 655

Cys Phe Ala Ala Val Cys Tyr Met Glu Lys Leu Ser His Thr Arg Met
        660                 665                 670

Gly Arg Tyr Asp Gly Cys Ser Pro Asp Cys Ser His Tyr Ala Gly Arg
    675                 680                 685

Lys Gln Gly His Ser His Cys Cys Tyr Arg Gly Thr Lys Met Cys Pro
690                 695                 700

Arg Ala Leu Trp Arg Glu Thr Gly His Asp Val Trp Gly Ile Ile Leu
705                 710                 715                 720

Asn Lys Cys Gln Arg Trp Phe His Ser Gly Gly Cys Ser Ala Pro Cys
                725                 730                 735

Ser Arg Ser Glu Lys Glu Asn Gln Gly Gln Gln Ile His Tyr Gln Ser
            740                 745                 750

Asn Arg Asp Gln Phe Gln Lys Val Thr Thr Asp Glu Leu Leu Gln
    755                 760                 765

Trp Leu Asn Pro Lys His Pro Trp Pro Val Lys Ser Ser Phe Pro Glu
770                 775                 780

Tyr Ile Cys Val Thr Tyr Leu Ala Leu Asn Arg Val Ala His Pro Thr
785                 790                 795                 800

Asp Thr Val Leu Trp Arg Val Tyr Ser Ala Gly Lys Pro Glu Pro Ser
                805                 810                 815

Ser Gln Val Pro Leu Glu Leu Trp Leu Phe Phe Val Leu Ser Gln Val
            820                 825                 830

Ile Trp Ala Leu Trp Leu Asn Arg Leu Val Met Ser Leu Gln Val Leu
        835                 840                 845

Lys Asp Asn Met Met Phe Leu Lys Trp Lys Lys Lys Lys
    850                 855                 860

<210> SEQ ID NO 36
<211> LENGTH: 902
<212> TYPE: PRT
<213> ORGANISM: Unknown Organism
<220> FEATURE:
<223> OTHER INFORMATION: Description of Unknown Organism: Tks 202

<400> SEQUENCE: 36

Phe Phe Phe Phe Phe Phe Thr Ile Leu Lys Thr Phe Thr Cys Tyr Leu
1               5                   10                  15

Leu Arg Pro Val Arg Thr Leu Val Tyr Leu Ala Arg Gly Pro Lys Ser
            20                  25                  30

Leu Thr Glu Thr Lys Gln Arg Arg Ala Lys Val Pro Glu Gly Pro Glu
        35                  40                  45

Ser Trp Val Gln Val Ser Leu His Cys Lys Leu Ser Ile Gly Gln Cys
    50                  55                  60

Gln Asp Val Pro Leu Cys Glu Pro Asn Lys Ser His Lys Phe Ser Ile
65                  70                  75                  80

Leu Glu Met Lys Thr Ser Gln Ala Lys Asp Val Trp Asp Leu Ala Ile
                85                  90                  95

Ala Thr Ile Leu His Leu Trp Leu Phe Gly Ile Gly Pro Gly Ile Gly
            100                 105                 110

Asn Gly Ser Ala Val Ile Leu Val Ser Ser Leu Phe His Phe Ser Ser
        115                 120                 125
```

-continued

```
Lys Val Gln Asn Ser Leu His Tyr Val Arg Thr Ile Phe Gly Thr Cys
130                 135                 140

Phe Thr Glu Cys Pro Ile Arg His Gly Gln Phe Leu Ser Lys Val Pro
145                 150                 155                 160

Trp Asp Thr Phe Leu Ser Leu Cys Ser Ser Val Thr Asn Val Ser
                165                 170                 175

Leu Val Ser Tyr Gln His Asn Gly Asn Ser Leu Met Gly Cys Ile Leu
                180                 185                 190

Asn His Ile Tyr Pro Phe Ser Tyr Val Lys Lys Ala Phe Leu Thr Cys
            195                 200                 205

Asn Ile Ile Gln Gln Asn Thr Ile Cys Leu Ser Glu Val Arg Leu
        210                 215                 220

Gly Asn Thr Ser Glu Ser Leu Leu Thr Ser Cys Ile Pro Glu Leu Gln
225                 230                 235                 240

Asn Cys Ser Phe Ser Ile His Asn Glu Gly Phe His Leu Glu Ile Asn
                245                 250                 255

Ser Gln Gly Gly Ala Tyr Ile Phe Ser Lys Phe Ile Leu Ala Lys Ser
                260                 265                 270

His Glu Glu Thr Arg Leu Pro His Cys Ser Val Pro Ser Lys Tyr Asn
                275                 280                 285

Leu Val Ser Leu Leu Ala Lys Arg Phe Ser Val Ile Tyr Gln Val
            290                 295                 300

Cys Leu Gly Arg Glu Cys Asp Gly Leu Ser Thr Asn Asn Ala Ala Phe
305                 310                 315                 320

Thr Asn Arg Pro Leu Gly Leu Pro Val Asp Gly Ser His Ile Phe Thr
                325                 330                 335

Lys Cys Leu Phe Ile Pro Tyr Val Arg Asn Ile Cys Val Ser Ile Thr
                340                 345                 350

Ser Lys Ala Leu Leu His Pro Val Pro Leu Lys Ser Pro Leu Val Leu
            355                 360                 365

Val Phe His Phe Val Ile Leu Ile Gly Ile Ser Gln Gly Arg Gln Ala
    370                 375                 380

Ala Val Glu Ala Ala Phe Arg Gln Ala Val Asn Phe Thr Ile Cys Pro
385                 390                 395                 400

Leu Gln Arg Ile Thr Glu Gly Gln Gly Val Thr Val Leu Ile His Ile
                405                 410                 415

Gly Arg Ala Gly Pro Val Ile Ala Arg Leu Arg Gly Met Thr Asn Glu
                420                 425                 430

Phe Gly Thr Ala Ser Arg Asn Cys Ile Pro Trp Asp Ile Ile Tyr Met
            435                 440                 445

Gln Arg Ser Val Glu Leu Ala Ile Thr Val Phe Lys Gly Thr Ser Lys
    450                 455                 460

Ala Ile Ile Thr Val Met Leu Pro Val Ser Cys Leu Glu Tyr Phe Asn
465                 470                 475                 480

Leu Pro Leu Lys Thr Ile Ser Ile Phe Cys Val Cys Ser Asp Tyr Phe
                485                 490                 495

Gln Ile Pro Phe Ser Ile Gln Thr Leu Ile Ser Ile Thr Phe Gln
                500                 505                 510

Ser Ile Leu Thr Leu Lys Lys Gly Tyr Val Cys Leu Cys Phe Lys Val
            515                 520                 525

Phe Leu Asn Phe Leu Val Phe His Ile Ile Asn Leu Phe Phe Gln Cys
    530                 535                 540

Ser His Ile Phe Leu Leu Thr Tyr Ala Phe Leu Phe Phe Glu Leu Ser
```

```
                545                 550                 555                 560
Leu Phe Asn Gly His Leu Gln Ile Ser Tyr Phe Ser Phe Ile Leu Thr
                565                 570                 575

Ser Glu Val Thr Glu Gly Phe Leu Ser Phe Ala Phe Phe Val Phe Pro
            580                 585                 590

Cys Leu Met Phe Cys Ser Leu Asn Pro Leu Ile His Phe Leu Phe Gln
            595                 600                 605

Leu Thr Gln Leu His Ser Cys Leu Val Leu Gly Ser Leu His Arg Asn
        610                 615                 620

Gly Gln Ile Phe His Phe Cys Ala Leu Lys Ser Asp Leu Thr Asp Glu
625                 630                 635                 640

Val Leu Tyr Asn Met Phe Ile Trp Leu Asn Ser Trp Leu His Lys Val
                645                 650                 655

Asp Val Leu Val Gln Gly Thr Asn Leu Leu Phe Ser Gly Asn Glu Leu
            660                 665                 670

Gly Phe Val Pro Lys Ser Arg Leu Glu Ile Leu Pro Ser Pro Ala Gly
            675                 680                 685

Thr Arg Arg Ala Ala Arg Gly Gly Gln Arg Arg Arg Val Leu Val
        690                 695                 700

Ala Phe Val Leu Leu Ala Val Val Cys Leu Arg Pro Arg Leu Arg His
705                 710                 715                 720

Gly Gly Arg Gly Ile Gln Arg Thr Pro Val Pro Ala Pro Pro Pro Ala
                725                 730                 735

Glu Gly Pro Glu Glu Ala Thr Arg Glu Leu Leu Glu Gly Asp Gly Ala
            740                 745                 750

Val Thr Val Gly Val Gln Pro Leu Glu Tyr Cys Leu Gly Val Gly Arg
            755                 760                 765

Pro His Pro Gln Leu Arg Ala Gln Cys Pro Glu Leu Leu Ala Leu Gln
        770                 775                 780

Ala Pro Arg Ala Val Arg Val Ala Gly Gly Glu Asp Ala Gln Pro Gly
785                 790                 795                 800

Gln Leu Leu Ser Val Pro Ile Arg Leu His Pro Ala Trp Arg Gly Arg
                805                 810                 815

Pro Arg Gly Leu Arg Ser Ala Ala Gly Arg Arg Ala Leu Pro Gly Arg
            820                 825                 830

Thr Gly Pro Pro Ala Ala Gly Arg Pro Gly Glu Phe Gly Ser Ser
        835                 840                 845

Gly Trp Phe Gly His Leu Arg Glu Arg Ala Gly Arg Gly Thr Ser
    850                 855                 860

Gly Val Ala Glu Arg Leu Pro Ser Thr Thr Val Arg Ala Ser Pro Gln
865                 870                 875                 880

Gln Val Pro Gly Ala Val Gly Cys Ala Arg Ala Pro Gly Thr Ala Lys
                885                 890                 895

Glu Arg Leu Leu Arg Leu
            900

<210> SEQ ID NO 37
<211> LENGTH: 900
<212> TYPE: PRT
<213> ORGANISM: Unknown Organism
<220> FEATURE:
<223> OTHER INFORMATION: Description of Unknown Organism: Tks 202

<400> SEQUENCE: 37

Phe Phe Phe Phe Phe Leu Pro Phe Lys His Leu His Val Ile Phe Asp
```

-continued

```
  1               5                10               15
Leu Gly His Asp Ser Ile Pro Glu Gly Pro Asn His Ser Leu Arg Gln
             20                  25                  30

Asn Lys Glu Glu Pro Lys Phe Gln Arg Asp Leu Arg Ala Gly Phe Arg
             35                  40                  45

Phe Pro Cys Thr Val Asn Ser Pro Asp Ser Val Ser Arg Met Cys His
             50                  55                  60

Ser Val Lys Ser Gln Ile Ser His Thr Asn Ser Val Phe Trp Lys Arg
 65                  70                  75                  80

Leu His Arg Pro Arg Met Phe Gly Ile Pro Leu Gln Gln Phe Phe Ile
                 85                  90                  95

Cys Gly Asp Phe Leu Glu Leu Val Pro Val Arg Leu Val Met Asp Leu
                100                 105                 110

Leu Ser Ser Leu Ser Val Leu Phe Phe Thr Ser Arg Ala Arg Cys Arg
                115                 120                 125

Thr Ala Ser Thr Met Leu Glu Pro Ser Leu Ala Leu Val Ser Gln Asn
            130                 135                 140

Asn Ala Pro Tyr Val Met Ala Ser Phe Ser Pro Lys Cys Pro Gly Thr
145                 150                 155                 160

His Phe Cys Pro Ser Val Ala Ala Val Ser Arg Met Ser Ala Leu Phe
                165                 170                 175

Pro Thr Ser Ile Met Gly Thr Val Ser Trp Ala Ala Ser Ser Ile Ile
                180                 185                 190

Ser Thr His Ser Arg Met Leu Arg Lys Leu Phe Ser His Val Thr Ser
                195                 200                 205

Tyr Ser Ser Lys Thr Pro Ser Ala Phe Leu Lys Asp Leu Ala Ile Leu
            210                 215                 220

Leu Asn Leu Ser Pro Ala Val Ser Gln Ser Cys Arg Thr Val Arg Ser
225                 230                 235                 240

Pro Ser Thr Met Arg Val Phe Ile Trp Lys Ser Thr Pro Arg Val Ala
                245                 250                 255

Leu Ile Phe Ser Arg Asn Ser Phe Leu Gln Ser Leu Met Arg Lys Leu
                260                 265                 270

Asp Phe Pro Thr Ala Ala Ser Pro Ala Ser Thr Ile Leu Ala Phe Cys
            275                 280                 285

Glu Leu Lys Asp Leu Ala Leu Ser Ser Thr Arg Ser Val Trp Gly Glu
            290                 295                 300

Ser Ala Glu Met Gly Phe Leu Asp Glu Leu Thr Met Leu Pro Ser Leu
305                 310                 315                 320

Thr Asp Pro Trp Gly Phe Gln Ser Lys Thr Glu Ala Thr Ser Ser Lys
                325                 330                 335

Pro Asn Val Ser Ser Ser Leu Met Ser Gly Thr Ser Val Ser Glu Ala
            340                 345                 350

Ser Pro Pro Lys Leu Ser Cys Thr Pro Cys Asp Leu Asn Pro Leu Trp
            355                 360                 365

Cys Leu Tyr Ser Thr Ser Glu Ser Tyr Ser Leu Gly Ser Leu Lys Val
            370                 375                 380

Asp Lys Pro Leu Ser Lys Gln Leu Ser Gly Arg Leu Ser Thr Ser Gln
385                 390                 395                 400

Phe Val Leu Cys Arg Gly Ser Gln Arg Ala Arg Glu Ser Gln Ser Ser
                405                 410                 415

Ser Thr Glu Glu Arg Asp Asp Leu Ser Pro Arg Gly Gly Glu Pro Met
            420                 425                 430
```

-continued

```
Asn Leu Gly Leu Leu Leu Glu Ile Val Phe Pro Gly Glu Ile Leu Phe
            435                 440                 445

Ile Cys Lys Asp Leu Leu Asn Leu Leu Leu Phe Ser Arg Ala Leu Leu
        450                 455                 460

Arg Pro Ser Leu Leu Ser Cys Ser Phe Arg Leu Ala Val Trp Ser Ile
465                 470                 475                 480

Ser Ile Cys Leu Ser Arg Leu Phe Arg Ser Ser Val Tyr Ala Arg Ile
                485                 490                 495

Ile Ser Arg Ser Leu Ser Val Phe Arg Leu Ser Ala Ser Leu Phe Lys
            500                 505                 510

Ala Ser Asn Ser Leu Arg Lys Ala Met Phe Val Cys Ala Ser Lys Arg
        515                 520                 525

Ser Phe Leu Thr Phe Trp Phe Ser Ile Asp Lys Ser Ile Cys Phe Phe
    530                 535                 540

Asn Ala Ala Thr Ser Ser Phe Leu Thr Arg Phe Asp Cys Ser Ser Ser
545                 550                 555                 560

Phe Leu Ser Phe Leu Met Val Thr Cys Arg Ser Pro Thr Ser Val Ser
                565                 570                 575

Tyr Arg Leu Arg Ser Leu Arg Ala Ser Ser Ala Leu Arg Phe Ser Ser
            580                 585                 590

Phe Arg Val Leu Cys Ser Ala Ile Leu Ser Ile Ser Ser Ser Asn
        595                 600                 605

Ser Leu Asn Cys Ile Ala Ala Leu Ser Trp Ala Leu Phe Thr Ala Met
    610                 615                 620

Ala Lys Phe Ser Ile Ser Val Leu Ser Leu Ile Ser Arg Met Lys Phe
625                 630                 635                 640

Phe Ile Thr Cys Ser Tyr Gly Ile Asn Leu Gly Ser Thr Arg Leu Met
                645                 650                 655

Phe Trp Tyr Lys Val Leu Thr Cys Ser Ser Leu Gly Met Asn Leu Ala
            660                 665                 670

Ser Ser Pro Ser Arg Ala Trp Lys Ser Cys Gln Ala Arg Pro Gly Leu
        675                 680                 685

Ala Gly Pro His Glu Val Ala Ser Ala Ala Ala Ser Ser Ser Pro
    690                 695                 700

Ser Ser Ser Ser Leu Ser Cys Val Ser Gly Pro Ala Ser Asp Thr Ala
705                 710                 715                 720

Gly Ala Gly Ser Arg Gly Pro Gln Ser Arg Arg Pro Pro Arg Arg
                725                 730                 735

Asp Pro Arg Lys Pro Arg Ala Asn Ser Trp Lys Val Met Ala Pro Ser
            740                 745                 750

Arg Ser Ala Ser Ser Arg Trp Asn Thr Ala Ser Ala Ser Ala Gly Arg
        755                 760                 765

Thr Arg Ser Ser Val His Ser Ala Arg Asn Ser Ser Arg Ser Arg Arg
    770                 775                 780

Pro Glu Arg Phe Ala Ser Gln Ala Ala Lys Thr Glu Arg Ser Arg Ala
785                 790                 795                 800

Ser Ser Ser Pro Ser Pro Ser Ala Ser Ile Pro Gly Gly Gly
                805                 810                 815

Arg Glu Gly Ser Gly Ala Pro Arg Gly Ala Gly Pro Ser Leu Glu Gly
            820                 825                 830

Arg Gly His Leu Leu Pro Pro Gly Gly Pro Ala Ser Leu Ala Arg Pro
        835                 840                 845
```

-continued

```
Ala Gly Ser Ala Thr Gly Asn Val Gly Arg Gly Glu Arg Arg Gly
    850                 855                 860
Trp Pro Ser Gly Ser Leu Arg Arg Arg Phe Gly Pro Ala Pro Asn Arg
865                 870                 875                 880
Ser Arg Glu Arg Trp Gly Ala Pro Gly Leu Gln Ala Pro Pro Arg Ser
                885                 890                 895
Ala Ser Cys Asp
            900

<210> SEQ ID NO 38
<211> LENGTH: 891
<212> TYPE: PRT
<213> ORGANISM: Unknown Organism
<220> FEATURE:
<223> OTHER INFORMATION: Description of Unknown Organism: Tks 202

<400> SEQUENCE: 38

Phe Phe Phe Phe Phe Tyr His Phe Lys Asn Ile Tyr Met Leu Ser Phe
  1               5                  10                  15
Lys Thr Cys Lys Asp Met Thr Ser Leu Phe Ser Gln Arg Ala Gln Ile
             20                  25                  30
Thr His Asp Lys Thr Lys Lys Ser Gln Ser Ser Arg Gly Thr Glu Leu
         35                  40                  45
Gly Ser Gly Phe Pro Ala Leu Thr Leu His Arg Thr Val Ser Val Gly
     50                  55                  60
Cys Ala Thr Leu Leu Arg Ala Lys Val Thr Gln Ile Gln Tyr Ser Gly
 65                  70                  75                  80
Asn Glu Asp Phe Thr Gly Gln Gly Cys Leu Gly Phe Ser His Cys Asn
                 85                  90                  95
Asn Ser Ser Ser Val Val Thr Phe Trp Asn Trp Ser Arg Leu Asp Trp
            100                 105                 110
Trp Ile Cys Cys His Pro Cys Gln Phe Ser Phe Ser Leu Leu Glu Gln
        115                 120                 125
Gly Ala Glu Gln Pro Pro Leu Cys Asn His Leu Trp His Leu Phe His
    130                 135                 140
Arg Ile Met Pro His Thr Ser Trp Pro Val Ser Leu Gln Ser Ala Leu
145                 150                 155                 160
Gly His Ile Phe Val Pro Leu Gln Gln Cys His Glu Cys Gln Pro Cys
                165                 170                 175
Phe Leu Pro Ala Trp Glu Gln Ser His Gly Leu His Pro Gln Ser Tyr
            180                 185                 190
Leu Pro Ile Leu Val Cys Glu Ser Phe Ser His Met His His Thr Ala
        195                 200                 205
Ala Lys His His Leu Pro Phe Ser Lys Thr Trp Gln Tyr Phe Ile Ser
    210                 215                 220
Pro Asp Gln Leu Tyr Pro Arg Ala Ala Glu Leu Phe Val Leu His Pro
225                 230                 235                 240
Gln Gly Phe Ser Phe Gly Asn Gln Leu Pro Gly Trp Arg Leu Tyr Phe
                245                 250                 255
Leu Glu Ile His Ser Cys Lys Val Ser Gly Asn Thr Ser Pro Leu Gln
            260                 265                 270
Arg Pro Gln Gln Val Gln Ser Cys Lys Pro Ser Val Ser Lys Ile Arg
        275                 280                 285
Cys His Leu Pro Gly Leu Ser Gly Ala Arg Val Leu Arg Trp Ala Phe
    290                 295                 300
```

```
Leu Met Asn Gln Cys Cys Leu His Gln Thr Leu Gly Ala Ser Ser Leu
305                 310                 315                 320

Arg Arg Lys Pro His Leu Leu Asn Gln Met Ser Leu His Pro Leu Cys
            325                 330                 335

Gln Glu His Leu Cys Leu Lys His His Leu Gln Ser Ser Pro Ala Pro
                340                 345                 350

Arg Val Thr Ser Glu Ile Pro Ser Gly Ala Cys Ile Pro Leu Leu Ser
                355                 360                 365

His Thr His Trp Asp Leu Ser Arg Thr Ser Arg Cys Arg Ser Ser Phe
            370                 375                 380

Gln Ala Gly Cys Gln Leu His Asn Leu Ser Ser Ala Glu Asp His Arg
385                 390                 395                 400

Gly Pro Gly Ser His Ser Pro His Pro His Arg Lys Ser Gly Met Thr
                405                 410                 415

Cys His Ser Leu Glu Val Glu Gly Asn Asp Gln Ile Trp Asp Cys Phe
                420                 425                 430

Lys Leu Tyr Ser Leu Val Arg Tyr Tyr Leu Tyr Ala Lys Ile Cys Thr
            435                 440                 445

Cys Tyr Asn Cys Phe Gln Gly His Phe Gly His Tyr Cys His Val
450                 455                 460

Ala Ser Gly Leu Phe Gly Val Phe Gln Phe Ala Ser Gln Asp Tyr Phe
465                 470                 475                 480

Asp Leu Leu Cys Met Leu Gly Leu Phe Pro Asp Pro Phe Gln Tyr Ser
                485                 490                 495

Asp Ser Asp Gln His Asn His Phe Ser Lys His Leu Thr His Ser Glu
                500                 505                 510

Glu Arg Leu Cys Leu Ser Val Leu Leu Lys Gly Leu Ser Leu Ser Gly
            515                 520                 525

Phe Pro Leu Ile Asn His Lys Phe Val Phe Ser Met Gln Pro His Leu
530                 535                 540

Pro Phe Asp Leu Arg Val Leu Ile Val Leu Arg Ala Phe Leu Ala Phe
545                 550                 555                 560

Trp Ser Pro Ala Asp Leu Leu Leu Gln Phe His Thr Asp Val Gly His
                565                 570                 575

Gly Leu Pro Gln Leu Cys Val Phe Arg Leu Ser Val Ser Tyr Val Leu
                580                 585                 590

Gln Pro Glu Ser Ser Asp Pro Phe Pro Leu Pro Thr His Ser Thr Ala
            595                 600                 605

Leu Pro Cys Pro Gly Leu Ser Ser Pro Gln Trp Pro Asn Phe Pro Phe
610                 615                 620

Leu Cys Phe Glu Val Ser His Gly Ser Ser Leu His Val His Met Ala
625                 630                 635                 640

Glu Leu Ile Leu Ala Pro Gln Gly Cys Phe Gly Thr Arg Tyr Leu Ala
                645                 650                 655

Leu Leu Trp Glu Thr Trp Leu Arg Pro Gln Val Ala Pro Gly Asn Pro
            660                 665                 670

Ala Lys Pro Gly Arg Asp Ser Pro Gly Arg Thr Arg Trp Pro Ala Pro
            675                 680                 685

Pro Pro Arg Pro Arg Arg Leu Arg Pro Pro Arg Cys Arg Val Ser Pro
690                 695                 700

Ala Pro Pro Gln Thr Arg Arg Ala Arg Asp Pro Glu Asp Pro Ser Pro
705                 710                 715                 720

Gly Ala Ala Pro Arg Gly Gly Thr Arg Gly Ser His Ala Arg Thr Pro
```

```
                    725                 730                 735
Gly Arg Trp Arg Arg His Gly Arg Arg Pro Ala Ala Gly Ile Leu Pro
            740                 745                 750

Arg Arg Arg Pro Ala Ala Pro Ala Ala Pro Cys Thr Val Pro Gly Thr
        755                 760                 765

Pro Arg Ala Pro Gly Ala Pro Ser Gly Ser Arg Arg Arg Arg Arg Arg
    770                 775                 780

Leu Ser Ala Ala Gly Pro Ala Pro Leu Arg Pro His Pro Pro Pro Ser
785                 790                 795                 800

Arg Leu Ala Gly Ala Ala Glu Arg Ala Pro Glu Arg Arg Gly Ala Gln
                805                 810                 815

Gly Pro Pro Trp Lys Asp Gly Ala Thr Cys Cys Arg Arg Glu Ala Arg
            820                 825                 830

Arg Val Trp Leu Val Arg Leu Val Arg Pro Leu Glu Gly Thr Ser Gly
        835                 840                 845

Gly Ala Arg Asn Val Gly Gly Arg Ala Ala Pro Phe Asp Asp Gly
    850                 855                 860

Ser Gly Gln Pro Pro Thr Gly Pro Gly Ser Gly Gly Val Arg Pro Gly
865                 870                 875                 880

Ser Arg His Arg Gln Gly Ala Pro Pro Ala Thr
                885                 890

<210> SEQ ID NO 39
<211> LENGTH: 190
<212> TYPE: PRT
<213> ORGANISM: Unknown Organism
<220> FEATURE:
<223> OTHER INFORMATION: Description of Unknown Organism: dbl

<400> SEQUENCE: 39

Asp Val Leu Lys Asn His Val Leu Asn Glu Leu Ile Gln Thr Glu Arg
1               5                   10                  15

Val Tyr Val Arg Glu Leu Tyr Thr Val Leu Leu Gly Tyr Arg Ala Glu
            20                  25                  30

Met Asp Asn Pro Glu Met Phe Asp Leu Met Pro Pro Leu Leu Arg Asn
        35                  40                  45

Lys Lys Asp Ile Leu Phe Gly Asn Met Ala Glu Ile Tyr Glu Phe His
    50                  55                  60

Asn Asp Ile Phe Leu Ser Ser Leu Glu Asn Cys Ala His Ala Pro Glu
65                  70                  75                  80

Arg Val Gly Pro Cys Phe Leu Glu Arg Lys Asp Asp Phe Gln Met Tyr
                85                  90                  95

Ala Lys Tyr Cys Gln Asn Lys Pro Arg Ser Glu Thr Ile Trp Arg Lys
            100                 105                 110

Tyr Ser Glu Cys Ala Phe Phe Gln Glu Cys Gln Arg Lys Leu Lys His
        115                 120                 125

Arg Leu Arg Leu Asp Ser Tyr Leu Leu Lys Pro Val Gln Arg Ile Thr
    130                 135                 140

Lys Tyr Gln Leu Leu Leu Lys Glu Leu Leu Tyr Ser Lys Asp Cys
145                 150                 155                 160

Glu Gly Ser Ala Leu Leu Lys Lys Ala Leu Asp Ala Met Leu Asp Leu
                165                 170                 175

Leu Lys Ser Val Asn Asp Ser Met His Gln Ile Ala Ile Asn
            180                 185                 190
```

-continued

```
<210> SEQ ID NO 40
<211> LENGTH: 186
<212> TYPE: PRT
<213> ORGANISM: Unknown Organism
<220> FEATURE:
<223> OTHER INFORMATION: Description of Unknown Organism: cdc24

<400> SEQUENCE: 40

His Asn Glu Tyr Val Lys Ile Ile Lys Glu Phe Val Ala Thr Glu Arg
 1               5                  10                  15

Lys Tyr Val His Asp Leu Glu Ile Leu Asp Lys Tyr Arg Gln Gln Leu
            20                  25                  30

Leu Asp Ser Asn Leu Ile Thr Ser Glu Glu Leu Tyr Met Leu Phe Pro
        35                  40                  45

Asn Leu Gly Asp Ala Ile Asp Phe Gln Arg Arg Phe Leu Ile Ser Leu
    50                  55                  60

Glu Ile Asn Ala Leu Val Glu Pro Ser Lys Gln Arg Ile Gly Ala Leu
65                  70                  75                  80

Phe Met His Ser Lys His Phe Lys Leu Tyr Glu Pro Trp Ser Ile
                85                  90                  95

Gly Gln Asn Ala Ala Ile Glu Phe Leu Ser Ser Thr Leu His Lys Met
            100                 105                 110

Arg Val Asp Glu Ser Gln Arg Phe Ile Ile Asn Asn Lys Leu Glu Leu
        115                 120                 125

Gln Ser Phe Leu Tyr Lys Pro Val Gln Arg Leu Cys Arg Tyr Pro Leu
    130                 135                 140

Leu Val Lys Glu Leu Leu Ala Glu Ser Ser Asp Asp Asn Asn Thr Lys
145                 150                 155                 160

Glu Leu Glu Ala Ala Leu Asp Ile Ser Lys Asn Ile Ala Arg Ser Ile
                165                 170                 175

Asn Glu Asn Gln Arg Arg Thr Glu Asn His
            180                 185

<210> SEQ ID NO 41
<211> LENGTH: 190
<212> TYPE: PRT
<213> ORGANISM: Unknown Organism
<220> FEATURE:
<223> OTHER INFORMATION: Description of Unknown Organism: vav

<400> SEQUENCE: 41

Tyr Asp Lys Arg Cys Cys Cys Leu Arg Glu Ile Gln Gln Thr Glu Glu
 1               5                  10                  15

Lys Tyr Thr Asp Thr Leu Gly Ser Ile Gln Gln His Phe Met Lys Pro
            20                  25                  30

Leu Gln Arg Phe Leu Lys Pro Gln Asp Met Glu Thr Ile Phe Val Asn
        35                  40                  45

Ile Glu Glu Leu Leu Ser Val His Thr His Phe Leu Lys Glu Leu Lys
    50                  55                  60

Asp Ala Leu Ser Gly Pro Gly Ala Thr Met Leu Tyr Gln Val Phe Ile
65                  70                  75                  80

Lys Tyr Lys Glu Arg Phe Leu Val Tyr Gly Arg Tyr Cys Ser Gln Val
                85                  90                  95

Glu Ser Ala Ile Lys His Leu Asp Gln Val Ala Thr Ala Arg Glu Asp
            100                 105                 110

Val Gln Met Lys Leu Glu Glu Cys Ser Gln Arg Ala Asn Asn Gly Arg
        115                 120                 125
```

```
Phe Thr Leu Arg Asp Leu Leu Met Val Pro Met Gln Arg Val Leu Lys
    130                 135                 140

Tyr His Leu Leu Leu Gln Glu Leu Val Lys His Thr Gln Asp Thr Thr
145                 150                 155                 160

Glu Lys Glu Asn Leu Arg Leu Ala Leu Asp Ala Met Arg Asp Leu Ala
                165                 170                 175

Gln Cys Val Asn Glu Val Lys Arg Asp Asn Glu Thr Leu Arg
            180                 185                 190

<210> SEQ ID NO 42
<211> LENGTH: 203
<212> TYPE: PRT
<213> ORGANISM: Unknown Organism
<220> FEATURE:
<223> OTHER INFORMATION: Description of Unknown Organism: tiam

<400> SEQUENCE: 42

Ala Asp Asn Val Arg Lys Val Ile Cys Glu Leu Leu Glu Thr Glu Arg
1               5                   10                  15

Thr Tyr Val Lys Asp Leu Asn Cys Leu Met Glu Arg Tyr Leu Lys Pro
                20                  25                  30

Leu Gln Lys Glu Thr Phe Leu Thr Gln Asp Glu Leu Asp Val Leu Phe
            35                  40                  45

Gly Asn Leu Thr Glu Met Val Glu Phe Gln Val Glu Phe Leu Lys Thr
50                  55                  60

Leu Glu Asp Gly Val Arg Leu Val Pro Asp Leu Glu Lys Leu Glu Lys
65                  70                  75                  80

Val Asp Gln Phe Lys Lys Val Leu Phe Ser Leu Gly Gly Ser Phe Leu
                85                  90                  95

Tyr Tyr Ala Asp Arg Phe Lys Leu Tyr Ser Ala Phe Cys Ala Ile His
            100                 105                 110

Thr Lys Val Pro Lys Val Leu Val Lys Ala Lys Thr Asp Thr Ala Phe
        115                 120                 125

Lys Ala Phe Leu Asp Ala Gln Asn Pro Lys Gln Gln His Ser Ser Thr
130                 135                 140

Leu Glu Ser Tyr Leu Ile Lys Pro Ile Gln Arg Ile Leu Lys Tyr Pro
145                 150                 155                 160

Leu Leu Leu Arg Glu Leu Phe Ala Leu Thr Asp Ala Glu Ser Glu Glu
                165                 170                 175

His Tyr His Leu Asp Val Ala Ile Lys Thr Met Asn Lys Val Ala Ser
            180                 185                 190

His Ile Asn Glu Met Gln Lys Ile His Glu Glu
        195                 200

<210> SEQ ID NO 43
<211> LENGTH: 198
<212> TYPE: PRT
<213> ORGANISM: Unknown Organism
<220> FEATURE:
<223> OTHER INFORMATION: Description of Unknown Organism: fgdl

<400> SEQUENCE: 43

Gln Gln Lys Val Phe His Ile Ala Asn Glu Leu Leu Gln Thr Glu Lys
1               5                   10                  15

Ala Tyr Val Ser Arg Leu His Leu Leu Asp Gln Val Phe Cys Ala Arg
                20                  25                  30

Leu Leu Glu Glu Ala Arg Asn Arg Ser Ser Phe Pro Ala Asp Val Val
            35                  40                  45
```

```
His Gly Ile Phe Ser Asn Ile Cys Ser Ile Tyr Cys Phe His Gln Gln
        50                  55                  60

Phe Leu Leu Pro Glu Leu Glu Lys Arg Met Glu Glu Trp Asp Arg Tyr
 65                  70                  75                  80

Pro Arg Ile Gly Asp Ile Leu Gln Lys Leu Ala Pro Phe Leu Lys Met
                85                  90                  95

Tyr Gly Glu Tyr Val Lys Asn Phe Asp Arg Ala Val Glu Leu Val Asn
            100                 105                 110

Thr Trp Thr Glu Arg Ser Thr Gln Phe Lys Val Ile Ile His Glu Val
            115                 120                 125

Gln Lys Glu Glu Ala Cys Arg Asn Leu Thr Leu Gln His His Met Leu
130                 135                 140

Glu Pro Val Gln Arg Ile Pro Arg Tyr Glu Leu Leu Leu Lys Asp Tyr
145                 150                 155                 160

Leu Leu Lys Leu Pro His Gly Ser Pro Asp Ser Lys Asp Ala Gln Lys
                165                 170                 175

Ser Leu Glu Leu Ile Ala Thr Ala Ala Glu His Ser Asn Ala Ala Ile
            180                 185                 190

Arg Lys Met Glu Arg Met
        195

<210> SEQ ID NO 44
<211> LENGTH: 175
<212> TYPE: PRT
<213> ORGANISM: Unknown Organism
<220> FEATURE:
<223> OTHER INFORMATION: Description of Unknown Organism: Grub

<400> SEQUENCE: 44

Ile Ser Ala Gln Gln Arg Leu Val Ser Glu Leu Ile Ala Cys Glu Gln
 1               5                  10                  15

Asp Tyr Val Ala Thr Leu Ser Glu Pro Val Pro Pro Gly Pro Glu
            20                  25                  30

Leu Thr Pro Glu Leu Arg Gly Thr Trp Ala Ala Leu Ser Ala Arg
         35                  40                  45

Glu Arg Leu Arg Ser Phe His Arg Thr His Phe Leu Arg Glu Leu Gln
 50                  55                  60

Gly Cys Ala Thr His Pro Leu Arg Ile Gly Ala Cys Glu Leu Arg His
 65                  70                  75                  80

Gly Asp Gln Phe Ser Leu Tyr Ala Gln Tyr Val Lys His Arg His Lys
                85                  90                  95

Leu Glu Asn Gly Leu Ala Ala Leu Ser Pro Leu Ser Lys Gly Ser Met
            100                 105                 110

Glu Ala Gly Pro Tyr Leu Pro Arg Ala Leu Gln Gln Pro Leu Glu Gln
            115                 120                 125

Leu Thr Arg Tyr Gly Arg Leu Ile Glu Glu Leu Leu Arg Glu Ala Gly
            130                 135                 140

Pro Glu Leu Ser Ser Glu Cys Arg Ala Leu Gly Ala Ala Val Gln Leu
145                 150                 155                 160

Leu Arg Glu Gln Glu Ala Arg Gly Arg Asp Leu Leu Ala Val Glu
                165                 170                 175

<210> SEQ ID NO 45
<211> LENGTH: 123
<212> TYPE: PRT
<213> ORGANISM: Unknown Organism
```

```
<220> FEATURE:
<223> OTHER INFORMATION: Description of Unknown Organism: dbl

<400> SEQUENCE: 45

Asn Leu Asn Glu Leu Gly Lys Met Ile Met Gln Gly Gly Phe Ser Val
 1               5                  10                  15

Trp Ile Gly His Lys Lys Gly Ala Thr Lys Met Lys Asp Leu Ala Arg
                20                  25                  30

Phe Lys Pro Met Gln Arg His Leu Phe Leu Tyr Glu Lys Ala Ile Val
            35                  40                  45

Phe Cys Lys Arg Arg Val Glu Ser Gly Glu Gly Ser Asp Arg Tyr Pro
        50                  55                  60

Ser Tyr Ser Phe Lys His Cys Trp Lys Met Asp Glu Val Gly Ile Thr
65                  70                  75                  80

Glu Tyr Val Lys Gly Asp Asn Arg Lys Phe Glu Ile Trp Tyr Gly Glu
                85                  90                  95

Lys Glu Glu Val Tyr Ile Val Gln Ala Ser Asn Val Asp Val Lys Met
            100                 105                 110

Thr Trp Leu Lys Glu Ile Arg Asn Ile Leu Leu
        115                 120

<210> SEQ ID NO 46
<211> LENGTH: 115
<212> TYPE: PRT
<213> ORGANISM: Unknown Organism
<220> FEATURE:
<223> OTHER INFORMATION: Description of Unknown Organism: tiam

<400> SEQUENCE: 46

Thr Val Arg Lys Ala Gly Ala Leu Ala Val Lys Asn Phe Leu Val His
 1               5                  10                  15

Lys Lys Asn Lys Lys Val Glu Ser Ala Thr Arg Arg Lys Trp Lys His
                20                  25                  30

Tyr Trp Val Ser Leu Lys Gly Cys Thr Leu Phe Phe Tyr Glu Ser Asp
            35                  40                  45

Gly Arg Ser Gly Ile Asp His Asn Ser Ile Pro Lys His Ala Val Trp
        50                  55                  60

Val Glu Asn Ser Ile Val Gln Ala Val Pro Glu His Pro Lys Lys Asp
65                  70                  75                  80

Phe Val Phe Cys Leu Ser Asn Ser Leu Gly Asp Ala Phe Leu Phe Gln
                85                  90                  95

Thr Thr Ser Gln Thr Glu Leu Glu Asn Trp Ile Thr Ala Ile His Ser
            100                 105                 110

Ala Cys Ala
        115

<210> SEQ ID NO 47
<211> LENGTH: 101
<212> TYPE: PRT
<213> ORGANISM: Unknown Organism
<220> FEATURE:
<223> OTHER INFORMATION: Description of Unknown Organism: fgd1

<400> SEQUENCE: 47

Asn Ser Val Ile Cys Ser Phe Leu His Tyr Met Glu Lys Gly Gly Lys
 1               5                  10                  15

Gly Trp His Lys Ala Trp Phe Val Val Pro Glu Asn Glu Pro Leu Val
                20                  25                  30
```

-continued

```
Leu Tyr Ile Tyr Gly Ala Pro Gln Asp Val Lys Ala Gln Arg Ser Leu
         35                  40                  45

Pro Leu Ile Gly Phe Glu Val Gly Pro Pro Glu Ala Gly Glu Arg Pro
 50                  55                  60

Asp Arg Arg His Val Phe Lys Ile Thr Gln Ser His Leu Ser Trp Tyr
 65                  70                  75                  80

Phe Ser Pro Glu Thr Glu Glu Leu Gln Arg Arg Trp Met Ala Val Leu
                 85                  90                  95

Gly Arg Ala Gly Arg
            100

<210> SEQ ID NO 48
<211> LENGTH: 108
<212> TYPE: PRT
<213> ORGANISM: Unknown Organism
<220> FEATURE:
<223> OTHER INFORMATION: Description of Unknown Organism: Grub

<400> SEQUENCE: 48

Asp Leu Lys Glu Gln Gly Gln Leu Leu His Arg Asp Pro Phe Thr Val
 1               5                  10                  15

Ile Cys Gly Arg Lys Lys Cys Leu Arg His Val Phe Leu Phe Glu His
                20                  25                  30

Leu Leu Leu Phe Ser Lys Leu Lys Gly Pro Glu Gly Gly Ser Glu Met
         35                  40                  45

Phe Val Tyr Lys Gln Ala Phe Lys Thr Ala Asp Met Gly Leu Thr Glu
 50                  55                  60

Asn Ile Gly Asp Ser Gly Leu Cys Phe Glu Leu Trp Phe Arg Arg Arg
 65                  70                  75                  80

Arg Ala Arg Glu Ala Tyr Thr Leu Gln Ala Thr Ser Pro Glu Ile Lys
                 85                  90                  95

Leu Lys Trp Thr Ser Ser Ile Ala Gln Leu Leu Trp
            100                 105

<210> SEQ ID NO 49
<211> LENGTH: 228
<212> TYPE: PRT
<213> ORGANISM: Unknown Organism
<220> FEATURE:
<223> OTHER INFORMATION: Description of Unknown Organism: Drebrin E

<400> SEQUENCE: 49

Met Ala Gly Val Ser Phe Ser Gly His Arg Leu Glu Leu Leu Ala Ala
 1               5                  10                  15

Tyr Glu Glu Val Ile Arg Glu Glu Ser Ala Ala Asp Trp Ala Leu Tyr
                20                  25                  30

Thr Tyr Glu Asp Gly Ser Asp Asp Leu Lys Leu Ala Ala Ser Gly Glu
         35                  40                  45

Gly Gly Leu Gln Glu Leu Ser Gly His Phe Glu Asn Gln Lys Val Met
 50                  55                  60

Tyr Gly Phe Cys Ser Val Lys Asp Ser Gln Ala Ala Leu Pro Lys Tyr
 65                  70                  75                  80

Val Leu Ile Asn Trp Val Gly Glu Asp Val Pro Asp Ala Arg Lys Cys
                 85                  90                  95

Ala Cys Ala Ser His Val Ala Lys Val Ala Glu Phe Phe Gln Gly Val
            100                 105                 110

Asp Val Ile Val Asn Ala Ser Ser Val Glu Asp Ile Asp Ala Gly Ala
        115                 120                 125
```

```
Ile Gly Gln Arg Leu Ser Asn Gly Leu Ala Arg Leu Ser Ser Pro Val
        130                 135                 140

Leu His Arg Leu Arg Leu Arg Glu Asp Glu Asn Ala Glu Pro Val Gly
145                 150                 155                 160

Thr Thr Tyr Gln Lys Thr Asp Ala Ala Val Glu Met Lys Arg Ile Asn
                165                 170                 175

Arg Glu Gln Phe Trp Glu Gln Ala Lys Lys Glu Glu Leu Arg Lys
                180                 185                 190

Glu Glu Glu Arg Lys Lys Ala Leu Asp Glu Arg Leu Arg Phe Glu Gln
                195                 200                 205

Glu Arg Met Glu Gln Glu Arg Gln Gln Gln Glu Arg Glu Arg Arg
        210                 215                 220

Tyr Arg Glu Arg
225

<210> SEQ ID NO 50
<211> LENGTH: 431
<212> TYPE: PRT
<213> ORGANISM: Unknown Organism
<220> FEATURE:
<223> OTHER INFORMATION: Description of Unknown Organism: Tks 118

<400> SEQUENCE: 50

Met Ala Ala Asn Leu Ser Arg Asn Gly Pro Ala Leu Gln Glu Ala Tyr
1               5                   10                  15

Val Arg Val Val Thr Glu Lys Ser Pro Thr Asp Trp Ala Leu Phe Thr
                20                  25                  30

Tyr Glu Gly Asn Ser Asn Asp Ile Arg Val Ala Gly Thr Gly Glu Gly
            35                  40                  45

Gly Leu Glu Glu Met Val Glu Leu Asn Ser Gly Lys Val Met Tyr
    50                  55                  60

Ala Phe Cys Arg Val Lys Asp Pro Asn Ser Gly Leu Pro Lys Phe Val
65                  70                  75                  80

Leu Ile Asn Trp Thr Gly Glu Gly Val Asn Asp Val Arg Lys Gly Ala
                85                  90                  95

Cys Ala Ser His Val Ser Thr Met Ala Ser Phe Leu Lys Gly Ala His
                100                 105                 110

Val Thr Ile Asn Ala Arg Ala Glu Glu Asp Val Glu Pro Glu Cys Ile
            115                 120                 125

Met Glu Lys Val Ala Lys Ala Ser Gly Ala Asn Tyr Ser Phe His Lys
        130                 135                 140

Glu Ser Gly Arg Phe Gln Asp Val Gly Pro Gln Ala Pro Val Gly Ser
145                 150                 155                 160

Val Tyr Gln Lys Thr Asn Ala Val Ser Glu Ile Lys Arg Val Gly Lys
                165                 170                 175

Asp Ser Phe Trp Ala Lys Ala Glu Lys Glu Glu Asn Arg Arg Leu
                180                 185                 190

Glu Glu Lys Arg Arg Ala Glu Glu Ala Gln Arg Gln Leu Glu Gln Glu
                195                 200                 205

Arg Arg Glu Arg Glu Leu Arg Glu Ala Ala Arg Glu Gln Arg Tyr
        210                 215                 220

Gln Glu Gln Gly Gly Glu Ala Ser Pro Gln Ser Arg Thr Trp Glu Gln
225                 230                 235                 240

Gln Gln Glu Val Val Ser Arg Asn Arg Asn Glu Gln Glu Ser Ala Val
                245                 250                 255
```

-continued

```
His Pro Arg Glu Ile Phe Lys Gln Lys Glu Arg Ala Met Ser Thr Thr
            260                 265                 270
Ser Ile Ser Ser Pro Gln Pro Gly Lys Leu Arg Ser Pro Phe Leu Gln
            275                 280                 285
Lys Gln Leu Thr Gln Pro Glu Thr His Phe Gly Arg Glu Pro Ala Ala
290                 295                 300
Ala Ile Ser Arg Pro Arg Ala Asp Leu Pro Ala Glu Glu Pro Ala Pro
305                 310                 315                 320
Ser Thr Pro Pro Cys Leu Val Gln Ala Glu Glu Ala Val Tyr Glu
            325                 330                 335
Glu Pro Pro Glu Gln Glu Thr Phe Tyr Glu Gln Pro Pro Leu Val Gln
            340                 345                 350
Gln Gln Gly Ala Gly Ser Glu His Ile Asp His His Ile Gln Gly Gln
            355                 360                 365
Gly Leu Ser Gly Gln Gly Leu Cys Ala Arg Ala Leu Tyr Asp Tyr Gln
            370                 375                 380
Ala Ala Asp Asp Thr Glu Ile Ser Phe Asp Pro Glu Asn Leu Ile Thr
385                 390                 395                 400
Gly Ile Glu Val Ile Asp Gly Trp Trp Arg Gly Tyr Gly Pro Asp
            405                 410                 415
Gly His Phe Gly Met Phe Pro Ala Asn Tyr Val Glu Leu Ile Glu
            420                 425                 430

<210> SEQ ID NO 51
<211> LENGTH: 433
<212> TYPE: PRT
<213> ORGANISM: Unknown Organism
<220> FEATURE:
<223> OTHER INFORMATION: Description of Unknown Organism: mSH3P7

<400> SEQUENCE: 51

Met Ala Val Asn Leu Ser Arg Asn Gly Pro Ala Leu Gln Glu Ala Tyr
1               5                   10                  15
Val Arg Val Val Thr Glu Lys Ser Pro Thr Asp Trp Ala Leu Phe Thr
            20                  25                  30
Tyr Glu Gly Asn Ser Asn Asp Ile Arg Val Ala Gly Thr Gly Glu Gly
            35                  40                  45
Gly Leu Glu Glu Leu Val Glu Glu Leu Asn Ser Gly Lys Val Met Tyr
        50                  55                  60
Ala Phe Cys Arg Val Lys Asp Pro Asn Ser Gly Leu Pro Lys Phe Val
65                  70                  75                  80
Leu Ile Asn Trp Thr Gly Glu Gly Val Asn Asp Val Arg Lys Gly Ala
            85                  90                  95
Cys Ala Asn His Val Ser Thr Met Ala Asn Phe Leu Lys Gly Ala His
            100                 105                 110
Val Thr Ile Asn Ala Arg Ala Glu Glu Asp Val Glu Pro Glu Cys Ile
            115                 120                 125
Met Glu Lys Val Ala Lys Ala Ser Gly Ala Asn Tyr Ser Phe His Lys
130                 135                 140
Glu Ser Thr Ser Phe Gln Asp Val Gly Pro Gln Ala Pro Val Gly Ser
145                 150                 155                 160
Val Tyr Gln Lys Thr Asn Ala Ile Ser Glu Ile Lys Arg Val Gly Lys
            165                 170                 175
Asp Asn Phe Trp Ala Lys Ala Glu Lys Glu Glu Asn Arg Arg Leu
            180                 185                 190
```

```
Glu Glu Lys Arg Arg Ala Glu Glu Arg Gln Arg Leu Glu Glu Glu
        195                 200                 205

Arg Arg Glu Arg Glu Leu Gln Glu Ala Ala Arg Arg Glu Gln Arg Tyr
    210                 215                 220

Gln Glu Gln His Arg Ser Ala Gly Ala Pro Ser Arg Thr Gly Glu Pro
225                 230                 235                 240

Glu Gln Glu Ala Val Ser Arg Thr Arg Gln Glu Trp Glu Ser Ala Gly
                245                 250                 255

Gln Gln Ala Pro His Pro Arg Glu Ile Phe Lys Gln Lys Glu Arg Ala
            260                 265                 270

Met Ser Thr Thr Ser Val Thr Ser Ser Gln Pro Gly Lys Leu Arg Ser
        275                 280                 285

Pro Phe Leu Gln Lys Gln Leu Thr Gln Pro Glu Thr Ser Tyr Gly Arg
    290                 295                 300

Glu Pro Thr Ala Pro Val Ser Arg Pro Ala Ala Gly Val Cys Glu Glu
305                 310                 315                 320

Pro Ala Pro Ser Thr Leu Ser Ser Ala Gln Thr Glu Glu Pro Thr
                325                 330                 335

Tyr Glu Val Pro Pro Glu Gln Asp Thr Leu Tyr Glu Pro Pro Leu
                340                 345                 350

Val Gln Gln Gln Gly Ala Gly Ser Glu His Ile Asp Asn Tyr Met Gln
            355                 360                 365

Ser Gln Gly Phe Ser Gly Gln Gly Leu Cys Ala Arg Ala Leu Tyr Asp
    370                 375                 380

Tyr Gln Ala Ala Asp Asp Thr Glu Ile Ser Phe Asp Pro Glu Asn Leu
385                 390                 395                 400

Ile Thr Gly Ile Glu Val Ile Asp Glu Gly Trp Trp Arg Gly Tyr Gly
                405                 410                 415

Pro Asp Gly His Phe Gly Met Phe Pro Ala Asn Tyr Val Glu Leu Ile
            420                 425                 430

Glu

<210> SEQ ID NO 52
<211> LENGTH: 64
<212> TYPE: PRT
<213> ORGANISM: Homo sapiens

<400> SEQUENCE: 52

Gly Gly Val Thr Thr Phe Val Ala Leu Tyr Asp Tyr Glu Ser Arg Thr
1               5                   10                  15

Glu Thr Asp Leu Ser Phe Lys Lys Gly Glu Arg Leu Gln Ile Val Asn
            20                  25                  30

Asn Thr Glu Gly Asp Trp Trp Leu Ala His Ser Leu Ser Thr Gly Gln
        35                  40                  45

Thr Gly Tyr Ile Pro Ser Asn Tyr Val Ala Pro Ser Asp Ser Ile Gln
    50                  55                  60

<210> SEQ ID NO 53
<211> LENGTH: 206
<212> TYPE: PRT
<213> ORGANISM: Unknown Organism
<220> FEATURE:
<223> OTHER INFORMATION: Description of Unknown Organism: c-mel

<400> SEQUENCE: 53

Met Ala Lys Thr Tyr Asp Tyr Leu Phe Lys Leu Leu Leu Ile Gly Asp
```

-continued

```
                1               5                   10                  15
Ser Gly Val Gly Lys Thr Cys Val Leu Phe Arg Phe Ser Glu Asp Ala
                    20                  25                  30

Phe Asn Ser Thr Phe Ile Ser Thr Ile Gly Ile Asp Phe Lys Ile Arg
                35                  40                  45

Thr Ile Glu Leu Asp Gly Lys Arg Ile Lys Leu Gln Ile Trp Asp Thr
            50                  55                  60

Ala Gly Gln Glu Arg Phe Arg Thr Ile Thr Thr Ala Tyr Tyr Arg Gly
 65                 70                  75                  80

Ala Met Gly Ile Met Leu Val Tyr Asp Ile Thr Asn Glu Lys Ser Phe
                    85                  90                  95

Asp Asn Ile Arg Asn Trp Ile Arg Asn Ile Glu Glu His Ala Ser Ala
                100                 105                 110

Asp Val Glu Lys Met Ile Leu Gly Asn Lys Cys Asp Val Asn Asp Lys
                115                 120                 125

Arg Gln Val Ser Lys Glu Arg Gly Glu Lys Leu Ala Leu Asp Tyr Gly
            130                 135                 140

Ile Lys Phe Met Glu Thr Ser Ala Lys Ala Asn Ile Asn Val Glu Asn
145                 150                 155                 160

Ala Phe Phe Thr Leu Ala Arg Asp Ile Lys Ala Lys Met Asp Lys Asn
                165                 170                 175

Trp Lys Ala Thr Ala Ala Gly Ser Ser His Gly Val Lys Ile Thr Val
                180                 185                 190

Glu Gln Gln Lys Arg Thr Ser Phe Phe Arg Cys Ser Leu Leu
            195                 200                 205
```

<210> SEQ ID NO 54
<211> LENGTH: 207
<212> TYPE: PRT
<213> ORGANISM: Unknown Organism
<220> FEATURE:
<223> OTHER INFORMATION: Description of Unknown Organism: rab8

<400> SEQUENCE: 54

```
Met Ala Lys Thr Tyr Asp Tyr Leu Phe Lys Leu Leu Leu Ile Gly Asp
 1               5                  10                  15

Ser Gly Val Gly Lys Thr Cys Val Leu Phe Arg Phe Ser Glu Asp Ala
                    20                  25                  30

Phe Asn Ser Thr Phe Ile Ser Thr Ile Gly Ile Asp Phe Lys Ile Arg
                35                  40                  45

Thr Ile Glu Leu Asp Gly Lys Arg Ile Lys Leu Gln Ile Trp Asp Thr
            50                  55                  60

Ala Gly Gln Glu Arg Phe Arg Thr Ile Thr Thr Ala Tyr Tyr Arg Gly
 65                 70                  75                  80

Ala Met Gly Ile Met Leu Val Tyr Asp Ile Thr Asn Glu Lys Ser Phe
                    85                  90                  95

Asp Asn Ile Arg Asn Trp Ile Arg Asn Ile Glu Glu His Ala Ser Ala
                100                 105                 110

Asp Val Glu Lys Met Ile Leu Gly Asn Lys Cys Asp Val Asn Asp Lys
                115                 120                 125

Arg Gln Val Ser Lys Glu Arg Gly Glu Lys Leu Ala Leu Asp Tyr Gly
            130                 135                 140

Ile Lys Phe Met Glu Thr Ser Ala Lys Ala Asn Ile Asn Val Glu Asn
145                 150                 155                 160

Ala Phe Phe Thr Leu Ala Arg Asp Ile Lys Ala Lys Met Asp Lys Lys
```

-continued

```
                    165                 170                 175
Leu Glu Gly Asn Ser Pro Gln Gly Ser Asn Gln Gly Val Lys Ile Thr
                180                 185                 190
Pro Asp Gln Gln Lys Arg Ser Ser Phe Phe Arg Cys Val Leu Leu
            195                 200                 205

<210> SEQ ID NO 55
<211> LENGTH: 203
<212> TYPE: PRT
<213> ORGANISM: Unknown Organism
<220> FEATURE:
<223> OTHER INFORMATION: Description of Unknown Organism: Tks 202

<400> SEQUENCE: 55

Ser Gln Lys Ala Tyr Lys Ile Val Leu Ala Gly Asp Ala Ala Val Gly
  1               5                  10                  15
Lys Ser Ser Phe Leu Met Arg Leu Cys Lys Asn Glu Phe Arg Glu Asn
                 20                  25                  30
Ile Ser Ala Thr Leu Gly Val Asp Phe Gln Met Lys Thr Leu Ile Val
             35                  40                  45
Asp Gly Glu Arg Thr Val Leu Gln Leu Trp Asp Thr Ala Gly Gln Glu
 50                  55                  60
Arg Phe Arg Ser Ile Ala Lys Ser Tyr Phe Arg Lys Ala Asp Gly Val
 65                  70                  75                  80
Leu Leu Leu Tyr Asp Val Thr Cys Glu Lys Ser Phe Leu Asn Ile Arg
                 85                  90                  95
Glu Trp Val Asp Met Ile Glu Asp Ala Ala His Glu Thr Val Pro Ile
                100                 105                 110
Met Leu Val Gly Asn Lys Ala Asp Ile Arg Asp Thr Ala Ala Thr Glu
            115                 120                 125
Gly Gln Lys Cys Val Pro Gly His Phe Gly Glu Lys Leu Ala Met Thr
130                 135                 140
Tyr Gly Ala Leu Phe Cys Glu Thr Ser Ala Lys Asp Gly Ser Asn Ile
145                 150                 155                 160
Val Glu Ala Val Leu His Leu Ala Arg Glu Val Lys Lys Arg Thr Asp
                165                 170                 175
Lys Asp Asp Ser Arg Ser Ile Thr Asn Leu Thr Gly Thr Asn Ser Lys
            180                 185                 190
Lys Ser Pro Gln Met Lys Asn Cys Cys Asn Gly
            195                 200
```